(12) United States Patent
Ling et al.

(10) Patent No.: US 8,519,096 B2
(45) Date of Patent: Aug. 27, 2013

(54) CITRULLINATED PEPTIDES FOR DIAGNOSING AND PROGNOSING RHEUMATOID ARTHRITIS

(75) Inventors: Nicholas Chi-Kwan Ling, San Diego, CA (US); Shui Long Wang, San Diego, CA (US); Dunrui Wang, San Diego, CA (US); Sharat Singh, Rancho Santa Fe, CA (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/239,329

(22) Filed: Sep. 21, 2011

(65) Prior Publication Data

US 2012/0295280 A1 Nov. 22, 2012

Related U.S. Application Data

(63) Continuation of application No. PCT/US2010/028946, filed on Mar. 26, 2010.

(60) Provisional application No. 61/164,840, filed on Mar. 30, 2009, provisional application No. 61/243,496, filed on Sep. 17, 2009, provisional application No. 61/255,058, filed on Oct. 26, 2009.

(51) Int. Cl.
*G01N 33/531* (2006.01)
*G01N 33/533* (2006.01)
*C07K 17/00* (2006.01)

(52) U.S. Cl.
USPC ............. 530/300; 530/324; 530/326; 435/7.1

(58) Field of Classification Search
None
See application file for complete search history.

(56) References Cited

U.S. PATENT DOCUMENTS

2009/0155822 A1 6/2009 Bang et al.

FOREIGN PATENT DOCUMENTS

| WO | WO 99/28344 A2 | 6/1999 |
| WO | WO 2007/000320 A2 | 1/2007 |

OTHER PUBLICATIONS

Bang, Holger et al., "Mutation and citrullination modifies vimentin to a novel autoantigen for rheumatoid arthritis," Arthritis & Rheumatism, Aug. 2007, vol. 56, No. 8, pp. 2503-2511.
Nicaise, Roland Pascale et al., "Antibodies to mutated citrullinated vimentin for diagnosing rheumatoid arthritis in anti-CCP-negative patients and for monitoring infliximab therapy," Arthritis Research & Therapy, 2008, vol. 10, No. 6, p. R142.
Schellekens, G.A. et al., "Citrulline is an Essential Constituent of Antigenic Determinants Recognized by Rheumatoid Arthritis—specific Autoantibodies," J. Clin. Invest., 101(1):273-281, 1998.

*Primary Examiner* — Jacob Cheu
*Assistant Examiner* — Carmencita M Belei
(74) *Attorney, Agent, or Firm* — Kilpatrick Townsend & Stockton LLP

(57) ABSTRACT

The present invention provides novel citrullinated peptides, their use in methods for aiding, assisting, improving, or facilitating the diagnosis or prognosis of rheumatic diseases such as rheumatoid arthritis (RA), and methods for identifying novel citrullinated peptides that are immunoreactive with anti-citrullinated protein antibodies (ACPAs). The present invention also provides methods for detecting rheumatoid factor (RF) using novel RF detection reagents as a means to aid, assist, improve, or facilitate the diagnosis or prognosis of rheumatic diseases such as RA. Kits comprising at least one of the novel citrullinated peptides and/or RF detection reagents of the present invention are also provided.

20 Claims, 27 Drawing Sheets

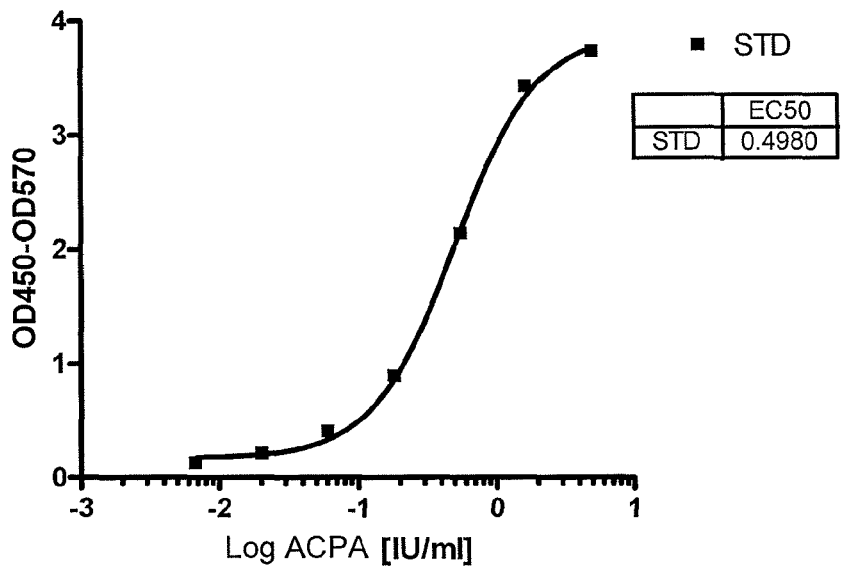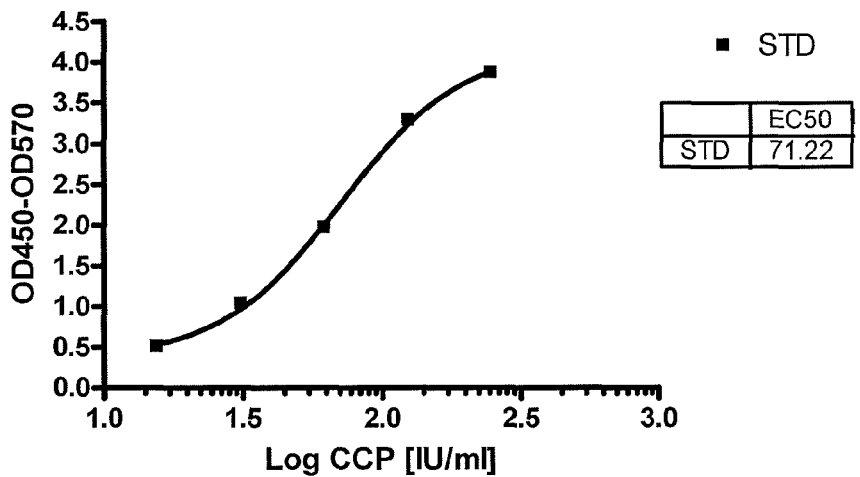
FIG. 4

|  | Samples | OD | | Average (IU/ml) | Stdev | %CV |
|---|---|---|---|---|---|---|
| INOVA anti-CCP Kit | NHS 1:100 | 0.01 | 0.01 | BDL | N/A | N/A |
|  | NHS 1:500 | 0.00 | 0.01 | BDL | N/A | N/A |
|  | C 1:100 | 3.84 | 3.76 | ADL | N/A | N/A |
|  | C 1:500 | 1.01 | 1.04 | 164.72 | 4.05 | 2.46 |
|  | C 1:2500 | 0.19 | 0.18 | 148.39 | 4.55 | 3.07 |
| [Arg$^{25}$]Cit-a32 Peptide | NHS 1:100 | 1.11 | 1.09 | 23.52 | 0.41 | 1.75 |
|  | NHS 1:500 | 0.35 | 0.33 | 31.53 | 1.46 | 4.64 |
|  | C 1:100 | 3.78 | 3.71 | ADL |  |  |
|  | C 1:500 | 2.63 | 2.54 | 379.76 | 20.73 | 5.46 |
|  | C 1:2500 | 0.80 | 0.82 | 426.14 | 7.06 | 1.66 |

BDL: Below detection limit. ADL: Above detection limit.

*FIG. 5*

A
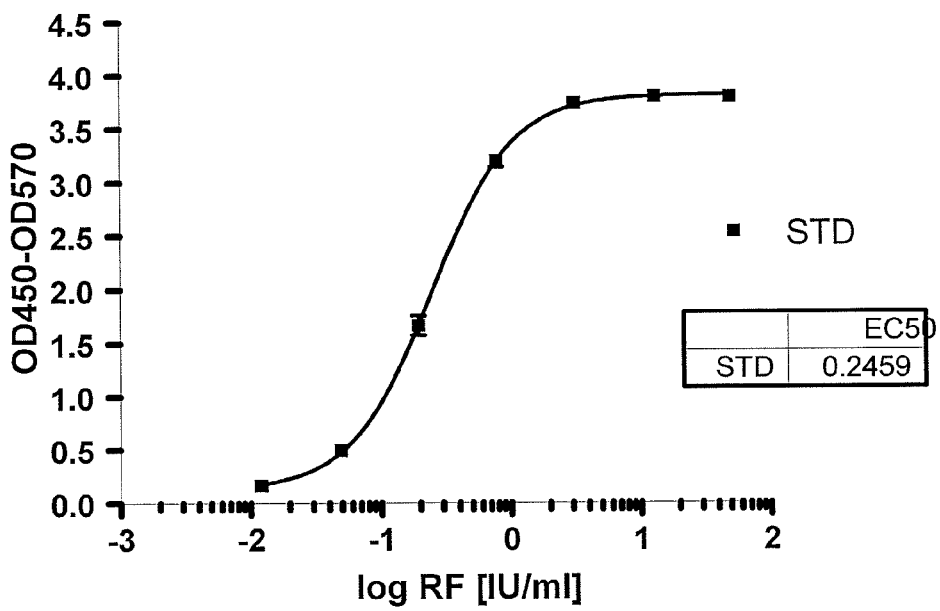
B
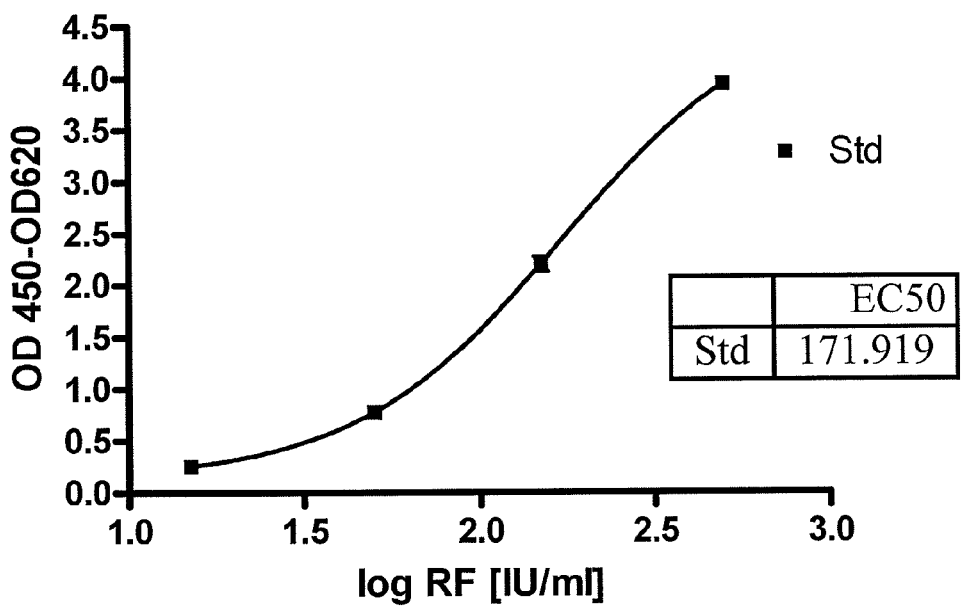
FIG. 8

| | Samples | OD | | Average RF (IU/ml) | STDEV | %CV |
|---|---|---|---|---|---|---|
| Orgentec RF Screen | NHS 1:100 | 0.51 | 0.50 | 32.72 | 0.56 | 1.70 |
| | NHS 1:500 | 0.14 | 0.13 | 43.94 | 2.24 | 5.09 |
| | NHS 1:2500 | 0.04 | 0.04 | BDL | N/A | N/A |
| | C 1:100 | 3.94 | 3.94 | ADL | N/A | N/A |
| | C 1:500 | 1.95 | 1.85 | 612.99 | 20.99 | 3.42 |
| | C 1:2500 | 0.42 | 0.41 | 663.65 | 10.15 | 1.53 |
| | C 1:12500 | 0.09 | 0.09 | BDL | N/A | N/A |
| HRP-Protein L | NHS 1:100 | 0.89 | 0.87 | 9.32 | 0.18 | 1.88 |
| | NHS 1:500 | 0.23 | 0.21 | 9.37 | 0.94 | 9.98 |
| | NHS 1:2500 | 0.10 | 0.07 | BDL | N/A | N/A |
| | C 1:100 | 3.61 | 3.84 | ADL | N/A | N/A |
| | C 1:500 | 3.43 | 3.46 | 593.32 | 29.92 | 5.04 |
| | C 1:2500 | 1.31 | 1.41 | 376.66 | 22.12 | 5.87 |
| | C 1:12500 | 0.30 | 0.36 | 402.32 | 58.86 | 14.63 |

*BDL: Below detection limit. ADL: Above detection limit.*

FIG. 9

|   | P1 | P2 | P3 | P4 | P5 | P6 | P7 | P8 | P9 |
|---|---|---|---|---|---|---|---|---|---|
| A | -2 | 0 | 0 | 0 | 0 | 0 | 0 | 0 | 0 |
| D | -2 | -1.3 | -1.3 | 1.7 | -0.2 | 0 | -1.1 | -1.1 | -2.6 |
| E | -2 | 0.1 | -1.2 | 0.8 | -0.1 | -1.2 | -0.2 | -0.2 | -1.8 |
| F | 0 | 0.8 | 0.8 | -0.8 | 0.3 | -1.3 | -0.8 | 0.1 | -0.8 |
| G | -2 | 0.5 | 0.2 | -1.5 | -0.2 | -1.1 | -1.5 | -0.5 | -0.2 |
| H | -2 | 0.8 | 0.2 | 0.8 | -0.1 | -1.6 | -0.8 | 0 | 0.3 |
| I | -1 | 1.1 | 1.5 | 0.8 | 0.1 | -0.2 | -0.2 | -0.1 | -0.4 |
| K | -2 | 1.1 | 0 | -2.2 | 0.3 | -2.3 | -1.2 | 0.9 | -0.9 |
| L | -1 | 1 | 1 | -0.6 | 0.1 | -1.3 | 0.4 | 0.6 | -1.3 |
| M | -1 | 1.1 | 1.4 | 1.4 | 0.3 | -1.3 | 0.7 | 0.4 | -0.4 |
| N | -2 | 0.8 | 0.5 | 0.5 | 0.2 | 1.7 | -0.1 | 0.7 | -1.1 |
| P | -2 | -0.5 | 0.3 | -2.1 | 0.5 | 0.1 | -0.3 | -0.2 | -1.6 |
| Q | -2 | 1.2 | 0 | 1.1 | 0.1 | -1.2 | -0.5 | 1.6 | 0.7 |
| R | -2 | 2.2 | 0.7 | -1.5 | 0 | -2.2 | -1.2 | 0.7 | -0.9 |
| S | -2 | -0.3 | 0.2 | 1.1 | 0.4 | 1.7 | -0.4 | 0.6 | 1.2 |
| T | -1 | 2.1 | 0 | 0.8 | 0.6 | 1.9 | -0.2 | 0.5 | -0.3 |
| V | 0 | -0.1 | 0.5 | 0.5 | 0.4 | 1.3 | 0.5 | 0.4 | 0.5 |
| W | 0 | -0.1 | 0 | -1.2 | -0.1 | -0.9 | -1.3 | 0.6 | -0.3 |
| Y | 0 | 0.9 | 0.8 | -1 | -0.2 | -1.1 | -0.7 | 1.3 | -1.5 |

*FIG. 10*

```
1    MSTRSVSSSS  YRRMFGGPGT  ASRPSSSRSY  VTTSTRTYSL  GSALRPSTSR  SLYASSPGGV
61   YATRSSAVRL  ⁷¹RSSVPGVRL  QDSVDFSLAD  AINTEFKNTR  TNEKVELQEL  NDRFANYIDK
```

| Successive 9-residue peptides centered around the selected ⁷¹R to Q change | P1 , P2 , P3 , P4 , P5 , P6 , P7 , P8 , P9 values for each residue side chain from table | Score equals to the sum of the values |
|---|---|---|
| TRSSAVRLQ | -2.0,

```
              +2.9         +3.5 +4.2        +1.6    +2.3                      +1.8  +3.7
  1    MSTRSVSSSS  YRRMFGGPGT  ASRPSSSRSY  VTTSTRTYSL  GSALRPSTSR  SLYASSPGGV
             +2.7 +2.2      +5.5  +2.6                          +3.4               +1.3
 61    YATRSSAVRL  RSSVPGVRLL  QDSVDFSLAD  AINTEFKNTR  TNEKVELQEL  NDRFANYIDK
        +2.0                              -1.1    -0.2 +2.2 +2.5         +0.7   +1.0
121    VRFLEQQNKI  LLAELEQLKG  QGKSRLGDLY  EEEMRELRRQ  VDQLTNDKAR  VEVERDNLAE
        +0.6 +1.1           +1.1              +4.4           +2.1        +2.7
181    DIMRLREKLQ  EEMLQREEAE  NTLQSFRQDV  DNASLARLDL  ERKVESLQEE  IAFLKKLHEE
                                                 +2.3        +1.1
241    EIQELQAQIQ  EQHVQIDVDV  SKPDLTAALR  DVRQQYESVA  AKNLQEAEEW  YKSKFADLSE
            +1.8       +3.7          +4.0  +2.4                      +1.5 +1.6
301    AANRNNDALR  QAKQESTEYR  RQVQSLTCEV  DALKGTNESL  EROMREMEEN  FAVEAANYQD
           +2.4            +0.4     +1.2                         +1.9   +2.3
361    TIGRLQDEIQ  NMKEEMARHL  REYQDLLNVK  MALDIEIATY  RKLLEGEESR  ISLPLPNFSS
        +2.6                            +2.3           +2.2
421    LNLRETNLDS  LPLVDTHSKR  TLLIKTVETR  DGQVINETSQ  HHDDLE
```

FIG. 12

(1) Biotin-GST$\overset{+2.9}{X}$SVSSSS YR$\overset{+4.2}{X}$RSVSSSS Y$\overset{+3.5}{X}$SRPSSS$\overset{+2.3}{X}$S YV (2) Biotin-GRSYVTTST$\overset{+3.7}{X}$ TYSALRPSTS $\overset{+3.7}{X}$SLYAT$\overset{+2.7}{X}$SSA VRL (3) Biotin-GTRSSAV$\overset{+2.2}{X}$LR SSVPGV$\overset{+2.6}{X}$VRL $\overset{+5.5}{X}$SSVPG
   +3.4           +2.0 +2.2

(4) Biotin-GFKNT$\overset{}{X}$TNEK NYIDKV$\overset{}{X}$EL$\overset{}{X}$ RQVDQLT (5) Biotin-GLR$\overset{+2.5}{X}$QVDQLT SF$\overset{+4.4}{X}$DVDNAS LA$\overset{+2.1}{X}$ARLDLE$\overset{+2.7}{X}$$\overset{}{X}$ KV
   +2.3

(6) Biotin-GTAAL$\overset{}{X}$DVRQ QYR$\overset{+2.4}{X}$QVQSLT S (7) Biotin-GANRNNDAL$\overset{+3.7}{X}$ QAKQESTEY$\overset{+4.0}{X}$ RQVQSLT
   +2.4           +1.9

(8) Biotin-GRANYQDTIG $\overset{}{X}$LDIEIATY$\overset{}{X}$ KLLEGEES$\overset{+2.3}{X}$I SR
   +2.6                                  +2.3                    +2.2

(9) Biotin-GNFSSLNL$\overset{}{X}$E TNLDSLPLVD THSK$\overset{}{X}$TLLIK TVET$\overset{}{X}$DG

FIG. 13

Thrombin Cleavage Site

```
        Signal Peptide Sequence                                      -0.1  +1.9
  1   MFSMRIVCLV LSVVGTAWTA DSGEGDFLAE GGGVRGPRVV ERHQSACKDS DWPFCSDEDW
                                                                        +3.2
 61   NYKCPSGCRM KGLIDEVNQD FTNRINKLKN SLFEYQKNNK DSHSLTTNIM EILRGDFSSA
            +0.3                                                          +2.6
            +4.0           +4.9 +1.6                 +5.2            +1.0
121   NNRDNTYNRV SEDLRSRIEV LKRKVIEKVQ HIQLLQKNVR AQLVDMKRLE VDIDIKIRSC
       +1.9
      +3.0 +0.3                        +2.2 +2.8
181   RGSCSRALAR EVDLKDYEDQ QKQLEQVIAK DLLPSRDRQH LPLIKMKPVP DLVPGNFKSQ
       +3.4                             +0.9                             +0.4
241   LQKVPPEWKA LTDMPQMRME LERPGGNEIT RGGSTSYGTG SETESPRNPS SAGSWNSGSS
            +0.7                                                         -1.0
301   GPGSTGNRNP GSSGTGGTAT GHWTSESSVS GSTGQWHSES GSFRPDSPGS TGSWNSGSSG TGSTGNQNPG SPRPGTGTW
                                  +2.9                +2.6                   +0.3
361   NPGSSERGSA GHWTSESSVS GSTGQWHSES GSFRPDSPGS TGSWNSGSSG TGSTGNQNPG GNARPNNPDW GTFEEVSGNV
           +0.3 +1.0                  +1.8                    +2.5 +3.2
421   SPGTRREYHT EKLVTSKGDK ELRTGKEKVT SGSTTTTRRS CSKTVTKTVI GPDGHKEVTK
                                            +0.6                      +2.2
481   EVVTSEDGSD CPEAMDLGTL SGIGTLDGFR DTASTGKTFP HRHPDEAAFF GFFSPMLGEF
                                             +1.4                        +4.3
541   VSETESRGSE SGIFTNTKES SSHHPGIAEF PSRGKSSSYS KQFTSSTSYN RGDSTFESKS
       +3.5                  +2.1    +0.5 +3.2
601   YKMADEAGSE ADHEGTHSTK RGHAKSRPVR GIHTSPLGKP SLSP
```

FIG. 14

(1) Biotin-GRGPRVVEX$^{+1.9}$H    EVNQDFTNX$^{+4.8}$I    NKLKIRSSX$^{+3.0}$G    S
(2) Biotin-GTNIMEILX$^{+3.2}$G    DFSSANNRDN             TYNX$^{+4.0}$VSEDLR    S
(3) Biotin-GYNRVSEDLX$^{+4.9}$    SRIEVLKX$^{+2.4}$KV    IEKQLLQKNV             X$^{+5.2}$A
(4) Biotin-GDIKIX$^{+2.6}$SSRG    SSSX$^{+3.4}$ALLPSX$^{+2.2}$  DRQHLLPSRD       X$^{+2.8}$QH
(5) Biotin-GREX$^{+2.6}$PDSPGS    GTWNPGSSEX$^{+2.9}$    GTSGSTTTTX$^{+2.5}$    RS
(6) Biotin-GSGSTTTTRX$^{+3.2}$    SSSKTVFRHX$^{+2.2}$    HPDEA
(7) Biotin-GREFVSETES             X$^{+3.5}$GSFTSSTSY    NX$^{+4.3}$GDSTFESK
(8) Biotin-GHEGTHSTKX$^{+2.1}$    GHAKSRPVX$^{+3.2}$G    IHTSPLGK

*FIG. 15*

Thrombin Cleavage Site

```
                Signal Peptide Sequence                              -0.2  -0.1    +1.9
  1   MKRMVSWSFH KLKTMKHLLL LLLCVFLVKS QGVNDNEEGF FSARGHRPLD KKREEAPSLR
             -0.1 +2.6           -1.0
 61   PAPPPISGGG YRARPAKAAA TQKKVERKAP DAGGCLHADP DLGVLCPTGC QLQEALLQQE
     +0.6 +1.5                                    +2.0
121   RPIRNSVDEL NNNVEAVSQT SSSSFQYMYL LKDLWQKRQK QVKDNENVVN EYSSELEKHQ
                     +3.0 +2.4      +3.4                     +2.7
181   LYIDETVNSN IPTNLRVLRS ILENLRSKIQ KLESDVSAQM EYCRTPCTVS CNIPVVSGKE
                                                      +1.6            +0.4
241   CEEIRKGGE  TSEMYLIQPD SSVKPYRVYC DMNTENGGWT VIQNRQDGSV DFGRKWDPYK
                                                 +2.1
301   QGFGNVATNT DGKNYCGLPG EYWLGNDKIS QLTRMGPTEL LIEMEDWKGD KVKAHYGGFT
              +6.7                                  +1.6  +0.3
361   VQNEANKYQI SVNKYRGTAG NALMDGASQL MGENRTMTIH NGMFFSTYDR DNDGWLTSDP
           +0.5                            +1.2                        +1.9
421   RKQCSKEDGG GWWYNRCHAA NPNGRYYWGG QYTWDMAKHG TDDGVVWMNW KGSWYSMRKM
     +3.1
      +1.6
481   SMKIRPFFPQ Q
```

FIG. 16

(1) Biotin-GYRAXPAKAA LLKDLWQKXXN SNIPTNLXVL RS
                +2.6                      +2.0         +3.0

(2) Biotin-GPTNLRVLXXS ILENLR

```
                        +0.1            +3.1                          +2.4            +2.2
  1   MSILKIHARE IFDSRGNPTV EVDLFTSKGL FRAAVPSGAS TGIYEALELR DNDKTRYMGK
                                                                      +1.6
 61   GVSKAVEHIN KTIAPALVSK KLNVTEQEKI DKLMIEMDGT ENKSKFGANA ILGVSLAVCK
                 +2.4
121   AGAVEKGVPL YRHIADLAGN SEVILPVPAF NVINGGSHAG NKLAMQEFMI LPVGAANFRE
      +1.1                                        +2.1
181   AMRIGAEVYH NLKNVIKEKY GKDATNVGDE GGFAPNILEN KEGLELLKTA IGKAGYTDKV
                 +0.7
241   VIGMDVAASE FFRSGKYDLD FKSPDDPSRY ISPDQLADLY KSFIKDYPVV SIEDPFDQDD
                                       +3.1
301   WGAWQKFTAS AGIQVVGDDL TVTNPKRIAK AVNEKSCNCL LLKVNQIGSV TESLQACKLA
                 +6.5                             +1.5           +1.4             +2.3
361   QANGNGWVMVS HRSGETEDTF IADLVVGLCT GQIKTGAPCR SERLAKYNQL LRIEEELGSK
      +0.9 +2.0
421   AKFAGRNFRN PLAK
```

*FIG. 18*

(1) Biotin-GFDSXGNPTV EVGLFXAAVP SGASLELXDN DKTR
                 +3.1           +2.4          +2.2

(2) Biotin-GLYXHIADLA GSXYISPDQL ADLTVTNPKXX IAK
               +2.4       +2.1             +3.1

(3) Biotin-GGWGVMVSHX SGETLXIEEE LGSGRNFXNP LAK
                    +6.5     +2.3         +2.0

FIG. 19

CITRULLINATED PEPTIDES FOR DIAGNOSING AND PROGNOSING RHEUMATOID ARTHRITIS

CROSS-REFERENCES TO RELATED APPLICATIONS

The present application is a continuation of PCT/US2010/028946, filed Mar. 26, 2010, which application claims the benefit of priority to U.S. Provisional Patent Application Nos. 61/164,840, filed Mar. 30, 2009; 61/243,496, filed Sep. 17, 2009; and 61/255,058, filed Oct. 26, 2009, the disclosures of which are hereby incorporated by reference in their entirety for all purposes.

Reference to a "Sequence Listing," a Table, or a Computer Program Listing Appendix Submitted as an ASCII Text File The Sequence Listing written in file—152-3.TXT, created on Jul. 2, 2012, 434,176 bytes, machine format IBM-PC, MS-Windows operating system, is hereby incorporated by reference in its entirety for all purposes.

BACKGROUND OF THE INVENTION

Rheumatoid arthritis (RA) is a chronic inflammatory disease, generally regarded as an autoimmune disorder, that affects approximately 1% of the adult population. It is characterized primarily by inflammation of the peripheral joints, in many cases ultimately leading to destruction of these joints. However, RA is a systemic disease, as especially long-standing (and severe) cases also develop extra-articular manifestations of symptoms. As the structural damage is progressive and largely irreversible, it is important to diagnose RA as early as possible to be able to start an adequate treatment. This holds especially true for patients at risk of or having severe RA, which is characterized, for example, by increased joint destruction (as measured by a higher radiological progression rate).

RA is caused by Chronic Inflammation of the Synovium that does not heal (Firestein, *Nature,* 423:356-361 (2003)). The synovium is a thin layer of tissue composed of 3 to 4 layer of cells that form a membrane encapsulating the joint fluid in a synovial joint (Iwanaga et al., *Arch. Histol. Cytol.,* 63:17-31 (2000)). Chronic inflammation of the synovium leads to unchecked proliferation of the synovial tissue, which is composed mainly of two types of cells, the A cells which are macrophage-like and the B cells which are fibroblast-like (Iwanaga et al., supra). The outgrowth of the proliferating synovium into the joint cavity causes swelling of the joint and the formation of a destructive piece of hanging tissue called the "Pannus" (Sanchez-Pernaute et al., *Rheumatology,* 42:19-25 (2003)). It is the Pannus which acts like a "warhead" of a missile that does most of the damage to the articular cartilage by the generation and secretion of the matrix metalloproteinases (MMPs) that break up the cartilage matrix proteins in the joint (Pap et al., *Arthritis Res.,* 2:361-367 (2000); Konttinen et al., *Matrix Biology,* 17:585-601 (1998)). Once the cartilage starts to erode, the disease becomes very serious because joint swelling and pain starts to develop which is the hallmark of RA (Firestein, *Nature,* 423:356-361 (2003)).

However, several fundamental questions on the etiology of RA remain. It is still unknown what mechanism initiates the inflammation in the synovium, and similarly, what mechanism sustains the chronic inflammation in the synovium. What is known, is that chronic inflammation in any bodily tissue has to be driven and sustained by the continuous presence of a foreign antigen (or antigens) in the inflamed tissue. Unfortunately, no animal models of arthritis can truly mimic the chronic inflammatory condition of RA because the so-called "collagen-induced arthritis", "albumen-induced arthritis" and "bacterial cell wall-induced arthritis" animal models of arthritis (Brahn *Clin. Orthop. Relat. Res.,* 265:42-53 (1991)) are all acute animal models, as the arthritic disease is induced by immunizing the animals with a subcutaneous injection of the antigen mixed with Freund's complete adjuvant and then followed later by an injection of the antigen into the synovial joint cavity in one of the knees of the animal while the non-injected knee serves as the control. After the injection, arthritic disease will develop in the injected knee joint within a week while the non-injected knee joint is disease-free. However, appearance of the disease is only transient because the diseased joint will eventually heal itself and the animal recovers spontaneously. This phenomenon occurs because the antigen that causes the disease is no longer present in the diseased joint to sustain the disease. As such, in all of the animal models of arthritis, the antigen that induces the disease is delivered exogenously by manual injection into the joint cavity. Thus, in order to properly diagnose and treat RA it is of paramount importance to determine what mechanism(s) are responsible for generating and sustaining a continuous presence of one or more foreign antigens, as well as the identity of the foreign antigen(s) underlying the disease.

Due to the tremendous research efforts executed by numerous laboratories all over the world in the past 15 years, researchers believe that the foreign antigen (or antigens) responsible for inducing and sustaining RA in RA-prompt patients are the citrulline-containing peptides derived from citrullination of the endogenous cellular proteins by the intracellular enzymes, peptidyl-arginine deiminases (PADs) (Schellekens et al., *J. Clin. Invest.,* 101:273-281 (1998); Girbal-Neuhauser et al., *J. Immunol.,* 162:585-594 (1999)). PADs convert an arginine residue within a peptide sequence to a citrulline residue and this reaction only occurs in the presence of $>10^{-4}$M $Ca^{2+}$ concentration. There are five known members of PADs (I, II, III, IV and VI) present inside the cells, and PADs II and IV are the ones found in the synovial cells (Foulquier et al., *Arthritis & Rheumatism,* 56:3541-3553 (2007)). Once a PAD is released outside of the cell, it can citrullinate other extracellular proteins but the enzymatic activity also disappears rapidly. Therefore, to further explore the cause of RA, one has to determine how the citrullinated peptides are being generated in the synovium and what sustains the continuous generation of those citrullinated peptides.

A correct diagnosis of RA is often difficult because the symptoms develop insidiously, or may resemble those of other diseases (e.g., osteoarthritis, arthritis due to infection or gout, etc.). Traditionally, RA is diagnosed using the revised American College of Rheumatology (ACR) classification criteria. The ACR proposes seven classification criteria which indicate a poor prognosis:

1. Morning stiffness of the joints lasting more than one hour;
2. Arthritis of three or more joints;
3. Inflammation of at least three joint areas at the same time;
4. Hand joints or finger joints are likewise affected;
5. Bilateral tenderness of metacarpophalangeal joints to pressure;
6. Erosions on radiographs;
7. Detection of rheumatoid factors, anti-perinuclear factor (APF), and anti-keratin antibodies (AKA).

However, diagnosing RA according to this procedure is labor-intensive and a significant amount of time passes before a definite diagnosis is made.

Autoantibodies to the "anti-perinuclear factor" (APF) were first described by Nienhuis et al. in patients having rheumatoid arthritis (Nienhuis et al., *Ann. Rheum. Dis.*, 23:302-305 (1964)). These APF antibodies react with the keratohyaline scattered around the perinuclear region of human buccal epithelial cells. Owning to the subjective and labor-intensive immunofluorescence technique employed, an APF antibody test has never been put into wide use for RA diagnosis. Later, Young et al. reported that RA patient sera reacted to the keratinous epithelium of the stratum corneum on rat esophagus tissue sections and designated these RA-specific antibodies as anti-keratin antibodies (AKA) (Young et al., *B.M.J.*, 2:97-99 (1979)). In 1993, Simon et al. found that a majority of the RA patient sera recognized a 40 kDa protein from human skin tissue (Simon et al., *J. Clin. Invest.*, 92:1387-93 (1993)). They further demonstrated that this protein identified as filaggrin was the target antigen of AKA and went on to show that AKA and APF antibodies are the same RA-specific antibodies (Sebbag et al., *J. Clin. Invest.*, 95:2672-2679 (1995)). For this reason, the APF autoantibodies are even today referred to as antikeratin antibodies (AKAs) (Vincent et al., *J. of Autoimmunity*, 4:493-505 (1991); Paimela et al., *Ann. Rheumat. Dis.*, 51:743-746 (1992)). The 40 kDa filaggrin protein aggregates cytokeratin filaments and assists in forming the intracellular fiber matrix of the keratinous cells (Simon et al., *J. Clin. Invest.*, 92:1387-93 (1993)). However, filaggrin is not present in the synovial joint tissue of RA patients. Furthermore, anti-filaggrin antibodies are found in the serum of only about 40% of RA patients.

As such, there is a need in the art for the identification and design of novel peptides that find utility in detecting antibodies associated with rheumatic diseases, e.g., antibodies associated with RA, which peptides make possible a sensitive and specific diagnosis, classification, and/or prognosis of rheumatic diseases such as RA. The present invention satisfies this need and provides related advantages as well.

BRIEF SUMMARY OF THE INVENTION

The present invention provides novel citrullinated peptides, their use in methods for aiding, assisting, improving, or facilitating the diagnosis or prognosis of rheumatic diseases such as rheumatoid arthritis (RA), and methods for identifying novel citrullinated peptides that are immunoreactive with anti-citrullinated protein antibodies (ACPAs). The present invention also provides methods for detecting rheumatoid factor (RF) using novel RF detection reagents as a means to aid, assist, improve, or facilitate the diagnosis or prognosis of rheumatic diseases such as RA. Kits comprising at least one of the novel citrullinated peptides and/or RF detection reagents of the present invention are also provided.

The compositions and methods of the present invention are advantageous because they make possible the early diagnosis of RA, and provide important prognostic information regarding the course of the disease (e.g., early stage, middle stage, and late stage) and the recommended therapy at the time of diagnosis. As such, the present invention enables a clinician to practice "personalized medicine" by guiding treatment decisions for RA such that the right drug is given to the right patient at the right time.

In one aspect, the present invention provides a synthetic peptide comprising a fragment of about 5 to about 50 contiguous amino acids of a human protein selected from the group consisting of SEQ ID NOS:1-39, wherein at least one of the contiguous amino acids is an arginine residue in the native protein, and wherein at least one of the arginine residues is citrullinated in the synthetic peptide.

In another aspect, the present invention provides a synthetic peptide comprising a first fragment of about 5 to about 50 contiguous amino acids of a human protein selected from the group consisting of SEQ ID NOS:1-39 linked to at least a second fragment of about 5 to about 50 contiguous amino acids of a human protein selected from the group consisting of SEQ ID NOS:1-39, wherein at least one residue of the first fragment is an arginine residue in the native protein and at least one residue of the second fragment is an arginine residue in the native protein, and wherein at least one of the arginine residues in the first and/or second fragments is citrullinated in the synthetic peptide.

The synthetic peptide comprising first and second fragments may further comprise at least a third or fourth fragment of about 5 to about 50 contiguous amino acids of SEQ ID NOS:1-39, wherein at least one residue of each of the third or fourth fragments is an arginine residue in the native protein, and wherein the third or fourth fragments are linked to the first and second fragments, e.g., by a peptide bond.

In yet another aspect, the present invention provides a synthetic peptide comprising a first synthetic fragment of about 5 to about 50 amino acids having homology to a first fragment of about 5 to about 50 contiguous amino acids of a human protein selected from the group consisting of SEQ ID NOS:1-39 linked to at least a second (and optionally a third or fourth) synthetic fragment of about 5 to about 50 amino acids having homology to a second (and optionally third or fourth) fragment of about 5 to about 50 contiguous amino acids of a human protein selected from the group consisting of SEQ ID NOS:1-39, wherein at least one residue of the first synthetic fragment is an arginine residue in the human protein and at least one residue of the second (and optionally third or fourth) synthetic fragment is an arginine residue in the human protein, wherein at least one of the arginine residues is citrullinated in the synthetic peptide, and wherein the composite amino acid sequence of the first synthetic fragment and the second (and optionally third or fourth) synthetic fragment is at least about 85%, 90%, 95%, or more identical to the composite amino acid sequence of the first and second fragments of the human protein.

In particular embodiments, the human protein is vimentin (SEQ ID NO:1), and the synthetic peptide comprises one or more fragments independently selected from the group consisting of amino acid residues 2-13, 4-12, 22-31, 28-38, 42-52, 61-70, 63-78, 68-76, 96-104, 116-124, 158-165, 157-165, 205-217, 216-224, 266-276, 320-328, 302-327, 356-364, 393-412, and 417-452 of SEQ ID NO:1, wherein the fragments are linked together (e.g., by a peptide bond), and wherein at least one of the arginine residues in each of the fragments is citrullinated.

In another aspect, the present invention provides synthetic peptides comprising an amino acid sequence selected from the group consisting of SEQ ID NOS:40-355. In certain embodiments, the synthetic peptides of the invention may be labeled, tagged, amidated, or otherwise chemically modified.

In a related aspect, the present invention provides synthetic peptides comprising an amino acid sequence that is at least about 85%, 90%, 95%, or more identical to a sequence selected from the group consisting of SEQ ID NOS:40-355. In certain embodiments, the synthetic peptides may be labeled, tagged, amidated, or otherwise chemically modified.

In some embodiments, the synthetic peptide comprises an amino acid sequence selected from the group consisting of SEQ ID NOS:41, 43, 45, 47, 49, 51, 53, 55, 57, 59, 61, 63, 65, and 67. In other embodiments, the synthetic peptide comprises an amino acid sequence that is at least about 85%, 90%, 95%, or more identical to an amino acid sequence selected from the group consisting of SEQ ID NOS:41, 43, 45, 47, 49, 51, 53, 55, 57, 59, 61, 63, 65, and 67. In yet other embodiments, the synthetic peptide is selected from the group consisting of SEQ ID NOS:40, 42, 44, 46, 48, 50, 52, 54, 56, 58, 60, 62, 64, and 66.

In yet another aspect, the present invention provides a method for detecting an anti-citrullinated protein antibody in a biological sample, the method comprising the steps of:
(a) contacting the biological sample with a synthetic peptide described herein under conditions suitable to transform said synthetic peptide into a complex comprising the synthetic peptide and the anti-citrullinated protein antibody; and
(b) detecting the presence (or absence) or level of the complex.

In another aspect, the present invention provides a method for performing an assay to aid in the diagnosis or prognosis of rheumatoid arthritis, the method comprising:
(a) detecting the presence (or absence) or level of an anti-citrullinated protein antibody in a biological sample by contacting the sample with a synthetic peptide described herein; and
(b) reporting the presence (or absence) or level of the anti-citrullinated protein antibody in the sample to aid in the diagnosis or prognosis of rheumatoid arthritis.

In a related aspect, the present invention provides a method for improving the sensitivity of diagnosing or prognosing rheumatoid arthritis, the method comprising:
(a) detecting the presence (or absence) or level of an anti-citrullinated protein antibody in a biological sample by contacting the sample with a synthetic peptide described herein; and
(b) reporting the presence (or absence) or level of the anti-citrullinated protein antibody in the sample to improve the sensitivity of diagnosing or prognosing rheumatoid arthritis.

In a related aspect, the present invention provides an assay for diagnosing or prognosing rheumatoid arthritis, the assay comprising:
(a) contacting a biological sample with a synthetic peptide described herein under conditions suitable to transform the synthetic peptide into a complex comprising the synthetic peptide and an anti-citrullinated protein antibody; and
(b) detecting the presence (or absence) or level of the complex.

In yet another aspect, the present invention provides a kit comprising:
(a) at least one synthetic peptide described herein; and
(b) at least one detectable moiety.

In another aspect, the present invention provides a method for identifying a peptide that is immunologically reactive with an anti-citrullinated protein antibody, the method comprising:
(a) identifying at least one antigenic peptide epitope in at least one synovial fluid polypeptide, wherein the antigenic peptide epitope is predicted to be immunologically reactive with an anti-citrullinated protein antibody, wherein the antigenic peptide epitope contains at least one citrullinated arginine residue;
(b) synthesizing a peptide that comprises at least one of the antigenic peptide epitopes;
(c) contacting a biological sample from a rheumatoid arthritis (RA) individual with the peptide under conditions suitable to transform the peptide into a complex comprising the peptide and the anti-citrullinated protein antibody; and
(d) identifying the peptide as being immunologically reactive with the anti-citrullinated protein antibody based on the presence of the complex.

Other objects, features, and advantages of the present invention will be apparent to one of skill in the art from the following detailed description and figures.

BRIEF DESCRIPTION OF THE DRAWINGS

FIG. 4 illustrates the dose-response curve for the [Arg$^{25}$] Cit-α32 peptide using an ELISA to detect the presence or level of IgG ACPAs.

FIG. 5 illustrates a comparison of the IgG ACPA values obtained using the INOVA CCP assay versus the [Arg$^{25}$]Cit-α32 peptide assay for normal human serum (NHS) and RF-positive (C) samples.

FIG. 7 also illustrates the dose-response curves for citrullinated fibrinogen beta-chain peptides of the invention using an ELISA to detect the presence or level of ACPAs.

FIG. 8 illustrates the dose-response curve for HRP-labeled Protein L using an ELISA to detect the presence or level of RF.

FIG. 9 illustrates a comparison of the RF values obtained using the Orgentec RF assay versus the inventive Protein L assay for normal human serum (NHS) and RF-positive samples (C).

FIG. 10 illustrates an exemplary peptide epitope side-chain scanning table suitable for use in the prediction and design of novel citrullinated peptides.

FIG. 11 illustrates how the score of a selected 9-residue peptide (SEQ ID NOS:357-365) epitope in the vimentin polypeptide (SEQ ID NO:356) in which an arginine was replaced with glutamine is determined by the RA antigenic peptide prediction program of the present invention.

FIG. 12 illustrates the scoring results determined by the RA antigenic peptide prediction program of the present invention for each of the arginine residues present in a 9-residue peptide epitope in the vimentin amino acid sequence (SEQ ID NO:1), wherein the arginines were replaced with glutamines.

FIG. 13 illustrates non-limiting examples of synthetic peptides (SEQ ID NOS:366-374) having composite amino acid sequences derived from high scoring vimentin peptide epitopes (>+2.0), which were determined by the RA antigenic peptide prediction program of the present invention. "X"=citrulline.

FIG. 14 illustrates the scoring results determined by the RA antigenic peptide prediction program of the present invention for each of the arginine residues present in a 9-residue peptide epitope in the fibrinogen alpha-chain amino acid sequence (SEQ ID NO:2), wherein the arginines were replaced with glutamine.

FIG. 15 illustrates non-limiting examples of synthetic peptides (SEQ ID NOS:375-382) having composite amino acid sequences derived from high scoring fibrinogen alpha-chain peptide epitopes (≧+2.0), which were determined by the RA antigenic peptide prediction program of the present invention. "X"=citrulline.

FIG. 16 illustrates the scoring results determined by the RA antigenic peptide prediction program of the present invention for each of the arginine residues present in a 9-residue peptide epitope in the fibrinogen beta-chain amino acid sequence (SEQ ID NO:3), wherein the arginines were replaced with glutamine.

FIG. 17 illustrates non-limiting examples of synthetic peptides (SEQ ID NOS:383-385) having composite amino acid sequences derived from high scoring fibrinogen beta-chain peptide epitopes (≧+2.0), which were determined by the RA antigenic peptide prediction program of the present invention. "X"=citrulline.

FIG. 18 illustrates the scoring results determined by the RA antigenic peptide prediction program of the present invention for each of the arginine residues present in a 9-residue peptide epitope in the alpha-enolase amino acid sequence (SEQ ID NO:5), wherein the arginines were replaced with glutamine.

FIG. 19 illustrates non-limiting examples of synthetic peptides (SEQ ID NOS:386-388) having composite amino acid sequences derived from high scoring alpha-enolase peptide epitopes (≧+2.0), which were determined by the RA antigenic peptide prediction program of the present invention. "X"=citrulline.

FIG. 20 illustrates the IgG ACPA dose-response curve of synthetic citrullinated peptides derived from Apolipoprotein a.

DETAILED DESCRIPTION OF THE INVENTION

I. Introduction

Figure 1:
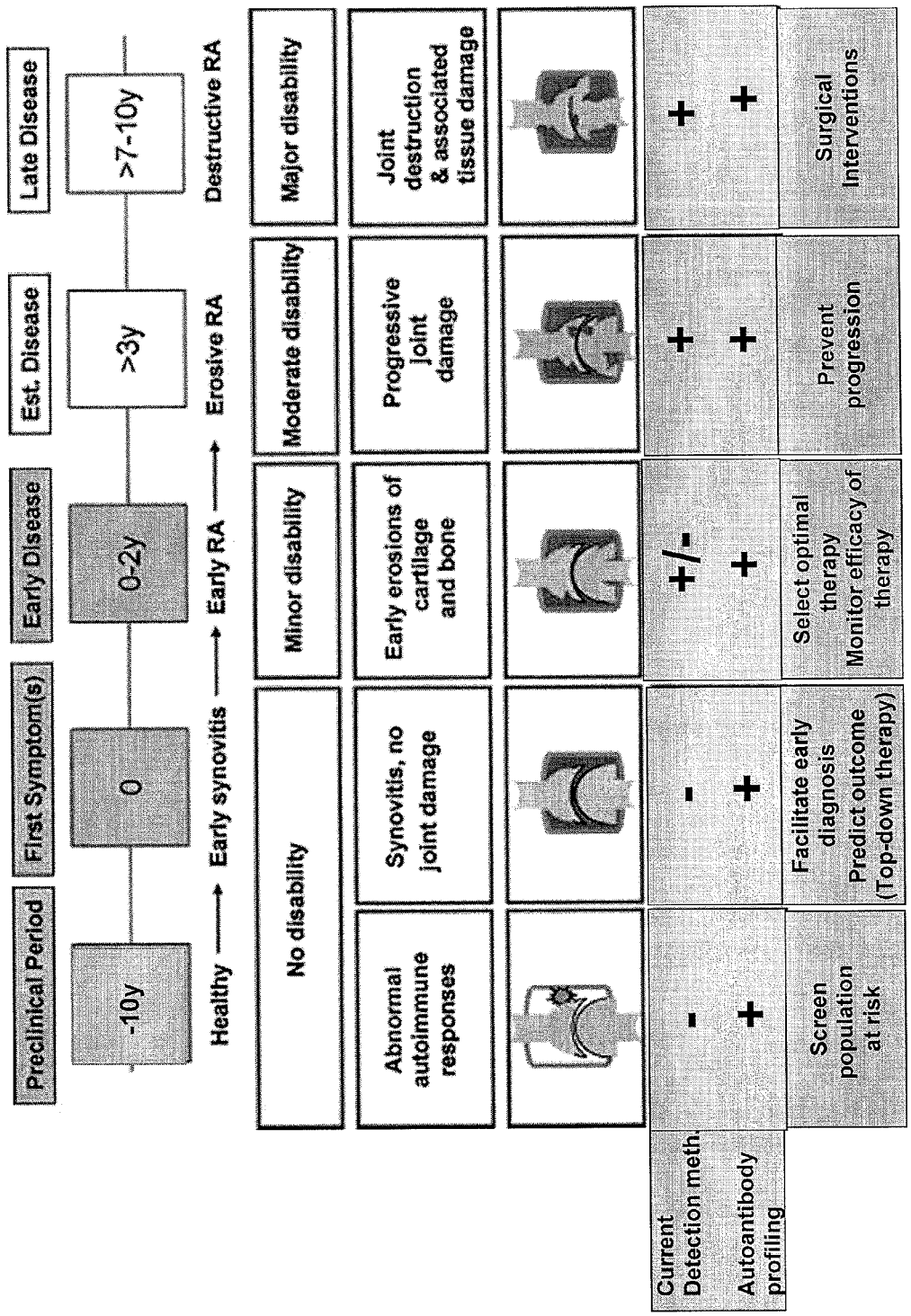
FIG. 1 illustrates the different stages of rheumatoid arthritis (RA) and an overview of autoantibody profiling in RA.

Rheumatoid arthritis (RA) is a heterogeneous autoimmune disease. Currently, the prevalence of RA is estimated at 1% of the U.S. population; 3 million adults in the U.S. have been diagnosed with RA. If not adequately managed, progressive deformity can lead to joint replacement surgery. In the U.S. in 1997 alone, there were 256,000 knee replacements and 117,000 hip replacements associated with arthritis. However, the clinical presentation and outcomes vary greatly among different patients.

One of the first reactions to an inflammatory insult, such as a viral or bacterial infection, or a minor tissue damage is the massive influx of the white blood cells to the injured area from the capillaries to repair the damage and the influx is facilitated by the release of TNFα by the immune surveillance cells (Moisan et al., *J. Leukoc. Biol.*, 79:489-498 (2006)). Over 60% of the granulocytes in the white blood cells in circulation are neutrophils, whose function is to phagocytize the viruses, bacteria and damaged tissues to clean up the damage area. However, in so doing, these "well-fed" neutrophils trapped in the extracellular matrix of the synovium also die there by "spontaneous apoptosis" (SA) and the apoptotic process is also induced by TNFα (Moisan et al., supra). When the neutrophils undergo SA, it lets in the extracellular $Ca^{2+}$, which is present at $10^{-3}$ M concentration, into the cytoplasm of the cells where the $Ca^{2+}$ concentration is normally maintained at $10^{-6}$ M to inhibit the enzymatic activity of the intracellular peptidyl-arginine deiminases (PADs). Once the intracellular PADs are activated by the influx of $Ca^{2+}$, they start to citrullinate the endogenous intermediate filament proteins, such as vimentin and lamin B1 as well as other intracellular proteins such as the histones and the heat shock protein, BiP (Moisan et al., supra). Moreover, in the process of being citrullinated, these normally intracellular intermediate filament proteins, vimentin and lamin B1, are translocated to the cell surface and thus are being exposed for phagocytosis by the resident macrophages (the A cells in the synovium), which can serve as antigen presenting cells (APCs) for potential generation of autoantibodies against these citrullinated proteins.

To induce antibody formation against an antigen in human beings, the antigen has to be bound to an allele-specific major histocompatibility complex (MHC) class II molecule expressed on the APC's cell surface. The bound antigenic peptide in the MHC-II complex is then recognized by a receptor on the CD4 helper $T_{H2}$ cells (Yvonne Jones et al., *Nature Reviews/Immunology*, 6:271-282 (2006)). Most RA-prompt patients express the MHC-II molecule, HLA-DR4, which can bind the citrullinated peptides (Yvonne Jones et al., supra), whereas non-RA-prompt human beings do not express this MHC-II molecule on their APCs. Therefore, in non-RA-prompt human beings, neutrophil SA does not cause RA because the citrullinated peptides are not being presented by the APCs to the helper $T_{H2}$ cells due to the absence of the MHC-II allele, HLA-DR4, and the inflammation is resolved. However, in the RA-prompt patients the MHC-II allele, HLA-DR4, is able to bind and present the bound citrullinated peptides to activate the CD4 helper $T_{H2}$ cells to induce antibody formation against these citrullinated peptides. And because of a special property of the synovial fibroblast-like cells (the B cells in the synovium), the synovium acts like the germinal center of the lymph node to foster activated $T_{H2}$ and B cells interaction to induce maturation of the activated B cells to differentiate into plasma cells to produce and secrete the anti-citrullinated peptide autoantibodies to drive the disease into a self-perpetuating inflammatory process (Dechanet et al., *J. Clin. Invest.*, 95:456-463 (1995); Edwards, *Clin. Exp. Immunol.*, 108:407-414 (1997)). The self-perpetuating process is sustained by the binding of the locally generated autoantibodies to the citrullinated peptide epitopes translocated to the surface of the apoptotic neutrophils to form immune complexes. These immune complexes, in turn, attract more naive neutrophils from the circulation to carry out the phagocytosis, followed by SA to repeat the inflammatory cycle. When the disease develops to this chronic stage, fibrin aggregates start to appear inside the joint cavity and adhere to the synovial lining (Sanchez-Permute et al., *Rheumatology*, 42:19-25 (2003)). The adhered fibrin aggregates, in turn, trigger an invasion by the synovial fibroblasts, ending with the complete incorporation of the aggregates within the tissue by development of a new lining layer at their surface and this is how a Pannus tissue develops (Sanchez-Pernaute et al., supra). At this stage, many citrullinated autoantibodies against other cellular and extracellular matrix proteins will appear in the patient because, in addition to neutrophil SA, other immune cells, such as macrophages and even fibroblasts will also undergo apoptosis and release massive amounts of PADs to citrullinate other proteins for autoantibody generation and this is how the phenomenon of epitope spreading occurs (Kidd et al., *Arthritis Res. Ther.*, 10:R119 (2008)). However, these spreading epitopes are not useful as diagnostic peptides for the detection of early RA because, when autoantibodies against these spreading epitopes start to appear, the disease has already progressed to a very serious stage, which may not be treatable with an anti-TNFα agent.

Therefore, in order to effectively treat RA, the disease should be diagnosed in its early stage by detecting the presence of anti-citrullinated intermediate filament proteins, vimentin and lamin B1 as well as, possibly, anti-citrullinated histone and BiP peptide autoantibodies in the patient serum and treat the patient immediately with an anti-TNFα agent to block the early inflammatory process. If the early inflammatory process is inhibited, the inflammation will be resolved and the patient will not proceed to develop RA a few years later. Moreover, the healthy status of the patient can be monitored by measuring the reappearance of the anti-citrullinated vimentin, lamin B1, histone and BiP autoantibodies in the serum. If these antibodies reappear, the patient can be treated with an anti-TNFα agent again to resolve the inflammation.

Thus, the heterogeneity in RA could be explained by the different autoantibodies against citrullinated synovial fluid proteins present in a patient. It has been discovered that the antigenic peptide which induces autoantibodies in RA patients contains an arginine residue that is transformed to citrulline by the endogenous enzyme PAD (Schellekens et al., *J. Clin Invest.*, 101:273-281 (1998); Girbal-Neuhauser et al., *J. Immunol.*, 162:585-594 (1999)). For example, one-half of RA patients who had the disease for more than 10 years had autoantibodies against the citrullinated β- and γ-chains of fibrin (Zhao et al., *Arthritis Res. & Ther.*, 10:R94 (2008)). However, current methods for detecting autoantibodies against citrullinated peptides are low in sensitivity and are unable to diagnose all stages of RA, especially early RA.

Currently, a citrullinated and mutated, recombinant vimentin ELISA, marketed by Orgentec, is the only RA diagnostic assay that can predict the severe outcome in patients with recent-onset polyarthritis (Mathsson et al., *Arthritis & Rheumatism*, 58: 36-45 (2008)), whereas the anti-CCP assay does not have this capability. However, the sensitivity of the Orgentic assay is less than 30%. The reason for the low sensitivity of this assay is because citrullinated vimentin is only one of the citrullinated proteins produced during SA of the neutrophils. Advantageously, the present invention provides, in one aspect, a computer program that can predict all of the potential citrullinated RA epitopes in any cellular protein. Through the use of this program, all of the citrullinated vimentin, lamin B1, as well as other intermediate filament-derived peptides can be predicted, for custom synthesis for use as auto-antigens to detect the citrullinated peptide autoantibodies present in early RA patients. Thus, the present invention also provides a comprehensive assay containing a plurality of auto-antigens generated in neutrophil SA, resulting in higher sensitivity for the early detection of RA.

FIG. 1 illustrates the different stages of RA and the use of the novel citrullinated peptides identified and designed in accordance with the present invention to provide valuable diagnostic and prognostic information for patients with any stage of RA, including early RA. In particular, autoantibody profiling using one or more (e.g., a pool) of the synthetic peptides described herein advantageously (1) enables the screening of patients at risk of developing RA, (2) facilitates early diagnosis and prognosis of RA, (3) enables the selection of optimal therapy or the monitoring of therapeutic efficacy in RA patients, (4) enables the prevention of the progression of RA, and (5) enables the identification of the need for surgical intervention in RA patients.

As such, the compositions and methods of the present invention make possible the early diagnosis of RA, and provide important prognostic information regarding the course of the disease and the recommended therapy at the time of diagnosis. For example, patients diagnosed with early RA and with a good prognosis may be recommended non-steroidal anti-inflammatory drug (NSAID) therapy, whereas patients diagnosed with early RA, but with a poor prognosis may be recommended disease-modifying antirheumatic drug (DMARD) therapy. In some embodiments, the present invention enables the classification of RA patients into different subsets and provides guidance on therapy selection based on the subset of RA. In other embodiments, the present invention enables the monitoring of a patient's response to treatment and provides guidance on the selection of the appropriate therapy or combination therapy for the patient. In particular, the present invention finds utility in guiding treatment decisions (e.g., which therapy to select, when that therapy should begin and end, etc.) to increase the likelihood of efficacy and decrease the likelihood of toxicity and failure since RA therapy is very expensive. Accordingly, the present invention enables a clinician to practice "personalized medicine" by guiding treatment decisions for rheumatic diseases such that the right drug is given to the right patient at the right time.

II. Definitions

As used herein, the following terms have the meanings ascribed to them unless specified otherwise.

The term "rheumatoid arthritis" or "RA" includes an autoimmune disease that causes chronic inflammation of the connective tissues in the body, most particularly, the joints and the tissue around the joints. In rheumatoid arthritis, multiple joints are usually inflamed in a symmetrical pattern (e.g., both sides of the body are affected). The small joints of both the hands and wrists as well as the feet are often involved. More rarely, the cricoarytenoid joint is involved, causing a hoarseness of the voice. The term "rheumatoid arthritis" also includes conditions such as Sjogren's syndrome, where the inflammation affects organs and areas of the body other than the joints, e.g., the glands of the eyes and mouth, causing dryness of these areas. Rheumatoid inflammation of the lung lining (pleuritis) causes chest pain with deep breathing or coughing. The lung tissue itself can also become inflamed and sometimes nodules of inflammation (rheumatoid nodules) develop within the lungs. Inflammation around the heart (pericarditis) can cause a chest pain that typically changes in intensity when lying down or leaning forward. Rheumatoid arthritis can reduce the number of red blood cells (anemia) and white blood cells. Decreased white blood cells can be associated with an enlarged spleen (referred to as Felty's syndrome) and can increase the risk of infections. Firm lumps under the skin (rheumatoid nodules) can occur around the elbows and fingers where there is frequent pressure. Even though these nodules usually do not cause symptoms, occasionally they can become infected. A rare, serious complication, usually with long-standing rheumatoid disease, is blood vessel inflammation (vasculitis). Vasculitis can impair blood supply to tissues and lead to tissue death. This is most often initially visible as tiny black areas around the nail beds or as leg ulcers.

The term "rheumatoid factor" or "RF" includes an autoantibody (i.e., an antibody directed against an organism's own tissues) that is typically directed against (i.e., binds to) the Fc (fragment crystallizable) portion of immunoglobulin G (IgG). Rheumatoid factor is most often an IgM autoantibody, but may also be an IgG or IgA autoantibody.

The term "anti-citrullinated protein antibody," "anti-citrullinated peptide antibody," or "ACPA" includes an autoantibody that specifically targets one or more epitopes in a peptide, polypeptide, or protein sequence where one or more arginine residues have been converted by the enzyme peptidylarginine deiminase into a citrulline residue during a post-translational modification. The presence or level of anti-citrullinated protein antibodies can be detected, determined, or measured using the natural or synthetic citrullinated peptides of the present invention, which are immunologically reactive (i.e., immunoreactive) with such antibodies. Anti-citrullinated protein antibodies are autoantibodies typically associated with rheumatoid arthritis.

The term "subject," "patient," or "individual" typically includes humans, but can also include other animals such as, e.g., other primates, rodents, canines, felines, equines, ovines, porcines, and the like.

The term "amino acid" includes naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., citrulline (Cit), γ-aminoglutamic acid, or O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

The term "substantially the same amino acid sequence" includes an amino acid sequence that is similar, but not identical to, the naturally-occurring amino acid sequence. For example, an amino acid sequence that has substantially the same amino acid sequence as a naturally-occurring peptide, polypeptide, or protein can have one or more modifications such as amino acid additions, deletions, or substitutions relative to the amino acid sequence of the naturally-occurring peptide, polypeptide, or protein, provided that the modified sequence retains substantially at least one biological activity of the naturally-occurring peptide, polypeptide, or protein such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a peptide, polypeptide, or protein of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

One of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally-occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, M, or V) is substituted with another member of the group. Similarly, an aliphatic polar-uncharged group such as C, S, T, N, or Q may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. In other embodiments, aromatic amino acids (e.g., F, Y, or W) may be substituted with another member of the group. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, 1993).

The term "peptide" includes a compound made up of a single chain of D- or L-amino acids or a mixture of D- and L-amino acids joined by peptide bonds. Generally, peptides are about 2 to about 100 (e.g., 2-100, 2-75, 2-50, 5-50, 5-45, 5-40, 5-35, 5-30, 5-25, 10-50, 10-45, 10-40, 15-40, 20-40, 10-30, 15-30, 20-30, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) amino acids in length. In certain embodiments, the citrullinated peptides of the present invention comprise or consist of about 5 to about 50 contiguous amino acids of a wild-type polypeptide or protein sequence (e.g., SEQ ID NOS:1-39), wherein at least one of the arginine (Arg) residues present in the sequence is citrullinated. In certain other embodiments, the citrullinated peptides of the present invention comprise or consist of about 5 to about 50 (e.g., about 5 to about 25) contiguous amino acids from two, three, four, or more regions (attached directly or via a linker) of a wild-type polypeptide or protein sequence (e.g., synthetic peptides having a composite amino acid sequence of about 10 to about 50 amino acids in length made up of fragments from SEQ ID NOS:1-39 linked together by peptide bonds), wherein at least one of the Arg residues present in the synthetic peptide sequence is citrullinated. In further embodiments, the citrullinated peptides of the present invention comprise or consist of about 5 to about 50 contiguous amino acids of a mutated version of a wild-type polypeptide or protein sequence (e.g., peptides having one of the mutated vimentin sequences described in PCT Publication No. WO 07/000,320), wherein at least one of the Arg residues present in the sequence is citrullinated.

A "cyclic peptide" includes a peptide in which the amino-terminus of the peptide or a side-chain on the peptide having a free amino group (e.g., lysine) is joined by a peptide bond to the carboxyl-terminus of the peptide or a side-chain on the peptide having a free carboxyl group (e.g., aspartic acid, glutamic acid). However, one skilled in the art will appreciate that heterodetic cyclic peptides formed by disulfide, ester, or ether bonds are also within the scope of the present invention.

The term "sensitivity" includes the probability that an assay described herein identifies a disease state (e.g., rheumatoid arthritis) among those who have the disease or the proportion of people with the disease who have a positive test result. Sensitivity can be expressed as the number of true positives/(the number of true positives+false negatives).

The term "specificity" includes the probability that an assay described herein does not identify a disease state (e.g., rheumatoid arthritis) among those who do not have the disease or the proportion of people free of the disease who have a negative test result. Specificity can be expressed as the number of true negatives/(the number of true negatives+false positives).

The term "immunoassay" includes an assay that utilizes a specific antibody to detect an antigen of interest or utilizes a specific antigen to detect an antibody of interest. An immunoassay is thus characterized by detection of the specific binding of an antigen to an antibody.

The term "sample" or "biological sample" includes a tissue sample or a bodily fluid sample. A tissue sample includes, but is not limited to, buccal cells, a brain sample, a skin sample, or an organ sample (e.g., liver). A bodily fluid sample includes all fluids that are present in the body including, but not limited to, blood, plasma, serum, saliva, synovial fluid, lymph, urine, or cerebrospinal fluid. The sample may also be obtained by subjecting it to a pre-treatment step, if necessary, e.g., by homogenizing the sample or by extracting or isolating a component of the sample. Suitable pre-treatment steps may be selected by one skilled in the art depending on nature of the biological sample. One skilled in the art will also appreciate that samples such as serum samples can be diluted prior to analysis.

As used herein, the terms "citrulline" and "citrullinated arginine" are equivalent, and refer to an arginine residue that has been deiminated. As such, it is envisioned that during the preparation of a citrullinated synthetic peptide, as provided herein, an arginine residue may be initially incorporated at a predetermined position in the peptide and subsequently citrullinated (i.e., deiminated). Alternatively, a citrulline residue may be substituted for the predetermined arginine residue during peptide synthesis. For the purposes of the present invention, when calculating the percent identity of a synthetic peptide with respect to a reference sequence (i.e., a human protein), a citrulline residue or citrullinated arginine residue is considered to be the same as an arginine residue found at the equivalent position of the reference sequence. Although citrulline (i.e., deiminated arginine) is structurally and functionally different than arginine, by definition, for purposes of determining a percent identity only, citrulline is considered to be analogous to arginine.

III. Description of the Embodiments

The present invention provides novel citrullinated peptides, their use in methods for aiding, assisting, improving, or facilitating the diagnosis or prognosis of rheumatic diseases such as rheumatoid arthritis (RA), and methods for identifying novel citrullinated peptides that are immunoreactive with anti-citrullinated protein antibodies (ACPAs). The present invention also provides methods for detecting rheumatoid factor (RF) using novel RF detection reagents as a means to aid, assist, improve, or facilitate the diagnosis or prognosis of rheumatic diseases such as RA. Kits comprising at least one of the novel citrullinated peptides and/or RF detection reagents of the present invention are also provided.

In one aspect, the present invention provides a synthetic peptide comprising a fragment of about 5 to about 50 contiguous amino acids of a human protein selected from the group consisting of SEQ ID NOS:1-39, wherein at least one of the contiguous amino acids is an arginine residue in the native protein, and wherein at least one of the arginine residues is citrullinated in the synthetic peptide.

In another aspect, the present invention provides a synthetic peptide comprising a first fragment of about 5 to about 50 contiguous amino acids of a human protein selected from the group consisting of SEQ ID NOS:1-39 linked to at least a second fragment of about 5 to about 50 contiguous amino acids of a human protein selected from the group consisting of SEQ ID NOS:1-39, wherein at least one residue of the first fragment is an arginine residue in the native protein and at least one residue of the second fragment is an arginine residue in the native protein, and wherein at least one of the arginine residues in the first and/or second fragments is citrullinated in the synthetic peptide. In some embodiments, the first and second fragments of the synthetic peptide each comprise at least one citrullinated arginine. In other embodiments, the first and second fragments are linked together by a peptide bond. The first and second fragments of the synthetic peptide may be derived from the same human protein set forth in SEQ ID NOS:1-39, or may be derived from different proteins.

The synthetic peptide comprising first and second fragments may further be linked to at least a third fragment of about 5 to about 50 contiguous amino acids of a human protein selected from the group consisting of SEQ ID NOS: 1-39, wherein at least one residue of the third fragment is an arginine residue in the native protein. In certain instances, at least one arginine residue in the third fragment is citrullinated. In some embodiments, the synthetic peptide comprising first, second, and third fragments may further be linked to at least a fourth fragment of about 5 to about 50 contiguous amino acids of a human protein selected from the group consisting of SEQ ID NOS:1-39, wherein at least one residue of the fourth fragment is an arginine residue in the native protein. In certain instances, at least one arginine residue in the fourth fragment is citrullinated. In other instances, the first, second, third, and/or fourth fragments are linked together by a peptide bond. In other embodiments, the synthetic peptide may further comprise at least a fifth, sixth, seventh, eighth, ninth, or tenth fragment. Each of the fragments of the synthetic peptide may be derived from the same human protein set forth in SEQ ID NOS:1-39, or may be derived from different proteins.

In yet another aspect, the present invention provides a synthetic peptide comprising a first synthetic fragment of about 5 to about 50 amino acids having homology to a first fragment of about 5 to about 50 contiguous amino acids of a human protein selected from the group consisting of SEQ ID NOS:1-39 linked to at least a second (and optionally a third or fourth) synthetic fragment of about 5 to about 50 amino acids having homology to a second (and optionally third or fourth) fragment of about 5 to about 50 contiguous amino acids of a human protein selected from the group consisting of SEQ ID NOS:1-39, wherein at least one residue of the first synthetic fragment is an arginine residue in the human protein and at least one residue of the second (and optionally third or fourth) synthetic fragment is an arginine residue in the human protein, wherein at least one of the arginine residues is citrullinated in the synthetic peptide, and wherein the composite amino acid sequence of the first synthetic fragment and the second (and optionally third or fourth) synthetic fragment is at least about 80%, 85%, 86%, 87%, 88%, 89%, 90%, 91%, 92%, 93%, 94%, 95%, 96%, 97%, 98%, or 99% identical to the composite amino acid sequence of the first and second fragments of the human protein. In other embodiments, the synthetic peptide may further comprise at least a fifth, sixth, seventh, eighth, ninth, or tenth synthetic fragment of about 5 to about 50 amino acids having homology to a fragment of about 5 to about 50 contiguous amino acids of a human protein selected from the group consisting of SEQ ID NOS: 1-39. Each of the synthetic fragments present in the synthetic peptide may be derived from the same human protein set forth in SEQ ID NOS:1-39, or may be derived from different proteins.

In one particular embodiment, the present invention provides a synthetic peptide comprising a fragment of about 5 to about 50 contiguous amino acids of human vimentin (SEQ ID NO:1), wherein at least one of the contiguous amino acids is an arginine residue, and wherein at least one arginine residue is citrullinated in the synthetic peptide.

In certain embodiments, the fragment comprises at least one of the arginine residues at positions 4, 12, 13, 28, 36, 50, 64, 69, 71, 78, 100, 122, 158, 159, 207, 217, 222, 270, 310, 320, 321, 364, 401, 410, 424, 440, and 450 of SEQ ID NO:1, wherein at least one of the arginine residues is citrullinated.

In other instances, the present invention provides a synthetic peptide comprising a first fragment of about 5 to about 50 contiguous amino acids of SEQ ID NO:1 linked to at least a second fragment of about 5 to about 50 contiguous amino acids of SEQ ID NO:1, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 4, 12, 13, 28, 36, 50, 64, 69, 71, 78, 100, 122, 158, 159, 207, 217, 222, 270, 310, 320, 321, 364, 401, 410, 424, 440, and 450 of SEQ ID NO:1, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:1, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 4, 12, 13, 28, 36, 50, 64, 69, 71, 78, 100, 122, 158, 159, 207, 217, 222, 270, 310, 320, 321, 364, 401, 410, 424, 440, and 450 of SEQ ID NO:1, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:1, wherein at least one residue of each of the fragments is an arginine residue in the native protein.

In certain other embodiments, the present invention provides a synthetic peptide comprising one or more fragments independently selected from the group consisting of amino acid residues 2-13, 4-12, 22-31, 28-38, 42-52, 61-70, 63-78, 68-76, 96-104, 116-124, 158-165, 157-165, 205-217, 216-224, 266-276, 320-328, 302-327, 356-364, 393-412, and 417-452 of SEQ ID NO:1, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:1. In some embodiments, the synthetic peptide comprises one, two, or three independently selected fragments of SEQ ID NO:1. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In particular embodiments, the synthetic peptide of the invention comprises a first fragment of amino acids 28-38 of SEQ ID NO:1, linked (e.g., by a peptide bond) to a second fragment of amino acids 42-52 of SEQ ID NO:1, linked (e.g., by a peptide bond) to a third fragment of amino acids 61-70 SEQ ID NO:1, wherein at least one of the arginine residues in each of the fragments is citrullinated (e.g., VMT7 core sequence set forth in SEQ ID NO:53). In alternative embodiments, the synthetic peptide comprises a first fragment of amino acids 42-52 or 61-70 of SEQ ID NO:1, linked (e.g., by a peptide bond) to a second fragment of amino acids 28-38 or 61-70 of SEQ ID NO:1, linked (e.g., by a peptide bond) to a third fragment of amino acids 28-38 or 42-52 of SEQ ID NO:1, wherein at least one of the arginine residues in each of the fragments is citrullinated. In other embodiments, the synthetic peptide may comprise alternative and/or additional fragments of SEQ ID NO:1.

In other particular embodiments, the synthetic peptide of the invention comprises a first fragment of amino acids 63-78 of SEQ ID NO:1, linked (e.g., by a peptide bond) to a second fragment of amino acids 68-76 of SEQ ID NO:1, wherein at least one of the arginine residues in each of the fragments is citrullinated (e.g., VMT8 core sequence set forth in SEQ ID NO:55). In alternative embodiments, the synthetic peptide comprises a first fragment of amino acids 68-76 of SEQ ID NO:1, linked (e.g., by a peptide bond) to a second fragment of amino acids 63-78 of SEQ ID NO:1, wherein at least one of the arginine residues in each of the fragments is citrullinated. In other embodiments, the synthetic peptide may comprise alternative and/or additional fragments of SEQ ID NO:1.

In further particular embodiments, the synthetic peptide of the invention comprises a first fragment of amino acids 356-364 of SEQ ID NO:1, linked (e.g., by a peptide bond) to a second fragment of amino acids 393-412 of SEQ ID NO:1, wherein at least one of the arginine residues in each of the fragments is citrullinated (e.g., VMT13 core sequence set forth in SEQ ID NO:65). In alternative embodiments, the synthetic peptide comprises a first fragment of amino acids 393-412 of SEQ ID NO:1, linked (e.g., by a peptide bond) to a second fragment of amino acids 356-364 of SEQ ID NO:1, wherein at least one of the arginine residues in each of the fragments is citrullinated. In other embodiments, the synthetic peptide may comprise alternative and/or additional fragments of SEQ ID NO:1.

In certain instances, the synthetic peptide comprising one or more fragments of SEQ ID NO:1 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human fibrinogen alpha-chain (SEQ ID NO:2), wherein at least one of the contiguous amino acids is an arginine residue, and wherein at least one arginine residue is citrullinated in the synthetic peptide.

In certain embodiments, the fragment comprises at least one of the arginine residues at positions 38, 42, 84, 114, 129, 135, 143, 160, 178, 181, 186, 216, 218, 367, 394, 458, 459, 512, 547, 591, 621, 627, and 630 of SEQ ID NO:2, wherein at least one of the arginine residues is citrullinated.

In other embodiments, the present invention provides a synthetic peptide comprising a first fragment of about 5 to about 50 contiguous amino acids of SEQ ID NO:2 linked to at least a second fragment of about 5 to about 50 contiguous amino acids of SEQ ID NO:2, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 38, 42, 84, 114, 129, 135, 143, 160, 178, 181, 186, 216, 218, 367, 394, 458, 459, 512, 547, 591, 621, 627, and 630 of SEQ ID NO:2, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:2, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 38, 42, 84, 114, 129, 135, 143, 160, 178, 181, 186, 216, 218, 367, 394, 458, 459, 512, 547, 591, 621, 627, and 630 of SEQ ID NO:2, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:2, wherein at least one residue of each of the fragments is an arginine residue in the native protein.

In certain other embodiments, the present invention provides a synthetic peptide comprising one or more fragments independently selected from the group consisting of amino acid residues 35-43, 76-89, 107-136, 127-148, 153-161, 174-188, 177-183, 212-220, 213-220, 359-368, 393-401, 440-450, 451-465, 509-517, 539-549, 583-599, and 613-639 of SEQ ID NO:2, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:2. In some embodiments, the synthetic peptide comprises one, two, or three independently selected fragments of SEQ ID NO:2. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:2 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human fibrinogen beta-chain (SEQ ID NO:3), wherein at least one of the contiguous amino acids is an arginine residue, and wherein at least one arginine residue is citrullinated in the synthetic peptide.

In certain embodiments, the fragment comprises at least one of the arginine residues at positions 47, 53, 60, 72, 74, 158, 196, 199, 206, 224, 334, 376, and 421 of SEQ ID NO:3, wherein at least one of the arginine residues is citrullinated.

In other embodiments, the present invention provides a synthetic peptide comprising a first fragment of about 5 to about 50 contiguous amino acids of SEQ ID NO:3 linked to at least a second fragment of about 5 to about 50 contiguous amino acids of SEQ ID NO:3, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 47, 53, 60, 72, 74, 158, 196, 199, 206, 224, 334, 376, and 421 of SEQ ID NO:3, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:3, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 47, 53, 60, 72, 74, 158, 196, 199, 206, 224, 334, 376, and 421 of SEQ ID NO:3, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:3, wherein at least one residue of each of the fragments is an arginine residue in the native protein.

In certain other embodiments, the present invention provides a synthetic peptide comprising one or more fragments independently selected from the group consisting of amino acid residues 70-79, 150-158, 188-200, 192-204, 198-207, 220-230, 327-336, 368-376, and 415-423 of SEQ ID NO:3, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:3. In some embodiments, the synthetic peptide comprises one, two, or three independently selected fragments of SEQ ID NO:3. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:3 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human fibrinogen gamma-chain (SEQ ID NO:4), wherein at least one of the contiguous amino acids is an arginine residue, and wherein at least one arginine residue is citrullinated in the synthetic peptide.

In certain embodiments, the fragment comprises at least one of the arginine residues at positions 31, 40, 134, 223, 301, and 417 of SEQ ID NO:4, wherein at least one of the arginine residues is citrullinated.

In other embodiments, the present invention provides a synthetic peptide comprising a first fragment of about 5 to about 50 contiguous amino acids of SEQ ID NO:4 linked to at least a second fragment of about 5 to about 50 contiguous amino acids of SEQ ID NO:4, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 31, 40, 134, 223, 301, and 417 of SEQ ID NO:4, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:4, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 31, 40, 134, 223, 301, and 417 of SEQ ID NO:4, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:4, wherein at least one residue of each of the fragments is an arginine residue in the native protein.

In certain other embodiments, the present invention provides a synthetic peptide comprising one or more fragments independently selected from the group consisting of amino acid residues 27-43, 126-135, 219-230, 300-308, and 409-419 of SEQ ID NO:4, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:4. In some embodiments, the synthetic peptide comprises one, two, or three independently selected fragments of SEQ ID NO:4. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:4 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human alpha-enolase (SEQ ID NO:5), wherein at least one of the contiguous amino acids is an arginine residue, and wherein at least one arginine residue is citrullinated in the synthetic peptide.

In certain embodiments, the fragment comprises at least one of the arginine residues at positions 9, 15, 32, 50, 132, 269, 327, 372, 412, and 429 of SEQ ID NO:5, wherein at least one of the arginine residues is citrullinated.

In other embodiments, the present invention provides a synthetic peptide comprising a first fragment of about 5 to about 50 contiguous amino acids of SEQ ID NO:5 linked to at least a second fragment of about 5 to about 50 contiguous amino acids of SEQ ID NO:5, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 9, 15, 32, 50, 132, 269, 327, 372, 412, and 429 of SEQ ID NO:5, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:5, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 9, 15, 32, 50, 132, 269, 327, 372, 412, and 429 of SEQ ID NO:5, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:5, wherein at least one residue of each of the fragments is an arginine residue in the native protein.

In certain other embodiments, the present invention provides a synthetic peptide comprising one or more fragments independently selected from the group consisting of amino acid residues 12-22, 29-40, 47-56, 130-139, 268-279, 321-330, 364-376, 411-419, and 425-434 of SEQ ID NO:5, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:5. In some embodiments, the synthetic peptide comprises one, two, or three independently selected fragments of SEQ ID NO:5. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:5 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human fibronectin 1 (SEQ ID NO:6), wherein at least one of the contiguous amino acids is an arginine residue, and wherein at least one arginine residue is citrullinated in the synthetic peptide.

In certain embodiments, the fragment comprises at least one of the arginine residues at positions 222, 228, 230, 237, 241, 1016, 1021, 1028, 1035, 1197, 1207, 1382, 1389, 1391, 1402, 1405, 1410, 1524, 1539, 1661, 1663, 1821, 1835, 1859, 1866, 2058, and 2059 of SEQ ID NO:6, wherein at least one of the arginine residues is citrullinated.

In other embodiments, the present invention provides a synthetic peptide comprising a first fragment of about 5 to about 50 contiguous amino acids of SEQ ID NO:6 linked to at least a second fragment of about 5 to about 50 contiguous amino acids of SEQ ID NO:6, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 222, 228, 230, 237, 241, 1016, 1021, 1028, 1035, 1197, 1207, 1382, 1389, 1391, 1402, 1405, 1410, 1524, 1539, 1661, 1663, 1821, 1835, 1859, 1866, 2058, and 2059 of SEQ ID NO:6, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:6, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 222, 228, 230, 237, 241, 1016, 1021, 1028, 1035, 1197, 1207, 1382, 1389, 1391, 1402, 1405, 1410, 1524, 1539, 1661, 1663, 1821, 1835, 1859, 1866, 2058, and 2059 of SEQ ID NO:6, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:6, wherein at least one residue of each of the fragments is an arginine residue in the native protein.

In certain other embodiments, the present invention provides a synthetic peptide comprising one or more fragments independently selected from the group consisting of amino acid residues 215-229, 221-229, 221-230, 231-239, 233-241, 1013-1021, 1014-1023, 1020-1035, 1027-1035, 1189-1214, 1379-1387, 1381-1389, 1388-1396, 1401-1409, 1401-1417, 1517-1546, 1655-1668, 1818-1837, 1851-1872, 2056-2065, and 2057-2066 of SEQ ID NO:6, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:6. In some embodiments, the synthetic peptide comprises one, two, or three independently selected fragments of SEQ ID NO:6. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:6 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human lamin B1 (SEQ ID NO:7), wherein at least one of the contiguous amino acids is an arginine residue, and wherein at least one arginine residue is citrullinated in the synthetic peptide.

In certain embodiments, the fragment comprises at least one of the arginine residues at positions 208, 220, 226, 234, 397, 402, 407, 410, 413, 416, 542, and 577 of SEQ ID NO:7, wherein at least one of the arginine residues is citrullinated.

In other embodiments, the present invention provides a synthetic peptide comprising a first fragment of about 5 to about 50 contiguous amino acids of SEQ ID NO:7 linked to at least a second fragment of about 5 to about 50 contiguous amino acids of SEQ ID NO:7, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 208, 220, 226, 234, 397, 402, 407, 410, 413, 416, 542, and 577 of SEQ ID NO:7, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:7, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 208, 220, 226, 234, 397, 402, 407, 410, 413, 416, 542, and 577 of SEQ ID NO:7, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:7, wherein at least one residue of each of the fragments is an arginine residue in the native protein.

In certain other embodiments, the present invention provides a synthetic peptide comprising one or more fragments independently selected from the group consisting of amino acid residues 205-229, 220-235, 395-409, 395-415, 406-425, 533-548, and 570-582 of SEQ ID NO:7, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:7. In some embodiments, the synthetic peptide comprises one, two, or three independently selected fragments of SEQ ID NO:7. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:7 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human lamin B2 (SEQ ID NO:8), wherein at least one of the contiguous amino acids is an arginine residue, and wherein at least one arginine residue is citrullinated in the synthetic peptide.

In certain embodiments, the fragment comprises at least one of the arginine residues at positions 185, 191, 219, 220, 228, 391, 396, 555, 564, and 591 of SEQ ID NO:8, wherein at least one of the arginine residues is citrullinated.

In other embodiments, the present invention provides a synthetic peptide comprising a first fragment of about 5 to about 50 contiguous amino acids of SEQ ID NO:8 linked to at least a second fragment of about 5 to about 50 contiguous amino acids of SEQ ID NO:8, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 185, 191, 219, 220, 228, 391, 396, 555, 564, and 591 of SEQ ID NO:8, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:8, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 185, 191, 219, 220, 228, 391, 396, 555, 564, and 591 of SEQ ID NO:8, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:8, wherein at least one residue of each of the fragments is an arginine residue in the native protein.

In certain other embodiments, the present invention provides a synthetic peptide comprising one or more fragments independently selected from the group consisting of amino acid residues 178-192, 184-193, 218-227, 219-231, 383-392, 389-404, 550-569, and 584-595 of SEQ ID NO:8, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:8. In some embodiments, the synthetic peptide comprises one, two, or three independently selected fragments of SEQ ID NO:8. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:8 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human lamin A/C (SEQ ID NO:9), wherein at least one of the contiguous amino acids is an arginine residue, and wherein at least one arginine residue is citrullinated in the synthetic peptide.

In certain embodiments, the fragment comprises at least one of the arginine residues at positions 7, 8, 11, 48, 50, 62, 72, 220, 221, 225, 235, 288, 296, 298, 399, 401, 419, 427, 435, 541, 545, 582, 584, 624, 627, 644, and 654 of SEQ ID NO:9, wherein at least one of the arginine residues is citrullinated.

In other embodiments, the present invention provides a synthetic peptide comprising a first fragment of about 5 to about 50 contiguous amino acids of SEQ ID NO:9 linked to at least a second fragment of about 5 to about 50 contiguous amino acids of SEQ ID NO:9, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 7, 8, 11, 48, 50, 62, 72, 220, 221, 225, 235, 288, 296, 298, 399, 401, 419, 427, 435, 541, 545, 582, 584, 624, 627, 644, and 654 of SEQ ID NO:9, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:9, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 7, 8, 11, 48, 50, 62, 72, 220, 221, 225, 235, 288, 296, 298, 399, 401, 419, 427, 435, 541, 545, 582, 584, 624, 627, 644, and 654 of SEQ ID NO:9, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:9, wherein at least one residue of each of the fragments is an arginine residue in the native protein.

In certain other embodiments, the present invention provides a synthetic peptide comprising one or more fragments independently selected from the group consisting of amino acid residues 5-13, 7-15, 7-16, 43-52, 43-58, 58-78, 218-227, 219-227, 219-236, 294-305, 296-305, 284-296, 399-407, 410-428, 418-441, 537-549, 541-552, 574-588, 580-590, 617-629, 619-628, and 636-657 of SEQ ID NO:9, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:9. In some embodiments, the synthetic peptide comprises one, two, or three independently selected fragments of SEQ ID NO:9. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:9 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human β-actin (SEQ ID NO:10), wherein at least one of the contiguous amino acids is an arginine residue, and wherein at least one arginine residue is citrullinated in the synthetic peptide.

In certain embodiments, the fragment comprises at least one of the arginine residues at positions 196 and 206 of SEQ ID NO:10, wherein at least one of the arginine residues is citrullinated.

In other embodiments, the present invention provides a synthetic peptide comprising a first fragment of about 5 to about 50 contiguous amino acids of SEQ ID NO:10 linked to at least a second fragment of about 5 to about 50 contiguous amino acids of SEQ ID NO:10, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 196 and 206 of SEQ ID NO:10, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:10, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 196 and 206 of SEQ ID NO:10, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:10, wherein at least one residue of each of the fragments is an arginine residue in the native protein.

In certain other embodiments, the present invention provides a synthetic peptide comprising one or more fragments independently selected from the group consisting of amino acid residues 188-207 of SEQ ID NO:10, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:10. In some embodiments, the synthetic peptide comprises one, two, or three independently selected fragments of SEQ ID NO:10. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:10 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human myeloblastin (SEQ ID NO:11), wherein at least one of the contiguous amino acids is an arginine residue, and wherein at least one arginine residue is citrullinated in the synthetic peptide.

In certain embodiments, the fragment comprises at least one of the arginine residues at positions 39, 48, 79, 91, 227, 235, 244, 248, and 249 of SEQ ID NO:11, wherein at least one of the arginine residues is citrullinated.

In other embodiments, the present invention provides a synthetic peptide comprising a first fragment of about 5 to about 50 contiguous amino acids of SEQ ID NO:11 linked to at least a second fragment of about 5 to about 50 contiguous amino acids of SEQ ID NO:11, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 39, 48, 79, 91, 227, 235, 244, 248, and 249 of SEQ ID NO:11, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:11, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 39, 48, 79, 91, 227, 235, 244, 248, and 249 of SEQ ID NO:11, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:11, wherein at least one residue of each of the fragments is an arginine residue in the native protein.

In certain other embodiments, the present invention provides a synthetic peptide comprising one or more fragments independently selected from the group consisting of amino acid residues 37-54, 71-99, 218-241, 241-249, 241-250, and 242-251 of SEQ ID NO:11, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:11. In some embodiments, the synthetic peptide comprises one, two, or three independently selected fragments of SEQ ID NO:11. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:11 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human PL scramblase (SEQ ID NO:12), wherein at least one of the contiguous amino acids is an arginine residue, and wherein at least one arginine residue is citrullinated in the synthetic peptide.

In certain embodiments, the fragment comprises at least one of the arginine residues at positions 163, 177, and 180 of SEQ ID NO:12, wherein at least one of the arginine residues is citrullinated.

In other embodiments, the present invention provides a synthetic peptide comprising a first fragment of about 5 to about 50 contiguous amino acids of SEQ ID NO:12 linked to at least a second fragment of about 5 to about 50 contiguous amino acids of SEQ ID NO:12, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 163, 177, and 180 of SEQ ID NO:12, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:12, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 163, 177, and 180 of SEQ ID NO:12, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:12, wherein at least one residue of each of the fragments is an arginine residue in the native protein.

In certain other embodiments, the present invention provides a synthetic peptide comprising one or more fragments independently selected from the group consisting of amino acid residues 161-181 and 173-182 of SEQ ID NO:12, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:12. In some embodiments, the synthetic peptide comprises one, two, or three independently selected fragments of SEQ ID NO:12. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:12 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human apolipoprotein (a) (SEQ ID NO:13), wherein at least one of the contiguous amino acids is an arginine residue, and wherein at least one arginine residue is citrullinated in the synthetic peptide.

In certain embodiments, the fragment comprises at least one of the arginine residues at positions 37, 47, 91, 96, 136, 3571, 3695, 3710, 3722, 3726, 3905, 3915, 3930, 3942, 3946, 4019, 4029, 4133, 4143, 4155, 4158, 4533, and 4536 of SEQ ID NO:13, wherein at least one of the arginine residues is citrullinated.

In other embodiments, the present invention provides a synthetic peptide comprising a first fragment of about 5 to about 50 contiguous amino acids of SEQ ID NO:13 linked to at least a second fragment of about 5 to about 50 contiguous amino acids of SEQ ID NO:13, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 37, 47, 91, 96, 136, 3571, 3695, 3710, 3722, 3726, 3905, 3915, 3930, 3942, 3946, 4019, 4029, 4133, 4143, 4155, 4158, 4533, and 4536 of SEQ ID NO:13, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:13, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 37, 47, 91, 96, 136, 3571, 3695, 3710, 3722, 3726, 3905, 3915, 3930, 3942, 3946, 4019, 4029, 4133, 4143, 4155, 4158, 4533, and 4536 of SEQ ID NO:13, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:13, wherein at least one residue of each of the fragments is an arginine residue in the native protein.

In certain other embodiments, the present invention provides a synthetic peptide comprising one or more fragments independently selected from the group consisting of amino acid residues 29-51, 89-97, 128-136, 3563-3572, 3687-3699, 3706-3722, 3718-3727, 3897-3919, 3926-3942, 3938-3947, 4011-4033, 4131-4156, 4155-4162, 4529-4541, and 4530-4539 of SEQ ID NO:13, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:13. In some embodiments, the synthetic peptide comprises one, two, or three independently selected fragments of SEQ ID NO:13. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:13 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human BiP (SEQ ID NO:14), wherein at least one of the contiguous amino acids is an arginine residue, and wherein at least one arginine residue is citrullinated in the synthetic peptide.

In certain embodiments, the fragment comprises at least one of the arginine residues at positions 181, 197, 283, 290, 297, 324, 336, 367, 439, and 532 of SEQ ID NO:14, wherein at least one of the arginine residues is citrullinated.

In other embodiments, the present invention provides a synthetic peptide comprising a first fragment of about 5 to about 50 contiguous amino acids of SEQ ID NO:14 linked to at least a second fragment of about 5 to about 50 contiguous amino acids of SEQ ID NO:14, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 181, 197, 283, 290, 297, 324, 336, 367, 439, and 532 of SEQ ID NO:14, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:14, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 181, 197, 283, 290, 297, 324, 336, 367, 439, and 532 of SEQ ID NO:14, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:14, wherein at least one residue of each of the fragments is an arginine residue in the native protein.

In certain other embodiments, the present invention provides a synthetic peptide comprising one or more fragments independently selected from the group consisting of amino acid residues 175-183, 190-203, 277-304, 315-324, 333-341, 359-367, 435-444, and 524-534 of SEQ ID NO:14, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:14. In some embodiments, the synthetic peptide comprises one, two, or three independently selected fragments of SEQ ID NO:14. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:14 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human histone H2A (SEQ ID NO:15), wherein at least one of the contiguous amino acids is an arginine residue, and wherein at least one arginine residue is citrullinated in the synthetic peptide.

In certain embodiments, the fragment comprises at least one of the arginine residues at positions 72 and 82 of SEQ ID NO:15, wherein at least one of the arginine residues is citrullinated.

In other embodiments, the present invention provides a synthetic peptide comprising a first fragment of about 5 to about 50 contiguous amino acids of SEQ ID NO:15 linked to at least a second fragment of about 5 to about 50 contiguous amino acids of SEQ ID NO:15, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 72 and 82 of SEQ ID NO:15, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:15, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 72 and 82 of SEQ ID NO:15, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:15, wherein at least one residue of each of the fragments is an arginine residue in the native protein.

In certain other embodiments, the present invention provides a synthetic peptide comprising one or more fragments independently selected from the group consisting of amino acid residues 64-85 of SEQ ID NO:15, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:15. In some embodiments, the synthetic peptide comprises one, two, or three independently selected fragments of SEQ ID NO:15. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:15 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human histone H2B (SEQ ID NO:16), wherein at least one of the contiguous amino acids is an arginine residue, and wherein at least one arginine residue is citrullinated in the synthetic peptide.

In certain embodiments, the fragment comprises at least one of the arginine residues at positions 34, 73, 80, 87, 93, and 100 of SEQ ID NO:16, wherein at least one of the arginine residues is citrullinated.

In other embodiments, the present invention provides a synthetic peptide comprising a first fragment of about 5 to about 50 contiguous amino acids of SEQ ID NO:16 linked to at least a second fragment of about 5 to about 50 contiguous amino acids of SEQ ID NO:16, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 34, 73, 80, 87, 93, and 100 of SEQ ID NO:16, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:16, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 34, 73, 80, 87, 93, and 100 of SEQ ID NO:16, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:16, wherein at least one residue of each of the fragments is an arginine residue in the native protein.

In certain other embodiments, the present invention provides a synthetic peptide comprising one or more fragments independently selected from the group consisting of amino acid residues 31-44, 65-94, and 79-101 of SEQ ID NO:16, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:16. In some embodiments, the synthetic peptide comprises one, two, or three independently selected fragments of SEQ ID NO:16. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:16 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human histone H3 (SEQ ID NO:17), wherein at least one of the contiguous amino acids is an arginine residue, and wherein at least one arginine residue is citrullinated in the synthetic peptide.

In certain embodiments, the fragment comprises at least one of the arginine residues at positions 24, 50, 53, 64, 84, and 135 of SEQ ID NO:17, wherein at least one of the arginine residues is citrullinated.

In other embodiments, the present invention provides a synthetic peptide comprising a first fragment of about 5 to about 50 contiguous amino acids of SEQ ID NO:17 linked to at least a second fragment of about 5 to about 50 contiguous amino acids of SEQ ID NO:17, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 24, 50, 53, 64, 84, and 135 of SEQ ID NO:17, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:17, wherein at least one residue of each of the third or fourth fragments is an arginine residue in the native protein.

In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 24, 50, 53, 64, 84, and 135 of SEQ ID NO:17, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:17, wherein at least one residue of each of the fragments is an arginine residue in the native protein.

In certain other embodiments, the present invention provides a synthetic peptide comprising one or more fragments independently selected from the group consisting of amino acid residues 41-70, 78-91, and 128-136 of SEQ ID NO:17, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:17. In some embodiments, the synthetic peptide comprises one, two, or three independently selected fragments of SEQ ID NO:17. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:17 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In a further particular embodiment, the present invention provides a synthetic peptide comprising a fragment of about 5 to about 50 contiguous amino acids of human histone H4 (SEQ ID NO:21), wherein at least one of the contiguous amino acids is an arginine residue, and wherein at least one arginine residue is citrullinated in the synthetic peptide.

In certain embodiments, the fragment comprises at least one of the arginine residues at positions 24, 56, 68, 79, and 96 of SEQ ID NO:21, wherein at least one of the arginine residues is citrullinated.

In other embodiments, the present invention provides a synthetic peptide comprising a first fragment of about 5 to about 50 contiguous amino acids of SEQ ID NO:21 linked to at least a second fragment of about 5 to about 50 contiguous amino acids of SEQ ID NO:21, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 24, 56, 68, 79, and 96 of SEQ ID NO:21, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:21, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 24, 56, 68, 79, and 96 of SEQ ID NO:21, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:21, wherein at least one residue of each of the fragments is an arginine residue in the native protein.

In certain other embodiments, the present invention provides a synthetic peptide comprising one or more fragments independently selected from the group consisting of amino acid residues 20-29, 49-84, and 92-100 of SEQ ID NO:21, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:21. In some embodiments, the synthetic peptide comprises one, two, or three independently selected fragments of SEQ ID NO:21. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:21 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human collagen T2α1 (SEQ ID NO:22), wherein at least one of the contiguous amino acids is an arginine residue, and wherein at least one arginine residue is citrullinated in the synthetic peptide.

In certain embodiments, the fragment comprises at least one of the arginine residues at positions 1270, 1379, 1422, 1428, 1453, and 1459 of SEQ ID NO:22, wherein at least one of the arginine residues is citrullinated.

In other embodiments, the present invention provides a synthetic peptide comprising a first fragment of about 5 to about 50 contiguous amino acids of SEQ ID NO:22 linked to at least a second fragment of about 5 to about 50 contiguous amino acids of SEQ ID NO:22, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 1270, 1379, 1422, 1428, 1453, and 1459 of SEQ ID NO:22, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:22, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 1270, 1379, 1422, 1428, 1453, and 1459 of SEQ ID NO:22, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:22, wherein at least one residue of each of the fragments is an arginine residue in the native protein.

In certain other embodiments, the present invention provides a synthetic peptide comprising one or more fragments independently selected from the group consisting of amino acid residues 1263-1271, 1371-1386, 1420-1429, 1421-1436, 1444-1460, and 1452-1460 of SEQ ID NO:22, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:22. In some embodiments, the synthetic peptide comprises one, two, or three independently selected fragments of SEQ ID NO:22. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:22 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human collagen T9α1 (SEQ ID NO:23), wherein at least one of the contiguous amino acids is an arginine residue, and wherein at least one arginine residue is citrullinated in the synthetic peptide.

In certain embodiments, the fragment comprises at least one of the arginine residues at positions 30, 71, 76, 100, 118, 189, 200, 768, and 783 of SEQ ID NO:23, wherein at least one of the arginine residues is citrullinated.

In other embodiments, the present invention provides a synthetic peptide comprising a first fragment of about 5 to about 50 contiguous amino acids of SEQ ID NO:23 linked to at least a second fragment of about 5 to about 50 contiguous amino acids of SEQ ID NO:23, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 30, 71, 76, 100, 118, 189, 200, 768, and 783 of SEQ ID NO:23, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:23, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 30, 71, 76, 100, 118, 189, 200, 768, and 783 of SEQ ID NO:23, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:23, wherein at least one residue of each of the fragments is an arginine residue in the native protein.

In certain other embodiments, the present invention provides a synthetic peptide comprising one or more fragments independently selected from the group consisting of amino acid residues 26-35, 63-71, 72-81, 73-80, 96-104, 111-126, 181-207, and 760-783 of SEQ ID NO:23, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:23. In some embodiments, the synthetic peptide comprises one, two, or three independently selected fragments of SEQ ID NO:23. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:23 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human collagen T10α1 (SEQ ID NO:24), wherein at least one of the contiguous amino acids is an arginine residue, and wherein at least one arginine residue is citrullinated in the synthetic peptide.

In certain embodiments, the fragment comprises at least one of the arginine residues at positions 531, 578, and 585 of SEQ ID NO:24, wherein at least one of the arginine residues is citrullinated.

In other embodiments, the present invention provides a synthetic peptide comprising a first fragment of about 5 to about 50 contiguous amino acids of SEQ ID NO:24 linked to at least a second fragment of about 5 to about 50 contiguous amino acids of SEQ ID NO:24, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 531, 578, and 585 of SEQ ID NO:24, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:24, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 531, 578, and 585 of SEQ ID NO:24, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:24, wherein at least one residue of each of the fragments is an arginine residue in the native protein.

In certain other embodiments, the present invention provides a synthetic peptide comprising one or more fragments independently selected from the group consisting of amino acid residues 527-536, 572-580, and 585-593 of SEQ ID NO:24, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:24. In some embodiments, the synthetic peptide comprises one, two, or three independently selected fragments of SEQ ID NO:24. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:24 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human collagen T11α1 (SEQ ID NO:25), wherein at least one of the contiguous amino acids is an arginine residue, and wherein at least one arginine residue is citrullinated in the synthetic peptide.

In certain embodiments, the fragment comprises at least one of the arginine residues at positions 64, 75, 155, 166, 192, 195, and 1555 of SEQ ID NO:25, wherein at least one of the arginine residues is citrullinated.

In other embodiments, the present invention provides a synthetic peptide comprising a first fragment of about 5 to about 50 contiguous amino acids of SEQ ID NO:25 linked to at least a second fragment of about 5 to about 50 contiguous amino acids of SEQ ID NO:25, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 64, 75, 155, 166, 192, 195, and 1555 of SEQ ID NO:25, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:25, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 64, 75, 155, 166, 192, 195, and 1555 of SEQ ID NO:25, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:25, wherein at least one residue of each of the fragments is an arginine residue in the native protein.

In certain other embodiments, the present invention provides a synthetic peptide comprising one or more fragments independently selected from the group consisting of amino acid residues 61-83, 150-174, 187-196, 188-196, and 1555-1564 of SEQ ID NO:25, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:25. In some embodiments, the synthetic peptide comprises one, two, or three independently selected fragments of SEQ ID NO:25. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:25 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human collagen T11α2 (SEQ ID NO:27), wherein at least one of the contiguous amino acids is an arginine residue, and wherein at least one arginine residue is citrullinated in the synthetic peptide.

In certain embodiments, the fragment comprises at least one of the arginine residues at positions 61, 64, 73, 91, 93, 243, 246, 254, and 257 of SEQ ID NO:27, wherein at least one of the arginine residues is citrullinated.

In other embodiments, the present invention provides a synthetic peptide comprising a first fragment of about 5 to about 50 contiguous amino acids of SEQ ID NO:27 linked to at least a second fragment of about 5 to about 50 contiguous amino acids of SEQ ID NO:27, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 61, 64, 73, 91, 93, 243, 246, 254, and 257 of SEQ ID NO:27, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:27, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 61, 64, 73, 91, 93, 243, 246, 254, and 257 of SEQ ID NO:27, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:27, wherein at least one residue of each of the fragments is an arginine residue in the native protein.

In certain other embodiments, the present invention provides a synthetic peptide comprising one or more fragments independently selected from the group consisting of amino acid residues 52-68, 60-74, 82-92, 85-98, 238-262, and 242-262 of SEQ ID NO:27, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:27. In some embodiments, the synthetic peptide comprises one, two, or three independently selected fragments of SEQ ID NO:27. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:27 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human syndecan-I (SEQ ID NO:28), wherein at least one of the contiguous amino acids is an arginine residue, and wherein at least one arginine residue is citrullinated in the synthetic peptide.

In certain embodiments, the fragment comprises at least one of the arginine residues at positions 126, 190, 229, and 230 of SEQ ID NO:28, wherein at least one of the arginine residues is citrullinated.

In other embodiments, the present invention provides a synthetic peptide comprising a first fragment of about 5 to about 50 contiguous amino acids of SEQ ID NO:28 linked to at least a second fragment of about 5 to about 50 contiguous amino acids of SEQ ID NO:28, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 126, 190, 229, and 230 of SEQ ID NO:28, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:28, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 126, 190, 229, and 230 of SEQ ID NO:28, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:28, wherein at least one residue of each of the fragments is an arginine residue in the native protein.

In certain other embodiments, the present invention provides a synthetic peptide comprising one or more fragments independently selected from the group consisting of amino acid residues 123-131, 183-191, 225-238, and 229-238 of SEQ ID NO:28, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:28. In some embodiments, the synthetic peptide comprises one, two, or three independently selected fragments of SEQ ID NO:28. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:28 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In a further particular embodiment, the present invention provides a synthetic peptide comprising a fragment of about 5 to about 50 contiguous amino acids of human syndecan-111 (SEQ ID NO:29), wherein at least one of the contiguous amino acids is an arginine residue, and wherein at least one arginine residue is citrullinated in the synthetic peptide.

In certain embodiments, the fragment comprises at least one of the arginine residues at positions 98, 155, 204, 209, 210, 223, 247, 255, 261, and 273 of SEQ ID NO:29, wherein at least one of the arginine residues is citrullinated.

In other embodiments, the present invention provides a synthetic peptide comprising a first fragment of about 5 to about 50 contiguous amino acids of SEQ ID NO:29 linked to at least a second fragment of about 5 to about 50 contiguous amino acids of SEQ ID NO:29, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 98, 155, 204, 209, 210, 223, 247, 255, 261, and 273 of SEQ ID NO:29, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:29, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 98, 155, 204, 209, 210, 223, 247, 255, 261, and 273 of SEQ ID NO:29, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:29, wherein at least one residue of each of the fragments is an arginine residue in the native protein.

In certain other embodiments, the present invention provides a synthetic peptide comprising one or more fragments independently selected from the group consisting of amino acid residues 91-99, 147-161, 196-209, 201-211, 202-211, 222-224, and 246-274 of SEQ ID NO:29, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:29. In some embodiments, the synthetic peptide comprises one, two, or three independently selected fragments of SEQ ID NO:29. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:29 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human CD44 (SEQ ID NO:30), wherein at least one of the contiguous amino acids is an arginine residue, and wherein at least one arginine residue is citrullinated in the synthetic peptide.

In certain embodiments, the fragment comprises at least one of the arginine residues at positions 29, 41, 46, 78, 90, 150, 154, 186, 218, 313, 343, 349, 417, 440, 469, 470, 537, 544, 545, 600, and 643 of SEQ ID NO:30, wherein at least one of the arginine residues is citrullinated.

In other embodiments, the present invention provides a synthetic peptide comprising a first fragment of about 5 to about 50 contiguous amino acids of SEQ ID NO:30 linked to at least a second fragment of about 5 to about 50 contiguous amino acids of SEQ ID NO:30, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 29, 41, 46, 78, 90, 150, 154, 186, 218, 313, 343, 349, 417, 440, 469, 470, 537, 544, 545, 600, and 643 of SEQ ID NO:30, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:30, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 29, 41, 46, 78, 90, 150, 154, 186, 218, 313, 343, 349, 417, 440, 469, 470, 537, 544, 545, 600, and 643 of SEQ ID NO:30, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:30, wherein at least one residue of each of the fragments is an arginine residue in the native protein.

In certain other embodiments, the present invention provides a synthetic peptide comprising one or more fragments independently selected from the group consisting of amino acid residues 22-42, 40-50, 72-97, 142-156, 149-156, 179-187, 211-226, 306-314, 335-345, 343-350, 411-420, 437-445, 469-477, 530-538, 537-544, 543-551, 593-604, and 641-647 of SEQ ID NO:30, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:30. In some embodiments, the synthetic peptide comprises one, two, or three independently selected fragments of SEQ ID NO:30. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:30 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human ICAM-1 (SEQ ID NO:31), wherein at least one of the contiguous amino acids is an arginine residue, and wherein at least one arginine residue is citrullinated in the synthetic peptide.

In certain embodiments, the fragment comprises at least one of the arginine residues at positions 143, 152, 159, 176, 187, 193, 460, 468, and 478 of SEQ ID NO:31, wherein at least one of the arginine residues is citrullinated.

In other embodiments, the present invention provides a synthetic peptide comprising a first fragment of about 5 to about 50 contiguous amino acids of SEQ ID NO:31 linked to at least a second fragment of about 5 to about 50 contiguous amino acids of SEQ ID NO:31, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 143, 152, 159, 176, 187, 193, 460, 468, and 478 of SEQ ID NO:31, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:31, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 143, 152, 159, 176, 187, 193, 460, 468, and 478 of SEQ ID NO:31, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:31, wherein at least one residue of each of the fragments is an arginine residue in the native protein.

In certain other embodiments, the present invention provides a synthetic peptide comprising one or more fragments independently selected from the group consisting of amino acid residues 140-152, 151-159, 168-179, 181-188, 186-194, and 456-480 of SEQ ID NO:31, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:31. In some embodiments, the synthetic peptide comprises one, two, or three independently selected fragments of SEQ ID NO:31. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:31 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human VCAM-I (SEQ ID NO:32), wherein at least one of the contiguous amino acids is an arginine residue, and wherein at least one arginine residue is citrullinated in the synthetic peptide.

In certain embodiments, the fragment comprises at least one of the arginine residues at positions 499 and 512 of SEQ ID NO:32, wherein at least one of the arginine residues is citrullinated.

In other embodiments, the present invention provides a synthetic peptide comprising a first fragment of about 5 to about 50 contiguous amino acids of SEQ ID NO:32 linked to at least a second fragment of about 5 to about 50 contiguous amino acids of SEQ ID NO:32, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 499 and 512 of SEQ ID NO:32, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:32, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 499 and 512 of SEQ ID NO:32, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:32, wherein at least one residue of each of the fragments is an arginine residue in the native protein.

In certain other embodiments, the present invention provides a synthetic peptide comprising one or more fragments independently selected from the group consisting of amino acid residues 496-520 of SEQ ID NO:32, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:32. In some embodiments, the synthetic peptide comprises one, two, or three independently selected fragments of SEQ ID NO:32. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:32 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human glypican-I (SEQ ID NO:33), wherein at least one of the contiguous amino acids is an arginine residue, and wherein at least one arginine residue is citrullinated in the synthetic peptide.

In certain embodiments, the fragment comprises at least one of the arginine residues at positions 90, 94, 105, 139, 142, 149, 153, 212, 215, 221, 235, 248, 466, 468, 505, and 511 of SEQ ID NO:33, wherein at least one of the arginine residues is citrullinated.

In other embodiments, the present invention provides a synthetic peptide comprising a first fragment of about 5 to about 50 contiguous amino acids of SEQ ID NO:33 linked to at least a second fragment of about 5 to about 50 contiguous amino acids of SEQ ID NO:33, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 90, 94, 105, 139, 142, 149, 153, 212, 215, 221, 235, 248, 466, 468, 505, and 511 of SEQ ID NO:33, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:33, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 90, 94, 105, 139, 142, 149, 153, 212, 215, 221, 235, 248, 466, 468, 505, and 511 of SEQ ID NO:33, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:33, wherein at least one residue of each of the fragments is an arginine residue in the native protein.

In certain other embodiments, the present invention provides a synthetic peptide comprising one or more fragments independently selected from the group consisting of amino acid residues 87-95, 88-106, 131-140, 139-146, 141-158, 209-225, 211-219, 227-250, 459-469, 460-473, 499-512, and 504-512 of SEQ ID NO:33, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:33. In some embodiments, the synthetic peptide comprises one, two, or three independently selected fragments of SEQ ID NO:33. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:33 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human glypican-II (SEQ ID NO:34), wherein at least one of the contiguous amino acids is an arginine residue, and wherein at least one arginine residue is citrullinated in the synthetic peptide.

In certain embodiments, the fragment comprises at least one of the arginine residues at positions 76, 79, 86, 214, 219, 225, 281, 287, 355, 357, 358, 469, 471, and 480 of SEQ ID NO:34, wherein at least one of the arginine residues is citrullinated.

In other embodiments, the present invention provides a synthetic peptide comprising a first fragment of about 5 to about 50 contiguous amino acids of SEQ ID NO:34 linked to at least a second fragment of about 5 to about 50 contiguous amino acids of SEQ ID NO:34, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 76, 79, 86, 214, 219, 225, 281, 287, 355, 357, 358, 469, 471, and 480 of SEQ ID NO:34, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:34, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 76, 79, 86, 214, 219, 225, 281, 287, 355, 357, 358, 469, 471, and 480 of SEQ ID NO:34, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:34, wherein at least one residue of each of the fragments is an arginine residue in the native protein.

In certain other embodiments, the present invention provides a synthetic peptide comprising one or more fragments independently selected from the group consisting of amino acid residues 68-76, 76-87, 212-229, 213-223, 273-288, 283-288, 351-359, 461-470, and 470-482 of SEQ ID NO:34, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:34. In some embodiments, the synthetic peptide comprises one, two, or three independently selected fragments of SEQ ID NO:34. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:34 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In still yet another particular embodiment, the present invention provides a synthetic peptide comprising a fragment of about 5 to about 50 contiguous amino acids of human glypican-IV (SEQ ID NO:35), wherein at least one of the contiguous amino acids is an arginine residue, and wherein at least one arginine residue is citrullinated in the synthetic peptide.

In certain embodiments, the fragment comprises at least one of the arginine residues at positions 167, 174, 213, 219, 351, 354, 463, and 469 of SEQ ID NO:35, wherein at least one of the arginine residues is citrullinated.

In other embodiments, the present invention provides a synthetic peptide comprising a first fragment of about 5 to about 50 contiguous amino acids of SEQ ID NO:35 linked to at least a second fragment of about 5 to about 50 contiguous amino acids of SEQ ID NO:35, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 167, 174, 213, 219, 351, 354, 463, and 469 of SEQ ID NO:35, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:35, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 167, 174, 213, 219, 351, 354, 463, and 469 of SEQ ID NO:35, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:35, wherein at least one residue of each of the fragments is an arginine residue in the native protein.

In certain other embodiments, the present invention provides a synthetic peptide comprising one or more fragments independently selected from the group consisting of amino acid residues 160-181, 207-216, 212-223, 350-358, 350-362, 462-470, and 465-476 of SEQ ID NO:35, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:35. In some embodiments, the synthetic peptide comprises one, two, or three independently selected fragments of SEQ ID NO:35. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:35 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another particular embodiment, the present invention provides a synthetic peptide comprising a fragment of about 5 to about 50 contiguous amino acids of human glypican-V (SEQ ID NO:36), wherein at least one of the contiguous amino acids is an arginine residue, and wherein at least one arginine residue is citrullinated in the synthetic peptide.

In certain embodiments, the fragment comprises at least one of the arginine residues at positions 76, 82, 198, 199, 210, 343, 347, 350, 357, 392, and 395 of SEQ ID NO:36, wherein at least one of the arginine residues is citrullinated.

In other embodiments, the present invention provides a synthetic peptide comprising a first fragment of about 5 to about 50 contiguous amino acids of SEQ ID NO:36 linked to at least a second fragment of about 5 to about 50 contiguous amino acids of SEQ ID NO:36, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 76, 82, 198, 199, 210, 343, 347, 350, 357, 392, and 395 of SEQ ID NO:36, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:36, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 76, 82, 198, 199, 210, 343, 347, 350, 357, 392, and 395 of SEQ ID NO:36, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:36, wherein at least one residue of each of the fragments is an arginine residue in the native protein.

In certain other embodiments, the present invention provides a synthetic peptide comprising one or more fragments independently selected from the group consisting of amino acid residues 70-83, 75-87, 194-205, 197-214, 336-354, 346-358, 385-399, and 387-399 of SEQ ID NO:36, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:36. In some embodiments, the synthetic peptide comprises one, two, or three independently selected fragments of SEQ ID NO:36. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:36 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In yet another particular embodiment, the present invention provides a synthetic peptide comprising a fragment of about 5 to about 50 contiguous amino acids of human glypican-VI (SEQ ID NO:37), wherein at least one of the contiguous amino acids is an arginine residue, and wherein at least one arginine residue is citrullinated in the synthetic peptide.

In certain embodiments, the fragment comprises at least one of the arginine residues at positions 95, 101, 213, 219, 229, 234, 461, and 468 of SEQ ID NO:37, wherein at least one of the arginine residues is citrullinated.

In other embodiments, the present invention provides a synthetic peptide comprising a first fragment of about 5 to about 50 contiguous amino acids of SEQ ID NO:37 linked to at least a second fragment of about 5 to about 50 contiguous amino acids of SEQ ID NO:37, wherein at least one residue of the first fragment is an arginine residue and at least one residue of the second fragment is an arginine residue, and wherein at least one arginine residue is citrullinated in the synthetic peptide.

In some instances, the first and second fragments of the synthetic peptide each comprise at least one citrullinated arginine. In other instances, the first and second fragments are linked together by a peptide bond. In further instances, the first and second fragments independently comprise at least one of the arginine residues at positions 95, 101, 213, 219, 229, 234, 461, and 468 of SEQ ID NO:37, wherein at least one of the arginine residues in the first fragment is citrullinated, and wherein at least one of the arginine residues in the second fragment is citrullinated.

The synthetic peptide comprising first and second fragments may further comprise at least a third or fourth fragment of about 5 to about 50 contiguous amino acids of SEQ ID NO:37, wherein at least one residue of each of the third or fourth fragments is an arginine residue in the native protein. In certain instances, at least one arginine residue in the third and/or fourth fragment is citrullinated. In other instances, the first, second, third, and/or fourth fragments are linked together by a peptide bond. In further instances, the third and fourth fragments independently comprise at least one of the arginine residues at positions 95, 101, 213, 219, 229, 234, 461, and 468 of SEQ ID NO:37, wherein at least one of the arginine residues in the third and/or fourth fragment is citrullinated. In other embodiments, the synthetic peptide may further comprise at least a fifth, sixth, seventh, eighth, ninth, or tenth fragment of about 5 to about 50 contiguous amino acids of SEQ ID NO:37, wherein at least one residue of each of the fragments is an arginine residue in the native protein.

In certain other embodiments, the present invention provides a synthetic peptide comprising one or more fragments independently selected from the group consisting of amino acid residues 91-102, 93-102, 206-234, 226-241, 454-462, and 460-475 of SEQ ID NO:37, wherein the fragments are linked together (e.g., by a peptide bond), and wherein at least one of the arginine residues in each of the fragments is citrullinated. The synthetic peptides of the invention having a composite amino acid sequence may comprise at least two, three, four, five, six, seven, eight, nine, ten, or more independently selected fragments of SEQ ID NO:37. In some embodiments, the synthetic peptide comprises one, two, or three independently selected fragments of SEQ ID NO:37. Preferably, the fragments are linked together by peptide bonds, e.g., a first fragment is linked to a second fragment by a peptide bond, which is linked to a third fragment by a peptide bond, with the resulting synthetic peptide having a linear structure. The fragments of the synthetic peptide may be linked together in any order or orientation.

In certain instances, the synthetic peptide comprising one or more fragments of SEQ ID NO:37 is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, at least two, three, four, five, six, or more arginine residues present in the synthetic peptide are citrullinated. In other embodiments, all of the arginine residues present in the synthetic peptide are citrullinated. In certain instances, at least one, two, three, four, five, six, or more of the cysteine residues present in the synthetic peptide are substituted with a serine residue, e.g., to prevent disulfide bond formation. In certain other instances, all of the cysteine residues present in the synthetic peptide are substituted with a serine residue.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In a related aspect, the present invention provides a synthetic peptide comprising an amino acid sequence selected from the group consisting of SEQ ID NOS:40-355. In one embodiment, the present invention provides a synthetic peptide comprising an amino acid sequence that is at least about 80% identical to a peptide selected from the group consisting of SEQ ID NOS:40-355. In other embodiments, the synthetic peptide may be at least about 85% identical, or at least about 86%, 87%, 88%, 89%, 90%, 91%, 92%, 93%, 94%, 95%, 96%, 97%, 98%, 99%, or 100% identical to a peptide selected from SEQ ID NOS:40-355.

In certain instances, the synthetic peptide is about 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In certain embodiments, the synthetic peptide is immunologically reactive with an autoantibody associated with rheumatoid arthritis. Preferably, the autoantibody associated with rheumatoid arthritis is an anti-citrullinated protein antibody. In certain instances, the synthetic peptide may further comprise a tag or capture moiety (e.g., biotin), a spacer or linker (e.g., glycine spacer), be labeled (e.g., fluorescent label), be amidated (e.g., at the C-terminus), or be otherwise chemically modified.

In another aspect, the present invention provides a method for detecting an anti-citrullinated protein antibody in a biological sample, the method comprising the steps of:
(a) contacting the biological sample with a synthetic peptide described herein under conditions suitable to transform the synthetic peptide into a complex comprising the synthetic peptide and the anti-citrullinated protein antibody; and
(b) detecting the presence (or absence) or level of said complex.

Methods of detecting the presence or level of the complex are known in the art, and include, without limitation, ELISA, mass spectrometry, immunoassays, fluorescence polarization, fluorescence anisotropy, western blotting, size exclusion chromatography, dynamic or static light scattering, analytical ultracentrifugation, and the like.

Accordingly, in certain embodiments, a detectable moiety may be used to facilitate detection of the complex. In certain embodiments, the detectable moiety may be conjugated to the synthetic peptide. In other embodiments, the detectable moiety may be conjugated to a detection reagent that binds to the synthetic protein, the anti-citrullinated protein antibody, or the complex thereof. In certain embodiments, the detectable moiety is selected from the group consisting of radioactive groups, fluorescent groups, luminescent groups, enzymes, biotin, and dyes.

In a related aspect, the present invention provides a method for detecting an anti-citrullinated protein antibody in a biological sample, the method comprising the steps of:
(a) contacting the biological sample with a synthetic peptide described herein under conditions suitable to transform the synthetic peptide into a complex comprising the synthetic peptide and the anti-citrullinated protein antibody;
(b) contacting the complex with a detection reagent comprising a reporter group to transform the complex into a labeled complex; and
(c) detecting the presence (or absence) or level of the labeled complex.

Any biological sample such as a tissue or bodily fluid sample obtained from an individual is suitable for use in the methods of the present invention to aid, assist, facilitate, or improve the detection of ACPAs. Non-limiting examples of tissue samples include buccal cells, a brain sample, a skin sample, or an organ sample (e.g., liver). A bodily fluid sample includes all fluids that are present in the body such as, e.g., blood, plasma, serum, saliva, synovial fluid, lymph, urine, or cerebrospinal fluid. Preferably, the sample is human serum.

In some embodiments, the detection reagent is selected from the group consisting of an anti-IgA antibody, an anti-IgG antibody, an anti-IgM antibody, Protein L, Protein A, Protein G, and mixtures thereof. In other embodiments, the reporter group is selected from the group consisting of radioactive groups, fluorescent groups, luminescent groups, enzymes, biotin, and dyes.

In certain instances, the step of detecting the presence or level of the labeled complex comprises detecting the presence or level of a signal generated from the reporter group, e.g., using a detection device. As a non-limiting example, the detection device may comprise a spectrophotometer.

The assay method of the present invention is useful for aiding in the detection of IgA anti-citrullinated protein antibodies, IgG anti-citrullinated protein antibodies, IgM anti-citrullinated protein antibodies, or mixtures thereof. In preferred embodiments, the assay method is an enzyme-linked immunosorbent assay (ELISA) method.

In yet another aspect, the present invention provides a method for performing an assay to aid in the diagnosis or prognosis of rheumatoid arthritis, the method comprising:
  (a) detecting the presence (or absence) or level of an anti-citrullinated protein antibody in a biological sample by contacting the sample with a synthetic peptide described herein; and
  (b) reporting the presence (or absence) or level of the anti-citrullinated protein antibody in the sample to aid in the diagnosis or prognosis of rheumatoid arthritis.

In a related aspect, the present invention provides a method for improving the sensitivity of diagnosing or prognosing rheumatoid arthritis, the method comprising:
  (a) detecting the presence (or absence) or level of an anti-citrullinated protein antibody in a biological sample with a synthetic peptide described herein; and
  (b) reporting the presence (or absence) or level of the anti-citrullinated protein antibody in the sample to improve the sensitivity of diagnosing or prognosing rheumatoid arthritis.

Any of the biological samples described above are suitable for use in the assay methods of the present invention to aid, assist, facilitate, or improve the diagnosis or prognosis of RA. In a preferred embodiment, the sample is human serum.

In certain embodiments, the step of detecting the presence or level of anti-citrullinated protein antibodies in the sample is performed using an ELISA. In some instances, the ELISA comprises the steps of: (a) contacting the sample with an enzyme-labeled immunoglobulin-binding protein; (b) contacting the sample with an enzyme substrate; and (c) analyzing the sample using a detection device. In other embodiments, the step of detecting the presence or level of anti-citrullinated protein antibodies in the sample is performed using mass spectrometry, immunoassays, fluorescence polarization, fluorescence anisotropy, western blotting, size exclusion chromatography, dynamic or static light scattering, analytical ultracentrifugation, and the like.

Examples of immunoglobulin-binding proteins include, but are not limited to, an anti-IgA antibody, an anti-IgG antibody, an anti-IgM antibody, Protein L, Protein A, Protein G, and mixtures thereof. A non-limiting example of a suitable detection device comprises a spectrophotometer. In some embodiments, the step of analyzing the sample using a detection device comprises measuring the intensity of color from a product of enzymatic activity of the enzyme substrate. A non-limiting example of a suitable enzyme substrate is 3,3′,5,5′-tetramethylbenzidine (TMB) or any other chromogenic reagent known in the art.

In some embodiments, the step of reporting the presence or level of anti-citrullinated protein antibodies in the sample comprises sending or reporting the results to a clinician, e.g., a rheumatologist or a general practitioner. In other embodiments, the step of reporting the presence or level of anti-citrullinated protein antibodies in the sample comprises recording or storing the results in a computer database or other suitable machine or device for storing information, e.g., at a laboratory.

In certain instances, the present invention may provide a diagnosis of RA in the form of a probability that an individual has RA or is at risk of developing RA based on the presence or absence of ACPAs in the sample. For example, an individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having RA or being at risk of developing RA. In other instances, the present invention may provide a prognosis of RA in an individual based on the presence or level of ACPAs in the sample. As non-limiting examples, the prognosis can be surgery, development of a more severe form of RA, development of a more advanced stage of RA, development of one or more symptoms associated with RA, and/or recovery from the disease.

In certain embodiments, the method further comprises:
  (a) contacting the sample with an anti-rheumatoid factor (RF) antibody (e.g., immunoglobulin G (IgG)), or antigenic fragment (e.g., Fc fragment) thereof, under conditions suitable to transform the anti-rheumatoid factor (RF) antibody, or antigenic fragment thereof, into a complex comprising the anti-rheumatoid factor (RF) antibody, or antigenic fragment thereof, and rheumatoid factor (RF);
  (b) detecting the presence or level of the complex, thereby determining the presence or level of rheumatoid factor (RF) in the sample; and
  (c) reporting the presence or level of rheumatoid factor (RF) in the sample to further improve the sensitivity of diagnosing or prognosing rheumatoid arthritis.

In preferred embodiments, the step of detecting the presence or level of the complex is performed using an ELISA. In other embodiments, the step of detecting the presence or level of the complex comprises mass spectrometry, immunoassays, fluorescence polarization, fluorescence anisotropy, western blotting, size exclusion chromatography, dynamic or static light scattering, analytical ultracentrifugation, and the like.

In yet another aspect, the present invention provides an assay for diagnosing or prognosing rheumatoid arthritis, the assay comprising:
  (a) contacting a sample with a synthetic peptide described herein under conditions suitable to transform the synthetic peptide into a complex comprising the synthetic peptide and an anti-citrullinated protein antibody; and
  (b) detecting the presence or level of the complex.

In certain embodiments, the step of detecting the presence or level of the complex comprises ELISA, mass spectrometry, immunoassays, fluorescence polarization, fluorescence anisotropy, western blotting, size exclusion chromatography, dynamic or static light scattering, analytical ultracentrifugation, and the like.

In a certain embodiment, the method comprises the steps of:
  (a) contacting a sample with a synthetic peptide described herein under conditions suitable to transform the synthetic peptide into a complex comprising the synthetic peptide and an anti-citrullinated protein antibody;
  (b) contacting the complex with a detection reagent comprising a reporter group to transform the complex into a labeled complex;
  (c) detecting the presence or level of the labeled complex, thereby determining the presence or level of the anti-citrullinated protein antibody; and
  (d) associating the presence or level of the anti-citrullinated protein antibody in the sample with rheumatoid arthritis.

In preferred embodiments, the anti-citrullinated protein antibodies are detected with an ELISA. In other embodiments, the anti-citrullinated protein antibodies are detected with mass spectrometry, an immunoassay, fluorescence polarization, fluorescence anisotropy, western blotting, size exclusion chromatography, dynamic or static light scattering, analytical ultracentrifugation, and the like.

In still yet another aspect, the present invention provides a kit comprising:
 (a) at least one synthetic peptide described herein; and
 (b) at least one detectable moiety.

In some embodiments, the detectable moiety is linked to the synthetic peptide. In certain instances, the detectable moiety is selected from the group consisting of radioactive groups, fluorescent groups, luminescent groups, enzymes, biotin, and dyes. In certain other instances, the detectable moiety comprises a detection reagent comprising a reporter group.

In other embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, or all of the synthetic peptides present in the kit are immobilized on a solid support. Non-limiting examples of solid supports include magnetic or chromatographic matrix particles, the surface of an assay plate (e.g., microtiter wells), pieces of a solid substrate material or membrane (e.g., plastic, nylon, paper), and the like. Other examples of solid supports include, but are not limited to, glass (e.g., a glass slide), chips, pins, filters, beads (e.g., magnetic beads, polystyrene beads, etc.), other membrane material (e.g., nitrocellulose, polyvinylidene fluoride (PVDF), etc.), fiber bundles, or any other suitable substrate. The peptides are generally immobilized or restrained on the solid support via covalent or noncovalent interactions (e.g., ionic bonds, hydrophobic interactions, hydrogen bonds, Van der Waals forces, dipole-dipole bonds). In certain instances, the peptides comprise capture tags (e.g., biotin) which interact with capture agents (e.g., avidin) bound to the solid support. In certain other instances, the kits described herein may comprise a plurality of peptides coupled to the surface of a solid support in different known/addressable locations.

In certain other instances, the kits described herein may comprise a plurality of anti-rheumatoid factor (RF) antibodies (e.g., IgGs), or antigenic fragments (e.g., Fc fragments) thereof, coupled to the surface of a solid support in different known/addressable locations.

In other embodiments, the detection reagent may comprise, for example, an anti-IgA antibody, an anti-IgG antibody, an anti-IgM antibody, Protein L, Protein A, Protein G, and mixtures thereof. Examples of reporter groups include, without limitation, radioactive groups, fluorescent groups, luminescent groups, enzymes, biotin, dyes, and mixtures thereof.

In a further aspect, the present invention provides an assay method to aid in the detection of rheumatoid factor (RF), the assay method comprising:
 (a) contacting a biological sample with an anti-rheumatoid factor (RF) antibody (e.g., immunoglobulin G (IgG)), or antigenic fragment (e.g., Fc fragment) thereof, under conditions suitable to transform the anti-rheumatoid factor (RF) antibody, or antigenic fragment thereof, into a complex comprising the anti-rheumatoid factor (RF) antibody, or antigenic fragment thereof, and rheumatoid factor (RF);
 (b) contacting the complex with a detection reagent comprising a reporter group to transform the complex into a labeled complex, wherein the detection reagent is Protein L; and
 (c) detecting the presence (or absence) or level of the labeled complex.

In another aspect, the present invention provides a method for improving the sensitivity of diagnosing or prognosing rheumatoid arthritis, the method comprising:
 (a) contacting a biological sample with an anti-rheumatoid factor (RF) antibody (e.g., immunoglobulin G (IgG)), or antigenic fragment (e.g., Fc fragment) thereof, under conditions suitable to transform the anti-rheumatoid factor (RF) antibody, or antigenic fragment thereof, into a complex comprising the anti-rheumatoid factor (RF) antibody, or antigenic fragment thereof, and rheumatoid factor (RF);
 (b) contacting the complex with a detection reagent comprising a reporter group to transform the complex into a labeled complex, wherein the detection reagent is Protein L;
 (c) detecting the presence (or absence) or level of the labeled complex, thereby determining the presence (or absence) or level of rheumatoid factor in the sample; and
 (d) reporting the presence (or absence) or level of rheumatoid factor in the sample to improve the sensitivity of diagnosing or prognosing rheumatoid arthritis.

Any of the biological samples described above is suitable for use in the methods of the present invention to aid, assist, facilitate, or improve the detection of RF or the diagnosis or prognosis of RA. In a preferred embodiment, the sample is human serum.

Non-limiting examples of reporter groups include radioactive groups, fluorescent groups, luminescent groups, enzymes, biotin, dyes, and mixtures thereof. In some instances, the step of detecting the presence or level of the labeled complex comprises detecting the presence or level of a signal generated from the reporter group, e.g., using a detection device. The detection device may comprise, for example, a spectrophotometer. Preferably, the assay method is an enzyme-linked immunosorbent assay (ELISA) method.

In some embodiments, the step of reporting the presence or level of RF in the sample comprises sending or reporting the results to a clinician, e.g., a rheumatologist or a general practitioner. In other embodiments, the step of reporting the presence or level of RF in the sample comprises recording or storing the results in a computer database or other suitable machine or device for storing information, e.g., at a laboratory.

In certain instances, the present invention may provide a diagnosis of RA in the form of a probability that an individual has RA or is at risk of developing RA based on the presence or absence of RF in the sample. For example, an individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having RA or being at risk of developing RA. In other instances, the present invention may provide a prognosis of RA in an individual based on the presence or level of RF in the sample. As non-limiting examples, the prognosis can be surgery, development of a more severe form of RA, development of a more advanced stage of RA, development of one or more symptoms associated with RA, and/or recovery from the disease.

In yet another aspect, the present invention provides an ELISA assay method, the ELISA assay method comprising:
  (a) contacting a biological sample with an anti-rheumatoid factor (RF) antibody (e.g., immunoglobulin G (IgG)), or antigenic fragment (e.g., Fc fragment) thereof, under conditions suitable to transform the anti-rheumatoid factor (RF) antibody, or antigenic fragment thereof, into a complex comprising the anti-rheumatoid factor (RF) antibody, or antigenic fragment thereof, and rheumatoid factor (RF);
  (b) contacting the complex with a detection reagent comprising an enzyme label to transform the complex into a labeled complex, wherein the detection reagent is Protein L;
  (c) contacting the labeled complex with an enzyme substrate; and
  (d) detecting the presence (or absence) or level of the labeled complex with a detection device.

Any of the biological samples described above is suitable for use in the ELISA assay methods of the present invention. In a preferred embodiment, the sample is human serum.

In some embodiments, the anti-rheumatoid factor (RF) antibody (e.g., IgG), or antigenic fragment (e.g., Fc fragment) thereof, is immobilized on a solid support. Non-limiting examples of suitable solid supports are described above. In certain instances, the enzyme label comprises horseradish peroxidase (HRP). In certain other instances, the detection device comprises a spectrophotometer.

In other embodiments, the step of detecting the presence or level of the labeled complex with a detection device comprises measuring the intensity of color from a product of enzymatic activity of the enzyme substrate. Examples of suitable enzyme substrates include, but are not limited to, 3,3',5,5'-tetramethylbenzidine (TMB) or any other chromogenic reagent known in the art.

In still yet another aspect, the present invention provides an assay for diagnosing or prognosing rheumatoid arthritis, the assay comprising:
  (a) contacting a biological sample with an anti-rheumatoid factor (RF) antibody (e.g., immunoglobulin G (IgG)), or antigenic fragment (e.g., Fc fragment) thereof, under conditions suitable to transform the anti-rheumatoid factor (RF) antibody, or antigenic fragment thereof, into a complex comprising the anti-rheumatoid factor (RF) antibody, or antigenic fragment thereof, and rheumatoid factor (RF);
  (b) contacting the complex with a detection reagent comprising an enzyme label to transform the complex into a labeled complex, wherein the detection reagent is Protein L;
  (c) detecting the presence (or absence) or level of the labeled complex, thereby determining the presence (or absence) or level of rheumatoid factor; and
  (d) associating the presence (or absence) or level of rheumatoid factor in the sample with rheumatoid arthritis.

In preferred embodiments, the presence or level of rheumatoid factor is detected with an ELISA. In other embodiments, the presence or level of rheumatoid factor is detected with mass spectrometry, an immunoassay, fluorescence polarization, fluorescence anisotropy, western blotting, size exclusion chromatography, dynamic or static light scattering, analytical ultracentrifugation, and the like.

In an additional aspect, the present invention provides a kit comprising:
  (a) an anti-rheumatoid factor (RF) antibody (e.g., IgG), or antigenic fragment (e.g., Fc fragment) thereof; and
  (b) a detection reagent optionally comprising a reporter group, wherein the detection reagent is Protein L.

In some embodiments, the anti-rheumatoid factor (RF) antibody (e.g., IgG), or antigenic fragment (e.g., Fc fragment) thereof, is immobilized on a solid support. Non-limiting examples of suitable solid supports are described above. The anti-rheumatoid factor (RF) antibody (e.g., IgG), or antigenic fragment (e.g., Fc fragment) thereof, is generally immobilized or restrained on the solid support via covalent or non-covalent interactions (e.g., ionic bonds, hydrophobic interactions, hydrogen bonds, Van der Waals forces, dipole-dipole bonds). In certain instances, the anti-rheumatoid factor (RF) antibody (e.g., IgG), or antigenic fragment (e.g., Fc fragment) thereof, comprises capture tags (e.g., biotin) which interact with capture agents (e.g., avidin) bound to the solid support.

In other embodiments, the reporter group may comprise, e.g., radioactive groups, fluorescent groups, luminescent groups, enzymes, biotin, dyes, and mixtures thereof. In certain instances, the reporter group comprises horseradish peroxidase (HRP).

In a further aspect, the present invention provides a method for identifying a peptide that is immunologically reactive with an anti-citrullinated protein antibody, the method comprising:
  (a) identifying at least one antigenic peptide epitope in at least one synovial fluid polypeptide, wherein the antigenic peptide epitope is predicted to be immunologically reactive with an anti-citrullinated protein antibody, wherein the antigenic peptide epitope contains at least one citrullinated arginine residue;
  (b) synthesizing a peptide that comprises at least one of the antigenic peptide epitopes;
  (c) contacting a sample from a rheumatoid arthritis (RA) individual with the peptide under conditions suitable to transform the peptide into a complex comprising the peptide and anti-citrullinated protein antibody; and
  (d) identifying the peptide as being immunologically reactive with the anti-citrullinated protein antibody based on the presence or level of the complex.

In one embodiment, step (c) of the above-described method further comprises:
  contacting the complex with a detection reagent comprising a reporter group to transform the complex into a labeled complex; and
  detecting the presence (or absence) or level of the labeled complex.

Examples of synovial fluid polypeptides include, but are not limited to, vimentin, fibrinogen alpha-chain, fibrinogen beta-chain, fibrinogen gamma-chain, alpha-enolase, β-actin, aggrecan, gelsolin, lumican, fibronectin, tropomyosin, cartilage oligomeric matrix protein, glucose-6-phosphate isomerase, lamin B1, lamin B2, lamin A/C, myeloblastin (proteinase 3), phospholipid (PL) scramblase 1, apolipoprotein (a), BiP (heat shock 70 kDa protein 5), histone H2A, histone H2B, histone H3, histone H4, COL2A1, COL9A1, COL10A1, COL11A1, COL11A2, syndecan 1, syndecan 3, CD44, intercellular adhesion molecule 1 (ICAM1), vascular cell adhesion molecule 1 (VCAM1), glypican 1, glypican 2, glypican 4, glypican 5, glypican 6, vitronectin, nidogen, and combinations thereof.

In certain embodiments, the antigenic peptide epitope comprises at least 5, 6, 7, 8, 9, 10, 11, 12, 13, 14, 15, 16, 17, 18, 19, 20, 25, 30, 35, 40, 45, 50, or more contiguous amino acids of a synovial fluid polypeptide sequence. Preferably, the antigenic peptide epitope comprises or consists of 9 contiguous amino acids of a synovial fluid polypeptide sequence.

In certain other embodiments, the antigenic peptide epitope is predicted to be immunologically reactive with an anti-citrullinated protein antibody when a score calculated for the antigenic peptide epitope is greater than or equal to a predetermined score. In certain instances, the score for the antigenic peptide epitope is calculated by adding up a value given to each amino acid in the antigenic peptide epitope based on the position and side-chain of the amino acid. In one embodiment, the peptide epitope comprises at least about 5 amino acids, or at least about 6, 7, 8, 9, 10, 11, 12, 13, 14, 15, 20, or more amino acids. In a specific embodiment, the peptide epitope is 9 amino acids long. As a non-limiting example, the value given to each amino acid in the antigenic peptide epitope may be a value shown in FIG. 10, wherein the value given to each amino acid is dependent upon the position of the amino acid in the peptide epitope sequence and the nature of the amino acid side-chain.

In certain instances, the predetermined score is +2.0. In certain other instances, the predetermined score is 0, +0.5, +1.0, +1.5, +2.0, +2.5, +3.0, +3.5, +4.0, +4.5, +5.0, +5.5, +6.0, +6.5, +7.0, +7.5, +8.0, +8.5, +9.0, +9.5, +10.0, or any fraction thereof. One skilled in the art will understand that the predetermined score may vary (e.g., be a positive or negative value) and will depend upon the specific value assigned to each amino acid at a particular position in the antigenic peptide epitope sequence.

In some embodiments, at least two, three, four, five, six, or more of the arginine residues present in the antigenic peptide epitope or epitopes are substituted with a citrulline residue. In other embodiments, all of the arginine residues present in the antigenic peptide epitope or epitopes are substituted with a citrulline residue.

Peptides comprising at least one, two, three, four, five, six, or more of the antigenic peptide epitopes identified in step (a) may be synthesized using any technique known in the art. Non-limiting examples of suitable peptide synthesis techniques are described below and include classical chemical synthesis and synthesis by recombinant means. Peptides may be linear or cyclized. For example, a peptide containing three of the antigenic peptide epitopes identified in step (a) may be linked by peptide bonds, such that a first peptide epitope is linked to a second peptide epitope by a peptide bond, which is linked to a third peptide epitope by a peptide bond, with the resulting peptide having a linear structure.

In certain embodiments, the detection reagent may comprise, for example, an anti-IgA antibody, an anti-IgG antibody, an anti-IgM antibody, Protein L, Protein A, Protein G, and mixtures thereof. Examples of reporter groups include, without limitation, radioactive groups, fluorescent groups, luminescent groups, enzymes, biotin, dyes, and mixtures thereof.

In some instances, the step of detecting the presence or level of the labeled complex comprises detecting the presence or level of a signal generated from the reporter group, e.g., using a detection device. The detection device may comprise, e.g., a spectrophotometer.

The method described above is particularly useful for identifying peptides that are immunologically reactive with IgA anti-citrullinated protein antibodies, IgG anti-citrullinated protein antibodies, IgM anti-citrullinated protein antibodies, or mixtures thereof.

Example 4 provides an exemplary embodiment of the method described above for predicting antigenic peptide epitopes in polypeptides present in synovial fluid and identifying novel citrullinated peptides based upon one or more predicted antigenic peptide epitopes.

In an additional aspect, the present invention provides a synthetic peptide identified by the method described above. In certain embodiments, the citrullinated peptides identified using the above-described method are useful for detecting anti-citrullinated protein antibodies present in an individual's sample with improved sensitivity and/or specificity, thereby enabling the early detection and/or prognosis of RA.

In some embodiments, the synthetic peptide is from 5-50, 8-50, 8-25, 8-15, 10-50, 10-45, 10-40, 10-35, 10-30, 10-25, 10-20, 15-50, 15-45, 15-40, 15-35, 15-30, 15-25, 20-50, 20-45, 20-40, 20-35, 20-30, 25-50, 25-45, 25-40, 25-35, 30-50, 30-45, 30-40, 35-50, 35-45, 40-50, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In other embodiments, the peptide further comprises a tag (e.g., biotin).

In another aspect, the present invention provides a kit comprising:
  (a) at least one synthetic peptide identified by the method described above; and
  (b) a detection reagent comprising a reporter group.

In a related embodiment, the present invention provides a kit comprising:
  (a) at least one synthetic peptide identified by the method described above; and
  (b) a detectable moiety.

In certain embodiments, the detectable moiety may be conjugated to the synthetic peptide. In other embodiments, the detectable moiety may be conjugated to a detection reagent that binds to the synthetic protein, the anti-citrullinated protein, or the complex thereof. In certain embodiments, the detectable moiety is selected from the group consisting of radioactive groups, fluorescent groups, luminescent groups, enzymes, biotin, dyes, or a combination thereof.

In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, or all of the synthetic peptides present in the kit are immobilized on a solid support. Non-limiting examples of suitable solid supports are described above. The peptides are generally immobilized or restrained on the solid support via covalent or noncovalent interactions (e.g., ionic bonds, hydrophobic interactions, hydrogen bonds, Van der Waals forces, dipole-dipole bonds). In certain instances, the peptides comprise capture tags (e.g., biotin) which interact with capture agents (e.g., avidin) bound to the solid support. In certain other instances, the kits described herein may comprise a plurality of peptides coupled to the surface of a solid support in different known/addressable locations.

In other embodiments, the detection reagent may comprise, for example, an anti-IgA antibody, an anti-IgG antibody, an anti-IgM antibody, Protein L, Protein A, Protein G, and mixtures thereof. Examples of reporter groups include, without limitation, radioactive groups, fluorescent groups, luminescent groups, enzymes, biotin, dyes, and mixtures thereof.

IV. Methods of Peptide Synthesis

In some embodiments, the present invention provides a method for producing a peptide described herein by classical chemical synthesis, wherein citrulline residues are substituted for arginine residues at certain steps during the chemical synthesis. In other embodiments, the present invention provides a method for producing a peptide described herein, wherein the primary amino acid sequence is produced by classical chemical synthesis, and wherein at least one arginine residue is subsequently transformed to a citrulline residue by contacting the peptide with a peptidylarginine deiminase (PAD).

The peptides of the present invention may be prepared using methods known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyloxycarbonyl (Fmoc) chemistry. The synthesized peptides can then be isolated and/or purified by reversed phase-HPLC and lyophilized. Peptides may also be prepared according to the solid phase methods described by Atherton and Shepard, in "Solid phase peptide synthesis," IRL Press, Oxford, UK (1989). Peptide synthesis may alternatively be carried out in homogeneous solution. For example, the synthesis technique in homogeneous solution described by Houbenweyl, in "Methode der Organischen Chemie," edited by E. Wunsch, vol. 15-1 et 11, Thieme, Stuttgart, Germany (1974), can be used. The claimed peptides may be obtained by substituting the original arginine residues with citrulline residues during chemical synthesis, or by contacting the peptides after synthesis with a peptidylarginine deiminase of any eukaryotic origin.

In certain embodiments, peptides may be produced by recombinant means, e.g., using recombinant DNA techniques described by Sambrook et al., in "Molecular Cloning, A Laboratory Manual," 2nd edition, Cold Spring Harbor University Press, Cold Spring Harbor, N.Y. USA (1989) or Stemmer et al., Gene, 164:49-53 (1995), in prokaryotes or lower or higher eukaryotes. The term "lower eukaryote" includes host cells such as yeast, fungi, and the like. Lower eukaryotes are generally (but not necessarily) unicellular. Examples of lower eukaryotic host cells include, but are not limited to, yeast, particularly species within Schizosaccharomyces, Saccharomyces, Kluiveromyces, Pichia (e.g., Pichia pastoris), Hansenula (e.g., Hansenula polymorpha), Schwaniomyces, Schizosaccharomyces, Yarowia, Zygosaccharomyces, and the like. The term "higher eukaryote" includes host cells derived from higher animals, such as mammals, reptiles, insects, and the like. Examples of higher eukaryotic host cells include Chinese hamster cell lines (e.g., CHO cells), monkey cell lines (e.g., COS and Vero cells), baby hamster kidney cell lines (BHK cells), pig kidney cell lines (PK15 cells), rabbit kidney cell lines (RK13 cells), the human osteosarcoma cell line 143 B, the human cell line HeLa, human hepatoma cell lines like Hep G2, and insect cell lines (e.g., Spodoptera frugiperda). The term "prokaryote" includes hosts such as E. coli, Lactobacillus, Lactococcus, Salmonella, Streptococcus, Bacillus subtilis, or Streptomyces. In certain instances, the present invention provides host cells comprising an expression vector for one or more the peptides described herein. The host cells may be provided in suspension or flask cultures, tissue cultures, organ cultures, and the like. Alternatively, the host cells may be derived from transgenic animals. In some embodiments, the claimed peptides are obtained by contacting the recombinant peptides after isolation and/or purification from host cells with a peptidylarginine deiminase of any eukaryotic origin.

Peptides may alternatively be prepared by cleavage of a longer polypeptide or full-length protein sequence. The peptides described herein may then be obtained by contacting the peptide fragment after cleavage with a peptidylarginine deiminase of any eukaryotic origin. For example, a peptide fragment of the present invention that is immunologically reactive with an RA-associated autoantibody may be obtained by first cleaving any one of the proteins set forth in SEQ ID NOS:1-39 by contacting the protein with an endopeptidase under suitable conditions and then contacting the resulting peptide fragment of interest with a peptidylarginine deiminase under suitable conditions to transform at least one of the arginine residues present in the peptide sequence to a citrulline residue.

In other embodiments, the peptides of the present invention may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino-terminal amides and esters. A number of synthetic techniques have been developed to generate synthetic circular peptides (see, e.g., Tarn et al., Protein Sci., 7:1583-1592 (1998); Romanovskis et al., J. Pept. Res., 52: 356-374 (1998); Camarero et al., J. Amer. Chem. Soc., 121: 5597-5598 (1999); Valero et al., J. Pept. Res., 53(1): 56-67 (1999)). Generally, the role of cyclizing peptides is two fold: (1) to reduce hydrolysis in vivo; and (2) to thermodynamically destabilize the unfolded state and promote secondary structure formation.

V. Antibodies

In some embodiments, the present invention provides an antibody raised upon immunization with any of the citrullinated peptides described herein, wherein the antibody is specifically immunoreactive with the citrullinated peptide. In other embodiments, the present invention provides an anti-idiotype antibody raised upon immunization with an RA-associated antibody, wherein the anti-idiotype antibody is specifically immunoreactive with the RA-associated antibody, thereby mimicking any of the citrullinated peptides described herein. These antibodies may be polyclonal or monoclonal.

To prepare the antibodies of the present invention, a host animal may be immunized with any of the citrullinated peptides or RA-associated antibodies described herein in a pharmaceutically acceptable carrier. Examples of pharmaceutically acceptable carriers include, but are not limited to, any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, and amino acid copolymers as well as inactive virus particles. Such carriers are well known to those of ordinary skill in the art.

Preferred adjuvants to enhance effectiveness of the composition include, but are not limited to, aluminum hydroxide (alum), N-acetyl-muramyl-L-threonyl-D-isoglutamine (thr-MDP) as described in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), and RIBI (which contains three components extracted from bacteria—monophosphoryl lipid A, trehalose dimycolate, and cell wall skeleton (MPL+TDM+CWS) in a 2% squalene/Tween 80 emulsion). Any of the 3 components MPL, TDM or CWS may also be used alone or combined 2 by 2. Additionally, adjuvants such as Stimulon (Cambridge Bioscience; Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically contain pharmaceutically-acceptable vehicles, such as water, saline, glycerol, ethanol, etc. Additionally, auxiliary substances, such as wetting or emulsifying agents, pH buffering substances, preservatives, and the like, may be included in such vehicles. The term "immunogenic" includes the ability of a substance to cause a humoral and/or cellular response, whether alone or when linked to a carrier, in the presence or absence of an adjuvant.

In some embodiments, the immunogenic compositions are prepared as injectables, either as liquid solutions or suspensions. Solid forms suitable for solution in, or suspension in, liquid vehicles prior to injection may also be prepared. The preparation also may be emulsified or encapsulated in liposomes for enhanced adjuvant effect. The antigen may also be incorporated into immune-stimulating complexes together with saponins, for example, Quil A (ISCOMS).

Immunogenic compositions used to raise antibodies comprise a "sufficient amount" or an "immunologically effective amount" of the antigen, as well as any other of the abovementioned components, as needed. An immunologically effective amount includes situations where the administration of that amount to a host animal, either in a single dose or as part of a series of doses, is effective to provoke an immune response and to raise antibodies against the antigen (e.g., citrullinated peptide or RA-associated antibody). This amount varies depending upon the health and physical condition of the host animal, the taxonomic group of the host animal (e.g., nonhuman primate, primate, rabbit, rat, mouse, etc.), the capacity of the host animal's immune system to synthesize antibodies, the immunogenicity of the antigen, its mode of administration, and other relevant factors. It is expected that the amount will fall into a relatively broad range that can be determined through routine trials. Usually, the amount will vary from about 0.01 to about 1000 mg/dose, more particularly from about 0.1 to about 100 mg/dose.

In certain embodiments, the immunogenic compositions may be conventionally administered parenterally, typically by injection, for example, subcutaneously, intravenously, or intramuscularly. Additional formulations suitable for other methods of administration include oral formulations and suppositories. Dosages may be administered as a single dose schedule or following a multiple dose schedule. The immunogenic compositions may be administered in conjunction with other immunoregulatory agents.

The host serum or plasma is collected following an appropriate time interval to provide a composition comprising antibodies reactive with the peptides or RA-associated antibodies of the present invention. The gamma globulin fraction or the IgG antibodies can be obtained, for example, by use of saturated ammonium sulfate or DEAE Sephadex, or other techniques known to those skilled in the art.

Monoclonal antibodies may be produced by any hybridoma formed according to classical methods from the spleen cells of an animal, particularly from a mouse or rat, that is immunized against an antigen, and of cells of a myeloma cell line, wherein the hybridoma is selected by its ability to produce monoclonal antibodies recognizing the antigen initially used for immunization of the animal.

In certain instances, monoclonal antibodies may be humanized versions of mouse monoclonal antibodies made by means of recombinant DNA technology, departing from parts of mouse and/or human genomic DNA sequences coding for H and L chains or from cDNA clones coding for H and L chains. Alternatively, monoclonal antibodies may be human monoclonal antibodies. Such antibodies can also be derived from human peripheral blood lymphocytes of patients with RA. As a non-limiting example, human monoclonal antibodies may be prepared by means of human peripheral blood lymphocyte repopulation of severe combined immune deficiency (SCID) mice (Duchosal et al., Nature, 355:258 (1992)) or by screening vaccinated host animals for the presence of reactive B-cells using the antigen.

The present invention also provides truncated versions or single-chain versions of the antibodies and anti-idiotype antibodies described above that have retained their original specificity for reacting with the antigen initially used for immunization.

The present invention also provides a method for detecting RA-associated antibodies from an individual's sample that specifically bind to the peptides or anti-idiotype antibodies described herein, the method comprising: (i) contacting the sample to be analyzed for the presence (or absence) or level of the RA-associated antibodies with a peptide or anti-idiotype antibody as defined above (e.g., under conditions suitable to transform the peptide or anti-idiotype antibody into a complex between the peptide or anti-idiotype antibody and the RA-associated antibody); and (ii) detecting the presence (or absence) or level of the complex formed between the peptide or anti-idiotype antibody and the RA-associated antibody. These methods are particularly useful for aiding in, assisting in, or improving the sensitivity of a diagnosis or prognosis of rheumatoid arthritis.

In further embodiments, the present invention provides a reverse method for detecting the peptides and/or anti-idiotype antibodies of the present invention with RA-associated antibodies from an individual's sample that specifically bind to the peptides and/or anti-idiotype antibodies that mimic such peptides, the method comprising: (i) contacting the sample to be analyzed for the presence (or absence) or level of a peptide or anti-idiotype antibody described herein with an RA-associated antibody (e.g., under conditions suitable to transform the RA-associated antibody into a complex between the RA-associated antibody and the peptide or anti-idiotype antibody); and (ii) detecting the presence (or absence) or level of the complex formed between the RA-associated antibody and the peptide or anti-idiotype antibody. These methods are also useful for aiding in, assisting in, or improving the sensitivity of a diagnosis or prognosis of rheumatoid arthritis.

VI. Assays

Any of a variety of assays, techniques, and kits known in the art can be used to detect the presence (or absence) or level of RA-associated autoantibodies such as anti-citrullinated protein antibodies (ACPAs) or rheumatoid factor (RF) in a sample from an individual, e.g., to provide a clinician with guidance when making a diagnosis or prognosis of RA.

The present invention relies, in part, on detecting the presence (or absence) or level of at least one antibody or antibody complex in a sample obtained from an individual. In preferred embodiments, the presence (or absence) or level of at least one autoantibody associated with RA is detected in an individual's sample. In certain embodiments, RA-associated autoantibodies may be detected in an individual's sample by detecting the presence (or absence) or level of complexes formed between the autoantibody, an antigen specific for the autoantibody, and a suitable detection reagent (e.g., an antibody or protein specific for the autoantibody that comprises a reporter group).

As used herein, the term "detecting the presence or absence" includes detecting, measuring, or determining the presence or absence of each antibody or antibody complex of interest by using any quantitative or qualitative assay known to one of skill in the art. As used herein, the term "detecting the level" includes detecting, measuring, or determining the level of each antibody or antibody complex of interest by using any direct or indirect quantitative assay known to one of skill in the art. In certain instances, quantitative assays that determine, for example, the relative or absolute amount of an antibody of interest are suitable for use in the present invention. One skilled in the art will appreciate that any assay useful for detecting the level of an antibody or antibody complex is also useful for detecting its presence or absence.

Flow cytometry can be used to determine the presence or level of RA-associated autoantibodies in a sample from an individual. Such flow cytometric assays, including bead based immunoassays, can be used to determine, e.g., ACPA or RF levels in the same manner as described for detecting serum antibodies to *Candida albicans* and HIV proteins (see, e.g., Bishop and Davis, *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for RA-associated autoantibodies can also be used to determine the presence or level of ACPAs or RF in a sample. As a non-limiting example, phage particles expressing an antigen specific for, e.g., one or more ACPAs can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego Academic Press, Inc. (1996)).

According to a specific embodiment, the methods of the present invention comprise the detection of the presence or level of RA-associated autoantibodies such as ACPAs or RF in a sample by immunoassay. Immunoassays can be based on detecting the binding with an antigen or pool of antigens known to be recognized by these antibodies, e.g., a natural or synthetic citrullinated peptide or an anti-idiotype antibody for detecting ACPAs or an immunoglobulin G (IgG) or Fc fragment thereof for detecting RF. Binding to the antigen can be detected, e.g., by a labeled secondary antibody, e.g., a fluorescently labeled secondary antibody. Immunoassays may be either competitive or noncompetitive. Non-competitive immunoassays are assays in which the amount of captured analyte is directly measured. In competitive assays, the amount of analyte present in the sample is measured indirectly by measuring the amount of an added (exogenous) analyte displaced (or competed away) from a capture agent by the analyte present in the sample. Suitable immunological methods include, but are not limited to, enzyme-linked immunosorbent assays (ELISA), immunoblotting, immunospotting (such as line immunoassays or LIA), radioimmunoassays (RIA), fluid or gel precipitation reactions, immunodiffusion (single or double), agglutination assays, immunoelectrophoresis, time-resolved immunofluorometric assays (TRIFMA), Western blots, complement-fixation assays, immunoradiometric assays, fluorescent immunoassays, protein A immunoassays, and immunoPCR. An overview of different immunoassays is provided in, e.g., Self and Cook (*Curr. Opin. Biotechnol.,* 7:60-65 (1996)), Wild (Nature Press, London, UK (2001)), Ghindilis et al. (Humana Press, Totowa, N.J., US (2002)), and Kilpatrick (*Transfusion Medicine,* 12:335-351 (2002)).

Additional immunoassays suitable for use in the present invention include, without limitation, enzyme immunoassays (EIA) such as enzyme multiplied immunoassay technique (EMIT), antigen capture ELISA, sandwich ELISA, IgM antibody capture ELISA (MAC ELISA), and microparticle enzyme immunoassay (MEIA); capillary electrophoresis immunoassays (CEIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis,* 18:2184-2193 (1997); Bao, *J. Chromatogr. B. Biomed. Sci.,* 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.,* 27:261-276 (1989)).

Antigen capture ELISA can be useful for determining the presence or level of one or more RA-associated autoantibodies in a sample. For example, in an antigen capture ELISA, an anti-idiotype antibody directed to an ACPA of interest is bound to a solid phase and sample is added such that the ACPA is bound by the anti-idiotype antibody. After unbound proteins are removed by washing, the amount of bound ACPA can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first anti-idiotype antibody is bound to a solid support, and the ACPA of interest is allowed to bind to the first antibody. The amount of the ACPA is quantitated by measuring the amount of a second anti-idiotype antibody that binds the ACPA. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) or chemiluminescent labeled secondary antibody (Harlow and Lane, supra) is also suitable for determining the presence or level of one or more RA-associated autoantibodies in a sample. In certain instances, a chemiluminescence assay using a chemiluminescent secondary antibody is suitable for sensitive, non-radioactive detection of ACPA or RF levels. Such secondary antibodies can be obtained commercially from various sources, e.g., Amersham Lifesciences, Inc. (Arlington Heights, Ill.).

Specific immunological binding of the antigen or pool of antigens to the RA-associated autoantibody of interest can be detected directly or indirectly. Direct labels include fluorescent or luminescent tags, metals, dyes, radionuclides, and the like, attached to the antibody. An antigen or pool of antigens labeled with iodine-125 ($^{125}$I) can be used for determining the level of ACPAs or RF in a sample. A chemiluminescence assay using a chemiluminescent antigen is suitable for sensitive, non-radioactive detection of ACPAs or RF levels. An antigen labeled with a fluorochrome is also suitable for determining the levels of ACPAs or RF in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of ACPA or RF levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more RA-associated autoantibodies in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more RA-associated autoantibodies in a sample. As used herein, the term immunohistochemical assay encompasses techniques that utilize the visual detection of fluorescent dyes or enzymes coupled (i.e., conjugated) to antibodies that react with the RA-associated autoantibody of interest (e.g., ACPA or RF) using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. The concentration of an ACPA or RF in a sample can be quantitated, e.g., through endpoint titration or through measuring the visual intensity of fluorescence compared to a known reference standard.

Alternatively, the presence or level of an RA-associated autoantibody (e.g., ACPA or RF) can be determined by detecting or quantifying the amount of the purified autoantibody. Purification of the autoantibody can be achieved, for example, by high pressure liquid chromatography (HPLC), alone or in combination with mass spectrometry (e.g., MALDI/MS, MALDI-TOF/MS, SELDI-TOF/MS, tandem MS, etc.). Qualitative or quantitative detection of an autoantibody of interest can also be determined by well-known methods including, without limitation, Bradford assays, Coomassie blue staining, silver staining, assays for radiolabeled protein, and mass spectrometry.

The analysis of a plurality of RA-associated autoantibody markers may be carried out separately or simultaneously with one test sample. For separate or sequential assay of RA-associated autoantibodies, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of autoantibody markers on a single surface. Particularly useful physical formats comprise surfaces having a plurality of discrete, addressable locations for the detection of a plurality of different autoantibody markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise an antigen or a plurality of antigens to immobilize ACPAs or RF for detection at each location. Surfaces may alternatively comprise one or more discrete particles (e.g., microparticles or nanoparticles) immobilized at discrete locations of a surface, where the microparticles comprise an antigen or a plurality of antigens to immobilize ACPAs or RF for detection.

Several RA-associated autoantibody markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in ACPA or RF levels over time. Increases or decreases in ACPA or RF levels, as well as the absence of change in ACPA or RF levels, can provide useful information to guide treatment decisions during the course of therapy.

A panel for measuring one or more of RA-associated autoantibodies may be constructed to provide relevant information related to the approach of the present invention for diagnosing or prognosing RA. Such a diagnostic or prognostic panel may be constructed to determine the presence or level of RF and/or the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or more individual ACPAs that are present in an individual's sample. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of RA-associated autoantibody markers may be carried out in a variety of physical formats as well. For example, the use of microtiter plates or automation could be used to facilitate the processing of large numbers of test samples. Alternatively, single sample formats could be developed to facilitate treatment, diagnosis, and prognosis in a timely fashion.

VII. Kits

The present invention also provides kits to facilitate and/or standardize the use of the compositions provided herein, as well as to facilitate the methods or assays described herein. Materials and reagents to carry out these various methods or assays can be provided in kits to facilitate their execution. As used herein, the term "kit" includes a combination of articles that facilitates a method, process, assay, analysis, or manipulation. In particular, kits comprising the peptides of the present invention find utility in a wide range of applications including, but not limited to, detecting the presence (or absence) or level of one or more RA-associated antibodies such as anti-citrullinated protein antibodies (ACPAs) and/or rheumatoid factor (RF) to provide a sensitive and specific diagnosis, classification, and/or prognosis of rheumatic diseases such as rheumatoid arthritis.

Kits can contain chemical reagents (e.g., citrullinated peptides, labeled antibodies, etc.) as well as other components. In addition, the kits of the present invention can include, without limitation, instructions to the kit user (e.g., directions for use of the peptides described herein for performing diagnostic or prognostic assays, etc.), apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

In some embodiments, the present invention provides a diagnostic or prognostic kit for use in detecting autoimmune diseases such as RA, wherein said kit comprises at least one of the above-mentioned peptides or antibodies. In certain instances, the peptide or antibody is bound to a solid support. In other embodiments, the kit comprises a plurality of the peptides and/or antibodies described herein, optionally in combination with other epitopes useful in characterizing or differentiating autoimmune diseases, wherein the peptides, antibodies and/or other epitopes are attached to specific locations on a solid substrate. In certain instances, the solid support is a membrane strip and the peptides, antibodies and/or other epitopes are coupled to the membrane in the form of parallel lines. In other instances, certain peptides, antibodies and/or other epitopes as defined above are not attached to a solid support but are instead provided in the binding solution to be used as competitors and/or to block other antibodies that are present in the sera of patients with autoimmune diseases other than rheumatoid arthritis, thereby decreasing or eliminating possible cross-reaction and/or non-specific binding.

In certain instances, the present invention provides a diagnostic or prognostic kit that allows differentiation between those autoimmune diseases in which the characteristic antibodies often cross-react with the same antigen, thus resulting in difficult and/or slow diagnosis or prognostication. Such kits may be prepared by the simultaneous use of several peptides and/or anti-idiotype antibodies of the present invention.

In certain other instances, the present invention provides a diagnostic or prognostic kit for use in detecting the presence or absence of RA-associated antibodies (e.g., anti-citrullinated protein antibodies and/or rheumatoid factor). Preferably, the kit comprises at least one peptide or anti-idiotype antibody described herein, optionally bound to a solid support.

In yet other instances, the present invention provides a diagnostic or prognostic kit for use in determining the type of autoimmune disease. The kit may comprise at least one peptide or anti-idiotype antibody described herein, optionally bound to a solid support.

In further instances, the present invention provides a diagnostic or prognostic kit comprising a plurality of the peptides and/or anti-idiotype antibodies described herein, which are attached to specific locations on a solid support.

VIII. Therapy and Therapeutic Monitoring

Once a diagnosis or prognosis of RA is made based on the presence or level of anti-citrullinated protein antibodies (ACPAs) and/or rheumatoid factor (RF) in an individual's sample as described herein, the methods of the present invention may further comprise administering to the individual a therapeutically effective amount of a drug useful for treating one or more symptoms associated with RA (i.e., an RA drug). For therapeutic applications, the RA drug can be administered alone or co-administered in combination with one or more additional RA drugs and/or one or more drugs that reduce the side-effects associated with the RA drug. The present invention advantageously enables a clinician to practice "personalized medicine" by guiding treatment decisions and informing therapy selection for RA such that the right drug is given to the right patient at the right time.

RA drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an RA drug is administered at the same time, just prior to, or just after the administration of a second drug (e.g., another RA drug, a drug useful for reducing the side-effects of the RA drug, etc.).

A therapeutically effective amount of an RA drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an RA drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the RA drug.

Methods for preparing such dosage forms are known to those skilled in the art (see, e.g., *Remington's Pharmaceutical Sciences,* 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *Remington's Pharmaceutical Sciences,* supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an RA drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An RA drug can also be formulated into a suppository disposed, for example, in a polyethylene glycol (PEG) carrier.

Liquid dosage forms can be prepared by dissolving or dispersing an RA drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An RA drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an RA drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of RA, an RA drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of RA symptoms, and the RA drug being employed. For example, dosages can be empirically determined considering the severity of RA symptoms, the stage of RA, and/or the prognosis of RA in an individual. The dose administered to an individual, in the context of the present invention, should be sufficient to affect a beneficial therapeutic response in the individual over time. The size of the dose can also be determined by the existence, nature, and extent of any adverse side-effects that accompany the administration of a particular RA drug in an individual. Determination of the proper dosage for a particular situation is within the skill of the practitioner. Generally, treatment is initiated with smaller dosages which are less than the optimum dose of the RA drug. Thereafter, the dosage is increased by small increments until the optimum effect under circumstances is reached. For convenience, the total daily dosage may be divided and administered in portions during the day, if desired.

As used herein, the term "RA drug" includes all pharmaceutically acceptable forms of a drug that is useful for treating one or more symptoms associated with RA. For example, the RA drug can be in a racemic or isomeric mixture, a solid complex bound to an ion exchange resin, or the like. In addition, the RA drug can be in a solvated form. The term "RA drug" is also intended to include all pharmaceutically acceptable salts, derivatives, and analogs of the RA drug being described, as well as combinations thereof. For example, the pharmaceutically acceptable salts of an RA drug include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an RA drug is suitable for use in the methods of the present invention, e.g., a pharmaceutically acceptable salt of an RA drug, a free base of an RA drug, or a mixture thereof.

Suitable drugs that are useful for treating one or more symptoms associated with RA include, but are not limited to, disease-modifying anti-rheumatic drugs (DMARDs), non-steroidal anti-inflammatory drugs (NSAIDs), immunosuppressive drugs, corticosteroids, free bases thereof, pharmaceutically acceptable salts thereof, derivatives thereof, analogs thereof, and combinations thereof.

Non-limiting examples of DMARDs include methotrexate (MTX), leflunomide, D-penicillamine, gold salts (e.g., sodium aurothiomalate, auranofin, etc.), minocycline, anti-malarial medications (e.g., chloroquine, hydroxychloroquine, sulfasalazine, etc.), free bases thereof, pharmaceutically acceptable salts thereof, derivatives thereof, analogs thereof, and combinations thereof.

Examples of NSAIDs include, but are not limited to, ibuprofen, indomethacin, COX-2 inhibitors (e.g., Celecoxib), free bases thereof, pharmaceutically acceptable salts thereof, derivatives thereof, analogs thereof, and combinations thereof.

Examples of immunosuppressive drugs include, without limitation, thiopurine drugs such as azathioprine (AZA), 6-mercaptopurine (6-MP), and metabolites thereof (e.g., 6-thioguanine); sirolimus (rapamycin); temsirolimus; everolimus; tacrolimus (FK-506); FK-778; immunosuppressive antibodies such as anti-tumor necrosis factor (TNF) antibodies (e.g., adalimumab, infliximab, etc.), anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; cyclophosphamide; IL-1 inhibitors; metabolites thereof; pharmaceutically acceptable salts thereof; derivatives thereof; prodrugs thereof; and combinations thereof.

An individual can also be monitored at periodic time intervals to assess the efficacy of a certain therapeutic regimen once a diagnosis or prognosis of RA has been made. For example, the presence or level of certain RA-associated autoantibodies (e.g., ACPAs and/or RF) may change based on the therapeutic effect of a treatment such as an RA drug. In certain embodiments, the patient is monitored to assess response and understand the effects of certain RA drugs or treatments in an individualized approach. In certain other embodiments, patients may not respond to a drug, but the presence or level of certain RA-associated autoantibodies may change, indicating that these patients belong to a special population (not responsive) that can be identified by their autoantibody levels. These patients can be discontinued on their current therapy and alternative treatments prescribed.

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Immunoassay for Detecting Anti-Citrullinated Protein Antibodies

This example describes an enzyme-linked immunosorbent assay (ELISA) for detecting (e.g., measuring) the presence (or absence) or level of anti-citrullinated protein antibodies (ACPAs) in an individual's sample. As a non-limiting example, a 96-well immunoassay plate was coated with avidin (e.g., neutravidin) and the plate was blocked with 5% bovine serum albumin in phosphate buffered saline. Biotinylated synthetic citrullinated peptides of the present invention were incubated with the avidin-coated plate. After washing, ACPA-positive serum standards or human serum samples were added to the plate and incubated for 1 hour at room temperature. Unbound samples were washed out and RA-associated autoantibodies directed against the immobilized citrullinated peptide were detected with an enzyme-labeled (e.g., HRP-labeled) anti-human IgA, IgG, IgM, or IgA/G/M secondary antibody.

Example 2

Design and Application of Novel Citrullinated Peptides

This example describes the design of citrullinated peptide sequences based upon human vimentin (SEQ ID NO:1), fibrinogen alpha chain (SEQ ID NO:2), fibrinogen beta chain (SEQ ID NO:3), and alpha-enolase (SEQ ID NO:5) protein sequences. This example also demonstrates the utility of the novel citrullinated peptides of the present invention in detecting anti-citrullinated protein antibodies (ACPAs) with improved sensitivity and/or specificity.

Vimentin

The citrullinated peptides shown Table 1 were designed from the wild-type human vimentin sequence and characterized for their ability to bind to and detect ACPAs.

TABLE 1

Exemplary citrullinated vimentin peptides of the present invention.

VMT1: Biotin-Gly-Gly-Gly-Ala-Thr-Cit-Ser-Ser-Ala-Val-Arg-Leu-Arg-Ser-Ser-Val-Pro-Gly-Val-Arg-Leu-Leu-Gln-Asp-Ser-NH$_2$ (SEQ ID NO: 40)

VMT2: Biotin-Gly-Gly-Gly-Ala-Thr-Arg-Ser-Ser-Ala-Val-Cit-Leu-Arg-Ser-Ser-Val-Pro-Gly-Val-Arg-Leu-Leu-Gln-Asp-Ser-NH$_2$ (SEQ ID NO: 42)

VMT3: Biotin-Gly-Gly-Gly-Ala-Thr-Arg-Ser-Ser-Ala-Val-Arg-Leu-Cit-Ser-Ser-Val-Pro-Gly-Val-Arg-Leu-Leu-Gln-Asp-Ser-NH$_2$ (SEQ ID NO: 44)

VMT4: Biotin-Gly-Gly-Gly-Ala-Thr-Arg-Ser-Ser-Ala-Val-Arg-Leu-Arg-Ser-Ser-Val-Pro-Gly-Val-Cit-Leu-Leu-Gln-Asp-Ser-NH$_2$ (SEQ ID NO: 46)

VMT5: Biotin-Gly-Gly-Gly-Ala-Thr-Cit-Ser-Ser-Ala-Val-Cit-Leu-Cit-Ser-Ser-Val-Pro-Gly-Val-Cit-Leu-Leu-Gln-Asp-Ser-NH$_2$ (SEQ ID NO: 48)

Each peptide has a biotin coupled at the N-terminus for binding to the ELISA plate, a glycine (Gly) spacer between the biotin moiety and vimentin sequence, and an amide at the C-terminus.

Figure 2:
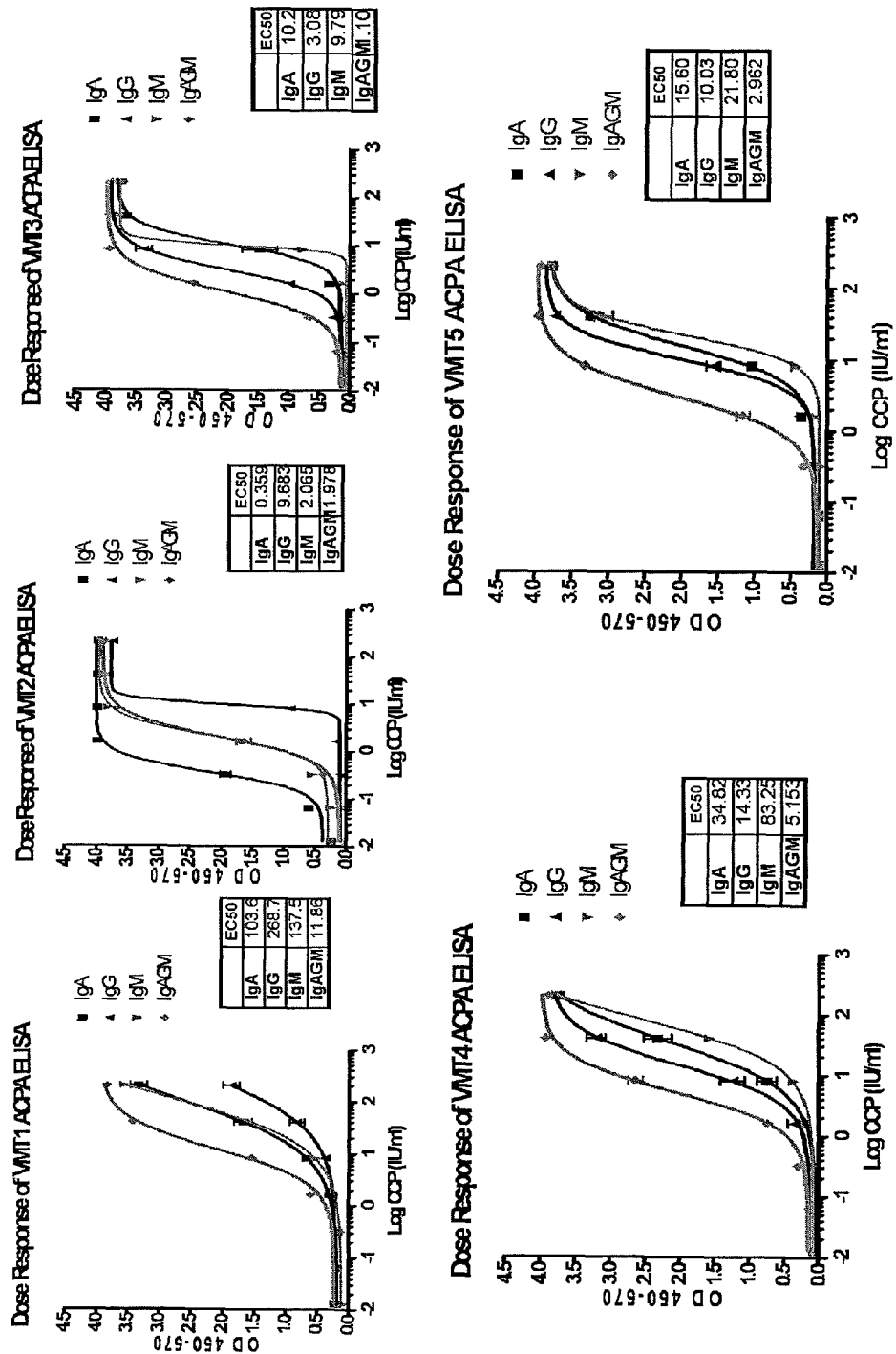
FIG. 2 illustrates dose-response curves for the citrullinated vimentin peptides shown in Table 1 using an ELISA to detect the presence or level of anti-citrullinated protein antibodies ("ACPAs").
Figure 3:
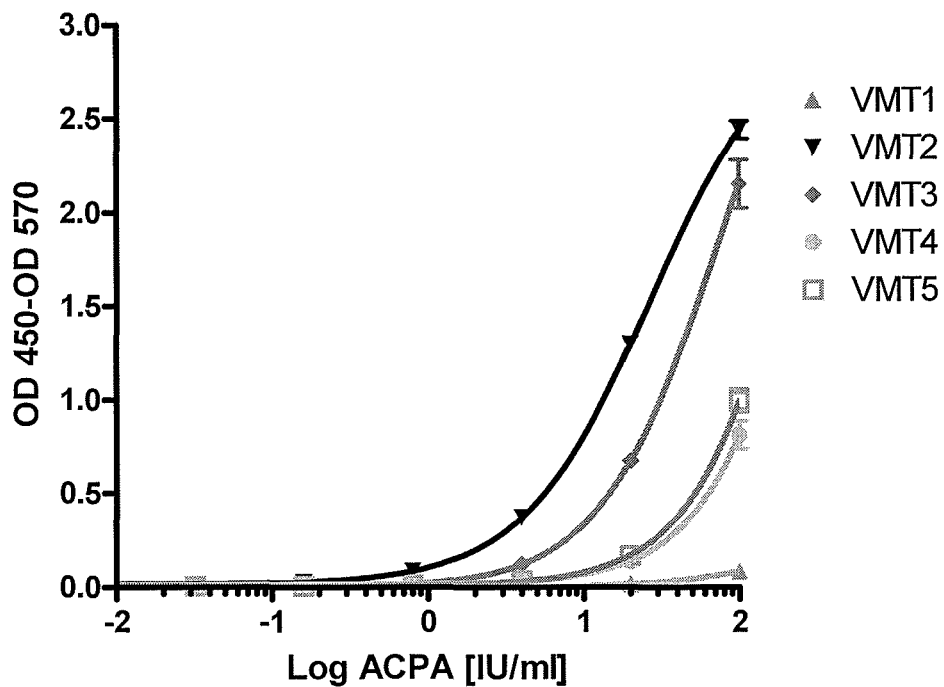
FIG. 3 illustrates a comparison of the dose-response curves for the citrullinated vimentin peptides shown in Table 1 using an ELISA to detect the presence or level of ACPAs.

FIG. 2 illustrates dose-response curves for each of these citrullinated vimentin peptides using an ELISA to detect the presence or absence of ACPAs. FIG. 3 illustrates a comparison of the dose-response curves for these citrullinated vimentin peptides using an ELISA to detect the presence or absence of ACPAs. All five of these peptides had peptide epitope scores ≧+2.0 (see, Example 4). As shown in FIG. 3, strong dose-response curves were observed for the VMT2 and VMT3 peptides compared to the other peptides tested. The weak dose-response curve observed for the VMT5 peptide may be due to the substitution of all four arginines with citrullines. This highlights the importance of balancing the degree of citrullination with antibody recognition such that the peptide contains a number of citrulline residues that is optimal for immunological reactivity with ACPAs.

Table 2 shows the affinity of each of these citrullinated vimentin peptides for IgA, IgG, IgM, or IgA/G/M ACPAs. As illustrated in Table 2, the VMT2 peptide exhibited a particularly high sensitivity for autoantibodies of the IgA and IgM classes, while the VMT3 peptide displayed a particularly high sensitivity for autoantibodies of the IgG and IgA/G/M classes. Since IgM and IgA are early markers for rheumatoid arthritis (RA), with IgM being an earlier marker than IgA, the VMT2 peptide may be useful for diagnosing an early form of the disease (e.g., early RA). Since IgG is a late/mature marker for RA, the VMT3 peptide is advantageous in diagnosing an established or late form of the disease (e.g., erosive RA or destructive RA).

TABLE 2

EC$_{50}$ of citrullinated vimentin peptides binding to different autoantibodies.
Antibody Binding Affinity of Vimentin Peptides Expressed in EC$_{50}$ Value

| | Peptides | VMT1 | VMT2 | VMT3 | VMT4 | VMT5 |
|---|---|---|---|---|---|---|
| Autoantibodies | IgA | 103.6 | 0.36 | 10.2 | 34.82 | 15.6 |
| | IgG | 268.7 | 9.68 | 3.08 | 14.33 | 10.03 |
| | IgM | 137.5 | 2.07 | 9.79 | 83.25 | 21.8 |
| | IgA/G/M | 11.86 | 1.98 | 1.1 | 5.15 | 2.96 |

Fibrinogen Alpha Chain

The citrullinated peptides shown in Table 3 were designed from the wild-type human fibrinogen alpha chain sequence and characterized for their ability to bind to and detect ACPAs.

TABLE 3

Exemplary citrullinated fibrinogen alpha chain peptides of the present invention.

α32: Biotin-Gly-Gly-Gly-Pro-Arg-Val-Val-Glu-Arg-His-Gln-Ser-Ala-Gly-Gly-Gly-Thr-Lys-Arg-Gly-His-Ala-Lys-Ser-Arg-Pro-Val-Arg-Gly-Ile-His-Thr (SEQ ID NO: 389)

Cit-α32: Biotin-Gly-Gly-Gly-Pro-Cit-Val-Val-Glu-Cit-His-Gln-Ser-Ala-Gly-Gly-Gly-Thr-Lys-Cit-Gly-His-Ala-Lys-Ser-Cit-Pro-Val-Cit-Gly-Ile-His-Thr (SEQ ID NO: 390)

[Arg$^{25}$]Cit-α32: Biotin-Gly-Gly-Gly-Pro-Cit-Val-Val-Glu-Cit-His-Gln-Ser-Ala-Gly-Gly-Gly-Thr-Lys-Cit-Gly-His-Ala-Lys-Ser-Arg-Pro-Val-Cit-Gly-Ile-His-Thr (SEQ ID NO: 391)

FB2-α(36-50)Cit$^{38,42}$: Biotin-Gly-Pro-Cit-Val-Val-Glu-Cit-His-Gln-Ser-Ala-<u>Ser</u>-Lys-Asp-Ser-NH$_2$ (SEQ ID NO: 86)

FB4-α(617-631)Cit$^{621,630}$: Biotin-His-Ser-Thr-Lys-Cit-Gly-His-Ala-Lys-Ser-Arg-Pro-Val-Cit-Gly-NH$_2$ (SEQ ID NO: 88)

Each of the first three peptides has a biotin coupled at the N-terminus for binding to the ELISA plate, a glycine (Gly) spacer between the N-terminal and C-terminal portions of the fibrinogen alpha chain sequence, and a carboxylic acid at the C-terminus.
Each of the last two peptides has a biotin coupled at the N-terminus for binding to the ELISA plate and is amidated at the C-terminus.
The underlined serine was substituted for cysteine present in the wild-type fibrinogen alpha chain sequence.

Figure 6:
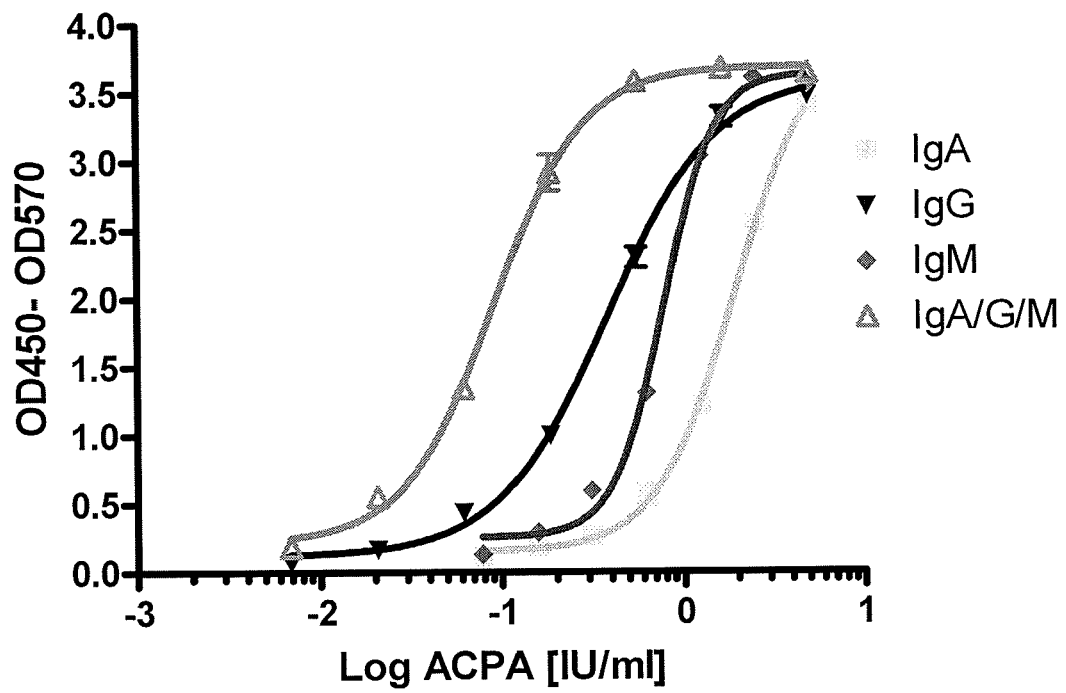
FIG. 6 illustrates the dose-response curves for the [Arg$^{25}$] Cit-α32 peptide using an ELISA to detect the presence or level of IgA, IgG, IgM, or IgA/G/M ACPAs.

FIG. 4 illustrates the dose-response curve for the [Arg$^{25}$]Cit-α32 peptide using an ELISA to detect the presence or absence of IgG ACPAs. This peptide was compared to a cyclic citrullinated peptide (CCP) IgG assay available from INOVA Diagnostics, Inc. (San Diego, Calif.). The EC50 of the INOVA assay was 143-fold higher than the EC$_{50}$ of the [Arg$^{25}$]Cit-α32 peptide assay, meaning that the inventive assay is 143 times more sensitive than NOVA's CCP assay for detecting IgG ACPAs. FIG. 5 illustrates a comparison of the IgG ACPA values obtained using the NOVA CCP assay versus the [Arg$^{25}$]Cit-α32 peptide assay for normal human serum (NHS) and RF-positive (C) samples. FIG. 6 illustrates the dose-response curves for the [Arg$^{25}$]Cit-α32 peptide using an ELISA to detect the presence or absence of IgA, IgG, IgM, or IgA/G/M ACPAs. These figures show that the [Arg$^{25}$]Cit-α32 peptide exhibited a particularly high sensitivity for autoantibodies of the IgG class. Since IgG is a late/mature marker for RA, the [Arg$^{25}$]Cit-α32 peptide is advantageous in diagnosing an established or late form of the disease (e.g., erosive RA or destructive RA).

Figure 7:
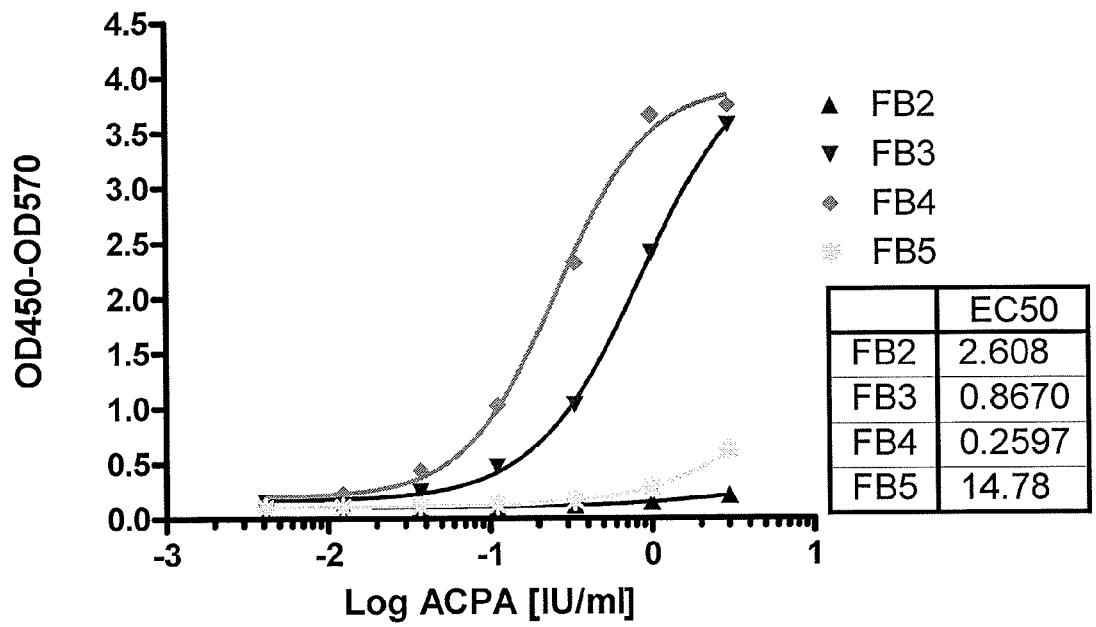
FIG. 7 illustrates the dose-response curves for additional citrullinated fibrinogen alpha-chain peptides of the invention using an ELISA to detect the presence or level of ACPAs.

FIG. 7 illustrates the dose-response curves for additional citrullinated fibrinogen alpha chain peptides of the invention using an ELISA to detect the presence or absence of ACPAs. The FB4 peptide, which had a peptide epitope score ≧+2.0, showed a stronger dose-response curve compared to the FB2 peptide, which had a peptide epitope score <+2.0 (see, Example 4).

Fibrinogen Beta Chain

The citrullinated peptides shown in Table 4 were designed from the wild-type human fibrinogen beta chain sequence and certain peptides were characterized for their ability to bind to and detect ACPAs.

TABLE 4

Exemplary citrullinated fibrinogen beta chain peptides of the present invention.

β32: Biotin-Gly-Gly-Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Ala-Arg-CO2H Biotin-Gly-Gly-Gly-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Ala-Arg-COOH (SEQ ID NO: 106)

Cit-β32: Biotin-Gly-Gly-Gly-His-Cit-Pro-Leu-Asp-Lys-Lys-Cit-Glu-Glu-Ala-Pro-Ser-Leu-Cit-Pro-Ala-Pro-Pro-Pro-Ile-Ser-Gly-Gly-Gly-Tyr-Cit-Ala-Cit-COOH (SEQ ID NO: 108)

[Arg[11]]Cit-β32: Biotin-Gly-Gly-Gly-His-Cit-Pro-Leu-Asp-Lys-Lys-Arg-Glu-Glu-Ala-Pro-Ser-Leu-Cit-Pro-Ala-Pro-Pro-Pro-Ile-Ser-Gly-Gly-Gly-Tyr-Cit-Ala-Cit-COOH (SEQ ID NO: 110)

FB3-β(60-74)Cit[60,72,74]: Biotin-Cit-Pro-Ala-Pro-Pro-Pro-Ile-Ser-Gly-Gly-Gly-Tyr-Cit-Ala-Cit-NH$_2$ (SEQ ID NO: 112)

FB5-β(43-62)Cit[47,60]: Biotin-Ala-Arg-Gly-His-Cit-Pro-Leu-Asp-Lys-Lys-Arg-Glu-Glu-Ala-Pro-Ser-Leu-Cit-Pro-Ala-NH$_2$ (SEQ ID NO: 114)

Each of the first three peptides has a biotin coupled at the N-terminus for binding to the ELISA plate, a glycine (Gly) spacer between the biotin moiety and fibrinogen beta chain sequence, and a carboxylic acid at the C-terminus.
Each of the last two peptides has a biotin coupled at the N-terminus for binding to the ELISA plate and is amidated at the C-terminus.

FIG. 7 illustrates the dose-response curves for the FB3 and FB5 peptides of the invention using an ELISA to detect the presence or absence of ACPAs. The FB3 peptide, which had a peptide epitope score $\geq +2.0$, showed a stronger dose-response curve compared to the FB5 peptide, which had a peptide epitope score $< +2.0$ (see, Example 4).

Alpha-Enolase

Figure 25:
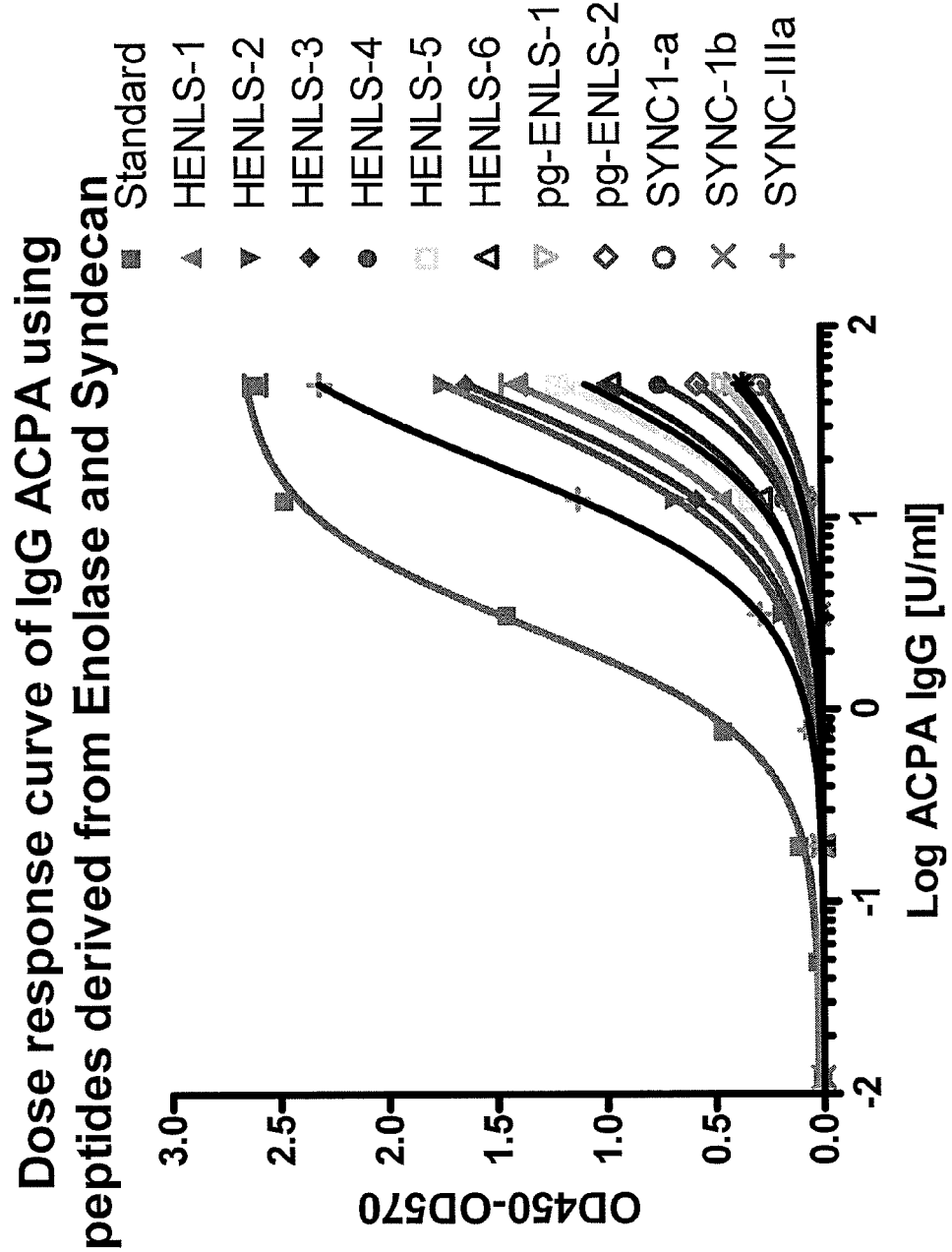
FIG. 25 illustrates the IgG ACPA dose-response curve of synthetic citrullinated peptides derived from alpha-enolase and syndecan.

The citrullinated peptides shown in Table 5 were designed from the wild-type human alpha-enolase sequence and characterized for their ability to bind to and detect ACPAs (see, FIG. 25 and Example 7).

bated in the wells coated with IgG Fc. Unbound samples were washed out and bound RF was incubated with Protein L-labeled with HRP. Unbound Protein L-HRP was washed out, TMB substrate was used to develop the color, and the presence or level of RF in the sample was detected or calculated using an RF standard curve.

FIG. 8 illustrates the dose-response curve for HRP-labeled Protein L using an ELISA to detect the presence or absence of RF. This detection agent was compared to a kit available from Orgentec Diagnostika GmbH (Mainz, Germany), which uses HRP-labeled secondary antibodies directed against each of

TABLE 5

Exemplary citrullinated alpha-enolase peptides of the present invention.

H-Enls 1: Biotin-Cys-Lys-Ile-His-Ala-Cit-Glu-Ile-Phe-Asp-Ser-Cit-Gly-Asn-Pro-Thr-Val-Glu-Cys-NH$_2$ (SEQ ID NO: 68)

H-Enls 2: Biotin-Cys-Lys-Ile-His-Ala-Arg-Glu-Ile-Phe-Asp-Ser-Cit-Gly-Asn-Pro-Thr-Val-Glu-Cys-NH$_2$ (SEQ ID NO: 70)

H-Enls 3: Biotin-Ala-Lys-Ile-His-Ala-Arg-Glu-Ile-Phe-Asp-Ser-Cit-Gly-Asn-Pro-Thr-Val-Glu-Ala-NH$_2$ (SEQ ID NO: 72)

Pg-Enls 1: Biotin-Cys-Lys-Ile-Ile-Gly-Cit-Glu-Ile-Leu-Asp-Ser-Cit-Gly-Asn-Pro-Thr-Val-Glu-Cys-NH$_2$ (SEQ ID NO: 392)

Pg-Enls 2: Biotin-Ala-Lys-Ile-Ile-Gly-Arg-Glu-Ile-Leu-Asp-Ser-Cit-Gly-Asn-Pro-Thr-Val-Glu-Ala-NH$_2$ (SEQ ID NO: 393)

Each peptide has a biotin coupled at the N-terminus for binding to the ELISA plate, a cysteine (Cys) or alanine (Ala) spacer at each end of the alpha-enolase sequence, and an amide at the C-terminus.

Example 3

Immunoassay for Detecting Rheumatoid Factor (RF)

This example describes an enzyme-linked immunosorbent assay (ELISA) for detecting (e.g., measuring) the presence (or absence) or level of rheumatoid factor (RF) in an individual's sample. The assay described herein uses Protein L having a reporter group attached thereto (e.g., Protein L labeled with HRP) as a detection agent to detect total autoantibodies associated with RA, e.g., human IgA, IgG, and IgM. As a non-limiting example, a 96-well immunoassay plate was coated with neutravidin. Biotinylated human IgG Fc fragment was bound to the neutravidin coated plate. Different concentrations of RF standards or patient serum samples were incuhuman IgA, IgG, and IgM. The $EC_{50}$ of the Orgentec assay was 697-fold higher than the $EC_{50}$ of the Protein L assay, meaning that the inventive assay is 697 times more sensitive than Orgentec's assay for detecting RF. FIG. 9 illustrates a comparison of the RF values obtained using the Orgentec RF assay versus the Protein L assay for normal human serum (NHS) and RF-positive samples (C). Without being bound to any particular theory, the inventive RF assay is substantially more sensitive than the commercially available Orgentec assay because it recognizes the Fab region of human IgA, IgG, and IgM autoantibodies without interfering with antibody-antigen binding.

Table 6 illustrates the sensitivity and specificity of the RF and ACPA assays of the present invention for normal human serum (Healthy Control) and rheumatoid arthritis serum (RA Patient) samples. As illustrated in Table 6, the RF and ACPA assays each on their own provided an extremely high level of specificity (>92%), but the combinatorial use of both assays resulted in an even higher level of specificity (>97%). Similar effects were observed with regard to the sensitivity detected for these assays.

TABLE 6

Sensitivity and specificity of the inventive RF and ACPA assays.

|  | Sample | Total Samples | Positive | Specificity (%) | Sensitivity (%) |
|---|---|---|---|---|---|
| RF | Healthy Control | 40 | 3.0 | 92.5 | |
|  | RA Patient | 53 | 31 |  | 58.5 |
| ACPA | Healthy Control | 37 | 2 | 94.6 | |
|  | RA Patient | 53 | 26 |  | 49.1 |
| RF & ACPA | Healthy Control | 36 | 1 | 97.2 | |
|  | RA Patient | 53 | 37 |  | 69.8 |

Example 4

Prediction and Design of Novel Citrullinated Peptides

This example describes an algorithm for predicting RA-specific antigenic peptide epitopes in proteins present in synovial fluid and the design of novel citrullinated peptides based upon one or more predicted antigenic peptide epitopes. The citrullinated peptides designed using the prediction method described herein are particularly useful for detecting and measuring anti-citrullinated protein antibodies (ACPAs) present in an individual's sample with improved sensitivity and/or specificity, thereby enabling the early detection and/or prognosis of RA.

To induce autoantibody formation against a protein, the protein has to be first internalized by the antigen presenting cell (APC). The internalized protein is then digested into small peptide fragments in the endosome and loaded onto the major histocompetability complex (MHC) class II molecule in the endoplasmic reticulum. The peptide/MHC complex is then transported to the surface of the APC through the Golgi Apparatus for presentation to the helper T cell through contact with the T cell receptor. Once the T cell recognizes the peptide/MHC complex, it will instruct the B cell to make an antibody that recognizes the antigenic peptide fragment present in the protein.

An MHC class II molecule is composed of two polypeptide chains: an α-chain and a β-chain. The overall shape of the molecule looks like a "hot dog bun" with the anti-parallel β-sheets forming the back of the bun and the two α-helixes, one from the α-chain and the other from the β-chain, forming the two loaves of the bun. An MHC class II molecule binds an antigenic peptide epitope that is composed of only 9 linear amino acid residues. The MHC molecule binds to the side-chains of the amino acids at positions P1, P4, P6, and P9 in the 9-residue peptide antigen. The peptide antigen backbone also forms H-bonds with some of the MHC protein residues to stabilize the overall structure. With the peptide antigen bound to the MHC molecule, the overall shape of the peptide/MHC complex looks exactly like a hot dog (peptide antigen) in a bun (MHC). The two ends of the bun are open so that it can accommodate a peptide hot dog that is longer than 9 amino acids. The extra amino acids from the peptide will just hang out at the two ends of the MHC molecule and not participate in the binding and antibody induction.

Table 7 illustrates the MHC Class II molecules associated with rheumatoid arthritis. The α-chain is identical for the three MHC class II alleles. It is only the β-chain that varies between the alleles and imparts the binding specificity to the peptide antigen.

TABLE 7

MHC Class II molecules associated with RA.

| MHC Class II Alleles | α-chain | β-chain |
|---|---|---|
| HLA-DR1 | HLA-DRA1*0101 | HLA-DRB1*0101 |
| HLA-DR4.1 (Dominant Allele) | HLA-DRA1*0101 | HLA-DRB1*0401 |
| HLA-DR4.4 | HLA-DRA1*0101 | HLA-DRB1*0404 |

A previous attempt to predict antigenic peptides that bind to the dominant RA HLA-DR4.1 MHC molecule employed side-chain scanning of a recombinant DRB1*0401 MHC molecule with a P1-anchored peptide library to determine the binding affinity of the test peptides (Hammer et al. *J. Exp. Med.*, 180:2353-2358 (1994)). The determined binding affinity was then divided by the binding affinity of a corresponding peptide that was substituted with alanine, which has the smallest side chain. If the affinity constant was better than alanine at that particular position, the score was positive; if the affinity constant was less than alanine at that particular position, the score was negative. A table was then compiled that gave the score of each of the 19 native amino acids (except cysteine) at positions 2-9 of the antigenic peptide. The peptide score was the sum of these values. If the 9-residue peptide epitope score was equal to or greater than +2.0, the epitope was considered to be an antigenic peptide. However, this prediction method is not particularly useful for identifying antigenic peptide epitopes and designing citrullinated peptides suitable for detecting RA-associated autoantibodies for at least the following reasons: (1) no values were given for amino acids A, D, E, G, H, K, N, P, Q, R, S, and T at the P1 position of the peptide, which limits the utility of the table and this prediction method because scores of the peptide epitopes that begin with any of these amino acids cannot be determined; and (2) the table does not have a value for citrulline, the crucial residue in the peptide antigen that is responsible for the induction of autoantibodies in RA patients.

The predictive algorithm of the present invention overcomes the limitations of Hammer et al. and is especially advantageous because it can accurately predict the scores of all of the RA antigenic peptide epitopes present in any protein. In certain embodiments, the inventive prediction method comprises a computer program which employs the peptide side-chain scanning table of Hammer et al., but with modifications in the P1 column so that all 9 amino acid positions in the peptide epitope are now used in the calculation. In addition, each of the arginine (R) residues present in the protein was replaced with glutamine (Q) because the side-chain binding affinity value for citrulline was not determined in the Hammer et al. table and the side-chain of citrulline is closely related to glutamine. Cysteine (C) residues present in the native protein sequence are replaced with serine (S). FIG. 10 illustrates an exemplary peptide epitope side-chain scanning table suitable for use in the prediction and design of novel citrullinated peptides.

FIG. 11 provides an illustration of how the score of a selected 9-residue peptide epitope in the vimentin polypeptide wherein an arginine residue was replaced with glutamine to mimic citrullination is determined by the RA antigenic peptide prediction program of the present invention. From the protein sequence shown in one letter code, the scores of each successive "frame-shifted" 9-residue peptide epitopes in the boxed peptide fragment and centered around the $^{71}$R (underlined and mutated to Q) were determined by summing up the individual 9-residue side-chain values obtained from the side-chain scanning table set forth in FIG. 10. The highest scoring peptide epitope from the nine successive frame-shifted epitope sequences was +5.5, which was assigned as the score for this $^{71}$R residue.

FIG. 12 illustrates the scoring results determined by the RA antigenic peptide prediction program of the present invention for each of the arginine residues present in a 9-residue peptide epitope in the vimentin sequence, wherein the arginines were replaced with glutamine. The scores of the calculated 9-residue peptide epitopes containing the arginine mutated to glutamine are shown above the corresponding arginine residue in FIG. 12. Those epitope scores that were ≧+2.0 (i.e., higher than 1.9) are underlined in FIG. 12. Such epitopes were used to design antigenic peptides for detecting autoantibodies in RA samples such as serum.

FIG. 13 illustrates non-limiting examples of synthetic peptides having composite amino acid sequences derived from high scoring vimentin 9-residue peptide epitopes (≧+2.0) determined by the RA antigenic peptide prediction program of the present invention. The scores for each of the calculated 9-residue peptide epitopes containing the arginine mutated to glutamine are shown above the corresponding citrulline (X) residue in FIG. 13. Each synthetic peptide may contain a biotin coupled at the N-terminus for binding to the ELISA plate, an optional amino acid spacer after the biotin moiety, an amide at the C-terminus, and an optional amino acid spacer before the C-terminal amide. Table 8 below sets forth these synthetic peptides as shown in FIG. 13 (i.e., with biotin and linker moieties) and as the core sequence only (see, SEQ ID NOS:50-67).

Referring to FIG. 13, Peptide (1), also known as "VMT6" in Table 8, is a 32-mer synthetic peptide containing amino acids 2-13 of human vimentin (SEQ ID NO:1) at the N-terminus, which is linked (i.e., by a peptide bond) to amino acids 4-12 of SEQ ID NO:1, which is linked to amino acids 22-31 of SEQ ID NO:1 at the C-terminus, wherein the "X" denotes substitution of arginine with citrulline. Peptide (2), also known as "VMT7" in Table 8, is a 33-mer synthetic peptide containing amino acids 28-38 of SEQ ID NO:1 at the N-terminus, which is linked to amino acids 42-52 of SEQ ID NO:1, which is linked to amino acids 61-70 of SEQ ID NO:1 at the C-terminus, wherein the "X" denotes substitution of arginine with citrulline. Peptide (3), also known as "VMT8" in Table 8, is a 26-mer synthetic peptide containing amino acids 63-78 of SEQ ID NO:1 at the N-terminus, which is linked to amino acids 68-76 of SEQ ID NO:1 at the C-terminus, wherein the "X" denotes substitution of arginine with citrulline. Peptide (4), also known as "VMT9" in Table 8, is a 27-mer synthetic peptide containing amino acids 96-104 of SEQ ID NO:1 at the N-terminus, which is linked to amino acids 116-124 of SEQ ID NO:1, which is linked to amino acids 158-165 of SEQ ID NO:1 at the C-terminus, wherein the "X" denotes substitution of arginine with citrulline. Peptide (5), also known as "VMT10" in Table 8, is a 32-mer synthetic peptide containing amino acids 157-165 of SEQ ID NO:1 at the N-terminus, which is linked to amino acids 205-217 of SEQ ID NO:1, which is linked to amino acids 216-224 of SEQ ID NO:1 at the C-terminus, wherein the "X" denotes substitution of arginine with citrulline. Peptide (6), also known as "VMT11" in Table 8, is a 21-mer synthetic peptide containing amino acids 266-276 of SEQ ID NO:1 at the N-terminus, which is linked to amino acids 320-328 of SEQ ID NO:1 at the C-terminus, wherein the "X" denotes substitution of arginine with citrulline, and wherein the cysteine at position 328 of SEQ ID NO:1 is replaced with a serine in the composite sequence. Peptide (7), also known as "VMT12" in Table 8, is a 27-mer synthetic peptide containing amino acids 302-327 of SEQ ID NO:1, wherein the "X" denotes substitution of arginine with citrulline. Peptide (8), also known as "VMT13" in Table 8, is a 31-mer synthetic peptide containing amino acids 356-364 of SEQ ID NO:1 at the N-terminus, which is linked to amino acids 393-412 of SEQ ID NO:1 at the C-terminus, wherein the "X" denotes substitution of arginine with citrulline. Peptide (9), also known as "VMT14" in Table 8, is a 37-mer synthetic peptide containing amino acids 417-452 of SEQ ID NO:1, wherein the "X" denotes substitution of arginine with citrulline. One skilled in the art will appreciate that the synthetic peptides shown in FIG. 13 are exemplary peptides of the present invention, and that other suitable RA antigenic peptides may be designed by linking the antigenic peptide epitope fragments of vimentin in alternative combinations or with antigenic peptide epitopes from other RA-associated polypeptides described herein (see, e.g., Example 5). As a non-limiting example, the synthetic peptide may contain one, two, three, four, five, six, or more peptide epitopes of human vimentin linked by peptide bonds, wherein each peptide epitope comprises at least 9 contiguous amino acids of SEQ ID NO:1 and includes at least one arginine residue with a score ≧+2.0 as determined by the RA antigenic peptide prediction program described herein, and wherein the synthetic peptide is immunoreactive against RA-associated autoantibodies present in an individual's sample.

FIG. 14 illustrates the scoring results determined by the RA antigenic peptide prediction program of the present invention for each of the arginine residues present in a 9-residue peptide epitope in the fibrinogen alpha chain sequence, wherein the arginines were replaced with glutamine. The scores of the calculated 9-residue peptide epitopes containing the arginine mutated to glutamine are shown above the corresponding arginine residue in FIG. 14. Those epitope scores that were ≧+2.0 are underlined in FIG. 14. Such epitopes were used to design antigenic peptides for detecting autoantibodies in RA samples such as serum.

FIG. 15 illustrates non-limiting examples of synthetic peptides having composite amino acid sequences derived from high scoring fibrinogen alpha chain 9-residue peptide epitopes (≧+2.0) determined by the RA antigenic peptide prediction program of the present invention. The scores for each of the calculated 9-residue peptide epitopes containing the arginine mutated to glutamine are shown above the corresponding citrulline (X) residue in FIG. 15. Each synthetic peptide may contain a biotin coupled at the N-terminus for binding to the ELISA plate, an optional amino acid spacer after the biotin moiety, an amide at the C-terminus, and an optional amino acid spacer before the C-terminal amide. Table 8 below sets forth these synthetic peptides as shown in FIG. 15 (i.e., with biotin and linker moieties) and as the core sequence only (see, SEQ ID NOS:90-105).

Referring to FIG. 15, Peptide (1), also known as "Fib-A1" in Table 8, is a 31-mer synthetic peptide containing amino acids 35-43 of human fibrinogen alpha chain (SEQ ID NO:2) at the N-terminus, which is linked (i.e., by a peptide bond) to amino acids 76-89 of SEQ ID NO:2, which is linked to amino acids 177-183 of SEQ ID NO:2 at the C-terminus, wherein the "X" denotes substitution of arginine with citrulline, and wherein the cysteine at position 180 of SEQ ID NO:2 is replaced with a serine in the composite sequence. Peptide (2), also known as "Fib-A2" in Table 8, is a 31-mer synthetic peptide containing amino acids 107-136 of SEQ ID NO:2, wherein the "X" denotes substitution of arginine with citrulline. Peptide (3), also known as "Fib-A3" in Table 8, is a 32-mer synthetic peptide containing amino acids 127-148 of SEQ ID NO:2 at the N-terminus, which is linked to amino acids 153-161 of SEQ ID NO:2 at the C-terminus, wherein the "X" denotes substitution of arginine with citrulline. Peptide (4), also known as "Fib-A4" in Table 8, is a 33-mer synthetic peptide containing amino acids 174-188 of SEQ ID NO:2 at the N-terminus, which is linked to amino acids 213-

220 of SEQ ID NO:2, which is linked to amino acids 212-220 of SEQ ID NO:2 at the C-terminus, wherein the "X" denotes substitution of arginine with citrulline, and wherein the cysteines at positions 180 and 184 of SEQ ID NO:2 are replaced with serines in the composite sequence. Peptide (5), also known as "Fib-A5" in Table 8, is a 32-mer synthetic peptide containing amino acids 393-401 of SEQ ID NO:2 at the N-terminus, which is linked to amino acids 359-368 of SEQ ID NO:2, which is linked to amino acids 450-460 at the C-terminus, wherein the "X" denotes substitution of arginine with citrulline. Peptide (6), also known as "Fib-A6" in Table 8, is a 25-mer synthetic peptide containing amino acids 451-465 at the N-terminus, which is linked to amino acids 509-517 at the C-terminus, wherein the "X" denotes substitution of arginine with citrulline, and wherein the cysteine at position 461 of SEQ ID NO:2 is replaced with a serine in the composite sequence. Peptide (7), also known as "Fib-A7" in Table 8, is a 30-mer synthetic peptide containing amino acids 539-549 at the N-terminus, which is linked to amino acids 583-599 at the C-terminus, wherein the "X" denotes substitution of arginine with citrulline. Peptide (8), also known as "Fib-A8" in Table 8, is a 28-mer synthetic peptide containing amino acids 613-639 of SEQ ID NO:2, wherein the "X" denotes substitution of arginine with citrulline. One skilled in the art will appreciate that the synthetic peptides shown in FIG. 15 are exemplary peptides of the present invention, and that other suitable RA antigenic peptides may be designed by linking the antigenic peptide epitope fragments of the fibrinogen alpha chain in alternative combinations or with antigenic peptide epitopes from other RA-associated polypeptides described herein (see, e.g., Example 5). As a non-limiting example, the synthetic peptide may contain one, two, three, four, five, six, or more peptide epitopes of the human fibrinogen alpha chain linked by peptide bonds, wherein each peptide epitope comprises at least 9 contiguous amino acids of SEQ ID NO:2 and includes at least one arginine residue with a score ≧+2.0 as determined by the RA antigenic peptide prediction program described herein, and wherein the synthetic peptide is immunoreactive against RA-associated autoantibodies present in an individual's sample.

FIG. 16 illustrates the scoring results determined by the RA antigenic peptide prediction program of the present invention for each of the arginine residues present in a 9-residue peptide epitope in the fibrinogen beta chain sequence, wherein the arginines were replaced with glutamine. The scores of the calculated 9-residue peptide epitopes containing the arginine mutated to glutamine are shown above the corresponding arginine residue in FIG. 16. Those epitope scores that were ≧+2.0 are underlined in FIG. 16. Such epitopes were used to design antigenic peptides for detecting autoantibodies in RA samples such as serum.

FIG. 17 illustrates non-limiting examples of synthetic peptides having composite amino acid sequences derived from high scoring fibrinogen beta chain 9-residue peptide epitopes (≧+2.0) determined by the RA antigenic peptide prediction program of the present invention. The scores for each of the calculated 9-residue peptide epitopes containing the arginine mutated to glutamine are shown above the corresponding citrulline (X) residue in FIG. 17. Each synthetic peptide may contain a biotin coupled at the N-terminus for binding to the ELISA plate, an optional amino acid spacer after the biotin moiety, an amide at the C-terminus, and an optional amino acid spacer before the C-terminal amide. Table 8 below sets forth these synthetic peptides as shown in FIG. 17 (i.e., with biotin and linker moieties) and as the core sequence only (see, SEQ ID NOS:116-121).

Referring to FIG. 17, Peptide (1), also known as "Fib-B1" in Table 8, is a 32-mer synthetic peptide containing amino acids 70-79 of human fibrinogen beta chain (SEQ ID NO:3) at the N-terminus, which is linked (i.e., by a peptide bond) to amino acids 150-158 of SEQ ID NO:3, which is linked to amino acids 188-200 of SEQ ID NO:3 at the C-terminus, wherein the "X" denotes substitution of arginine with citrulline. Peptide (2), also known as "Fib-B2" in Table 8, is a 35-mer synthetic peptide containing amino acids 192-204 of SEQ ID NO:3 at the N-terminus, which is linked to amino acids 198-207 of SEQ ID NO:3, which is linked to amino acids 220-230 of SEQ ID NO:3 at the C-terminus, wherein the "X" denotes substitution of arginine with citrulline, and wherein the cysteines at positions 223 and 227 of SEQ ID NO:3 are replaced with serines in the composite sequence. Peptide (3), also known as "Fib-B3" in Table 8, is a 29-mer synthetic peptide containing amino acids 327-336 of SEQ ID NO:3 at the N-terminus, which is linked to amino acids 368-376 of SEQ ID NO:3, which is linked to amino acids 415-423 of SEQ ID NO:3 at the C-terminus, wherein the "X" denotes substitution of arginine with citrulline. One skilled in the art will appreciate that the synthetic peptides shown in FIG. 17 are exemplary peptides of the present invention, and that other suitable RA antigenic peptides may be designed by linking the antigenic peptide epitope fragments of the fibrinogen beta chain in alternative combinations or with antigenic peptide epitopes from other RA-associated polypeptides described herein (see, e.g., Example 5). As a non-limiting example, the synthetic peptide may contain one, two, three, four, five, six, or more peptide epitopes of the human fibrinogen beta chain linked by peptide bonds, wherein each peptide epitope comprises at least 9 contiguous amino acids of SEQ ID NO:3 and includes at least one arginine residue with a score ≧+2.0 as determined by the RA antigenic peptide prediction program described herein, and wherein the synthetic peptide is immunoreactive against RA-associated autoantibodies present in an individual's sample.

FIG. 18 illustrates the scoring results determined by the RA antigenic peptide prediction program of the present invention for each of the arginine residues present in a 9-residue peptide epitope in the alpha-enolase sequence, wherein the arginines were replaced with glutamine. The scores of the calculated 9-residue peptide epitopes containing the arginine mutated to glutamine are shown above the corresponding arginine residue in FIG. 18. Those epitope scores that were ≧+2.0 are underlined in FIG. 18. Such epitopes were used to design antigenic peptides for detecting autoantibodies in RA samples such as serum.

FIG. 19 illustrates non-limiting examples of synthetic peptides having composite amino acid sequences derived from high scoring alpha-enolase 9-residue peptide epitopes (≧+2.0) determined by the RA antigenic peptide prediction program of the present invention. The scores for each of the calculated 9-residue peptide epitopes containing the arginine mutated to glutamine are shown above the corresponding citrulline (X) residue in FIG. 19. Each synthetic peptide may contain a biotin coupled at the N-terminus for binding to the ELISA plate, an optional amino acid spacer after the biotin moiety, an amide at the C-terminus, and an optional amino acid spacer before the C-terminal amide. Table 8 below sets forth these synthetic peptides as shown in FIG. 19 (i.e., with biotin and linker moieties) and as the core sequence only (see, SEQ ID NOS:74-79).

Referring to FIG. 19, Peptide (1), also known as "H-Enls-4" in Table 8, is a 34-mer synthetic peptide containing amino acids 12-22 of human alpha-enolase (SEQ ID NO:5) at the N-terminus, which is linked (i.e., by a peptide bond) to amino acids 29-40 of SEQ ID NO:5, which is linked to amino acids 47-56 of SEQ ID NO:5 at the C-terminus, wherein the "X" denotes substitution of arginine with citrulline. Peptide (2), also known as "H-Enls-5" in Table 8, is a 33-mer chimeric peptide containing amino acids 130-139 of SEQ ID NO:5 at the N-terminus, which is linked to amino acids 268-279 of SEQ ID NO:5, which is linked to amino acids 321-330 of SEQ ID NO:5 at the C-terminus, wherein the "X" denotes substitution of arginine with citrulline. Peptide (3), also known as "H-Enls-6" in Table 8, is a 33-mer chimeric peptide containing amino acids 364-376 of SEQ ID NO:5 at the N-terminus, which is linked to amino acids 411-419 of SEQ ID NO:5, which is linked to amino acids 425-434 of SEQ ID NO:5 at the C-terminus, wherein the "X" denotes substitution of arginine with citrulline. One skilled in the art will appreciate that the chimeric peptides shown in FIG. 19 are exemplary peptides of the present invention, and that other suitable RA antigenic peptides may be designed by linking the antigenic peptide epitope fragments of alpha-enolase in alternative combinations or with antigenic peptide epitopes from other RA-associated polypeptides described herein (see, e.g., Example 5). As a non-limiting example, the synthetic peptide may contain one, two, three, four, five, six, or more peptide epitopes of human alpha-enolase linked by peptide bonds, wherein each peptide epitope comprises at least 9 contiguous amino acids of SEQ ID NO:5 and includes at least one arginine residue with a score $\geq+2.0$ as determined by the RA antigenic peptide prediction program described herein, and wherein the synthetic peptide is immunoreactive against RA-associated autoantibodies present in an individual's sample.

In addition to the above-described proteins, any other protein present in synovial fluid may be analyzed to identify RA antigenic peptide epitopes by applying the prediction program of the present invention. Non-limiting examples of synovial fluid proteins are described in Gobezie et al., *Arthritis Res. & Ther.,* 9:R36 (2007). In certain embodiments, structural proteins or enzymes found in synovial fluid may be citrullinated. Structural proteins are more likely to be citrullinated because they are constantly present in high abundance in the synovium. Preferably, high scoring (e.g., $\geq+2.0$) citrullinated peptide epitopes from synovial fluid proteins such as collagen, actin, aggrecan, gelsolin, lumican, fibronectin, lamin, myeloblastin, PL scramblase, apolipoprotein (a), BiP, histone, syndecan, CD44, ICAM-I, VCAM-I, glypican, vitronectin, nidogen, tropomyosin, cartilage oligomeric matrix protein, and glucose-6-phosphate isomerase are identified using the algorithmic prediction program of the present invention, and citrullinated peptides based on one or more of the identified antigenic epitopes are chemically synthesized. In some instances, individual RA patient serum can be screened with a pool of synthetic citrullinated peptides derived from each synovial fluid protein to detect the presence of RA-associated autoantibodies. In other instances, all of the high affinity antigenic citrullinated peptides can be pooled and used as the antigen in an assay such as an ELISA to detect autoantibodies in patients with early RA.

In some embodiments, the present invention identifies and provides a profile of the autoantibodies against a particular set of citrullinated synovial fluid proteins in a patient sample, wherein the presence of autoantibodies against one or more of the citrullinated synovial fluid proteins in the set provides information on the stage of RA, thereby enabling the classification of RA patients into different disease stages, i.e., early stage, middle stage, or late stage. RA is a heterogeneous disease affecting a large population world-wide, and the heterogeneity in RA may be correlated with the presence of different autoantibodies against different citrullinated synovial fluid proteins in a patient at a given stage of the disease. As such, classification of RA patients into different stages or subsets in accordance with the present invention enables a clinician to practice "personalized medicine" by treating the heterogeneous population of RA patients with the appropriate medicine or therapy.

Example 5

Calculation of Percent Identity for the Composite Amino Acid Sequence of a Synthetic Peptide In one aspect, the present invention provides a synthetic peptide comprising two or more synthetic fragments of 5 to 50 amino acids, which each have homology to a fragment of 5 to 50 contiguous amino acids of a human protein selected from the group consisting of SEQ ID NOS:1 to 39. In certain embodiments, the composite amino acid sequence of the synthetic fragment will have at least about 80%, 85%, 90%, 95%, or more identity to the composite sequence of the corresponding fragments of the human protein(s).

In order to calculate the percent identity of the composite sequences, any linker residues should be removed from the amino acid sequence of the synthetic peptide to generate the composite amino acid sequence of the synthetic fragments. This sequence would then be compared to the composite sequence of the corresponding human protein fragments. For example, vimentin synthetic peptide (1), shown in FIG. 13, consists of three synthetic fragments corresponding to fragments of the human vimentin protein (SEQ ID NO:1), to which a biotin molecule is attached to the N-terminus through a glycine linker. After removing the glycine linker from the synthetic peptide, the composite sequence of the synthetic fragments is STXSVSSSSYRXRSVSSSSYXSRPSSSX-SYV (SEQ ID NO:51), where X is citrulline. The fragments of the human vimentin corresponding to the synthetic peptide consist of residues 2 to 13 (STRSVSSSSYRR; SEQ ID NO:394), 4 to 12 (RSVSSSSYR; SEQ ID NO:395), and 22 to 31 (SRPSSSRSYV; SEQ ID NO:396) of SEQ ID NO:1. Thus, the composite sequence of the corresponding human protein fragments is STRSVSSSSYRRRSVSSSSYR-SRPSSSRSYV (SEQ ID NO:397). When the composite sequence of the synthetic fragments is compared to the composite sequence of the corresponding human protein fragments, wherein for the purposes of the present invention citrulline is considered to be equivalent or identical to arginine, it is seen that the two sequences are 100% identical.

```
Synthetic Composite Sequence (SEQ ID NO: 51):   STXSVSSSSYRXRSVSSSSYXSRPSSSXSYV
                                                |||||||||||||||||||||||||||||||
Native Composite Sequence (SEQ ID NO: 397):     STRSVSSSSYRRRSVSSSSYRSRPSSSRSYV
```

Likewise, for a variant of vimentin synthetic peptide (1), wherein the valine residues are substituted with alanines (GSTXSASSSSYRXRSASSSSYXSRPSSSXSYA (SEQ ID NO:398), where X is citrulline), the composite amino acid sequence of the synthetic fragments is 90.3% identical to the composite sequence of the corresponding human protein fragments.

```
Variant Synthetic Composite Sequence (SEQ ID NO: 399):  STXSASSSSYRXRSASSSSYXSRPSSSXSYA
                                                        ||||  |||||||||  ||||||||||||||
Native Composite Sequence (SEQ ID NO: 397):             STRSVSSSSYRR TABLE 8-continued Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| VMT9 | Biotin-*Gly*-Phe$^{96}$-Lys-Asn-Thr-Cit-Thr-Asn-Glu-Lys$^{104}$-Asn$^{116}$-Tyr-Ile-Asp-Lys-Val-Cit-Phe-Leu$^{124}$-Cit$^{158}$-Arg-Gln-Val-Asp-Gln-Leu-Thr$^{165}$-NH$_2$ | 56 | Phe$^{96}$-Lys-Asn-Thr-Cit-Thr-Asn-Glu-Lys$^{104}$-Asn$^{116}$-Tyr-Ile-Asp-Lys-Val-Cit-Phe-Leu$^{124}$-Cit$^{158}$-Arg-Gln-Val-Asp-Gln-Leu-Thr$^{165}$ | 57 |
| VMT10 | Biotin-*Gly*-Leu$^{157}$-Arg-Cit-Gln-Val-Asp-Gln-Leu-Thr$^{165}$-Ser$^{205}$-Phe-Cit-Gln-Asp-Val-Asp-Asn-Ala-Ser-Leu-Ala-Cit$^{217}$-Ala$^{216}$-Arg-Leu-Asp-Leu-Glu-Cit-Lys-Val$^{224}$-NH$_2$ | 58 | Leu$^{157}$-Arg-Cit-Gln-Val-Asp-Gln-Leu-Thr$^{165}$-Ser$^{205}$-Phe-Cit-Gln-Asp-Val-Asp-Asn-Ala-Ser-Leu-Ala-Cit$^{217}$-Ala$^{216}$-Arg-Leu-Asp-Leu-Glu-Cit-Lys-Val$^{224}$ | 59 |
| VMT11 | Biotin-*Gly*-Thr$^{266}$-Ala-Ala-Leu-Cit-Asp-Val-Arg-Gln-Tyr$^{276}$-Arg$^{320}$-Cit-Gln-Val-Gln-Ser-Leu-Thr-Ser$^{328}$-NH$_2$ | 60 | Thr$^{266}$-Ala-Ala-Leu-Cit-Asp-Val-Arg-Gln-Tyr$^{276}$-Arg$^{320}$-Cit-Gln-Val-Gln-Ser-Leu-Thr-<u>Ser$^{328}$</u> | 61 |
| VMT12 | Biotin-*Gly*-Ala$^{302}$-Asn-Arg-Asn-Asn-Asp-Ala-Leu-Cit-Gln-Ala-Lys-Gln-Glu-Ser-Thr-Glu-Tyr-Cit-Arg-Gln-Val-Gln-Ser-Leu-Thr$^{327}$-NH$_2$ | 62 | Ala$^{302}$-Asn-Arg-Asn-Asn-Asp-Ala-Leu-Cit-Gln-Ala-Lys-Gln-Glu-Ser-Thr-Glu-Tyr-Cit-Arg-Gln-Val-Gln-Ser-Leu-Thr$^{327}$ | 63 |
| VMT13 | Biotin-*Gly-Arg*-Ala$^{356}$-Asn-Tyr-Gln-Asp-Thr-Ile-Gly-Cit$^{364}$-Leu$^{393}$-Asp-Ile-Glu-Ile-Ala-Thr-Tyr-Cit-Lys-Leu-Leu-Glu-Gly-Glu-Glu-Ser-Cit-Ile-Ser$^{412}$-*Arg*-NH$_2$ | 64 | Ala$^{356}$-Asn-Tyr-Gln-Asp-Thr-Ile-Gly-Cit$^{364}$-Leu$^{393}$-Asp-Ile-Glu-Ile-Ala-Thr-Tyr-Cit-Lys-Leu-Leu-Glu-Gly-Glu-Glu-Ser-Cit-Ile-Ser$^{412}$ | 65 |
| VMT14 | Biotin-*Gly*-Asn$^{417}$-Phe-Ser-Ser-Leu-Asn-Leu-Cit-Glu-Thr-Asn-Leu-Asp-Ser-Leu-Pro-Leu-Val-Asp-Thr-His-Ser-Lys-Cit-Thr-Leu-Leu-Ile-Lys-Thr-Val-Glu-Thr-Cit-Asp-Gly$^{452}$-NH$_2$ | 66 | Asn$^{417}$-Phe-Ser-Ser-Leu-Asn-Leu-Cit-Glu-Thr-Asn-Leu-Asp-Ser-Leu-Pro-Leu-Val-Asp-Thr-His-Ser-Lys-Cit-Thr-Leu-Leu-Ile-Lys-Thr-Val-Glu-Thr-Cit-Asp-Gly$^{452}$ | 67 |
| 2. Alpha Enolase Peptides (The underlined sequence contains a disulfide bond between the two Cys) | | | | |
| H-Enls-1 | Biotin-<u>*Cys*-Lys$^5$-Ile-His-Ala-Cit-Glu-Ile-Phe-Asp-Ser-Cit-Gly-Asn-Pro-Thr-Val-Glu$^{21}$-*Cys*</u>-NH$_2$ | 68 | Lys$^5$-Ile-His-Ala-Cit-Glu-Ile-Phe-Asp-Ser-Cit-Gly-Asn-Pro-Thr-Val-Glu$^{21}$ | 69 |
| H-Enls-2 | Biotin-<u>*Cys*-Lys$^5$-Ile-His-Ala-Arg-Glu-Ile-Phe-Asp-Ser-Cit-Gly-Asn-Pro-Thr-Val-Glu$^{21}$-*Cys*</u>-NH$_2$ | 70 | Lys$^5$-Ile-His-Ala-Arg-Glu-Ile-Phe-Asp-Ser-Cit-Gly-Asn-Pro-Thr-Val-Glu$^{21}$ | 71 |
| H-Enls-3 | Biotin-*Ala*-Lys$^5$-Ile-His-Ala-Arg-Glu-Ile-Phe-Asp-Ser-Cit-Gly-Asn-Pro-Thr-Val-Glu$^{21}$-*Ala*-NH$_2$ | 72 | Lys$^5$-Ile-His-Ala-Arg-Glu-Ile-Phe-Asp-Ser-Cit-Gly-Asn-Pro-Thr-Val-Glu$^{21}$ | 73 |
| H-Enls-4 | Biotin-*Gly*-Phe$^{12}$-Asp-Ser-Cit-Gly-Asn-Pro-Thr-Val-Glu-Val$^{22}$-Gly$^{29}$-Leu-Phe-Cit-Ala-Ala-Val-Pro-Ser-Gly-Ala-Ser$^{40}$-Leu$^{47}$-Glu-Leu-Cit-Asp-Asn-Asp-Lys-Thr-Arg$^{56}$-NH$_2$ | 74 | Phe$^{12}$-Asp-Ser-Cit-Gly-Asn-Pro-Thr-Val-Glu-Val$^{22}$-Gly$^{29}$-Leu-Phe-Cit-Ala-Ala-Val-Pro-Ser-Gly-Ala-Ser$^{40}$-Leu$^{47}$-Glu-Leu-Cit-Asp-Asn-Asp-Lys-Thr-Arg$^{56}$ | 75 |
| H-Enls-5 | Biotin-*Gly*-Leu$^{130}$-Tyr-Cit-His-Ile-Ala-Asp-Leu-Ala-Gly$^{139}$-Ser$^{268}$-Cit-Tyr-Ile-Ser-Pro-Asp-Gln-Leu-Ala-Asp-Leu$^{279}$-Thr$^{321}$-Val-Thr-Asn-Pro-Lys-Cit-Ile-Ala-Lys$^{330}$-NH$_2$ | 76 | Leu$^{130}$-Tyr-Cit-His-Ile-Ala-Asp-Leu-Ala-Gly$^{139}$-Ser$^{268}$-Cit-Tyr-Ile-Ser-Pro-Asp-Gln-Leu-Ala-Asp-Leu$^{279}$-Thr$^{321}$-Val-Thr-Asn-Pro-Lys-Cit-Ile-Ala-Lys$^{330}$ | 77 |
| H-Enls-6 | Biotin-*Gly*-Gly$^{364}$-Trp-Gly-Val-Met-Val-Ser-His-Cit-Ser-Gly-Glu-Thr$^{376}$-Leu$^{411}$-Cit-Ile-Glu-Glu-Glu-Leu-Gly-Ser$^{419}$-Gly$^{425}$-Arg-Asn-Phe-Cit-Asn-Pro-Leu-Ala-Lys$^{434}$-NH$_2$ | 78 | Gly$^{364}$-Trp-Gly-Val-Met-Val-Ser-His-Cit-Ser-Gly-Glu-Thr$^{376}$-Leu$^{411}$-Cit-Ile-Glu-Glu-Glu-Leu-Gly-Ser$^{419}$-Gly$^{425}$-Arg-Asn-Phe-Cit-Asn-Pro-Leu-Ala-Lys$^{434}$ | 79 |
| 3. Fibrin Alpha-Chain Peptides | | | | |
| α32 | Biotin-*Gly-Gly*-Gly$^{36}$-Pro-Arg-Val-Val-Glu-Arg-His-Gln-Ser-Ala$^{46}$-*Gly-Gly-Gly*-Thr$^{619}$-Lys-Arg-Gly-His-Ala-Lys-Ser-Arg-Pro-Val-Arg-Gly-Ile-His-Thr$^{634}$-NH$_2$ | 80 | Gly$^{36}$-Pro-Arg-Val-Val-Glu-Arg-His-Gln-Ser-Ala$^{46}$-Xaa-Thr$^{619}$-Lys-Arg-Gly-His-Ala-Lys-Ser-Arg-Pro-Val-Arg-Gly-Ile-His-Thr$^{634}$ | 81 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Cit-α32 | Biotin-*Gly-Gly*-Gly$^{36}$-Pro-Cit-Val-Val-Glu-Cit-His-Gln-Ser-Ala$^{46}$-*Gly-Gly-Gly*-Thr$^{619}$-Lys-Cit-Gly-His-Ala-Lys-Ser-Cit-Pro-Val-Cit-Gly-Ile-His-Thr$^{634}$-NH$_2$ | 82 | Gly$^{36}$-Pro-Cit-Val-Val-Glu-Cit-His-Gln-Ser-Ala$^{46}$-Xaa-Thr$^{619}$-Lys-Cit-Gly-His-Ala-Lys-Ser-Cit-Pro-Val-Cit-Gly-Ile-His-Thr$^{634}$ | 83 |
| [Arg$^{627}$] Cit-α32 | Biotin-*Gly-Gly*-Gly$^{36}$-Pro-Cit-Val-Val-Glu-Cit-His-Gln-Ser-Ala$^{46}$-*Gly-Gly-Gly*-Thr$^{619}$-Lys-Cit-Gly-His-Ala-Lys-Ser-Arg-Pro-Val-Cit-Gly-Ile-His-Thr$^{634}$-NH$_2$ | 84 | Gly$^{36}$-Pro-Cit-Val-Val-Glu-Cit-His-Gln-Ser-Ala$^{46}$-Xaa-Thr$^{619}$-Lys-Cit-Gly-His-Ala-Lys-Ser-Arg-Pro-Val-Cit-Gly-Ile-His-Thr$^{634}$ | 85 |
| [Cit$^{38,42}$] FB2-α(36-50) | Biotin-Gly$^{36}$-Pro-Cit-Val-Val-Glu-Cit-His-Gln-Ser-Ala-<u>Ser</u>-Lys-Asp-Ser$^{50}$-NH$_2$ | 86 | Gly$^{36}$-Pro-Cit-Val-Val-Glu-Cit-His-Gln-Ser-Ala-<u>Ser</u>-Lys-Asp-Ser$^{50}$ | 87 |
| [Cit$^{621,630}$] FB4-α(617-631) | Biotin-His$^{617}$-Ser-Thr-Lys-Cit-Gly-His-Ala-Lys-Ser-Arg-Pro-Val-Cit-Gly$^{631}$-NH$_2$ | 88 | His$^{617}$-Ser-Thr-Lys-Cit-Gly-His-Ala-Lys-Ser-Arg-Pro-Val-Cit-Gly$^{631}$ | 89 |
| Fib-A1 | Biotin-*Gly*-Arg$^{35}$-Gly-Pro-Arg-Val-Val-Glu-Cit-His$^{43}$-Glu$^{76}$-Val-Asn-Gln-Asp-Phe-Thr-Asn-Cit-Ile-Asn-Lys-Leu-Lys$^{89}$-Ile$^{177}$-Arg-Ser-<u>Ser</u>-Cit-Gly-Ser$^{183}$-NH$_2$ | 90 | Arg$^{35}$-Gly-Pro-Arg-Val-Val-Glu-Cit-His$^{43}$-Glu$^{76}$-Val-Asn-Gln-Asp-Phe-Thr-Asn-Cit-Ile-Asn-Lys-Leu-Lys$^{89}$-Ile$^{177}$-Arg-Ser-<u>Ser</u>-Cit-Gly-Ser$^{183}$ | 91 |
| Fib-A2 | Biotin-*Gly*-Thr$^{107}$-Asn-Ile-Met-Glu-Ile-Leu-Cit-Gly-Asp-Phe-Ser-Ser-Ala-Asn-Asn-Arg-Asp-Asn-Thr-Tyr-Asn-Cit-Val-Ser-Glu-Asp-Leu-Arg-Ser$^{136}$-NH$_2$ | 92 | Thr$^{107}$-Asn-Ile-Met-Glu-Ile-Leu-Cit-Gly-Asp-Phe-Ser-Ser-Ala-Asn-Asn-Arg-Asp-Asn-Thr-Tyr-Asn-Cit-Val-Ser-Glu-Asp-Leu-Arg-Ser$^{136}$ | 93 |
| Fib-A3 | Biotin-*Gly*-Tyr$^{127}$-Asn-Arg-Val-Ser-Glu-Asp-Leu-Cit-Ser-Arg-Gly-Ile-Glu-Val-Leu-Lys-Cit-Lys-Val-Ile-Glu-Lys$^{148}$-Gln$^{153}$-Leu-Leu-Gln-Lys-Asn-Val-Cit-Ala$^{161}$-NH$_2$ | 94 | Tyr$^{127}$-Asn-Arg-Val-Ser-Glu-Asp-Leu-Cit-Ser-Arg-Gly-Ile-Glu-Val-Leu-Lys-Cit-Lys-Val-Ile-Glu-Lys$^{148}$-Gln$^{153}$-Leu-Leu-Gln-Lys-Asn-Val-Cit-Ala$^{161}$ | 95 |
| Fib-A4 | Biotin-*Gly*-Asp$^{174}$-Ile-Lys-Ile-Cit-Ser-<u>Ser</u>-Arg-Gly-Ser-<u>Ser</u>-Ser-Cit-Ala-Leu$^{188}$-Leu$^{213}$-Pro-Ser-Cit-Asp-Arg-Gln-His$^{220}$-Leu$^{212}$-Leu-Pro-Ser-Arg-Asp-Cit-Gln-His$^{220}$-NH$_2$ | 96 | Asp$^{174}$-Ile-Lys-Ile-Cit-Ser-<u>Ser</u>-Arg-Gly-Ser-<u>Ser</u>-Ser-Cit-Ala-Leu$^{188}$-Leu$^{213}$-Pro-Ser-Cit-Asp-Arg-Gln-His$^{220}$-Leu$^{212}$-Leu-Pro-Ser-Arg-Asp-Cit-Gln-His$^{220}$ | 97 |
| Fib-A5 | Biotin-*Gly*-Arg-Phe$^{393}$-Cit-Pro-Asp-Ser-Pro-Gly-Ser-Gly$^{401}$-Thr$^{359}$-Trp-Asn-Pro-Gly-Ser-Ser-Glu-Cit-Gly$^{368}$-Thr$^{440}$-Ser-Gly-Ser-Thr-Thr-Thr-Thr-Cit-Arg-Ser$^{460}$-NH$_2$ | 98 | Phe$^{393}$-Cit-Pro-Asp-Ser-Pro-Gly-Ser-Gly$^{401}$-Thr$^{359}$-Trp-Asn-Pro-Gly-Ser-Ser-Glu-Cit-Gly$^{368}$-Thr$^{440}$-Ser-Gly-Ser-Thr-Thr-Thr-Thr-Cit-Arg-Ser$^{450}$ | 99 |
| Fib-A6 | Biotin-*Gly*-Ser$^{451}$-Gly-Ser-Thr-Thr-Thr-Thr-Arg-Cit-Ser-<u>Ser</u>-Ser-Lys-Thr-Val$^{465}$-Phe$^{509}$-Arg-His-Cit-His-Pro-Asp-Glu-Ala$^{517}$-NH$_2$ | 100 | Ser$^{451}$-Gly-Ser-Thr-Thr-Thr-Thr-Arg-Cit-Ser-<u>Ser</u>-Ser-Lys-Thr-Val$^{465}$-Phe$^{509}$-Arg-His-Cit-His-Pro-Asp-Glu-Ala$^{517}$ | 101 |
| Fib-A7 | Biotin-*Gly*-Arg-Glu$^{539}$-Phe-Val-Ser-Glu-Thr-Glu-Ser-Cit-Gly-Ser$^{549}$-Phe$^{583}$-Thr-Ser-Ser-Thr-Ser-Tyr-Asn-Cit-Gly-Asp-Ser-Thr-Phe-Glu-Ser-Lys$^{599}$-NH$_2$ | 102 | Glu$^{539}$-Phe-Val-Ser-Glu-Thr-Glu-Ser-Cit-Gly-Ser$^{549}$-Phe$^{583}$-Thr-Ser-Ser-Thr-Ser-Tyr-Asn-Cit-Gly-Asp-Ser-Thr-Phe-Glu-Ser-Lys$^{599}$ | 103 |
| Fib-A8 | Biotin-*Gly*-His$^{613}$-Glu-Gly-Thr-His-Ser-Thr-Lys-Cit-Gly-His-Ala-Lys-Ser-Arg-Pro-Val-Cit-Gly-Ile-His-Thr-Ser-Pro-Leu-Gly-Lys$^{639}$-NH$_2$ | 104 | His$^{613}$-Glu-Gly-Thr-His-Ser-Thr-Lys-Cit-Gly-His-Ala-Lys-Ser-Arg-Pro-Val-Cit-Gly-Ile-His-Thr-Ser-Pro-Leu-Gly-Lys$^{639}$ | 105 |
| 4. Fibrin Beta-Chain Peptides ||||||
| β32 | Biotin-*Gly-Gly*-Gly$^{45}$-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Ala-Arg$^{74}$-COOH | 106 | Gly$^{45}$-His-Arg-Pro-Leu-Asp-Lys-Lys-Arg-Glu-Glu-Ala-Pro-Ser-Leu-Arg-Pro-Ala-Pro-Pro-Pro-Ile-Ser-Gly-Gly-Gly-Tyr-Arg-Ala-Arg$^{74}$ | 107 |
| Cit-β32 | Biotin-*Gly-Gly*-Gly$^{45}$-His-Cit-Pro-Leu-Asp-Lys-Lys-Cit-Glu-Glu-Ala-Pro-Ser-Leu-Cit-Pro-Ala-Pro-Pro-Pro-Ile-Ser-Gly-Gly-Gly-Tyr-Cit-Ala-Cit$^{74}$-COOH | 108 | Gly$^{45}$-His-Cit-Pro-Leu-Asp-Lys-Lys-Cit-Glu-Glu-Ala-Pro-Ser-Leu-Cit-Pro-Ala-Pro-Pro-Pro-Ile-Ser-Gly-Gly-Gly-Tyr-Cit-Ala-Cit$^{74}$ | 109 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| [Arg$^{53}$]Cit-β32 | Biotin-*Gly-Gly*-Gly$^{45}$-His-Cit-Pro-Leu-Asp-Lys-Lys-Arg-Glu-Glu-Ala-Pro-Ser-Leu-Cit-Pro-Ala-Pro-Pro-Pro-Ile-Ser-Gly-Gly-Gly-Tyr-Cit-Ala-Cit$^{74}$-COOH | 110 | Gly$^{45}$-His-Cit-Pro-Leu-Asp-Lys-Lys-Arg-Glu-Glu-Ala-Pro-Ser-Leu-Cit-Pro-Ala-Pro-Pro-Pro-Ile-Ser-Gly-Gly-Gly-Tyr-Cit-Ala-Cit$^{74}$ | 111 |
| [Cit$^{60,72,74}$] FB3-β(60-74) | Biotin-Cit$^{60}$-Pro-Ala-Pro-Pro-Pro-Ile-Ser-Gly-Gly-Gly-Tyr-Cit-Ala-Cit$^{74}$-NH$_2$ | 112 | Cit$^{60}$-Pro-Ala-Pro-Pro-Pro-Ile-Ser-Gly-Gly-Gly-Tyr-Cit-Ala-Cit$^{74}$ | 113 |
| [Cit$^{47,60}$] FB5-β(43-62) | Biotin-Ala$^{43}$-Arg-Gly-His-Cit-Pro-Leu-Asp-Lys-Lys-Arg-Glu-Glu-Ala-Pro-Ser-Leu-Cit-Pro-Ala$^{62}$-NH$_2$ | 114 | Ala$^{43}$-Arg-Gly-His-Cit-Pro-Leu-Asp-Lys-Lys-Arg-Glu-Glu-Ala-Pro-Ser-Leu-Cit-Pro-Ala$^{62}$ | 115 |
| Fib-B1 | Biotin-Gly$^{70}$-Tyr-Arg-Ala-Cit-Pro-Ala-Lys-Ala-Ala$^{79}$-Leu$^{150}$-Leu-Lys-Asp-Leu-Trp-Gln-Lys-Cit$^{158}$-Asn$^{188}$-Ser-Asn-Ile-Pro-Thr-Asn-Leu-Cit-Val-Leu-Arg-Ser$^{200}$-NH$_2$ | 116 | Gly$^{70}$-Tyr-Arg-Ala-Cit-Pro-Ala-Lys-Ala-Ala$^{79}$-Leu$^{150}$-Leu-Lys-Asp-Leu-Trp-Gln-Lys-Cit$^{158}$-Asn$^{188}$-Ser-Asn-Ile-Pro-Thr-Asn-Leu-Cit-Val-Leu-Arg-Ser$^{200}$ | 117 |
| Fib-B2 | Biotin-*Gly*-Pro$^{192}$-Thr-Asn-Leu-Arg-Val-Leu-Cit-Ser-Ile-Leu-Glu-Asn$^{204}$-Leu$^{198}$-Arg-Ser-Ile-Leu-Glu-Asn-Leu-Cit-Ser$^{207}$-Met$^{220}$-Glu-Tyr-<u>Ser</u>-Cit-Thr-Pro-Ser-Thr-Val-Ser$^{230}$-NH$_2$ | 118 | Pro$^{192}$-Thr-Asn-Leu-Arg-Val-Leu-Cit-Ser-Ile-Leu-Glu-Asn$^{204}$-Leu$^{198}$-Arg-Ser-Ile-Leu-Glu-Asn-Leu-Cit-Ser$^{207}$-Met$^{220}$-Glu-Tyr-<u>Ser</u>-Cit-Thr-Pro-<u>Ser</u>-Thr-Val-Ser$^{230}$ | 119 |
| Fib-B3 | Biotin-*Gly*-Asp$^{327}$-Lys-Ile-Ser-Gln-Leu-Thr-Cit-Met-Gly$^{336}$-Tyr$^{368}$-Gln-Ile-Ser-Val-Asn-Lys-Tyr-Cit$^{376}$-Trp$^{415}$-Leu-Thr-Ser-Asp-Pro-Cit-Lys-Gln$^{423}$-NH$_2$ | 120 | Asp$^{327}$-Lys-Ile-Ser-Gln-Leu-Thr-Cit-Met-Gly$^{336}$-Tyr$^{368}$-Gln-Ile-Ser-Val-Asn-Lys-Tyr-Cit$^{376}$-Trp$^{415}$-Leu-Thr-Ser-Asp-Pro-Cit-Lys-Gln$^{423}$ | 121 |
| 5. Fibrin Gamma-Chain Peptides ||||||
| Fib-G1 | Biotin-*Gly*-Tyr$^{27}$-Val-Ala-Thr-Cit-Asp-Asn-<u>Ser</u>-<u>Ser</u>-Ile-Leu-Asp-Glu-Cit-Phe-Gly-Ser$^{43}$-*Arg*-Ile$^{126}$-Leu-Thr-His-Asp-Ser-Ser-Ile-Cit-Tyr$^{135}$-*Arg*-NH$_2$ | 122 | Tyr$^{27}$-Val-Ala-Thr-Cit-Asp-Asn-<u>Ser</u>-<u>Ser</u>-Ile-Leu-Asp-Glu-Cit-Phe-Gly-Ser$^{43}$-Xaa-Ile$^{126}$-Leu-Thr-His-Asp-Ser-Ser-Ile-Cit-Tyr$^{135}$ | 123 |
| Fib-G2 | Biotin-*Gly*-Val$^{219}$-Phe-Gln-Lys-Cit-Leu-Asp-Gly-Ser-Val-Asp-Phe$^{230}$-Tyr$^{300}$-Cit-Leu-Thr-Tyr-Ala-Tyr-Phe-Ala$^{308}$-Thr$^{409}$-Met-Lys-Ile-Ile-Pro-Phe-Asn-Cit-Leu-Thr$^{419}$-*Arg*-NH$_2$ | 124 | Val$^{219}$-Phe-Gln-Lys-Cit-Leu-Asp-Gly-Ser-Val-Asp-Phe$^{230}$-Tyr$^{300}$-Cit-Leu-Thr-Tyr-Ala-Tyr-Phe-Ala$^{308}$-Thr$^{409}$-Met-Lys-Ile-Ile-Pro-Phe-Asn-Cit-Leu-Thr$^{419}$ | 125 |
| 6. Fibronectin Peptides ||||||
| Fibronectin-1 | Biotin-*Gly*-<u>Ser</u>$^{215}$-Leu-Gly-Glu-Gly-Ser-Gly-Cit-Ile-Thr-<u>Ser</u>-Thr-Ser-Arg-Asn$^{229}$-Gly$^{221}$-Arg-Ile-Thr-<u>Ser</u>-Thr-Ser-Cit-Asn$^{229}$-*Gly*-NH$_2$ | 126 | <u>Ser</u>$^{215}$-Leu-Gly-Glu-Gly-Ser-Gly-Cit-Ile-Thr-<u>Ser</u>-Thr-Ser-Arg-Asn$^{229}$-Gly$^{221}$-Arg-Ile-Thr-<u>Ser</u>-Thr-Ser-Cit-Asn$^{229}$ | 127 |
| Fibronectin-2 | Biotin-Gly$^{221}$-Arg-Ile-Thr-<u>Ser</u>-Thr-Ser-Arg-Asn-Cit$^{230}$-Asp$^{233}$-Gln-Asp-Thr-Arg-Thr-Ser-Tyr-Cit$^{241}$-<u>Ser</u>$^{231}$-Asn-Asp-Gln-Asp-Thr-Cit-Thr-Ser$^{239}$-*Gly*-NH$_2$ | 128 | Gly$^{221}$-Arg-Ile-Thr-<u>Ser</u>-Thr-Ser-Arg-Asn-Cit$^{230}$-Asp$^{233}$-Gln-Asp-Thr-Arg-Thr-Ser-Tyr-Cit$^{241}$-<u>Ser</u>$^{231}$-Asn-Asp-Gln-Asp-Thr-Cit-Thr-Ser$^{239}$ | 129 |
| Fibronectin-3 | Biotin-*Gly*-Val$^{1013}$-Leu-Val-Cit-Trp-Thr-Pro-Pro-Arg$^{1021}$-Leu$^{1014}$-Val-Arg-Trp-Thr-Pro-Pro-Cit-Ala-Gln$^{1023}$-*Gly*-NH$_2$ | 130 | Val$^{1013}$-Leu-Val-Cit-Trp-Thr-Pro-Pro-Arg$^{1021}$-Leu$^{1014}$-Val-Arg-Trp-Thr-Pro-Pro-Cit-Ala-Gln$^{1023}$ | 131 |
| Fibronectin-4 | Biotin-*Gly*-Tyr$^{1027}$-Arg-Leu-Thr-Val-Gly-Leu-Thr-Cit$^{1035}$-Pro$^{1020}$-Arg-Ala-Gln-Ile-Thr-Gly-Tyr-Cit-Leu-Thr-Val-Gly-Leu-Thr-Arg$^{1035}$-*Gly*-NH$_2$ | 132 | Tyr$^{1027}$-Arg-Leu-Thr-Val-Gly-Leu-Thr-Cit$^{1035}$-Pro$^{1020}$-Arg-Ala-Gln-Ile-Thr-Gly-Tyr-Cit-Leu-Thr-Val-Gly-Leu-Thr-Arg$^{1035}$ | 133 |
| Fibronectin-5 | Biotin-*Arg*-Gly$^{1189}$-Val-Leu-Thr-Val-Ser-Trp-Glu-Cit-Ser-Thr-Thr-Pro-Asp-Ile-Thr-Gly-Tyr-Cit-Ile-Thr-Thr-Thr-Pro-Thr-Asn$^{1214}$-*Arg*-NH$_2$ | 134 | Gly$^{1189}$-Val-Leu-Thr-Val-Ser-Trp-Glu-Cit-Ser-Thr-Thr-Pro-Asp-Ile-Thr-Gly-Tyr-Cit-Ile-Thr-Thr-Thr-Pro-Thr-Asn$^{1214}$ | 135 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Fibronectin-6 | Biotin-Arg-Ile$^{1379}$-Ala-Pro-Cit-Ala-Thr-Ile-Thr-Gly$^{1387}$-Pro$^{1381}$-Arg-Ala-Thr-Ile-Thr-Gly-Tyr-Cit$^{1389}$-Tyr$^{1388}$-Arg-Ile-Cit-His-His-Pro-Glu-His$^{1396}$-Gly-NH$_2$ | 136 | Ile$^{1379}$-Ala-Pro-Cit-Ala-Thr-Ile-Thr-Gly$^{1387}$-Pro$^{1381}$-Arg-Ala-Thr-Ile-Thr-Gly-Tyr-Cit$^{1389}$-Tyr$^{1388}$-Arg-Ile-Cit-His-His-Pro-Glu-His$^{1396}$ | 137 |
| Fibronectin-7 | Biotin-Gly-Pro$^{1401}$-Cit-Glu-Asp-Arg-Val-Pro-His-Ser$^{1409}$-Pro$^{1401}$-Arg-Glu-Asp-Cit-Val-Pro-His-Ser-Cit-Asn-Ser-Ile-Thr-Leu-Thr-Asn$^{1417}$-Gly-NH$_2$ | 138 | Pro$^{1401}$-Cit-Glu-Asp-Arg-Val-Pro-His-Ser$^{1409}$-Pro$^{1401}$-Arg-Glu-Asp-Cit-Val-Pro-His-Ser-Cit-Asn-Ser-Ile-Thr-Leu-Thr-Asn$^{1417}$ | 139 |
| Fibronectin-8 | Biotin-Arg-Thr$^{1517}$-Val-Tyr-Ala-Val-Thr-Gly-Cit-Gly-Asp-Ser-Pro-Ala-Ser-Ser-Lys-Pro-Ile-Ser-Ile-Asn-Tyr-Cit-Thr-Glu-Ile-Asp-Lys-Pro-Ser$^{1546}$-Gly-NH$_2$ | 140 | Thr$^{1517}$-Val-Tyr-Ala-Val-Thr-Gly-Cit-Gly-Asp-Ser-Pro-Ala-Ser-Ser-Lys-Pro-Ile-Ser-Ile-Asn-Tyr-Cit-Thr-Glu-Ile-Asp-Lys-Pro-Ser$^{1546}$ | 141 |
| Fibronectin-9 | Biotin-Arg-Pro$^{1655}$-Gln-Gly-Gln-Val-Ser-Cit-Tyr-Arg-Val-Thr-Tyr-Ser-Ser$^{1668}$-Pro$^{1656}$-Gln-Gly-Gln-Val-Ser-Arg-Tyr-Cit-Val-Thr-Tyr-Ser-Ser$^{1668}$-Gly-NH$_2$ | 142 | Pro$^{1655}$-Gln-Gly-Gln-Val-Ser-Cit-Tyr-Arg-Val-Thr-Tyr-Ser-Ser$^{1668}$-Pro$^{1655}$-Gln-Gly-Gln-Val-Ser-Arg-Tyr-Cit-Val-Thr-Tyr-Ser-Ser$^{1668}$ | 143 |
| Fibronectin-10 | Biotin-Gly-Gly$^{2056}$-Phe-Arg-Cit-Thr-Thr-Pro-Pro-Thr-Thr$^{2065}$-Phe$^{2057}$-Cit-Arg-Thr-Thr-Pro-Pro-Thr-Thr-Ala$^{2066}$-Arg-NH$_2$ | 144 | Gly$^{2056}$-Phe-Arg-Cit-Thr-Thr-Pro-Pro-Thr-Thr$^{2065}$-Phe$^{2057}$-Cit-Arg-Thr-Thr-Pro-Pro-Thr-Thr-Ala$^{2066}$ | 145 |
| Fibronectin-11 | Biotin-Gly-Arg$^{1818}$-Arg-Ala-Cit-Val-Thr-Asp-Ala-Thr-Glu-Thr-Thr-Ile-Thr-Ile-Ser-Trp-Cit-Thr-Lys$^{1837}$-NH$_2$ | 146 | Arg$^{1818}$-Arg-Ala-Cit-Val-Thr-Asp-Ala-Thr-Glu-Thr-Thr-Ile-Thr-Ile-Ser-Trp-Cit-Thr-Lys$^{1837}$ | 147 |
| Fibronectin-12 | Biotin-Arg-Ala$^{1851}$-Asn-Gly-Gln-Thr-Pro-Ile-Gln-Cit-Thr-Ile-Lys-Pro-Asp-Val-Cit-Ser-Tyr-Thr-Ile-Thr-Gly$^{1872}$-Arg-NH$_2$ | 148 | Ala$^{1851}$-Asn-Gly-Gln-Thr-Pro-Ile-Gln-Cit-Thr-Ile-Lys-Pro-Asp-Val-Cit-Ser-Tyr-Thr-Ile-Thr-Gly$^{1872}$ | 149 |
| 7. Lamin B1 Peptides | | | | |
| Lamin-B1-1 | Biotin-Gly-Leu$^{205}$-Glu-Phe-Cit-Lys-Ser-Met-Tyr-Glu-Glu-Glu-Ile-Asn-Glu-Thr-Cit-Arg-Lys-His-Glu-Thr-Arg-Leu-Val-Glu$^{229}$-NH$_2$ | 150 | Leu$^{205}$-Glu-Phe-Cit-Lys-Ser-Met-Tyr-Glu-Glu-Glu-Ile-Asn-Glu-Thr-Cit-Arg-Lys-His-Glu-Thr-Arg-Leu-Val-Glu$^{229}$ | 151 |
| Lamin-B1-2 | Biotin-Gly-Arg$^{220}$-Arg-Lys-His-Glu-Thr-Cit-Leu-Val-Glu-Val-Asp-Ser-Gly-Cit-Gln$^{235}$-Gly-NH$_2$ | 152 | Arg$^{220}$-Arg-Lys-His-Glu-Thr-Cit-Leu-Val-Glu-Val-Asp-Ser-Gly-Cit-Gln$^{235}$ | 153 |
| Lamin-B1-3 | Biotin-Ser$^{395}$-Ser-Cit-Val-Thr-Val-Ser-Arg-Ala-Ser-Ser-Ser-Cit-Ser-Val$^{409}$-Ser$^{406}$-Arg-Ser-Val-Arg-Thr-Thr-Cit-Gly-Lys-Cit-Lys-Arg-Val-Asp-Val-Glu-Glu-Ser-Glu$^{425}$-NH$_2$ | 154 | Ser$^{395}$-Ser-Cit-Val-Thr-Val-Ser-Arg-Ala-Ser-Ser-Ser-Cit-Ser-Val$^{409}$-Ser$^{406}$-Arg-Ser-Val-Arg-Thr-Thr-Cit-Gly-Lys-Cit-Lys-Arg-Val-Asp-Val-Glu-Glu-Ser-Glu$^{425}$ | 155 |
| Lamin-B1-4 | Biotin-Gly-Ser$^{395}$-Ser-Arg-Val-Thr-Val-Ser-Cit-Ala-Ser-Ser-Ser-Arg-Ser-Val-Cit-Thr-Thr-Arg-Gly-Lys$^{415}$-NH$_2$ | 156 | Ser$^{395}$-Ser-Arg-Val-Thr-Val-Ser-Cit-Ala-Ser-Ser-Ser-Arg-Ser-Val-Cit-Thr-Thr-Arg-Gly-Lys$^{415}$ | 157 |
| Lamin-B1-5 | Biotin-Asn$^{533}$-Ser-Gln-Gly-Glu-Glu-Val-Ala-Gln-Cit-Ser-Thr-Val-Phe-Lys-Thr$^{548}$-Phe$^{570}$-His-Gln-Gly-Thr-Pro-Cit-Ala-Ser-Asn-Arg-Ser$^{582}$-Gly-NH$_2$ | 158 | Asn$^{533}$-Ser-Gln-Gly-Glu-Glu-Val-Ala-Gln-Cit-Ser-Thr-Val-Phe-Lys-Thr$^{548}$-Phe$^{570}$-His-Gln-Gly-Thr-Pro-Cit-Ala-Ser-Asn-Arg-Ser$^{582}$ | 159 |
| 8. Lamin B2 Peptides | | | | |
| Lamin-B2-1 | Biotin-Lys-Leu$^{178}$-Glu-Lys-Glu-Thr-Leu-Met-Cit-Val-Asp-Leu-Glu-Asn-Arg-<u>Ser</u>$^{192}$-Met$^{184}$-Arg-Val-Asp-Leu-Glu-Asn-Cit-<u>Ser</u>-Gln$^{193}$-NH$_2$ | 160 | Leu$^{178}$-Glu-Lys-Glu-Thr-Leu-Met-Cit-Val-Asp-Leu-Glu-Asn-Arg-<u>Ser</u>$^{192}$-Met$^{184}$-Arg-Val-Asp-Leu-Glu-Asn-Cit-<u>Ser</u>-Gln$^{193}$ | 161 |
| Lamin-B2-2 | Biotin-Glu$^{218}$-Cit-Arg-Leu-Val-Glu-Val-Asp-Ser-Ser$^{227}$-Arg$^{219}$-Cit-Leu-Val-Glu-Val-Asp-Ser-Ser-Cit-Gln-Gln-Glu$^{231}$-NH$_2$ | 162 | Glu$^{218}$-Cit-Arg-Leu-Val-Glu-Val-Asp-Ser-Ser$^{227}$-Arg$^{219}$-Cit-Leu-Val-Glu-Val-Asp-Ser-Ser-Cit-Gln-Gln-Glu$^{231}$ | 163 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Lamin-B2-3 | Biotin-Lys$^{383}$-Leu-Ser-Pro-Ser-Pro-Ser-Ser-Cit-Val$^{392}$-Ser$^{389}$-Ser-Arg-Val-Thr-Val-Ser-Cit-Ala-Thr-Ser-Ser-Ser-Ser-Gly-Ser$^{404}$-NH$_2$ | 164 | Lys$^{383}$-Leu-Ser-Pro-Ser-Pro-Ser-Ser-Cit-Val$^{392}$-Ser$^{389}$-Ser-Arg-Val-Thr-Val-Ser-Cit-Ala-Thr-Ser-Ser-Ser-Ser-Gly-Ser$^{404}$ | 165 |
| Lamin-B2-4 | Biotin-Glu$^{550}$-Glu-Val-Ala-Met-Cit-Thr-Val-Lys-Lys-Ser-Ser-Val-Met-Cit-Glu-Asn-Glu-Asn-Gly$^{569}$-Phe$^{584}$-His-Gln-Gln-Gly-Asp-Pro-Cit-Thr-Thr-Ser-Arg$^{595}$-NH$_2$ | 166 | Glu$^{550}$-Glu-Val-Ala-Met-Cit-Thr-Val-Lys-Lys-Ser-Ser-Val-Met-Cit-Glu-Asn-Glu-Asn-Gly$^{569}$-Phe$^{584}$-His-Gln-Gln-Gly-Asp-Pro-Cit-Thr-Thr-Ser-Arg$^{595}$ | 167 |
| 9. Lamin A/C Peptides | | | | |
| Lamin-A/C-1 | Biotin-*Gly*-Ser$^5$-Gln-Arg-Cit-Ala-Thr-Arg-Ser-Gly$^{13}$-Cit$^7$-Arg-Ala-Thr-Arg-Ser-Gly-Ala-Gln$^{15}$-Arg$^7$-Arg-Ala-Thr-Cit-Ser-Gly-Ala-Gln-Ala$^{16}$-NH$_2$ | 168 | Ser$^5$-Gln-Arg-Cit-Ala-Thr-Arg-Ser-Gly$^{13}$-Cit$^7$-Arg-Ala-Thr-Arg-Ser-Gly-Ala-Gln$^{15}$-Arg$^7$-Arg-Ala-Thr-Cit-Ser-Gly-Ala-Gln-Ala$^{16}$ | 169 |
| Lamin-A/C-2 | Biotin-*Gly*-Ala$^{43}$-Val-Tyr-Ile-Asp-Cit-Val-Arg-Ser-Leu$^{52}$-Ala$^{43}$-Val-Tyr-Ile-Asp-Arg-Val-Cit-Ser-Leu-Glu-Thr-Glu-Asn-Ala-Gly$^{58}$-NH$_2$ | 170 | Ala$^{43}$-Val-Tyr-Ile-Asp-Cit-Val-Arg-Ser-Leu$^{52}$-Ala$^{43}$-Val-Tyr-Ile-Asp-Arg-Val-Cit-Ser-Leu-Glu-Thr-Glu-Asn-Ala-Gly$^{58}$ | 171 |
| Lamin-A/C-3 | Biotin-Gly$^{58}$-Leu-Arg-Leu-Cit-Ile-Thr-Glu-Ser-Glu-Glu-Val-Val-Ser-Cit-Glu-Val-Ser-Gly-Ile-Lys$^{78}$-NH$_2$ | 172 | Gly$^{58}$-Leu-Arg-Leu-Cit-Ile-Thr-Glu-Ser-Glu-Glu-Val-Val-Ser-Cit-Glu-Val-Ser-Gly-Ile-Lys$^{78}$ | 173 |
| Lamin-A/C-4 | Biotin-Thr$^{218}$-Lys-Cit-Arg-His-Glu-Thr-Arg-Leu-Val-Val$^{227}$-Lys$^{219}$-Arg-Cit-His-Glu-Thr-Arg-Leu-Val$^{227}$-Lys$^{219}$-Arg-Arg-His-Glu-Thr-Cit-Leu-Val-Glu-Ile-Asp-Asn-Gly-Lys-Gln-Cit-Glu$^{236}$-NH$_2$ | 174 | Thr$^{218}$-Lys-Cit-Arg-His-Glu-Thr-Arg-Leu-Val$^{227}$-Lys$^{219}$-Arg-Cit-His-Glu-Thr-Arg-Leu-Val$^{227}$-Lys$^{219}$-Arg-Arg-His-Glu-Thr-Cit-Leu-Val-Glu-Ile-Asp-Asn-Gly-Lys-Gln-Cit-Glu$^{236}$ | 175 |
| Lamin-A/C-5 | Biotin-Gln$^{294}$-Ser-Arg-Ile-Cit-Ile-Asp-Ser-Leu-Ser-Ala-Gln$^{305}$-Cit$^{296}$-Ile-Arg-Ile-Asp-Ser-Leu-Ser-Ala-Gln$^{305}$-Gly-NH$_2$ | 176 | Gln$^{294}$-Ser-Arg-Ile-Cit-Ile-Asp-Ser-Leu-Ser-Ala-Gln$^{305}$-Cit$^{296}$-Ile-Arg-Ile-Asp-Ser-Leu-Ser-Ala-Gln$^{305}$ | 177 |
| Lamin-A/C-6 | Biotin-Glu$^{284}$-Glu-Arg-Leu-Cit-Leu-Ser-Pro-Ser-Pro-Thr-Ser-Gln$^{296}$-Cit$^{399}$-Gly-Arg-Ala-Ser-Ser-His-Ser-Ser$^{407}$-Arg$^{399}$-Gly-Cit-Ala-Ser-Ser-His-Ser-Ser$^{407}$-NH$_2$ | 178 | Glu$^{284}$-Glu-Arg-Leu-Cit-Leu-Ser-Pro-Ser-Pro-Thr-Ser-Gln$^{296}$-Cit$^{399}$-Gly-Arg-Ala-Ser-Ser-His-Ser-Ser$^{407}$-Arg$^{399}$-Gly-Cit-Ala-Ser-Ser-His-Ser-Ser$^{407}$ | 179 |
| Lamin-A/C-7 | Biotin-Gln$^{410}$-Gly-Gly-Gly-Ser-Val-Thr-Lys-Lys-Cit-Lys-Leu-Glu-Ser-Thr-Glu-Ser-Arg-Ser$^{428}$-NH$_2$ | 180 | Gln$^{410}$-Gly-Gly-Gly-Ser-Val-Thr-Lys-Lys-Cit-Lys-Leu-Glu-Ser-Thr-Glu-Ser-Arg-Ser$^{428}$ | 181 |
| Lamin-A/C-8 | Biotin-Lys$^{418}$-Arg-Lys-Leu-Glu-Ser-Thr-Glu-Ser-Cit-Ser-Ser-Phe-Ser-Gln-His-Ala-Cit-Thr-Ser-Gly-Arg-Val-Ala$^{441}$-NH$_2$ | 182 | Lys$^{418}$-Arg-Lys-Leu-Glu-Ser-Thr-Glu-Ser-Cit-Ser-Ser-Phe-Ser-Gln-His-Ala-Cit-Thr-Ser-Gly-Arg-Val-Ala$^{441}$ | 183 |
| Lamin-A/C-9 | Biotin-Glu$^{537}$-Val-Ala-Met-Cit-Lys-Leu-Val-Arg-Ser-Val-Thr-Val$^{549}$-Arg$^{541}$-Lys-Leu-Val-Cit-Ser-Val-Thr-Val-Val-Glu-Asp$^{552}$-NH$_2$ | 184 | Glu$^{537}$-Val-Ala-Met-Cit-Lys-Leu-Val-Arg-Ser-Val-Thr-Val$^{549}$-Arg$^{541}$-Lys-Leu-Val-Cit-Ser-Val-Thr-Val-Val-Glu-Asp$^{552}$ | 185 |
| Lamin-A/C-10 | Biotin-Gly$^{574}$-Asp-Pro-Ala-Glu-Tyr-Asn-Leu-Cit-Ser-Arg-Thr-Val-Leu-Ser$^{588}$-Asn$^{580}$-Leu-Arg-Ser-Cit-Thr-Val-Leu-Ser-Gly-Thr$^{590}$-NH$_2$ | 186 | Gly$^{574}$-Asp-Pro-Ala-Glu-Tyr-Asn-Leu-Cit-Ser-Arg-Thr-Val-Leu-Ser$^{588}$-Asn$^{580}$-Leu-Arg-Ser-Cit-Thr-Val-Leu-Ser-Gly-Thr$^{590}$ | 187 |
| Lamin-A/C-11 | Biotin-Ser$^{619}$-Val-Thr-Val-Thr-Arg-Ser-Tyr-Cit-Ser$^{628}$-Ala$^{617}$-Ser-Ser-Val-Thr-Val-Thr-Cit-Ser-Tyr-Arg-Ser-Val$^{629}$-NH$_2$ | 188 | Ser$^{619}$-Val-Thr-Val-Thr-Arg-Ser-Tyr-Cit-Ser$^{628}$-Ala$^{617}$-Ser-Ser-Val-Thr-Val-Thr-Cit-Ser-Tyr-Arg-Ser-Val$^{629}$ | 189 |
| Lamin-A/C-12 | Biotin-Ser$^{636}$-Phe-Gly-Asp-Asn-Leu-Val-Thr-Cit-Ser-Tyr-Leu-Leu-Gly-Asn-Ser-Ser-Pro-Cit-Thr-Gln-Ser$^{657}$-*Gly*-NH$_2$ | 190 | Ser$^{636}$-Phe-Gly-Asp-Asn-Leu-Val-Thr-Cit-Ser-Tyr-Leu-Leu-Gly-Asn-Ser-Ser-Pro-Cit-Thr-Gln-Ser$^{657}$ | 191 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| 10. β-Actin Peptide | | | | |
| β-Actin-1 | Biotin-Tyr$^{188}$-Leu-Met-Lys-Ile-Leu-Thr-Glu-Cit-Gly-Tyr-Ser-Phe-Thr-Thr-Thr-Ala-Glu-Cit-Glu$^{207}$-NH$_2$ | 192 | Tyr$^{188}$-Leu-Met-Lys-Ile-Leu-Thr-Glu-Cit-Gly-Tyr-Ser-Phe-Thr-Thr-Thr-Ala-Glu-Cit-Glu$^{207}$ | 193 |
| 11. Myeloblastin Peptides | | | | |
| Myelo-blastin-1 | Biotin-His$^{37}$-Ser-Cit-Pro-Tyr-Met-Ala-Ser-Leu-Gln-Met-Cit-Gly-Asn-Pro-Gly-Ser-His$^{54}$-NH$_2$ | 194 | His$^{37}$-Ser-Cit-Pro-Tyr-Met-Ala-Ser-Leu-Gln-Met-Cit-Gly-Asn-Pro-Gly-Ser-His$^{54}$ | 195 |
| Myelo-blastin-2 | Biotin-His$^{71}$-Ser-Leu-Arg-Asp-Ile-Pro-Gln-Cit-Leu-Val-Asn-Val-Val-Leu-Gly-Ala-His-Asn-Val-Cit-Thr-Gln-Glu-Pro-Thr-Gln-Gln-His$^{99}$-Gly-NH$_2$ | 196 | His$^{71}$-Ser-Leu-Arg-Asp-Ile-Pro-Gln-Cit-Leu-Val-Asn-Val-Val-Leu-Gly-Ala-His-Asn-Val-Cit-Thr-Gln-Glu-Pro-Thr-Gln-Gln-His$^{99}$ | 197 |
| Myelo-blastin-3 | Biotin-Ser$^{218}$-Phe-Val-Ile-Trp-Gly-Ser-Ala-Thr-Cit-Leu-Phe-Pro-Asp-Phe-Phe-Thr-Cit-Val-Ala-Leu-Tyr-Val-Asp$^{241}$-NH$_2$ | 198 | Ser$^{218}$-Phe-Val-Ile-Trp-Gly-Ser-Ala-Thr-Cit-Leu-Phe-Pro-Asp-Phe-Phe-Thr-Cit-Val-Ala-Leu-Tyr-Val-Asp$^{241}$ | 199 |
| Myelo-blastin-4 | Biotin-Gly-Asp$^{241}$-Trp-Ile-Cit-Ser-Thr-Leu-Arg-Arg$^{249}$-Asp$^{241}$-Trp-Ile-Arg-Ser-Thr-Leu-Arg-Cit-Val$^{250}$-Trp$^{242}$-Ile-Arg-Ser-Thr-Leu-Cit-Arg-Val-Glu$^{251}$-NH$_2$ | 200 | Asp$^{241}$-Trp-Ile-Cit-Ser-Thr-Leu-Arg-Arg$^{249}$-Asp$^{241}$-Trp-Ile-Arg-Ser-Thr-Leu-Arg-Cit-Val$^{250}$-Trp$^{242}$-Ile-Arg-Ser-Thr-Leu-Cit-Arg-Val-Glu$^{251}$ | 201 |
| 12. PL Scramblase Peptide | | | | |
| PL Scramblase-1 | Biotin-Thr$^{161}$-Leu-Cit-Ile-Ile-Asp-Asn-Met-Gly-Gln-Glu-Val-Ile-Thr-Leu-Glu-Cit-Pro-Leu-Arg-Ser$^{181}$-Ile$^{173}$-Thr-Leu-Glu-Arg-Pro-Leu-Cit-Ser-Ser$^{182}$-NH$_2$ | 202 | Thr$^{161}$-Leu-Cit-Ile-Ile-Asp-Asn-Met-Gly-Gln-Glu-Val-Ile-Thr-Leu-Glu-Cit-Pro-Leu-Arg-Ser$^{181}$-Ile$^{173}$-Thr-Leu-Glu-Arg-Pro-Leu-Cit-Ser-Ser$^{182}$ | 203 |
| 13. Apolipoprotein (a) Peptides | | | | |
| Apolipo(a)-1 | Biotin-Gly-Tyr$^{29}$-His-Gly-Asp-Gly-Gln-Ser-Tyr-Cit-Gly-Thr-Tyr-Ser-Thr-Thr-Val-Thr-Gly-Cit-Thr-Ser-Gln-Ala$^{51}$-Arg-NH$_2$ | 204 | Tyr$^{29}$-His-Gly-Asp-Gly-Gln-Ser-Tyr-Cit-Gly-Thr-Tyr-Ser-Thr-Thr-Val-Thr-Gly-Cit-Thr-Ser-Gln-Ala$^{51}$ | 205 |
| Apolipo(a)-2 | Biotin-Gly-Tyr$^{89}$-Thr-Cit-Asp-Pro-Gly-Val-Arg-Trp$^{97}$-Tyr$^{89}$-Thr-Arg-Asp-Pro-Gly-Val-Cit-Trp$^{97}$-Ser$^{128}$-Glu-Gln-Ala-Pro-Thr-Glu-Gln-Cit$^{136}$-Gly-NH$_2$ | 206 | Tyr$^{89}$-Thr-Cit-Asp-Pro-Gly-Val-Arg-Trp$^{97}$-Tyr$^{89}$-Thr-Arg-Asp-Pro-Gly-Val-Cit-Trp$^{97}$-Ser$^{128}$-Glu-Gln-Ala-Pro-Thr-Glu-Gln-Cit$^{136}$ | 207 |
| Apolipo(a)-3 | Biotin-Tyr$^{3563}$-Tyr-His-Tyr-Gly-Gln-Ser-Tyr-Cit-Gly$^{3572}$-Ser$^{3687}$-Phe-Ser-Thr-Thr-Val-Thr-Gly-Cit-Thr-Ser-Gln-Ser$^{3699}$-Arg-NH$_2$ | 208 | Tyr$^{3563}$-Tyr-His-Tyr-Gly-Gln-Ser-Tyr-Cit-Gly$^{3572}$-Ser$^{3687}$-Phe-Ser-Thr-Thr-Val-Thr-Gly-Cit-Thr-Ser-Gln-Ser$^{3699}$ | 209 |
| Apolipo(a)-4 | Biotin-His$^{3706}$-Trp-His-Gln-Cit-Thr-Thr-Glu-Tyr-Tyr-Pro-Asn-Gly-Gly-Leu-Thr-Cit$^{3722}$-Gly$^{3718}$-Gly-Leu-Thr-Arg-Asn-Tyr-Ser-Cit-Asn$^{3727}$-NH$_2$ | 210 | His$^{3706}$-Trp-His-Gln-Cit-Thr-Thr-Glu-Tyr-Tyr-Pro-Asn-Gly-Gly-Leu-Thr-Cit$^{3722}$-Gly$^{3718}$-Gly-Leu-Thr-Arg-Asn-Tyr-Ser-Cit-Asn$^{3727}$ | 211 |
| Apolipo(a)-5 | Biotin-Gly-Tyr$^{3897}$-Arg-Gly-Asp-Gly-Gln-Ser-Tyr-Cit-Gly-Thr-Leu-Ser-Thr-Thr-Ile-Thr-Gly-Cit-Thr-Ser-Gln-Ser$^{3919}$-Arg-NH$_2$ | 212 | Tyr$^{3897}$-Arg-Gly-Asp-Gly-Gln-Ser-Tyr-Cit-Gly-Thr-Leu-Ser-Thr-Thr-Ile-Thr-Gly-Cit-Thr-Ser-Gln-Ser$^{3919}$ | 213 |
| Apolipo(a)-6 | Biotin-His$^{3926}$-Trp-His-Arg-Cit-Ile-Pro-Leu-Tyr-Tyr-Pro-Asn-Ala-Gly-Leu-Thr-Cit$^{3942}$-Ala$^{3938}$-Gly-Leu-Thr-Arg-Asn-Tyr-Ser-Cit-Asn$^{3947}$-NH$_2$ | 214 | His$^{3926}$-Trp-His-Arg-Cit-Ile-Pro-Leu-Tyr-Tyr-Pro-Asn-Ala-Gly-Leu-Thr-Cit$^{3942}$-Ala$^{3938}$-Gly-Leu-Thr-Arg-Asn-Tyr-Ser-Cit-Asn$^{3947}$ | 215 |
| Apolipo(a)-7 | Biotin-Gly-Tyr$^{4011}$-His-Gly-Asp-Gly-Arg-Ser-Tyr-Cit-Gly-Ile-Ser-Ser-Thr-Thr-Val-Thr-Gly-Cit-Thr-Ser-Gln-Ser$^{4033}$-Arg-NH$_2$ | 216 | Tyr$^{4011}$-His-Gly-Asp-Gly-Arg-Ser-Tyr-Cit-Gly-Ile-Ser-Ser-Thr-Thr-Val-Thr-Gly-Cit-Thr-Ser-Gln-Ser$^{4033}$ | 217 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Apolipo (a)-8 | Biotin-Ser$^{4131}$-Tyr-Cit-Gly-Thr-Phe-Ser-Thr-Thr-Val-Thr-Gly-Cit-Thr-_Ser_-Gln-Ser-Trp-Ser-Ser-Met-Thr-Pro-His-Cit-His$^{4156}$-Arg$^{4155}$-His-Gln-Cit-Thr-Pro-Glu-Asn$^{4162}$-_Gly_-NH$_2$ | 218 | Ser$^{4131}$-Tyr-Cit-Gly-Thr-Phe-Ser-Thr-Thr-Val-Thr-Gly-Cit-Thr-_Ser_-Gln-Ser-Trp-Ser-Ser-Met-Thr-Pro-His-Cit-His$^{4156}$-Arg$^{4155}$-His-Gln-Cit-Thr-Pro-Glu-Asn$^{4162}$ | 219 |
| Apolipo (a)-9 | Biotin-_Gly_-Gly$^{4529}$-Val-Tyr-Ala-Arg-Val-Ser-Cit-Phe-Val-Thr-Trp-Ile$^{4541}$-Val$^{4530}$-Tyr-Ala-Cit-Val-Ser-Arg-Phe-Val-Thr$^{4539}$-NH$_2$ | 220 | Gly$^{4529}$-Val-Tyr-Ala-Arg-Val-Ser-Cit-Phe-Val-Thr-Trp-Ile$^{4541}$-Val$^{4530}$-Tyr-Ala-Cit-Val-Ser-Arg-Phe-Val-Thr$^{4539}$ | 221 |
| 14. BiP Peptides | | | | |
| BiP-1 | Biotin-_Arg_-Tyr$^{175}$-Phe-Asn-Asp-Ala-Gln-Cit-Gln-Ala$^{183}$-Ile$^{190}$-Ala-Gly-Leu-Asn-Val-Met-Cit-Ile-Ile-Asn-Glu-Pro-Thr$^{203}$-_Arg_-NH$_2$ | 222 | Tyr$^{175}$-Phe-Asn-Asp-Ala-Gln-Cit-Gln-Ala$^{183}$-Ile$^{190}$-Ala-Gly-Leu-Asn-Val-Met-Cit-Ile-Ile-Asn-Glu-Pro-Thr$^{203}$ | 223 |
| BiP-2 | Biotin-Asp$^{277}$-Val-Arg-Lys-Asp-Asn-Cit-Ala-Val-Gln-Lys-Leu-Arg-Cit-Glu-Val-Glu-Lys-Ala-Lys-Cit-Ala-Leu-Ser-Ser-Gln-His-Gln$^{304}$-NH$_2$ | 224 | Asp$^{277}$-Val-Arg-Lys-Asp-Asn-Cit-Ala-Val-Gln-Lys-Leu-Arg-Cit-Glu-Val-Glu-Lys-Ala-Lys-Cit-Ala-Leu-Ser-Ser-Gln-His-Gln$^{304}$ | 225 |
| BiP-3 | Biotin-Gly$^{315}$-Glu-Asp-Phe-Ser-Glu-Thr-Leu-Thr-Cit$^{324}$-Asp$^{333}$-Leu-Phe-Cit-Ser-Thr-Met-Lys-Pro$^{341}$-Ile$^{359}$-Val-Leu-Val-Gly-Gly-Ser-Thr-Cit$^{367}$-_Arg_-NH$_2$ | 226 | Gly$^{315}$-Glu-Asp-Phe-Ser-Glu-Thr-Leu-Thr-Cit$^{324}$-Asp$^{333}$-Leu-Phe-Cit-Ser-Thr-Met-Lys-Pro$^{341}$-Ile$^{359}$-Val-Leu-Val-Gly-Gly-Ser-Thr-Cit$^{367}$ | 227 |
| BiP-4 | Biotin-Lys$^{435}$-Leu-Ile-Pro-Cit-Asn-Thr-Val-Val-Pro$^{444}$-Ile$^{524}$-Thr-Ile-Thr-Asn-Asp-Gln-Asn-Cit-Leu-Thr$^{534}$-_Arg_-NH$_2$ | 228 | Lys$^{435}$-Leu-Ile-Pro-Cit-Asn-Thr-Val-Val-Pro$^{444}$-Ile$^{524}$-Thr-Ile-Thr-Asn-Asp-Gln-Asn-Cit-Leu-Thr$^{534}$ | 229 |
| 15. Histone Peptides | | | | |
| Histone H2A-1 | Biotin-_Gly_-Leu$^{64}$-Glu-Leu-Ala-Gly-Asn-Ala-Ala-Cit-Asp-Asn-Lys-Lys-Thr-Arg-Ile-Ile-Pro-Cit-His-Leu-Gln$^{85}$-_Gly_-NH$_2$ | 230 | Leu$^{64}$-Glu-Leu-Ala-Gly-Asn-Ala-Ala-Cit-Asp-Asn-Lys-Lys-Thr-Arg-Ile-Ile-Pro-Cit-His-Leu-Gln$^{85}$ | 231 |
| Histone H2B-1 | Biotin-_Ser_-Lys$^{31}$-Arg-Ser-Cit-Lys-Glu-Ser-Tyr-Ser-Val-Tyr-Val-Tyr-Lys$^{44}$-NH$_2$ | 232 | Lys$^{31}$-Arg-Ser-Cit-Lys-Glu-Ser-Tyr-Ser-Val-Tyr-Val-Tyr-Lys$^{44}$ | 233 |
| Histone H2B-2 | Biotin-Ser$^{65}$-Phe-Val-Asn-Asp-Ile-Phe-Glu-Cit-Ile-Ala-Gly-Glu-Ala-Ser-Cit-Leu-Ala-His-Tyr-Asn-Lys-Arg-Ser-Thr-Ile-Thr-Ser-Cit-Glu$^{94}$-_Gly_-NH$_2$ | 234 | Ser$^{65}$-Phe-Val-Asn-Asp-Ile-Phe-Glu-Cit-Ile-Ala-Gly-Glu-Ala-Ser-Cit-Leu-Ala-His-Tyr-Asn-Lys-Arg-Ser-Thr-Ile-Thr-Ser-Cit-Glu$^{94}$ | 235 |
| Histone H2B-3 | Biotin-Ser$^{79}$-Arg-Leu-Ala-His-Tyr-Asn-Lys-Ser-Cit-Ser-Thr-Ile-Thr-Ser-Arg-Glu-Ile-Gln-Thr-Ala-Val-Cit-Leu$^{101}$-_Gly_-NH$_2$ | 236 | Ser$^{79}$-Arg-Leu-Ala-His-Tyr-Asn-Lys-Cit-Ser-Thr-Ile-Thr-Ser-Arg-Glu-Ile-Gln-Thr-Ala-Val-Cit-Leu$^{101}$ | 237 |
| Histone H3-1 | Biotin-Arg$^{41}$-Tyr-Arg-Pro-Gly-Thr-Val-Ala-Leu-Cit-Glu-Ile-Cit-Arg-Tyr-Gln-Lys-Ser-Thr-Glu-Leu-Leu-Ile-Cit-Lys-Leu-Pro-Phe-Gln-Arg$^{70}$-NH$_2$ | 238 | Arg$^{41}$-Tyr-Arg-Pro-Gly-Thr-Val-Ala-Leu-Cit-Glu-Ile-Cit-Arg-Tyr-Gln-Lys-Ser-Thr-Glu-Leu-Leu-Ile-Cit-Lys-Leu-Pro-Phe-Gln-Arg$^{70}$ | 239 |
| Histone H3-2 | Biotin-Asp$^{78}$-Phe-Lys-Thr-Asp-Leu-Cit-Phe-Gln-Ser-Ser-Ala-Val-Met$^{91}$-Ala$^{128}$-Arg-Arg-Ile-Arg-Gly-Glu-Cit-Ala$^{136}$-_Gly_-NH$_2$ | 240 | Asp$^{78}$-Phe-Lys-Thr-Asp-Leu-Cit-Phe-Gln-Ser-Ser-Ala-Val-Met$^{91}$-Ala$^{128}$-Arg-Arg-Ile-Arg-Gly-Glu-Cit-Ala$^{136}$ | 241 |
| Histone H4-1 | Biotin-Arg$^{20}$-Lys-Val-Leu-Cit-Asp-Asn-Ile-Gln-Gly$^{29}$-Lys$^{92}$-Arg-Gln-Gly-Cit-Thr-Leu-Tyr-Gly$^{100}$-_Gly_-NH$_2$ | 242 | Arg$^{20}$-Lys-Val-Leu-Cit-Asp-Asn-Ile-Gln-Gly$^{29}$-Lys$^{92}$-Arg-Gln-Gly-Cit-Thr-Leu-Tyr-Gly$^{100}$ | 243 |
| Histone H4-2 | Biotin-Gly$^{49}$-Leu-Ile-Tyr-Glu-Glu-Thr-Cit-Gly-Val-Leu-Lys-Val-Phe-Leu-Glu-Asn-Val-Ile-Cit-Asp-Ala-Val-Thr-Tyr-Thr-Glu-His-Ala-Lys-Cit-Lys-Thr-Val-Thr-Ala$^{84}$-_Gly_-NH$_2$ | 244 | Gly$^{49}$-Leu-Ile-Tyr-Glu-Glu-Thr-Cit-Gly-Val-Leu-Lys-Val-Phe-Leu-Glu-Asn-Val-Ile-Cit-Asp-Ala-Val-Thr-Tyr-Thr-Glu-His-Ala-Lys-Cit-Lys-Thr-Val-Thr-Ala$^{84}$ | 245 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| 16. Collagen Peptides | | | | |
| Coll. T2α1-1 | Biotin-*Arg*-Asn$^{1263}$-Asn-Gln-Ile-Glu-Ser-Ile-Cit-Ser$^{1271}$-Ala$^{1371}$-Asn-Val-Gln-Met-Thr-Phe-Leu-Cit-Leu-Leu-Ser-Thr-Glu-Gly-Ser$^{1386}$-*Lys*-NH$_2$ | 246 | Asn$^{1263}$-Asn-Gln-Ile-Glu-Ser-Ile-Cit-Ser$^{1271}$-Ala$^{1371}$-Asn-Val-Gln-Met-Thr-Phe-Leu-Cit-Leu-Leu-Ser-Thr-Glu-Gly-Ser$^{1386}$ | 247 |
| Coll. T2α1-2 | Biotin-Glu$^{1420}$-Ile-Cit-Ala-Glu-Gly-Asn-Ser-Arg-Phe$^{1429}$-Ile$^{1421}$-Arg-Ala-Glu-Gly-Asn-Ser-Cit-Phe-Thr-Tyr-Thr-Ala-Leu-Lys-Asp$^{1436}$-NH$_2$ | 248 | Glu$^{1420}$-Ile-Cit-Ala-Glu-Gly-Asn-Ser-Arg-Phe$^{1429}$-Ile$^{1421}$-Arg-Ala-Glu-Gly-Asn-Ser-Cit-Phe-Thr-Tyr-Thr-Ala-Leu-Lys-Asp$^{1436}$ | 249 |
| Coll. T2α1-3 | Biotin-Lys$^{1444}$-Trp-Gly-Lys-Thr-Val-Ile-Glu-Tyr-Cit-Ser-Gln-Lys-Thr-Ser-Arg-Leu$^{1460}$-Tyr$^{1452}$-Arg-Ser-Gln-Lys-Thr-Ser-Cit-Leu$^{1460}$-*Gly*-NH$_2$ | 250 | Lys$^{1444}$-Trp-Gly-Lys-Thr-Val-Ile-Glu-Tyr-Cit-Ser-Gln-Lys-Thr-Ser-Arg-Leu$^{1460}$-Tyr$^{1452}$-Arg-Ser-Gln-Lys-Thr-Ser-Cit-Leu$^{1460}$ | 251 |
| Coll. T9α1-1 | Biotin-Lys$^{26}$-Arg-Arg-Pro-Cit-Phe-Pro-Val-Asn-Ser-$^{35}$-Phe$^{63}$-Gln-Val-Asp-Lys-Ala-Ala-Ser-Cit$^{71}$-Ala$^{73}$-Ile-Gln-Arg-Val-Val-Gly-Ser$^{80}$-Arg$^{72}$-Ala-Ile-Gln-Cit-Val-Val-Gly-Ser-Ala$^{81}$-NH$_2$ | 252 | Lys$^{26}$-Arg-Arg-Pro-Cit-Phe-Pro-Val-Asn-Ser$^{35}$-Phe$^{63}$-Gln-Val-Asp-Lys-Ala-Ala-Ser-Cit$^{71}$-Ala$^{73}$-Ile-Gln-Arg-Val-Val-Gly-Ser$^{80}$-Arg$^{72}$-Ala-Ile-Gln-Cit-Val-Val-Gly-Ser-Ala$^{81}$ | 253 |
| Coll. T9α1-2 | Biotin-*Gly*-Arg$^{96}$-Ile-Pro-Thr-Cit-Asn-Leu-Tyr-Pro$^{104}$-Tyr$^{111}$-Ser-Phe-Leu-Thr-Thr-Phe-Cit-Met-Thr-Gly-Ser-Thr-Leu-Lys-Lys$^{126}$-NH$_2$ | 254 | Arg$^{96}$-Ile-Pro-Thr-Cit-Asn-Leu-Tyr-Pro$^{104}$-Tyr$^{111}$-Ser-Phe-Leu-Thr-Thr-Phe-Cit-Met-Thr-Gly-Ser-Thr-Leu-Lys-Lys$^{126}$ | 255 |
| Coll. T9α1-3 | Biotin-*Gly*-His$^{181}$-Lys-Ile-Met-Ile-Gly-Val-Glu-Cit-Ser-Ser-Ala-Thr-Leu-Phe-Val-Asp-<u>Ser</u>-Asn-Cit-Ile-Glu-Ser-Leu-Pro-Ile-Lys$^{207}$-NH$_2$ | 256 | His$^{181}$-Lys-Ile-Met-Ile-Gly-Val-Glu-Cit-Ser-Ser-Ala-Thr-Leu-Phe-Val-Asp-<u>Ser</u>-Asn-Cit-Ile-Glu-Ser-Leu-Pro-Ile-Lys$^{207}$ | 257 |
| Coll. T9α1-4 | Biotin-Gln$^{760}$-His-Ile-Lys-Gln-Val-<u>Ser</u>-Met-Cit-Val-Ile-Gln-Glu-His-Phe-Ala-Glu-Met-Ala-Ala-Ser-Leu-Lys-Cit$^{783}$-*Gly*-NH$_2$ | 258 | Gln$^{760}$-His-Ile-Lys-Gln-Val-<u>Ser</u>-Met-Cit-Val-Ile-Gln-Glu-His-Phe-Ala-Glu-Met-Ala-Ala-Ser-Leu-Lys-Cit$^{783}$ | 259 |
| Coll. T10α1-1 | Biotin-Lys$^{527}$-Ala-Gly-Gln-Cit-Pro-Ser-Leu-Ser-Gly-$^{536}$-Asp$^{572}$-Lys-Ile-Leu-Tyr-Asn-Cit-Gln-Gln$^{580}$-Cit$^{585}$-Thr-Gly-Ile-Phe-Thr-<u>Ser</u>-Gln-Ile$^{593}$-*Arg*-NH$_2$ | 260 | Lys$^{527}$-Ala-Gly-Gln-Cit-Pro-Ser-Leu-Ser-Gly$^{536}$-Asp$^{572}$-Lys-Ile-Leu-Tyr-Asn-Cit-Gln-Gln$^{580}$-Cit$^{585}$-Thr-Gly-Ile-Phe-Thr-<u>Ser</u>-Gln-Ile$^{593}$ | 261 |
| Coll. T11α1-1 | Biotin-*Gly*-<u>Ser</u>$^{61}$-Thr-Asn-Cit-Lys-Asn-Ser-Lys-Gly-Ser-Asp-Thr-Ala-Tyr-Cit-Val-Ser-Lys-Gln-Ala-Gln-Leu-Ser$^{83}$-NH$_2$ | 262 | <u>Ser</u>$^{61}$-Thr-Asn-Cit-Lys-Asn-Ser-Lys-Gly-Ser-Asp-Thr-Ala-Tyr-Cit-Val-Ser-Lys-Gln-Ala-Gln-Leu-Ser$^{83}$ | 263 |
| Coll. T11α1-2 | Biotin-Asp$^{150}$-Tyr-Pro-Leu-Phe-Cit-Thr-Val-Asn-Ile-Ala-Asp-Gly-Lys-Trp-His-Cit-Val-Ala-Ile-Ser-Val-Glu-Lys-Lys$^{174}$-*Gly*-NH$_2$ | 264 | Asp$^{150}$-Tyr-Pro-Leu-Phe-Cit-Thr-Val-Asn-Ile-Ala-Asp-Gly-Lys-Trp-His-Cit-Val-Ala-Ile-Ser-Val-Glu-Lys-Lys$^{174}$ | 265 |
| Coll. T11α1-3 | Biotin-Thr$^{187}$-Lys-Pro-Leu-Asp-Cit-Ser-Glu-Arg-Ala$^{196}$-Lys$^{188}$-Pro-Leu-Asp-Arg-Ser-Glu-Cit-Ala$^{196}$-Cit$^{1555}$-Arg-His-Thr-Glu-Gly-Met-Gln-Ala-Asp$^{1564}$-NH$_2$ | 266 | Thr$^{187}$-Lys-Pro-Leu-Asp-Cit-Ser-Glu-Arg-Ala$^{196}$-Lys$^{188}$-Pro-Leu-Asp-Arg-Ser-Glu-Cit-Ala$^{196}$-Cit$^{1555}$-Arg-His-Thr-Glu-Gly-Met-Gln-Ala-Asp$^{1564}$ | 267 |
| Coll. T11α2-1 | Biotin-Gly$^{52}$-Ile-<u>Ser</u>-Pro-Ala-Asp-Val-Ala-Tyr-Cit-Val-Ala-Arg-Pro-Ala-Gln-Leu$^{68}$-Tyr$^{60}$-Arg-Val-Ala-Cit-Pro-Ala-Gln-Leu-Ser-Ala-Pro-Thr-Cit-Gln$^{74}$-*Arg*-NH$_2$ | 268 | Gly$^{52}$-Ile-<u>Ser</u>-Pro-Ala-Asp-Val-Ala-Tyr-Cit-Val-Ala-Arg-Pro-Ala-Gln-Leu$^{68}$-Tyr$^{60}$-Arg-Val-Ala-Cit-Pro-Ala-Gln-Leu-Ser-Ala-Pro-Thr-Cit-Gln$^{74}$ | 269 |
| Coll. T11α2-2 | Biotin-Lys$^{82}$-Asp-Phe-Ser-Leu-Leu-Thr-Val-Val-Cit-Thr$^{92}$-Ser$^{85}$-Leu-Leu-Thr-Val-Val-Arg-Thr-Cit-Pro-Gly-Leu-Gln-Ala$^{98}$-*Gly*-NH$_2$ | 270 | Lys$^{82}$-Asp-Phe-Ser-Leu-Leu-Thr-Val-Val-Cit-Thr$^{92}$-Ser$^{85}$-Leu-Leu-Thr-Val-Val-Arg-Thr-Cit-Pro-Gly-Leu-Gln-Ala$^{98}$ | 271 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Coll. T11α2-3 | Biotin-Asn$^{238}$-Gln-Gln-Pro-His-Arg-Ala-Gln-Cit-Ser-Pro-Gln-Gln-Gln-Pro-Ser-Arg-Leu-His-Cit-Pro-Gln-Asn-Gln-Glu$^{262}$-NH$_2$ | 272 | Asn$^{238}$-Gln-Gln-Pro-His-Arg-Ala-Gln-Cit-Ser-Pro-Gln-Gln-Gln-Pro-Ser-Arg-Leu-His-Cit-Pro-Gln-Asn-Gln-Glu$^{262}$ | 273 |
| Coll. T11α2-4 | Biotin-*Gly*-His$^{242}$-Cit-Ala-Gln-Arg-Ser-Pro-Gln-Gln-Gln-Pro-Ser-Cit-Leu-His-Arg-Pro-Gln-Asn-Gln-Glu$^{262}$-NH$_2$ | 274 | His$^{242}$-Cit-Ala-Gln-Arg-Ser-Pro-Gln-Gln-Gln-Pro-Ser-Cit-Leu-His-Arg-Pro-Gln-Asn-Gln-Glu$^{262}$ | 275 |

17. Syndecan Peptides

| Name | Biotinylated Sequence | SEQ ID NO: | Core Sequence | SEQ ID NO: |
|---|---|---|---|---|
| Syndecan-I-1 | Biotin-*Gly*-Pro$^{123}$-Arg-Pro-Cit-Glu-Thr-Thr-Gln-Leu$^{131}$-*Gly*$^{183}$-Gly-Pro-Ser-Ala-Thr-Glu-Cit-Ala$^{191}$-*Gly*-NH$_2$ | 276 | Pro$^{123}$-Arg-Pro-Cit-Glu-Thr-Thr-Gln-Leu$^{131}$-*Gly*$^{183}$-Gly-Pro-Ser-Ala-Thr-Glu-Cit-Ala$^{191}$ | 277 |
| Syndecan-I-2 | Biotin-*Gly*-Val$^{225}$-Glu-Pro-Asp-Arg-Cit-Asn-Gln-Ser-Pro-Val-Asp-Gln-Gly$^{238}$-Cit$^{229}$-Arg-Asn-Gln-Ser-Pro-Val-Asp-Gln-Gly$^{238}$-NH$_2$ | 278 | Val$^{225}$-Glu-Pro-Asp-Arg-Cit-Asn-Gln-Ser-Pro-Val-Asp-Gln-Gly$^{238}$-Cit$^{229}$-Arg-Asn-Gln-Ser-Pro-Val-Asp-Gln-Gly$^{238}$ | 279 |
| Syndecan-III-1 | Biotin-*Arg*-Ser$^{91}$-Gly-Ile-Glu-Thr-Ala-Met-Cit-Phe$^{99}$-Glu$^{147}$-Val-Pro-Glu-Glu-Pro-Ser-Gln-Cit-Ala-Thr-Thr-Val-Ser-Thr$^{161}$-Ala$^{222}$-Cit-Ala$^{224}$-*Arg*-NH$_2$ | 280 | Ser$^{91}$-Gly-Ile-Glu-Thr-Ala-Met-Cit-Phe$^{99}$-Glu$^{147}$-Val-Pro-Glu-Glu-Pro-Ser-Gln-Cit-Ala-Thr-Thr-Val-Ser-Thr$^{161}$-Ala$^{222}$-Cit-Ala$^{224}$ | 281 |
| Syndecan-III-2 | Biotin-*Arg*-Phe$^{196}$-Thr-Ala-Thr-Thr-Ala-Val-Ile-Cit-Thr-Thr-Gly-Val-Arg$^{209}$-Ala$^{201}$-Val-Ile-Arg-Thr-Thr-Gly-Val-Cit-Arg-Leu$^{211}$-Val$^{202}$-Ile-Arg-Thr-Thr-Gly-Val-Arg-Cit-Leu$^{211}$-*Gly*-NH$_2$ | 282 | Phe$^{196}$-Thr-Ala-Thr-Thr-Ala-Val-Ile-Cit-Thr-Thr-Gly-Val-Arg$^{209}$-Ala$^{201}$-Val-Ile-Arg-Thr-Thr-Gly-Val-Cit-Arg-Leu$^{211}$-Val$^{202}$-Ile-Arg-Thr-Thr-Gly-Val-Arg-Cit-Leu$^{211}$ | 283 |
| Syndecan-III-3 | Biotin-*Arg*-Pro$^{246}$-Cit-Leu-Val-Ser-Thr-Ala-Thr-Ser-Cit-Pro-Arg-Ala-Leu-Pro-Cit-Pro-Ala-Thr-Thr-Gln-Glu-Pro-Asp-Ile-Pro-Glu-Cit-Ser$^{274}$-*Gly*-NH$_2$ | 284 | Pro$^{246}$-Cit-Leu-Val-Ser-Thr-Ala-Thr-Ser-Cit-Pro-Arg-Ala-Leu-Pro-Cit-Pro-Ala-Thr-Thr-Gln-Glu-Pro-Asp-Ile-Pro-Glu-Cit-Ser$^{274}$ | 285 |

18. CD44 Peptides

| Name | Biotinylated Sequence | SEQ ID NO: | Core Sequence | SEQ ID NO: |
|---|---|---|---|---|
| CD44-1 | Biotin-*Arg*-Ile$^{22}$-Asp-Leu-Asn-Ile-Thr-<u>Ser</u>-Cit-Phe-Ala-Gly-Val-Phe-His-Val-Glu-Lys-Asn-Gly-Cit-Tyr$^{42}$-*Gly*$^{40}$-Arg-Tyr-Ser-Ile-Ser-Cit-Thr-Glu-Ala-Ala$^{50}$-*Gly*-NH$_2$ | 286 | Ile$^{22}$-Asp-Leu-Asn-Ile-Thr-<u>Ser</u>-Cit-Phe-Ala-Gly-Val-Phe-His-Val-Glu-Lys-Asn-Gly-Cit-Tyr$^{42}$-*Gly*$^{40}$-Arg-Tyr-Ser-Ile-Ser-Cit-Thr-Glu-Ala-Ala$^{50}$ | 287 |
| CD44-2 | Biotin-*Arg*-Ile$^{72}$-Gly-Phe-Glu-Thr-<u>Ser</u>-Cit-Tyr-Gly-Phe-Ile-Glu-Gly-His-Val-Val-Ile-Pro-Cit-Ile-His-Pro-Asn-Ser-Ile-<u>Ser</u>$^{97}$-*Arg*-NH$_2$ | 288 | Ile$^{72}$-Gly-Phe-Glu-Thr-<u>Ser</u>-Cit-Tyr-Gly-Phe-Ile-Glu-Gly-His-Val-Val-Ile-Pro-Cit-Ile-His-Pro-Asn-Ser-Ile-<u>Ser</u>$^{97}$ | 289 |
| CD44-3 | Biotin-*Arg*-Pro$^{142}$-Ile-Thr-Ile-Thr-Ile-Val-Asn-Cit-Asp-Gly-Thr-Arg-Tyr-Val$^{156}$-Asn$^{149}$-Arg-Asp-Gly-Thr-Cit-Tyr-Val$^{156}$-*Gly*-NH$_2$ | 290 | Pro$^{142}$-Ile-Thr-Ile-Thr-Ile-Val-Asn-Cit-Asp-Gly-Thr-Arg-Tyr-Val$^{156}$-Asn$^{149}$-Arg-Asp-Gly-Thr-Cit-Tyr-Val$^{156}$ | 291 |
| CD44-4 | Biotin-*Gly*-Ser$^{179}$-Ser-Gly-Ser-Ser-Ser-Glu-Cit-Ser$^{187}$-Trp$^{211}$-Ile-Thr-Asp-Ser-Thr-Asp-Cit-Ile-Pro-Ala-Thr-Thr-Leu-Met-Ser$^{226}$-*Gly*-NH$_2$ | 292 | Ser$^{179}$-Ser-Gly-Ser-Ser-Ser-Glu-Cit-Ser$^{187}$-Trp$^{211}$-Ile-Thr-Asp-Ser-Thr-Asp-Cit-Ile-Pro-Ala-Thr-Thr-Leu-Met-Ser$^{226}$ | 293 |
| CD44-5 | Biotin-*Arg*-Ser$^{306}$-Thr-Ile-Ser-Thr-Thr-Pro-Cit-Ala$^{314}$-Glu$^{335}$-Val-Leu-Leu-Gln-Thr-Thr-Thr-Cit-Met-Thr$^{345}$-Arg$^{343}$-Met-Thr-Asp-Val-Asp-Cit-Asn$^{350}$-*Gly*-NH$_2$ | 294 | Ser$^{306}$-Thr-Ile-Ser-Thr-Thr-Pro-Cit-Ala$^{314}$-Glu$^{335}$-Val-Leu-Leu-Gln-Thr-Thr-Thr-Cit-Met-Thr$^{345}$-Arg$^{343}$-Met-Thr-Asp-Val-Asp-Cit-Asn$^{350}$ | 295 |
| CD44-6 | Biotin-Gly$^{411}$-Tyr-Arg-Gln-Thr-Pro-Cit-Glu-Asp-Ser-$^{420}$-Met$^{437}$-Gln-Gly-Cit-Thr-Thr-Pro-Ser-Pro$^{445}$-Cit$^{469}$-Arg-Met-Asp-Met-Asp-Ser-Ser-His$^{477}$-Arg$^{469}$-Cit-Met-Asp-Met-Asp-Ser-Ser-His$^{477}$-*Gly*-NH$_2$ | 296 | Gly$^{411}$-Tyr-Arg-Gln-Thr-Pro-Cit-Glu-Asp-Ser-$^{420}$-Met$^{437}$-Gln-Gly-Cit-Thr-Thr-Pro-Ser-Pro$^{445}$-Cit$^{469}$-Arg-Met-Asp-Met-Asp-Ser-Ser-His$^{477}$-Arg$^{469}$-Cit-Met-Asp-Met-Asp-Ser-Ser-His$^{477}$ | 297 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| CD44-7 | Biotin-*Gly*-Ser$^{530}$-Thr-Leu-Thr-Ser-Ser-Asn-Cit-Asn$^{538}$-Arg$^{537}$-Asn-Asp-Val-Thr-Gly-Gly-Cit$^{544}$-Gly$^{543}$-Arg-Cit-Asp-Pro-Asn-His-Ser-Glu$^{551}$-*Gly*-NH$_2$ | 298 | Ser$^{530}$-Thr-Leu-Thr-Ser-Ser-Asn-Cit-Asn$^{538}$-Arg$^{537}$-Asn-Asp-Val-Thr-Gly-Gly-Cit$^{544}$-Gly$^{543}$-Arg-Cit-Asp-Pro-Asn-His-Ser-Glu$^{551}$ | 299 |
| CD44-8 | Biotin-*Arg*-Asp$^{593}$-Ser-Asn-Ser-Asn-Val-Asn-Cit-Ser-Leu-Ser-Gly$^{604}$-Pro$^{641}$-Ile-Cit-Thr-Pro-Gln-Ile$^{647}$-*Arg*-NH$_2$ | 300 | Asp$^{593}$-Ser-Asn-Ser-Asn-Val-Asn-Cit-Ser-Leu-Ser-Gly$^{604}$-Pro$^{641}$-Ile-Cit-Thr-Pro-Gln-Ile$^{647}$ | 301 |
| 19. ICAM-I Peptides | | | | |
| ICAM-I-1 | Biotin-*Arg*-Gly$^{140}$-Ala-Pro-Cit-Ala-Asn-Leu-Thr-Val-Val-Leu-Leu-Cit$^{152}$-Leu$^{151}$-Arg-Gly-Glu-Lys-Glu-Leu-Lys-Cit$^{159}$-*Gly*-NH$_2$ | 302 | Gly$^{140}$-Ala-Pro-Cit-Ala-Asn-Leu-Thr-Val-Val-Leu-Leu-Cit$^{152}$-Leu$^{151}$-Arg-Gly-Glu-Lys-Glu-Leu-Lys-Cit$^{159}$ | 303 |
| ICAM-I-2 | Biotin-*Gly*-Glu$^{168}$-Val-Thr-Thr-Thr-Val-Leu-Val-Cit-Arg-Asp-His$^{179}$-Gly$^{181}$-Ala-Asn-Phe-Ser-<u>Ser</u>-Cit-Thr$^{188}$-<u>Ser</u>$^{186}$-Arg-Thr-Glu-Leu-Asp-Leu-Cit-Pro$^{194}$-*Gly*-NH$_2$ | 304 | Glu$^{168}$-Val-Thr-Thr-Thr-Val-Leu-Val-Cit-Arg-Asp-His$^{179}$-Gly$^{181}$-Ala-Asn-Phe-Ser-<u>Ser</u>-Cit-Thr$^{188}$-<u>Ser</u>$^{186}$-Arg-Thr-Glu-Leu-Asp-Leu-Cit-Pro$^{194}$ | 305 |
| ICAM-I-3 | Biotin-*Gly*-Leu$^{456}$-<u>Ser</u>-Arg-Ala-Cit-Ser-Thr-Gln-Gly-Glu-Val-Thr-Cit-Lys-Val-Thr-Val-Asn-Val-Leu-Ser-Pro-Cit-Tyr-Glu$^{480}$-*Gly*-NH$_2$ | 306 | Leu$^{456}$-<u>Ser</u>-Arg-Ala-Cit-Ser-Thr-Gln-Gly-Glu-Val-Thr-Cit-Lys-Val-Thr-Val-Asn-Val-Leu-Ser-Pro-Cit-Tyr-Glu$^{480}$ | 307 |
| 20. VCAM-I Peptide | | | | |
| VCAM-I-1 | Biotin-*Gly*-Pro$^{496}$-Lys-Gln-Cit-Gln-Ser-Thr-Gln-Thr-Leu-Tyr-Val-Asn-Val-Ala-Pro-Cit-Asp-Thr-Thr-Val-Leu-Val-Ser-Pro$^{520}$-*Arg*-NH$_2$ | 308 | Pro$^{496}$-Lys-Gln-Cit-Gln-Ser-Thr-Gln-Thr-Leu-Tyr-Val-Asn-Val-Ala-Pro-Cit-Asp-Thr-Thr-Val-Leu-Val-Ser-Pro$^{520}$ | 309 |
| 21. Glypican Peptides | | | | |
| Glypican-I-1 | Biotin-*Gly*-Thr$^{87}$-Ala-Leu-Cit-Asp-Ser-Ser-Arg-Val$^{95}$-Ala$^{88}$-Leu-Arg-Asp-Ser-Ser-Cit-Val-Leu-Gln-Ala-Met-Leu-Ala-Thr-Gln-Leu-Cit-Ser$^{106}$-*Arg*-NH$_2$ | 310 | Thr$^{87}$-Ala-Leu-Cit-Asp-Ser-Ser-Arg-Val$^{95}$-Ala$^{88}$-Leu-Arg-Asp-Ser-Ser-Cit-Val-Leu-Gln-Ala-Met-Leu-Ala-Thr-Gln-Leu-Cit-Ser$^{106}$ | 311 |
| Glypican-I-2 | Biotin-Gly$^{131}$-Glu-Leu-Tyr-Thr-Gln-Asn-Ala-Cit-Ala$^{140}$-Arg$^{139}$-Ala-Phe-Cit-Asp-Leu-Tyr-Ser$^{146}$-Phe$^{141}$-Arg-Asp-Leu-Tyr-Ser-Glu-Leu-Cit-Leu-Tyr-Tyr-Cit-Gly-Ala-Asn-Leu-His$^{158}$-*Gly*-NH$_2$ | 312 | Gly$^{131}$-Glu-Leu-Tyr-Thr-Gln-Asn-Ala-Cit-Ala$^{140}$-Arg$^{139}$-Ala-Phe-Cit-Asp-Leu-Tyr-Ser$^{146}$-Phe$^{141}$-Arg-Asp-Leu-Tyr-Ser-Glu-Leu-Cit-Leu-Tyr-Tyr-Cit-Gly-Ala-Asn-Leu-His$^{158}$ | 313 |
| Glypican-I-3 | Biotin-*Gly*-Leu$^{211}$-Arg-Ala-Thr-Cit-Ala-Phe-Val-Ala$^{219}$-Leu$^{209}$-Arg-Leu-Ala-Thr-Arg-Ala-Phe-Val-Ala-Ala-Cit-Ser-Phe-Val-Gln$^{225}$-*Gly*-NH$_2$ | 314 | Leu$^{211}$-Arg-Ala-Thr-Cit-Ala-Phe-Val-Ala$^{219}$-Leu$^{209}$-Arg-Leu-Cit-Ala-Thr-Arg-Ala-Phe-Val-Ala-Ala-Cit-Ser-Phe-Val-Gln$^{225}$ | 315 |
| Glypican-I-4 | Biotin-*Arg*-Leu$^{227}$-Gly-Val-Ala-Ser-Asp-Val-Val-Cit-Lys-Val-Ala-Gln-Val-Pro-Leu-Gly-Pro-Glu-<u>Ser</u>-Ser-Cit-Ala-Val$^{250}$-*Arg*-NH$_2$ | 316 | Leu$^{227}$-Gly-Val-Ala-Ser-Asp-Val-Val-Cit-Lys-Val-Ala-Gln-Val-Pro-Leu-Gly-Pro-Glu-<u>Ser</u>-Ser-Cit-Ala-Val$^{250}$ | 317 |
| Glypican-I-5 | Biotin-*Gly*-Gln$^{459}$-Leu-Lys-Ile-Met-Thr-Asn-Cit-Leu-Arg-Ser$^{469}$-Leu$^{460}$-Lys-Ile-Met-Thr-Asn-Arg-Leu-Cit-Ser-Ala-Tyr-Asn-Gly$^{473}$-*Arg*-NH$_2$ | 318 | Gln$^{459}$-Leu-Lys-Ile-Met-Thr-Asn-Cit-Leu-Arg-Ser$^{469}$-Leu$^{460}$-Lys-Ile-Met-Thr-Asn-Arg-Leu-Cit-Ser-Ala-Tyr-Asn-Gly$^{473}$ | 319 |
| Glypican-I-6 | Biotin-*Gly*-Ser$^{499}$-Gly-Arg-Lys-Val-Ser-Cit-Lys-Ser-Ser-Ser-Ser-Arg-Thr$^{512}$-Ser$^{504}$-Arg-Lys-Ser-Ser-Ser-Ser-Ser-Cit-Thr$^{512}$-*Gly*-NH$_2$ | 320 | Ser$^{499}$-Gly-Arg-Lys-Val-Ser-Cit-Lys-Ser-Ser-Ser-Ser-Arg-Thr$^{512}$-Ser$^{504}$-Arg-Lys-Ser-Ser-Ser-Ser-Ser-Cit-Thr$^{512}$ | 321 |
| Glypican-II-1 | Biotin-*Gly*-Ser$^{68}$-<u>Ser</u>-Ser-Ser-Glu-Thr-Glu-Gln-Cit$^{76}$-Arg$^{76}$-Leu-Ile-Cit-Glu-Thr-Glu-Ala-Thr-Phe-Cit-Gly$^{87}$-*Arg*-NH$_2$ | 322 | Ser$^{68}$-<u>Ser</u>-Ser-Ser-Glu-Thr-Glu-Gln-Cit$^{76}$-Arg$^{76}$-Leu-Ile-<u>Cit</u>-Glu-Thr-Glu-Ala-Thr-Phe-<u>Cit</u>-Gly$^{87}$ | 323 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Glypican-II-2 | Biotin-Arg$^{212}$-Leu-Cit-Leu-Gln-Ile-Thr-Arg-Thr-Leu-Val-Ala-Ala-Cit-Ala-Phe-Val-Gln$^{229}$-Leu$^{213}$-Arg-Leu-Gln-Ile-Thr-Cit-Thr-Leu-Val-Ala$^{223}$-Arg-NH$_2$ | 324 | Arg$^{212}$-Leu-Cit-Leu-Gln-Ile-Thr-Arg-Thr-Leu-Val-Ala-Ala-Cit-Ala-Phe-Val-Gln$^{229}$-Leu$^{213}$-Arg-Leu-Gln-Ile-Thr-Cit-Thr-Leu-Val-Ala$^{223}$ | 325 |
| Glypican-II-3 | Biotin-Arg-Gln$^{273}$-Gly-Phe-Ser-Leu-Asn-Val-Val-Cit-Gly-Ser-Leu-Ser-Ser-Arg-Gly$^{288}$-Ser$^{283}$-Leu-Ser-Ser-Cit-Gly$^{288}$-Gly-NH$_2$ | 326 | Gln$^{273}$-Gly-Phe-Ser-Leu-Asn-Val-Val-Cit-Gly-Ser-Leu-Ser-Ser-Arg-Gly$^{288}$-Ser$^{283}$-Leu-Ser-Ser-Cit-Gly$^{288}$ | 327 |
| Glypican-II-4 | Biotin-Gly-Pro$^{351}$-Val-Pro-Ala-Cit-Asn-Arg-Arg-Ala$^{359}$-Pro$^{351}$-Val-Pro-Ala-Arg-Asn-Cit-Arg-Ala$^{359}$-Pro$^{351}$-Val-Pro-Ala-Arg-Asn-Arg-Cit-Ala$^{359}$-Gly-NH$_2$ | 328 | Pro$^{351}$-Val-Pro-Ala-Cit-Asn-Arg-Arg-Ala$^{359}$-Pro$^{351}$-Val-Pro-Ala-Arg-Asn-Cit-Arg-Ala$^{359}$-Pro$^{351}$-Val-Pro-Ala-Arg-Asn-Arg-Cit-Ala$^{359}$ | 329 |
| Glypican-II-5 | Biotin-Arg-Ser$^{461}$-Gly-Pro-Asp-Val-Pro-Thr-Arg-Cit-Arg$^{470}$-Arg$^{470}$-Cit-Leu-Gln-Leu-Arg-Ala-Ala-Thr-Ala-Cit-Met-Lys$^{482}$-NH$_2$ | 330 | Ser$^{461}$-Gly-Pro-Asp-Val-Pro-Thr-Arg-Cit-Arg$^{470}$-Arg$^{470}$-Cit-Leu-Gln-Leu-Arg-Ala-Ala-Thr-Ala-Cit-Met-Lys$^{482}$ | 331 |
| Glypican-IV-1 | Biotin-Arg-Met$^{160}$-Leu-Asn-Asp-Phe-Trp-Ala-Cit-Leu-Leu-Glu-Arg-Met-Phe-Cit-Leu-Val-Asn-Ser-Gln-Tyr-His$^{181}$-Gly-NH$_2$ | 332 | Met$^{160}$-Leu-Asn-Asp-Phe-Trp-Ala-Cit-Leu-Leu-Glu-Arg-Met-Phe-Cit-Leu-Val-Asn-Ser-Gln-Tyr-His$^{181}$ | 333 |
| Glypican-IV-2 | Biotin-Gly-Leu$^{207}$-Lys-Leu-Gln-Val-Thr-Cit-Ala-Phe-Val$^{216}$-Thr$^{212}$-Arg-Ala-Phe-Val-Ala-Ala-Cit-Thr-Phe-Ala-Gln$^{223}$-Arg-NH$_2$ | 334 | Leu$^{207}$-Lys-Leu-Gln-Val-Thr-Cit-Ala-Phe-Val$^{216}$-Thr$^{212}$-Arg-Ala-Phe-Val-Ala-Ala-Cit-Thr-Phe-Ala-Gln$^{223}$ | 335 |
| Glypican-IV-3 | Biotin-Gly-Gly$^{350}$-Cit-Ile-Ser-Arg-Ser-Ile-Ser-Glu$^{358}$-Gly$^{350}$-Arg-Ile-Ser-Cit-Ser-Ile-Ser-Glu-Ser-Ala-Phe-Ser$^{362}$-Arg-NH$_2$ | 336 | Gly$^{350}$-Cit-Ile-Ser-Arg-Ser-Ile-Ser-Glu$^{358}$-Gly$^{350}$-Arg-Ile-Ser-Cit-Ser-Ile-Ser-Glu-Ser-Ala-Phe-Ser$^{362}$ | 337 |
| Glypican-IV-4 | Biotin-Arg-Leu$^{462}$-Cit-Gln-Ile-Met-Ala-Leu-Arg-Val$^{470}$-Ile$^{465}$-Met-Ala-Leu-Cit-Val-Met-Thr-Ser-Lys-Met-Lys$^{476}$-Gly-NH$_2$ | 338 | Leu$^{462}$-Cit-Gln-Ile-Met-Ala-Leu-Arg-Val$^{470}$-Ile$^{465}$-Met-Ala-Leu-Cit-Val-Met-Thr-Ser-Lys-Met-Lys$^{476}$ | 339 |
| Glypican-V-1 | Biotin-Gly-Thr$^{70}$-Arg-Lys-Met-Glu-Glu-Cit-Tyr-Gln-Ile-Ala-Ala-Arg-Gln$^{83}$-Glu$^{75}$-Arg-Tyr-Gln-Ile-Ala-Ala-Cit-Gln-Asp-Met-Gln-Gln$^{87}$-Arg-NH$_2$ | 340 | Thr$^{70}$-Arg-Lys-Met-Glu-Glu-Cit-Tyr-Gln-Ile-Ala-Ala-Arg-Gln$^{83}$-Glu$^{75}$-Arg-Tyr-Gln-Ile-Ala-Ala-Cit-Gln-Asp-Met-Gln-Gln$^{87}$ | 341 |
| Glypican-V-2 | Biotin-Gly-Ile$^{194}$-Arg-Met-Ala-Arg-Cit-Asp-Val-Ser-Pro-Phe-Gly$^{205}$-Ala$^{197}$-Cit-Arg-Asp-Val-Ser-Pro-Phe-Gly-Asn-Ile-Pro-Gln-Cit-Val-Met-Gly-Gln$^{214}$-Arg-NH$_2$ | 342 | Ile$^{194}$-Arg-Met-Ala-Arg-Cit-Asp-Val-Ser-Pro-Phe-Gly$^{205}$-Ala$^{197}$-Cit-Arg-Asp-Val-Ser-Pro-Phe-Gly-Asn-Ile-Pro-Gln-Cit-Val-Met-Gly-Gln$^{214}$ | 343 |
| Glypican-V-3 | Biotin-Gly-Lys$^{336}$-Leu-Leu-Glu-Gln-Val-Asn-Cit-Ile-Ser-Gly-Cit-Pro-Val-Arg-Thr-Pro-Thr-Gln$^{354}$-Gly-$^{346}$-Arg-Pro-Val-Cit-Thr-Pro-Thr-Gln-Ser-Pro-Cit-Ser$^{358}$-Arg-NH$_2$ | 344 | Lys$^{336}$-Leu-Leu-Glu-Gln-Val-Asn-Cit-Ile-Ser-Gly-Cit-Pro-Val-Arg-Thr-Pro-Thr-Gln$^{354}$-Gly$^{346}$-Arg-Pro-Val-Cit-Thr-Pro-Thr-Gln-Ser-Pro-Cit-Ser$^{358}$ | 345 |
| Glypican-V-4 | Biotin-Gly-Lys$^{385}$-Glu-Phe-Ile-Asn-Ser-Leu-Cit-Leu-Tyr-Arg-Ser-Phe-Tyr-Gly$^{399}$-Phe$^{387}$-Ile-Asn-Ser-Leu-Arg-Leu-Tyr-Cit-Ser-Phe-Tyr-Gly$^{399}$-Arg-NH$_2$ | 346 | Lys$^{385}$-Glu-Phe-Ile-Asn-Ser-Leu-Cit-Leu-Tyr-Arg-Ser-Phe-Tyr-Gly$^{399}$-Phe$^{387}$-Ile-Asn-Ser-Leu-Arg-Leu-Tyr-Cit-Ser-Phe-Tyr-Gly$^{399}$ | 347 |
| Glypican-VI-1 | Biotin-Gly-Ser$^{91}$-His-Phe-Val-Cit-Thr-Thr-Phe-Val-Ser-Arg-His$^{102}$-Phe$^{93}$-Val-Arg-Thr-Thr-Phe-Val-Ser-Cit-His$^{102}$-Gly-NH$_2$ | 348 | Ser$^{91}$-His-Phe-Val-Cit-Thr-Thr-Phe-Val-Ser-Arg-His$^{102}$-Phe$^{93}$-Val-Arg-Thr-Thr-Phe-Val-Ser-Cit-His$^{102}$ | 349 |
| Glypican-VI-2 | Biotin-Gly-Lys$^{206}$-Leu-Lys-Ile-Gln-Val-Thr-Cit-Ala-Phe-Ile-Ala-Ala-Cit-Thr-Phe-Val-Gln-Gly-Leu-Thr-Val-Gly-Cit-Glu-Val-Ala-Asn-Arg$^{234}$-Gly-NH$_2$ | 350 | Lys$^{206}$-Leu-Lys-Ile-Gln-Val-Thr-Cit-Ala-Phe-Ile-Ala-Ala-Cit-Thr-Phe-Val-Gln-Gly-Leu-Thr-Val-Gly-Cit-Glu-Val-Ala-Asn-Arg$^{234}$ | 351 |

TABLE 8-continued

Exemplary synthetic citrullinated peptides of the present invention. The left column shows non-limiting examples of synthetic peptides with biotin and spacer moieties, while the right column shows the core amino acid sequence for each synthetic peptide.

| Name | Biotinylated Sequence | SEQ ID NO: | Core Sequence | SEQ ID NO: |
|---|---|---|---|---|
| Glypican-VI-3 | Biotin-$Gly$-Thr$^{226}$-Val-Gly-Arg-Glu-Val-Ala-Asn-Cit-Val-Ser-Lys-Val-Ser-Pro-Thr$^{241}$-$Arg$-NH$_2$ | 352 | Thr$^{226}$-Val-Gly-Arg-Glu-Val-Ala-Asn-Cit-Val-Ser-Lys-Val-Ser-Pro-Thr$^{241}$ | 353 |
| Glypican-VI-4 | Biotin-$Gly$-Thr$^{454}$-Arg-Pro-Asp-Thr-Phe-Ile-Cit-Gln$^{462}$-Ile$^{460}$-Arg-Gln-Gln-Ile-Met-Ala-Leu-Cit-Val-Met-Thr-Asn-Lys-Leu-Lys$^{475}$-$Gly$-NH$_2$ | 354 | Thr$^{454}$-Arg-Pro-Asp-Thr-Phe-Ile-Cit-Gln$^{462}$-Ile$^{460}$-Arg-Gln-Gln-Ile-Met-Ala-Leu-Cit-Val-Met-Thr-Asn-Lys-Leu-Lys$^{475}$ | 355 |

In particular embodiments, one, two, three, four, five, or more (e.g., all) of the "Cit" (citrulline) residues in any of SEQ ID NOS:40-355 shown in Table 8 is replaced with "Arg" (arginine). As one non-limiting example, the VMT8 core sequence (SEQ ID NO:55) has the following amino acid sequence: TRSSAVXLRSSVPGVXVRLXSSVPG (SEQ ID NO:400), wherein X=Arg or Cit. As another non-limiting example, the VMT7 core sequence (SEQ ID NO:53) has the following amino acid sequence: RSYVTTSTXTYSALRPSTSXSLYATXSSAVRL (SEQ ID NO:401), wherein X=Arg or Cit. As yet another non-limiting example, the VMT13 core sequence (SEQ ID NO:65) has the following amino acid sequence: ANYQDTIGXLDE-IATYXKLLEGEESXIS (SEQ ID NO:402), wherein X=Arg or Cit.

The synthetic citrullnated peptides set forth in Example 6, which were designed from synovial proteins, were synthesized and evaluated for their ability to diagnose and/or prognose RA. Table 9 shows that these citrullnated peptides find utility in diagnosing and prognosing various stages of RA, including early stage, middle stage, and late stage RA. The peptides were then tested for IgG ACPA dose-response in samples of synovial fluid taken from both healthy patients and patients with RA. Table 9 shows that many of the synthetic citrillunated peptides derived from synovial protein sequences showed either a strong or moderate IgG ACPA dose-response in a sample of synovial fluid from an individual with RA.

TABLE 9

Synthetic citrullinated peptides synthesized and tested for IgG ACPA response.

| RA | Protein | Peptides Designed | Peptides Synthesized | IgG ACPA Positive (Strong/Moderate) |
|---|---|---|---|---|
| Early Stage (Initiation of Disease) (Neutrophil) | Vimentin | 14 | 14 | 3/3 |
| | Lamin | 21 | 14 | N/A |
| | Bip (P60 Heat Shock Protein) | 4 | 4 | 0/2 |
| | Histone | 8 | 8 | 1/3 |
| | β-Actin | 1 | 1 | 0/0 |
| | Myeloblastin | 4 | 4 | 0/1 |
| | PL Scramblase | 1 | 1 | 0/1 |
| Middle Stage (Propagation of Disease) (Plasma) | Fibrin | 24 | 22 | 3/4 |
| | Apolipoprotein a | 9 | 6 | 2/0 |
| Late Stage (Destruction of Cartilage & Bone) | Collagen | 15 | 15 | 2/4 |
| | Syndecan | 5 | 5 | 0/1 |
| | Fibronectin | 12 | 11 | 1/4 |
| (Matrix) | Total Peptides | 126 | 113 | 12/23 |

Example 7

Synthesis and Testing of Designed Citrullinated Peptides

The present example demonstrates that the heterogeneity in RA can be correlated to the different autoantibodies against the various synovial proteins present in the patient at different stages of the disease, i.e., early stage, middle stage, and late stage.

Figure 20:
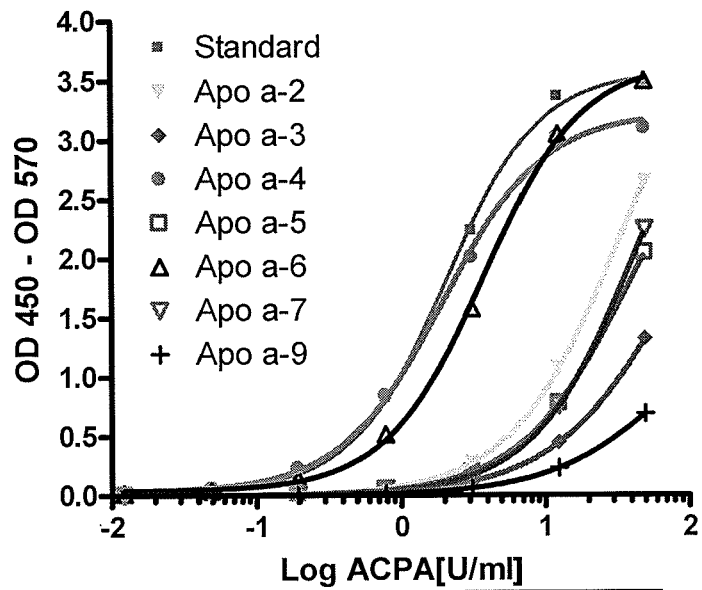
Figure 21:
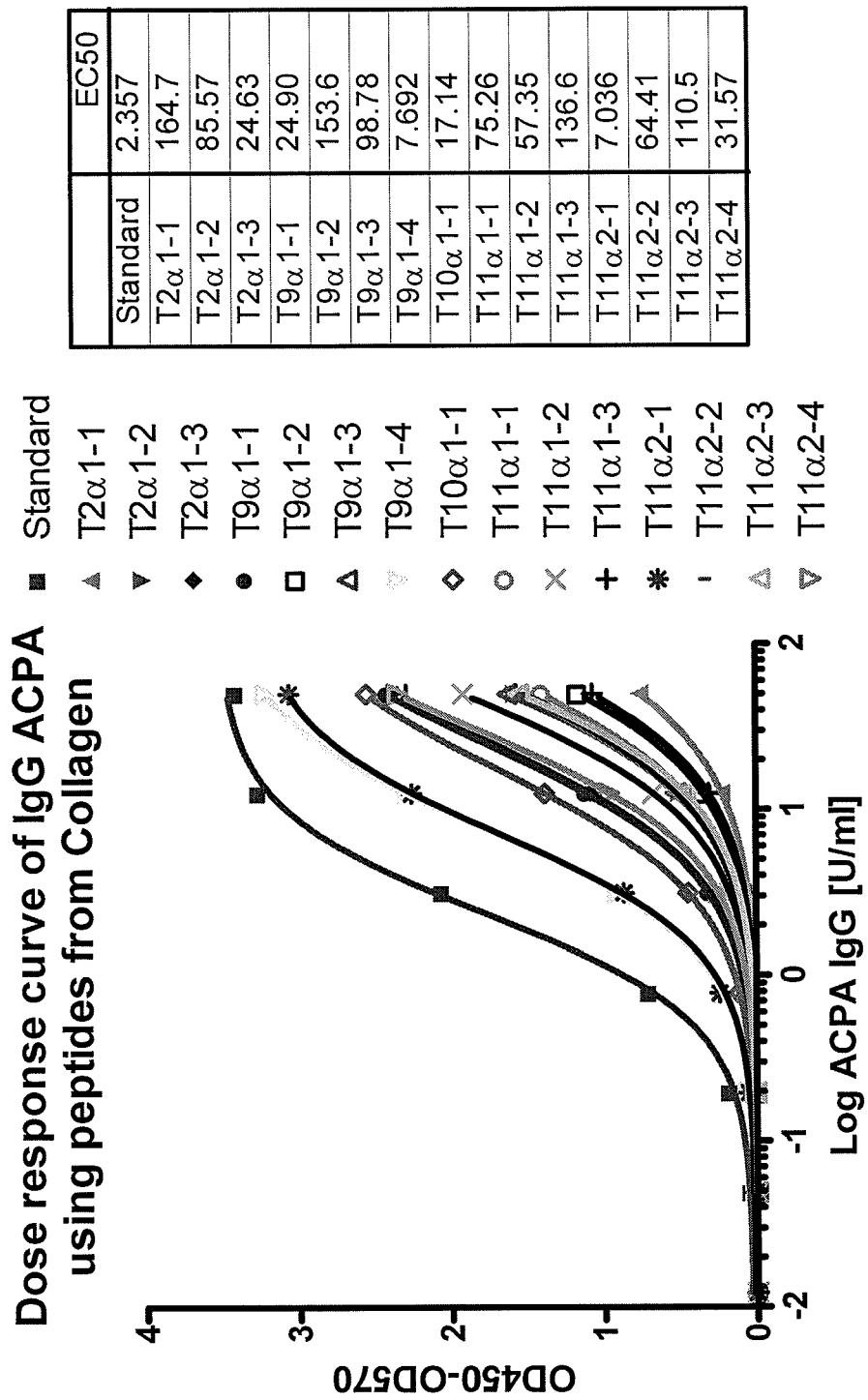
FIG. 21 illustrates the IgG ACPA dose-response curve of synthetic citrullinated peptides derived from collagen (e.g., Coll.T2α1, Coll.T9α1, Coll.T10α1, Coll.T11α1, and Coll.T11α2).

IgG ACPA (anti-citrullinated peptide antibody) dose-response curves of synthetic citrullinated peptides derived from Apolipoprotein a were calculated. FIG. 20 illustrates that several synthesized citrullinated Apolipoprotein a peptides displayed robust binding, as evidenced by the EC50 values calculated for each of the peptides. Significantly, Apo a-4 and Apo a-6 both displayed strong IgG ACPA positive responses (i.e., EC50 values of 1.959 and 3.797, respectively).

IgG ACPA dose-response curves of synthetic citrullinated peptides derived from collagen (e.g., Coll.T2α1, Coll.T9α1, Coll.T10α1, Coll.T11α1, Coll.T11α2) were calculated. FIG.

21 illustrates that several synthesized citrullinated collagen peptides displayed robust binding, as evidenced by the EC50 values calculated for each of the peptides. Significantly, T9α1-4 and T11α2-1 both displayed strong IgG ACPA positive responses (i.e., EC50 values of 7.692 and 7.036, respectively), while T2α1-3, T9α1-1, T10α1-1, and T11α2-4 displayed moderate IgG ACPA positive responses (i.e., EC50 values of 24.63, 24.90, 17.14, and 31.57, respectively).

Figure 22:
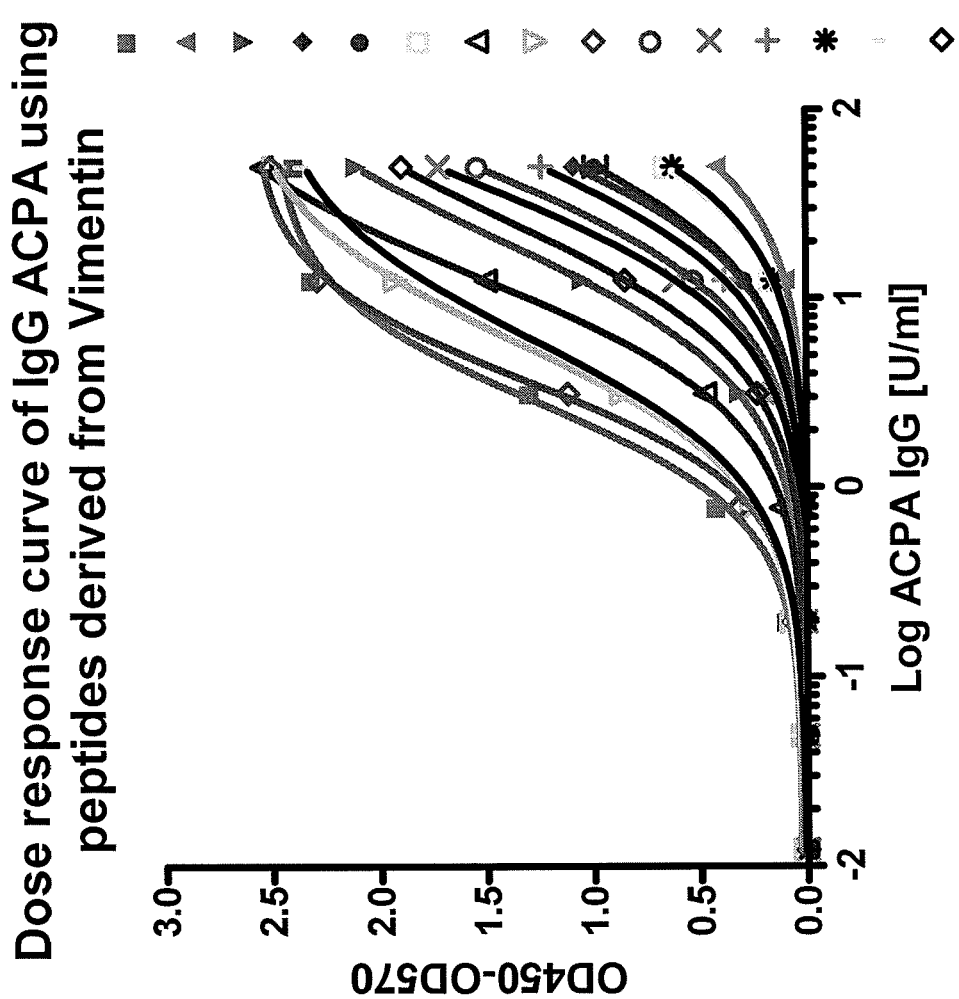
FIG. 22 illustrates the IgG ACPA dose-response curve of synthetic citrullinated peptides derived from vimentin.

IgG ACPA dose-response curves of synthetic citrullinated peptides derived from vimentin were calculated. FIG. 22 illustrates that several synthesized citrullinated vimentin peptides displayed robust binding, as evidenced by the EC50 values calculated for each of the peptides. Significantly, VMT7, VMT8, and VMT13 displayed strong IgG ACPA positive responses (i.e., EC50 values of 5.826, 3.639, and 6.020, respectively), while VMT2, VMT6, and VMT14 displayed moderate IgG ACPA positive responses (i.e., EC50 values of 21.29, 12.96, and 25.99, respectively).

Figure 23:
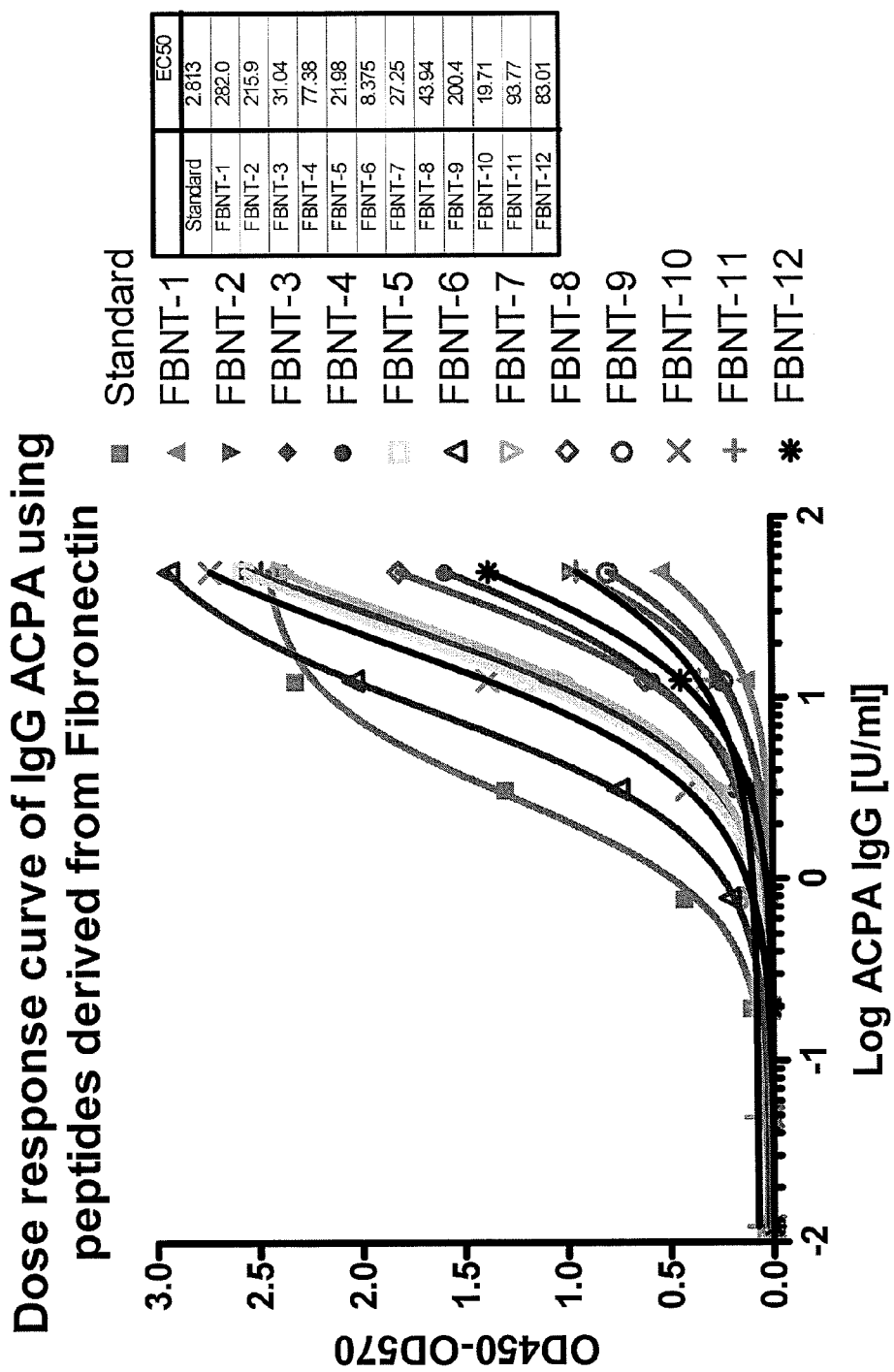
FIG. 23 illustrates the IgG ACPA dose-response curve of synthetic citrullinated peptides derived from fibronectin.

IgG ACPA dose-response curves of synthetic citrullinated peptides derived from fibronectin were calculated. FIG. 23 illustrates that several synthesized citrullinated fibronectin peptides displayed robust binding, as evidenced by the EC50 values calculated for each of the peptides. Significantly, FBNT-6 displayed a strong IgG ACPA positive response (i.e., EC50 value of 8.375), while FBNT-3, FBNT-5, FBNT-7, and FBNT-10 displayed moderate IgG ACPA positive responses (i.e., EC50 values of 31.04, 21.98, 27.25, and 19.71, respectively).

Figure 24:
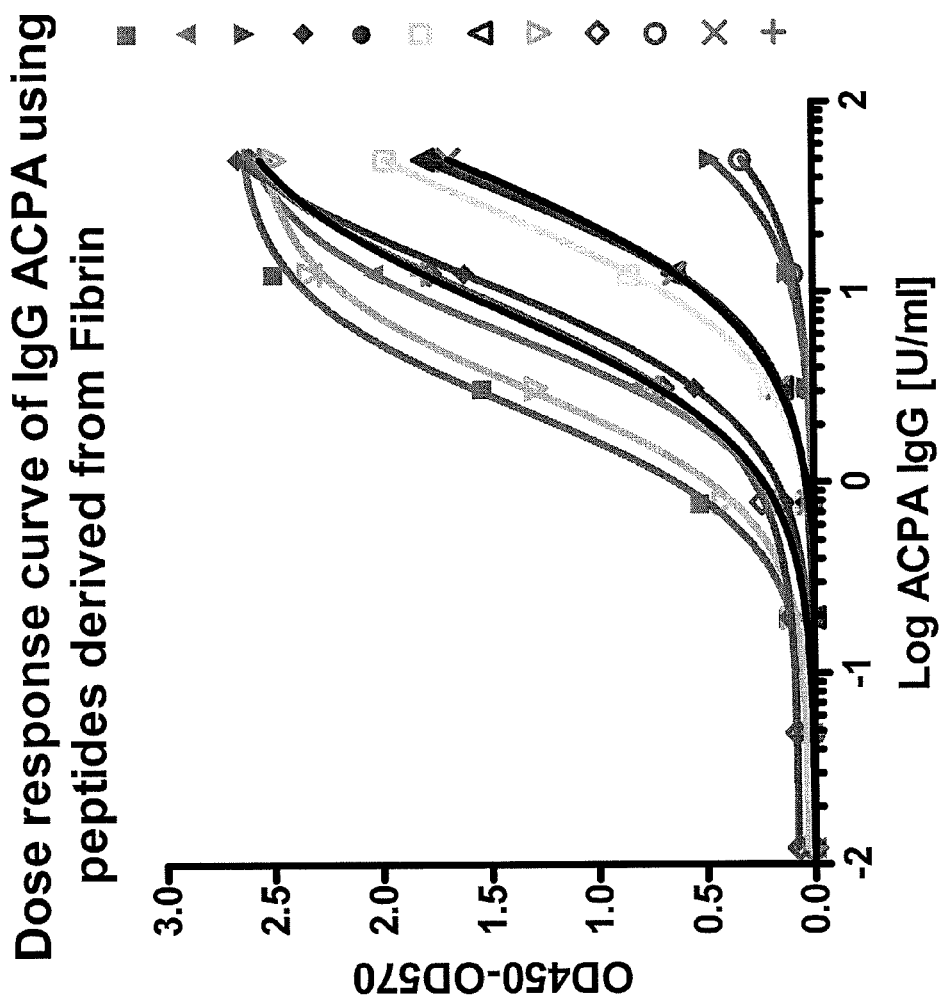
FIG. 24 illustrates the IgG ACPA dose-response curve of synthetic citrullinated peptides derived from fibrin (e.g., fibrin alpha-chain, beta-chain, and gamma-chain).

IgG ACPA dose-response curves of synthetic citrullinated peptides derived from fibrin (e.g., fibrin alpha-chain, fibrin beta-chain, fibrin gamma-chain) were calculated. FIG. 24 illustrates that several synthesized citrullinated fibrin peptides displayed robust binding, as evidenced by the EC50 values calculated for each of the peptides. Significantly, FIB-A1, FIB-A8, and FIB-G1 displayed strong IgG ACPA positive responses (i.e., EC50 values of 5.682, 3.030, and 7.863, respectively), while FIB-A3, FIB-A5, FIB-A6, and FIB-B1 displayed moderate IgG ACPA positive responses (i.e., EC50 values of 12.19, 25.90, 38.12, and 9.207, respectively).

IgG ACPA dose-response curves of synthetic citrullinated peptides derived from enolase and syndecan were calculated. FIG. 25 illustrates that SYNC-IIIa displayed a moderate IgG ACPA positive response (i.e., EC50 value of 18.93).

Figure 26:
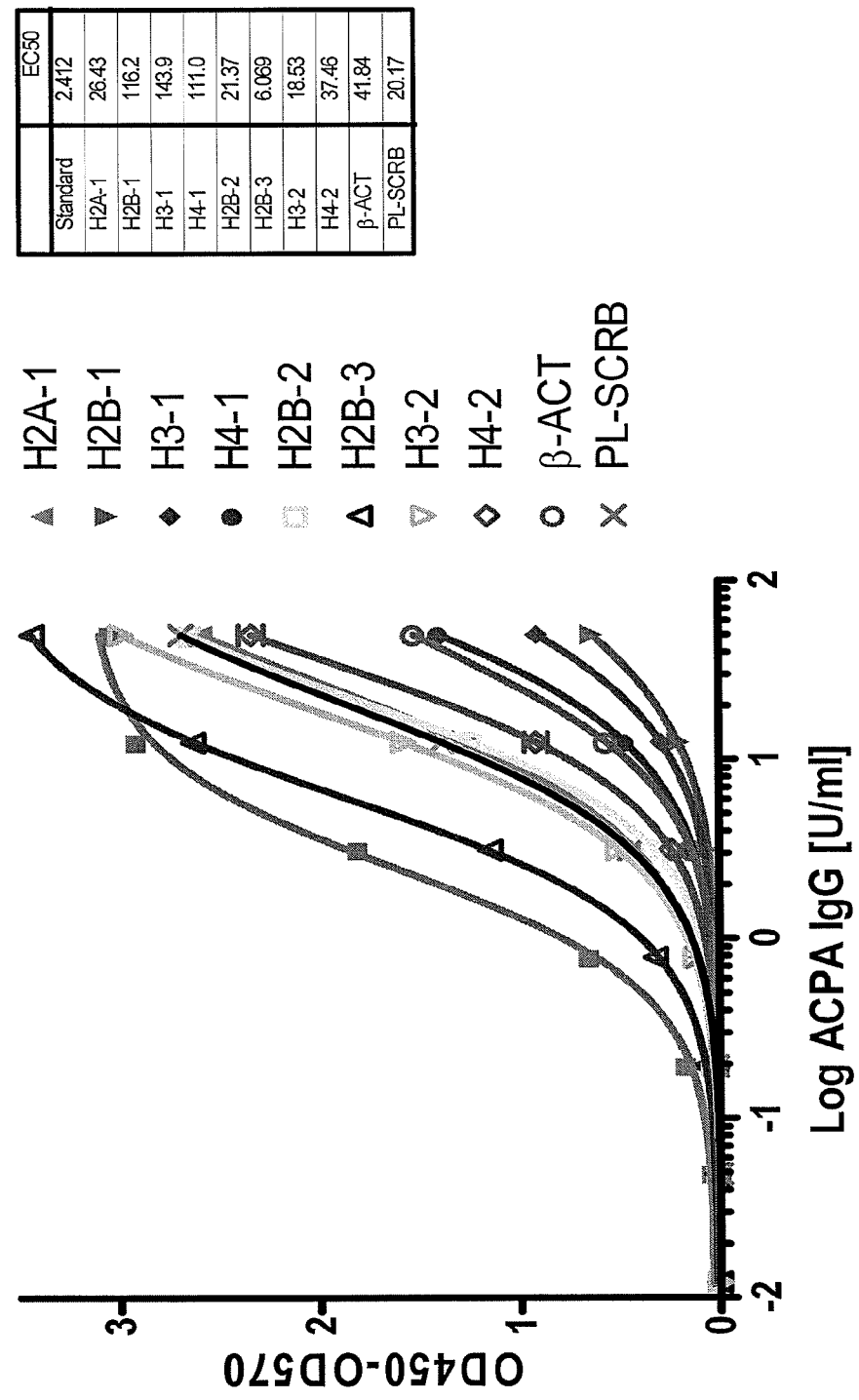
FIG. 26 illustrates the IgG ACPA dose-response curve of synthetic citrullinated peptides derived from histone, β-actin, and PL scramblase.

IgG ACPA dose-response curves of synthetic citrullinated peptides derived from histone, β-actin, and PL scramblase were calculated. FIG. 26 illustrates that several of these synthesized citrullinated peptides displayed robust binding, as evidenced by the EC50 values calculated for each of the peptides. Significantly, H2B-3 displayed a strong IgG ACPA positive response (i.e., EC50 value of 6.069), while H2A-1, H2B-2, H3-2, and PL-SCRB displayed moderate IgG ACPA positive responses (i.e., EC50 values of 26.43, 21.37, 18.53, and 20.17, respectively).

Figure 27:
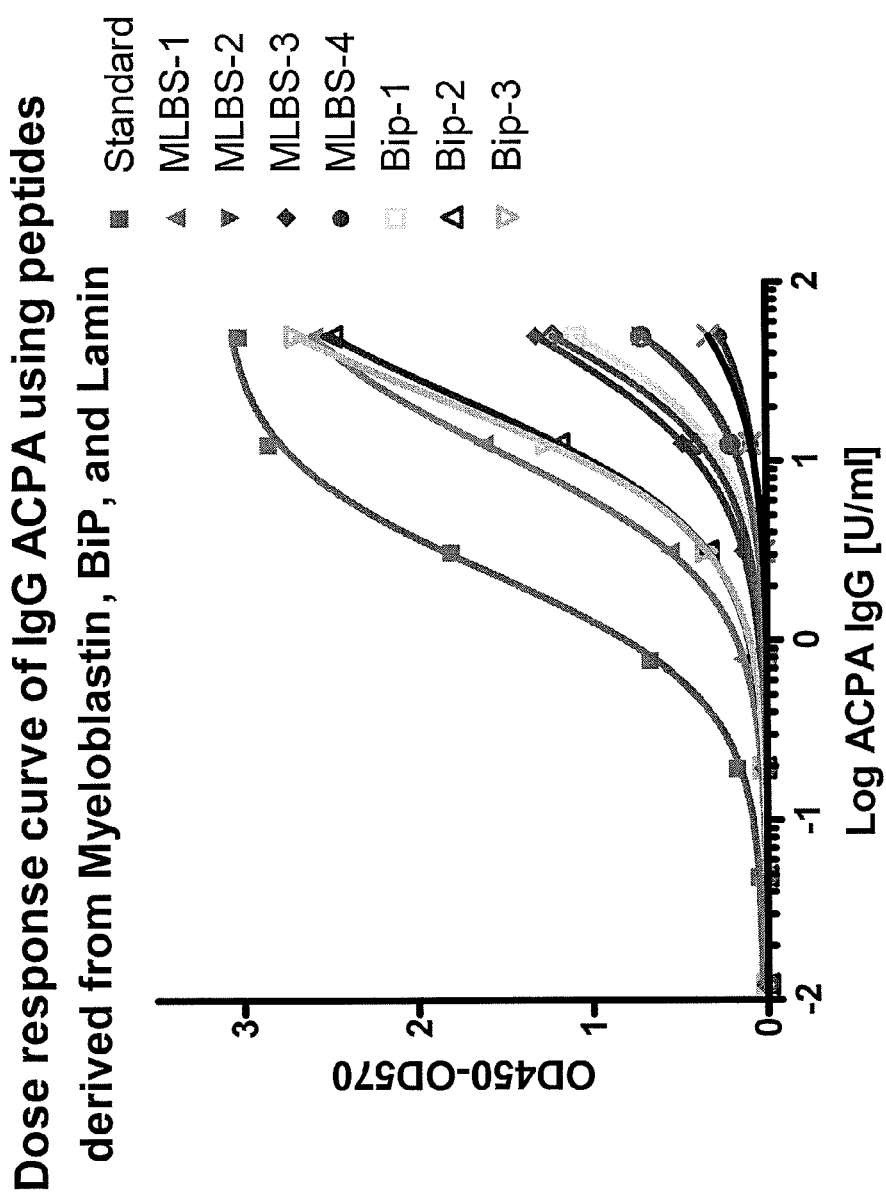
FIG. 27 illustrates the IgG ACPA dose-response curve of synthetic citrullinated peptides derived from myeloblastin, BiP, and lamin (e.g., lamin B1, B2, and A/C)

IgG ACPA dose-response curves of synthetic citrullinated peptides derived from myeloblastin, BiP, and lamin (e.g., lamin B1, lamin B2, lamin A/C) were calculated. FIG. 27 illustrates that several of these synthesized citrullinated peptides displayed robust binding, as evidenced by the EC50 values calculated for each of the peptides. Significantly, MLBS-1, Bip-2, and Bip-3 displayed moderate IgG ACPA positive responses (i.e., EC50 values of 11.20, 22.66, and 22.74, respectively).

As demonstrated in this example, the ability to classify RA patients into different stages of the disease will enable the clinician to practice personalized medicine to treat the heterogeneous population of RA patients with the appropriate medicine at earlier time points and change the course of the disease. This ability to identify autoantibodies against each individual citrullinated synovial protein in a patient allows the classification of RA patients into different stages of the disease.

Example 8

Diagnosing RA Using a Combination of Citrullinated Peptides

The present example demonstrates the development of an assay which incorporates multiple endogenous synovial protein autoantigens to diagnose, prognose, and/or differentiate RA patients into various stages for specialized treatment. Although the specificity for each of the currently marketed RA diagnostic assays is good (>90%), none of the assays can achieve a sensitivity of greater than 75%. This discrepancy is due to the fact that the current anti-CCP-based and anti-filaggrin-based assays are not measuring the endogenous autoantigens that are actually present in the synovial joint. This example demonstrates the ability of the present invention to fulfill this need in the art.

The sensitivity and specificity of RA diagnosis was calculated for a synthesized fibrin citrullinated peptide and three synthesized vimentin citrullinated peptides. Table 10 shows that the sensitivity for RA diagnosis using the fibrin peptide was 80%, with 100% specificity. Similarly, the VMT2 peptide demonstrated a 75% sensitivity with a 95% specificity. Significantly, when the fibrin and VMT2 peptides were used in conjunction with each other, 95% sensitivity was achieved.

TABLE 10

Sensitivity and specificity of RA diagnosis using synthetic citrullinated fibrin and vimentin peptides.

| | Normal Control | | | | RA Patients | | | |
|---|---|---|---|---|---|---|---|---|
| | Fibrin | VMT 1 | VMT3 | VMT2 | Fibrin | VMT 1 | VMT3 | VMT2 |
| Sensitivity (%) | | | | | 80 | 45 | 50 | 75 |
| Fibrin + VMT2 Sensitivity | | | | | | 95% | | |
| Specificity (%) | 100 | 95 | 95 | 95 | | | | |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, Genbank Accession Nos., and Swiss-Prot Accession Nos., are incorporated herein by reference for all purposes.

SEQUENCE LISTING

<160> NUMBER OF SEQ ID NOS: 402

<210> SEQ ID NO 1
<211> LENGTH: 466
<212> TYPE: PRT
<213> ORGANISM: Homo sapiens
<220> FEATURE:
<223> OTHER INFORMATION: vimentin

<400> SEQUENCE: 1

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

```
Val Glu Ala Ala Asn Tyr Gln Asp Thr Ile Gly Arg Leu Gln Asp Glu
            355                 360                 365

Ile Gln Asn Met Lys Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
                405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
450                 455                 460

Leu Glu
465

<210> SEQ ID NO 2
<211> LENGTH: 644
<212> TYPE: PRT
<213> ORGANISM: Homo sapiens
<220> FEATURE:
<223> OTHER INFORMATION: fibrinogen alpha chain preproprotein

<400> SEQUENCE: 2

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
```

```
                245                 250                 255
Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
            275                 280                 285

Pro Ser Ser Ala Gly Ser Trp Asn Ser Gly Ser Ser Gly Pro Gly Ser
            290                 295                 300

Thr Gly Asn Arg Asn Pro Gly Ser Ser Gly Thr Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
                370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Thr Arg Arg Ser Cys Ser Lys Thr
                450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
                580                 585                 590

Asp Ser Thr Phe Glu Ser Lys Ser Tyr Lys Met Ala Asp Glu Ala Gly
                595                 600                 605

Ser Glu Ala Asp His Glu Gly Thr His Ser Thr Lys Arg Gly His Ala
                610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 3
<211> LENGTH: 491
<212> TYPE: PRT
```

-continued

```
<213> ORGANISM: Homo sapiens
<220> FEATURE:
<223> OTHER INFORMATION: fibrinogen beta chain preproprotein

<400> SEQUENCE: 3

Met Lys Arg Met Val Ser Trp Ser Phe His Lys Leu Lys Thr Met Lys
 1               5                  10                  15

His Leu Leu Leu Leu Leu Leu Cys Val Phe Leu Val Lys Ser Gln Gly
             20                  25                  30

Val Asn Asp Asn Glu Glu Gly Phe Phe Ser Ala Arg Gly His Arg Pro
         35                  40                  45

Leu Asp Lys Lys Arg Glu Glu Ala Pro Ser Leu Arg Pro Ala Pro Pro
 50                  55                  60

Pro Ile Ser Gly Gly Gly Tyr Arg Ala Arg Pro Ala Lys Ala Ala Ala
 65                  70                  75                  80

Thr Gln Lys Lys Val Glu Arg Lys Ala Pro Asp Ala Gly Gly Cys Leu
                 85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
370                 375                 380

Asp Gly Ala Ser Gln Leu Met Gly Glu Asn Arg Thr Met Thr Ile His
385                 390                 395                 400
```

```
Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
            435                 440                 445

Gly Gly Gln Tyr Thr Trp Asp Met Ala Lys His Gly Thr Asp Asp Gly
    450                 455                 460

Val Val Trp Met Asn Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 4
<211> LENGTH: 453
<212> TYPE: PRT
<213> ORGANISM: Homo sapiens
<220> FEATURE:
<223> OTHER INFORMATION: fibrinogen gamma chain preproprotein

<400> SEQUENCE: 4

Met Ser Trp Ser Leu His Pro Arg Asn Leu Ile Leu Tyr Phe Tyr Ala
 1               5                  10                  15

Leu Leu Phe Leu Ser Ser Thr Cys Val Ala Tyr Val Ala Thr Arg Asp
             20                  25                  30

Asn Cys Cys Ile Leu Asp Glu Arg Phe Gly Ser Tyr Cys Pro Thr Thr
         35                  40                  45

Cys Gly Ile Ala Asp Phe Leu Ser Thr Tyr Gln Thr Lys Val Asp Lys
     50                  55                  60

Asp Leu Gln Ser Leu Glu Asp Ile Leu His Gln Val Glu Asn Lys Thr
 65                  70                  75                  80

Ser Glu Val Lys Gln Leu Ile Lys Ala Ile Gln Leu Thr Tyr Asn Pro
                 85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270
```

```
Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
        290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
                340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
        370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln His His Leu Gly Gly Ala Lys
                420                 425                 430

Gln Val Arg Pro Glu His Pro Ala Glu Thr Glu Tyr Asp Ser Leu Tyr
        435                 440                 445

Pro Glu Asp Asp Leu
        450

<210> SEQ ID NO 5
<211> LENGTH: 434
<212> TYPE: PRT
<213> ORGANISM: Homo sapiens
<220> FEATURE:
<223> OTHER INFORMATION: alpha-enolase preproprotein

<400> SEQUENCE: 5

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
```

-continued

```
                180                 185                 190
Lys Asn Val Ile Lys Glu Lys Tyr Gly Lys Asp Ala Thr Asn Val Gly
                    195                 200                 205

Asp Glu Gly Gly Phe Ala Pro Asn Ile Leu Glu Asn Lys Glu Gly Leu
        210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys

<210> SEQ ID NO 6
<211> LENGTH: 2386
<212> TYPE: PRT
<213> ORGANISM: Homo sapiens
<220> FEATURE:
<223> OTHER INFORMATION: fibronectin 1 (FN1)

<400> SEQUENCE: 6

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110
```

-continued

```
Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
        130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
530                 535                 540
```

```
Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
            930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
```

```
                965                 970                 975
Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                1000                1005

Thr Asp Ser Thr Val Leu Val Arg Trp Thr Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
                1060                1065                1070

Gln Glu Ser Pro Lys Ala Thr Gly Val Phe Thr Thr Leu Gln Pro Gly
                1075                1080                1085

Ser Ser Ile Pro Pro Tyr Asn Thr Glu Val Thr Glu Thr Thr Ile Val
                1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
                1140                1145                1150

Ile Gln Val Leu Arg Asp Gly Gln Glu Arg Asp Ala Pro Ile Val Asn
                1155                1160                1165

Lys Val Val Thr Pro Leu Ser Pro Pro Thr Asn Leu His Leu Glu Ala
1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
                1220                1225                1230

Thr Phe Asp Asn Leu Ser Pro Gly Leu Glu Tyr Asn Val Ser Val Tyr
                1235                1240                1245

Thr Val Lys Asp Asp Lys Glu Ser Val Pro Ile Ser Asp Thr Ile Ile
                1250                1255                1260

Pro Ala Val Pro Pro Pro Thr Asp Leu Arg Phe Thr Asn Ile Gly Pro
1265                1270                1275                1280

Asp Thr Met Arg Val Thr Trp Ala Pro Pro Pro Ser Ile Asp Leu Thr
                1285                1290                1295

Asn Phe Leu Val Arg Tyr Ser Pro Val Lys Asn Glu Glu Asp Val Ala
                1300                1305                1310

Glu Leu Ser Ile Ser Pro Ser Asp Asn Ala Val Val Leu Thr Asn Leu
                1315                1320                1325

Leu Pro Gly Thr Glu Tyr Val Val Ser Val Ser Ser Val Tyr Glu Gln
                1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
                1365                1370                1375

His Trp Ile Ala Pro Arg Ala Thr Ile Thr Gly Tyr Arg Ile Arg His
                1380                1385                1390
```

```
His Pro Glu His Phe Ser Gly Arg Pro Arg Glu Asp Arg Val Pro His
        1395                1400                1405

Ser Arg Asn Ser Ile Thr Leu Thr Asn Leu Thr Pro Gly Thr Glu Tyr
    1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
                1460                1465                1470

Val Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala Thr
    1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
        1540                1545                1550

Val Gln Asp Asn Ser Ile Ser Val Lys Trp Leu Pro Ser Ser Ser Pro
    1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile
        1620                1625                1630

Asp Arg Pro Lys Gly Leu Ala Phe Thr Asp Val Asp Val Asp Ser Ile
    1635                1640                1645

Lys Ile Ala Trp Glu Ser Pro Gln Gly Gln Val Ser Arg Tyr Arg Val
    1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
            1685                1690                1695

Glu Tyr Thr Val Ser Val Val Ala Leu His Asp Asp Met Glu Ser Gln
        1700                1705                1710

Pro Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr Pro
    1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
            1765                1770                1775

Val Val Val Ser Gly Leu Met Val Ala Thr Lys Tyr Glu Val Ser Val
    1780                1785                1790

Tyr Ala Leu Lys Asp Thr Leu Thr Ser Arg Pro Ala Gln Gly Val Val
        1795                1800                1805

Thr Thr Leu Glu Asn Val Ser Pro Pro Arg Arg Ala Arg Val Thr Asp
    1810                1815                1820
```

```
Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
            1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
            1875                1880                1885

Asn Ala Arg Ser Ser Pro Val Val Ile Asp Ala Ser Thr Ala Ile Asp
            1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
            1925                1930                1935

Tyr Glu Lys Pro Gly Ser Pro Pro Arg Glu Val Val Pro Arg Pro Arg
            1940                1945                1950

Pro Gly Val Thr Glu Ala Thr Ile Thr Gly Leu Glu Pro Gly Thr Glu
            1955                1960                1965

Tyr Thr Ile Tyr Val Ile Ala Leu Lys Asn Asn Gln Lys Ser Glu Pro
            1970                1975                1980

Leu Ile Gly Arg Lys Lys Thr Asp Glu Leu Pro Gln Leu Val Thr Leu
1985                1990                1995                2000

Pro His Pro Asn Leu His Gly Pro Glu Ile Leu Asp Val Pro Ser Thr
            2005                2010                2015

Val Gln Lys Thr Pro Phe Val Thr His Pro Gly Tyr Asp Thr Gly Asn
            2020                2025                2030

Gly Ile Gln Leu Pro Gly Thr Ser Gly Gln Gln Pro Ser Val Gly Gln
            2035                2040                2045

Gln Met Ile Phe Glu Glu His Gly Phe Arg Arg Thr Thr Pro Pro Thr
            2050                2055                2060

Thr Ala Thr Pro Ile Arg His Arg Pro Arg Pro Tyr Pro Pro Asn Val
2065                2070                2075                2080

Gly Glu Glu Ile Gln Ile Gly His Ile Pro Arg Glu Asp Val Asp Tyr
            2085                2090                2095

His Leu Tyr Pro His Gly Pro Gly Leu Asn Pro Asn Ala Ser Thr Gly
            2100                2105                2110

Gln Glu Ala Leu Ser Gln Thr Thr Ile Ser Trp Ala Pro Phe Gln Asp
            2115                2120                2125

Thr Ser Glu Tyr Ile Ile Ser Cys His Pro Val Gly Thr Asp Glu Glu
            2130                2135                2140

Pro Leu Gln Phe Arg Val Pro Gly Thr Ser Thr Ser Ala Thr Leu Thr
2145                2150                2155                2160

Gly Leu Thr Arg Gly Ala Thr Tyr Asn Ile Ile Val Glu Ala Leu Lys
            2165                2170                2175

Asp Gln Gln Arg His Lys Val Arg Glu Glu Val Val Thr Val Gly Asn
            2180                2185                2190

Ser Val Asn Glu Gly Leu Asn Gln Pro Thr Asp Asp Ser Cys Phe Asp
            2195                2200                2205

Pro Tyr Thr Val Ser His Tyr Ala Val Gly Asp Glu Trp Glu Arg Met
            2210                2215                2220

Ser Glu Ser Gly Phe Lys Leu Leu Cys Gln Cys Leu Gly Phe Gly Ser
2225                2230                2235                2240

Gly His Phe Arg Cys Asp Ser Ser Arg Trp Cys His Asp Asn Gly Val
```

-continued

```
                    2245                2250                2255
Asn Tyr Lys Ile Gly Glu Lys Trp Asp Arg Gln Gly Glu Asn Gly Gln
                2260                2265                2270

Met Met Ser Cys Thr Cys Leu Gly Asn Gly Lys Gly Glu Phe Lys Cys
            2275                2280                2285

Asp Pro His Glu Ala Thr Cys Tyr Asp Asp Gly Lys Thr Tyr His Val
        2290                2295                2300

Gly Glu Gln Trp Gln Lys Glu Tyr Leu Gly Ala Ile Cys Ser Cys Thr
2305                2310                2315                2320

Cys Phe Gly Gly Gln Arg Gly Trp Arg Cys Asp Asn Cys Arg Arg Pro
                2325                2330                2335

Gly Gly Glu Pro Ser Pro Glu Gly Thr Thr Gly Gln Ser Tyr Asn Gln
            2340                2345                2350

Tyr Ser Gln Arg Tyr His Gln Arg Thr Asn Thr Asn Val Asn Cys Pro
        2355                2360                2365

Ile Glu Cys Phe Met Pro Leu Asp Val Gln Ala Asp Arg Glu Asp Ser
    2370                2375                2380

Arg Glu
2385

<210> SEQ ID NO 7
<211> LENGTH: 586
<212> TYPE: PRT
<213> ORGANISM: Homo sapiens
<220> FEATURE:
<223> OTHER INFORMATION: lamin B1 (LMNB1)

<400> SEQUENCE: 7

Met Ala Thr Ala Thr Pro Val Pro Pro Arg Met Gly Ser Arg Ala Gly
 1               5                  10                  15

Gly Pro Thr Thr Pro Leu Ser Pro Thr Arg Leu Ser Arg Leu Gln Glu
            20                  25                  30

Lys Glu Glu Leu Arg Glu Leu Asn Asp Arg Leu Ala Val Tyr Ile Asp
        35                  40                  45

Lys Val Arg Ser Leu Glu Thr Glu Asn Ser Ala Leu Gln Leu Gln Val
    50                  55                  60

Thr Glu Arg Glu Glu Val Arg Gly Arg Glu Leu Thr Gly Leu Lys Ala
65                  70                  75                  80

Leu Tyr Glu Thr Glu Leu Ala Asp Ala Arg Arg Ala Leu Asp Asp Thr
                85                  90                  95

Ala Arg Glu Arg Ala Lys Leu Gln Ile Glu Leu Gly Lys Cys Lys Ala
            100                 105                 110

Glu His Asp Gln Leu Leu Leu Asn Tyr Ala Lys Lys Glu Ser Asp Leu
        115                 120                 125

Asn Gly Ala Gln Ile Lys Leu Arg Glu Tyr Glu Ala Ala Leu Asn Ser
    130                 135                 140

Lys Asp Ala Ala Leu Ala Thr Ala Leu Gly Asp Lys Lys Ser Leu Glu
145                 150                 155                 160

Gly Asp Leu Glu Asp Leu Lys Asp Gln Ile Ala Gln Leu Glu Ala Ser
                165                 170                 175

Leu Ala Ala Ala Lys Lys Gln Leu Ala Asp Glu Thr Leu Leu Lys Val
            180                 185                 190

Asp Leu Glu Asn Arg Cys Gln Ser Leu Thr Glu Asp Leu Glu Phe Arg
        195                 200                 205

Lys Ser Met Tyr Glu Glu Glu Ile Asn Glu Thr Arg Arg Lys His Glu
    210                 215                 220
```

Thr Arg Leu Val Glu Val Asp Ser Gly Arg Gln Ile Glu Tyr Glu Tyr
225                 230                 235                 240

Lys Leu Ala Gln Ala Leu His Glu Met Arg Glu Gln His Asp Ala Gln
            245                 250                 255

Val Arg Leu Tyr Lys Glu Glu Leu Glu Gln Thr Tyr His Ala Lys Leu
        260                 265                 270

Glu Asn Ala Arg Leu Ser Ser Glu Met Asn Thr Ser Thr Val Asn Ser
    275                 280                 285

Ala Arg Glu Glu Leu Met Glu Ser Arg Met Arg Ile Glu Ser Leu Ser
290                 295                 300

Ser Gln Leu Ser Asn Leu Gln Lys Glu Ser Arg Ala Cys Leu Glu Arg
305                 310                 315                 320

Ile Gln Glu Leu Glu Asp Leu Leu Ala Lys Lys Asp Asn Ser Arg
                325                 330                 335

Arg Met Leu Thr Asp Lys Glu Arg Glu Met Ala Glu Ile Arg Asp Gln
            340                 345                 350

Met Gln Gln Gln Leu Asn Asp Tyr Glu Gln Leu Leu Asp Val Lys Leu
        355                 360                 365

Ala Leu Asp Met Glu Ile Ser Ala Tyr Arg Lys Leu Leu Glu Gly Glu
    370                 375                 380

Glu Glu Arg Leu Lys Leu Ser Pro Ser Pro Ser Ser Arg Val Thr Val
385                 390                 395                 400

Ser Arg Ala Ser Ser Ser Arg Ser Val Arg Thr Thr Arg Gly Lys Arg
                405                 410                 415

Lys Arg Val Asp Val Glu Glu Ser Glu Ala Ser Ser Ser Val Ser Ile
            420                 425                 430

Ser His Ser Ala Ser Ala Thr Gly Asn Val Cys Ile Glu Glu Ile Asp
        435                 440                 445

Val Asp Gly Lys Phe Ile Arg Leu Lys Asn Thr Ser Glu Gln Asp Gln
450                 455                 460

Pro Met Gly Gly Trp Glu Met Ile Arg Lys Ile Gly Asp Thr Ser Val
465                 470                 475                 480

Ser Tyr Lys Tyr Thr Ser Arg Tyr Val Leu Lys Ala Gly Gln Thr Val
                485                 490                 495

Thr Ile Trp Ala Ala Asn Ala Gly Val Thr Ala Ser Pro Pro Thr Asp
            500                 505                 510

Leu Ile Trp Lys Asn Gln Asn Ser Trp Gly Thr Gly Glu Asp Val Lys
        515                 520                 525

Val Ile Leu Lys Asn Ser Gln Gly Glu Glu Val Ala Gln Arg Ser Thr
530                 535                 540

Val Phe Lys Thr Thr Ile Pro Glu Glu Glu Glu Glu Glu Glu Glu Ala
545                 550                 555                 560

Ala Gly Val Val Val Glu Glu Leu Phe His Gln Gln Gly Thr Pro
                565                 570                 575

Arg Ala Ser Asn Arg Ser Cys Ala Ile Met
            580                 585

<210> SEQ ID NO 8
<211> LENGTH: 600
<212> TYPE: PRT
<213> ORGANISM: Homo sapiens
<220> FEATURE:
<223> OTHER INFORMATION: lamin B2 (LMNB2)

<400> SEQUENCE: 8

```
Met Ala Thr Pro Leu Pro Gly Arg Ala Gly Pro Ala Thr Pro Leu
  1               5                  10                 15

Ser Pro Thr Arg Leu Ser Arg Leu Gln Glu Lys Glu Glu Leu Arg Glu
             20                  25                  30

Leu Asn Asp Arg Leu Ala His Tyr Ile Asp Arg Val Arg Ala Leu Glu
             35                  40                  45

Leu Glu Asn Asp Arg Leu Leu Leu Lys Ile Ser Glu Lys Glu Glu Val
 50                  55                  60

Thr Thr Arg Glu Val Ser Gly Ile Lys Ala Leu Tyr Glu Ser Glu Leu
 65                  70                  75                  80

Ala Asp Ala Arg Arg Val Leu Asp Glu Thr Ala Arg Glu Arg Ala Arg
                 85                  90                  95

Leu Gln Ile Glu Ile Gly Lys Leu Arg Ala Glu Leu Asp Glu Val Asn
                100                 105                 110

Lys Ser Ala Lys Lys Arg Glu Gly Glu Leu Thr Val Ala Gln Gly Arg
                115                 120                 125

Val Lys Asp Leu Glu Ser Leu Phe His Arg Ser Glu Val Glu Leu Ala
                130                 135                 140

Ala Ala Leu Ser Asp Lys Arg Gly Leu Glu Ser Asp Val Ala Glu Leu
145                 150                 155                 160

Arg Ala Gln Leu Ala Lys Ala Glu Asp Gly His Ala Val Ala Lys Lys
                165                 170                 175

Gln Leu Glu Lys Glu Thr Leu Met Arg Val Asp Leu Glu Asn Arg Cys
                180                 185                 190

Gln Ser Leu Gln Glu Glu Leu Asp Phe Arg Lys Ser Val Phe Glu Glu
                195                 200                 205

Glu Val Arg Glu Thr Arg Arg His Glu Arg Arg Leu Val Glu Val
210                 215                 220

Asp Ser Ser Arg Gln Gln Glu Tyr Asp Phe Lys Met Ala Gln Ala Leu
225                 230                 235                 240

Glu Glu Leu Arg Ser Gln His Asp Glu Gln Val Arg Leu Tyr Lys Leu
                245                 250                 255

Glu Leu Glu Gln Thr Tyr Gln Ala Lys Leu Asp Ser Ala Lys Leu Ser
                260                 265                 270

Ser Asp Gln Asn Asp Lys Ala Ala Ser Ala Ala Arg Glu Glu Leu Lys
                275                 280                 285

Glu Ala Arg Met Arg Leu Glu Ser Leu Ser Tyr Gln Leu Ser Gly Leu
                290                 295                 300

Gln Lys Gln Ala Ser Ala Glu Asp Arg Ile Arg Glu Leu Glu Glu
305                 310                 315                 320

Ala Met Ala Gly Glu Arg Asp Lys Phe Arg Lys Met Leu Asp Ala Lys
                325                 330                 335

Glu Gln Glu Met Thr Glu Met Arg Asp Val Met Gln Gln Leu Ala
                340                 345                 350

Glu Tyr Gln Glu Leu Leu Asp Val Lys Leu Ala Leu Asp Met Glu Ile
                355                 360                 365

Asn Ala Tyr Arg Lys Leu Leu Glu Gly Glu Glu Arg Leu Lys Leu
370                 375                 380

Ser Pro Ser Pro Ser Ser Arg Val Thr Val Ser Arg Ala Thr Ser Ser
385                 390                 395                 400

Ser Ser Gly Ser Leu Ser Ala Thr Gly Arg Leu Gly Arg Ser Lys Arg
                405                 410                 415

Lys Arg Leu Glu Val Glu Glu Pro Leu Gly Ser Gly Pro Ser Val Leu
                420                 425                 430
```

```
Gly Thr Gly Thr Gly Ser Gly Gly Phe His Leu Ala Gln Gln Ala
            435                 440                 445

Ser Ala Ser Gly Ser Val Ser Ile Glu Glu Ile Asp Leu Glu Gly Lys
450                 455                 460

Phe Val Gln Leu Lys Asn Asn Ser Asp Lys Asp Gln Ser Leu Gly Asn
465                 470                 475                 480

Trp Arg Ile Lys Arg Gln Val Leu Glu Gly Glu Ile Ala Tyr Lys
            485                 490                 495

Phe Thr Pro Lys Tyr Ile Leu Arg Ala Gly Gln Met Val Thr Val Trp
            500                 505                 510

Ala Ala Gly Ala Gly Val Ala His Ser Pro Pro Ser Thr Leu Val Trp
            515                 520                 525

Lys Gly Gln Ser Ser Trp Gly Thr Gly Glu Ser Phe Arg Thr Val Leu
530                 535                 540

Val Asn Ala Asp Gly Glu Glu Val Ala Met Arg Thr Val Lys Lys Ser
545                 550                 555                 560

Ser Val Met Arg Glu Asn Glu Asn Gly Glu Glu Glu Glu Glu Glu Ala
            565                 570                 575

Glu Phe Gly Glu Glu Asp Leu Phe His Gln Gln Gly Asp Pro Arg Thr
            580                 585                 590

Thr Ser Arg Gly Cys Tyr Val Met
            595                 600

<210> SEQ ID NO 9
<211> LENGTH: 664
<212> TYPE: PRT
<213> ORGANISM: Homo sapiens
<220> FEATURE:
<223> OTHER INFORMATION: lamin A/C (LMNA)

<400> SEQUENCE: 9

Met Glu Thr Pro Ser Gln Arg Arg Ala Thr Arg Ser Gly Ala Gln Ala
 1               5                  10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
                100                 105                 110

Phe Lys Glu Leu Lys Ala Arg Asn Thr Lys Lys Glu Gly Asp Leu Ile
            115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
                180                 185                 190
```

```
Ala Glu Asn Arg Leu Gln Thr Met Lys Glu Leu Asp Phe Gln Lys
    195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Gly Asp Asp
545                 550                 555                 560

Leu Leu His His His His Gly Ser His Cys Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620
```

```
Ser Tyr Arg Ser Val Gly Gly Ser Gly Gly Ser Phe Gly Asp Asn
625                 630                 635                 640

Leu Val Thr Arg Ser Tyr Leu Leu Gly Asn Ser Ser Pro Arg Thr Gln
            645                 650                 655

Ser Pro Gln Asn Cys Ser Ile Met
            660

<210> SEQ ID NO 10
<211> LENGTH: 375
<212> TYPE: PRT
<213> ORGANISM: Homo sapiens
<220> FEATURE:
<223> OTHER INFORMATION: beta actin (ACTB)

<400> SEQUENCE: 10

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320
```

```
Ala Pro Ser Thr Met Lys Ile Lys Ile Ile Ala Pro Pro Glu Arg Lys
            325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
            355                 360                 365

Ile Val His Arg Lys Cys Phe
            370             375

<210> SEQ ID NO 11
<211> LENGTH: 256
<212> TYPE: PRT
<213> ORGANISM: Homo sapiens
<220> FEATURE:
<223> OTHER INFORMATION: myeloblastin, proteinase 3 (PRTN3)

<400> SEQUENCE: 11

Met Ala His Arg Pro Pro Ser Pro Ala Leu Ala Ser Val Leu Leu Ala
 1               5                  10                  15

Leu Leu Leu Ser Gly Ala Ala Arg Ala Ala Glu Ile Val Gly Gly His
            20                  25                  30

Glu Ala Gln Pro His Ser Arg Pro Tyr Met Ala Ser Leu Gln Met Arg
        35                  40                  45

Gly Asn Pro Gly Ser His Phe Cys Gly Gly Thr Leu Ile His Pro Ser
    50                  55                  60

Phe Val Leu Thr Ala Ala His Cys Leu Arg Asp Ile Pro Gln Arg Leu
65                  70                  75                  80

Val Asn Val Val Leu Gly Ala His Asn Val Arg Thr Gln Glu Pro Thr
                85                  90                  95

Gln Gln His Phe Ser Val Ala Gln Val Phe Leu Asn Asn Tyr Asp Ala
            100                 105                 110

Glu Asn Lys Leu Asn Asp Val Leu Leu Ile Gln Leu Ser Ser Pro Ala
        115                 120                 125

Asn Leu Ser Ala Ser Val Ala Thr Val Gln Leu Pro Gln Gln Asp Gln
    130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
            180                 185                 190

Arg Arg Lys Ala Gly Ile Cys Phe Gly Asp Ser Gly Gly Pro Leu Ile
        195                 200                 205

Cys Asp Gly Ile Ile Gln Gly Ile Asp Ser Phe Val Ile Trp Gly Cys
    210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

<210> SEQ ID NO 12
<211> LENGTH: 318
<212> TYPE: PRT
<213> ORGANISM: Homo sapiens
<220> FEATURE:
<223> OTHER INFORMATION: phospholipid scramblase 1 (PLSCR1), PL
      scramblase

<400> SEQUENCE: 12
```

Met Asp Lys Gln Asn Ser Gln Met Asn Ala Ser His Pro Glu Thr Asn
1               5                   10                  15

Leu Pro Val Gly Tyr Pro Gln Tyr Pro Thr Ala Phe Gln Gly
            20                  25                  30

Pro Pro Gly Tyr Ser Gly Tyr Pro Gly Pro Gln Val Ser Tyr Pro Pro
            35                  40                  45

Pro Pro Ala Gly His Ser Gly Pro Gly Pro Ala Gly Phe Pro Val Pro
        50                  55                  60

Asn Gln Pro Val Tyr Asn Gln Pro Val Tyr Asn Gln Pro Val Gly Ala
65                  70                  75                  80

Ala Gly Val Pro Trp Met Pro Ala Pro Gln Pro Pro Leu Asn Cys Pro
                85                  90                  95

Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Pro Cys Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
        210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Trp Thr Gly Ile Leu Arg Glu Ala Phe Thr
            260                 265                 270

Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
290                 295                 300

Phe Glu Ser Thr Gly Ser Gln Glu Gln Lys Ser Gly Val Trp
305                 310                 315

<210> SEQ ID NO 13
<211> LENGTH: 4548
<212> TYPE: PRT
<213> ORGANISM: Homo sapiens
<220> FEATURE:
<223> OTHER INFORMATION: apolipoprotein (a)

<400> SEQUENCE: 13

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
            20                  25                  30

Gly Gln Ser Tyr Arg Gly Thr Tyr Ser Thr Thr Val Thr Gly Arg Thr
        35                  40                  45

```
-continued

Cys Gln Ala Trp Ser Ser Met Thr Pro His Gln His Asn Arg Thr Thr
     50                  55                  60

Glu Asn Tyr Pro Asn Ala Gly Leu Ile Met Asn Tyr Cys Arg Asn Pro
 65                  70                  75                  80

Asp Ala Val Ala Ala Pro Tyr Cys Tyr Thr Arg Asp Pro Gly Val Arg
                 85                  90                  95

Trp Glu Tyr Cys Asn Leu Thr Gln Cys Ser Asp Ala Glu Gly Thr Ala
            100                 105                 110

Val Ala Pro Pro Thr Val Thr Pro Val Pro Ser Leu Glu Ala Pro Ser
        115                 120                 125

Glu Gln Ala Pro Thr Glu Gln Arg Pro Gly Val Gln Glu Cys Tyr His
    130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
        195                 200                 205

Val Arg Trp Glu Tyr Cys Asn Leu Thr Gln Cys Ser Asp Ala Glu Gly
    210                 215                 220

Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
                245                 250                 255

Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
        275                 280                 285

Ser Arg Thr Pro Glu Tyr Tyr Pro Asn Ala Gly Leu Ile Met Asn Tyr
    290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
                325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
        355                 360                 365

Glu Cys Tyr His Gly Asn Gly Gln Ser Tyr Arg Gly Thr Tyr Ser Thr
    370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
        435                 440                 445

Asp Ala Glu Gly Thr Ala Val Ala Pro Pro Thr Val Thr Pro Val Pro
    450                 455                 460

Ser Leu Glu Ala Pro Ser Glu Gln Ala Pro Thr Glu Gln Arg Pro Gly
465                 470                 475                 480
```

-continued

```
Val Gln Glu Cys Tyr His Gly Asn Gly Gln Ser Tyr Arg Gly Thr Tyr
            485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
            515                 520                 525

Ile Met Asn Tyr Cys Arg Asn Pro Asp Ala Val Ala Ala Pro Tyr Cys
530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
                580                 585                 590

Pro Gly Val Gln Glu Cys Tyr His Gly Asn Gly Gln Ser Tyr Arg Gly
            595                 600                 605

Thr Tyr Ser Thr Thr Val Thr Gly Arg Thr Cys Gln Ala Trp Ser Ser
            610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                645                 650                 655

Tyr Cys Tyr Thr Arg Asp Pro Gly Val Arg Trp Glu Tyr Cys Asn Leu
                660                 665                 670

Thr Gln Cys Ser Asp Ala Glu Gly Thr Ala Val Ala Pro Pro Thr Val
            675                 680                 685

Thr Pro Val Pro Ser Leu Glu Ala Pro Ser Glu Gln Ala Pro Thr Glu
            690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
            835                 840                 845

Ala Trp Ser Ser Met Thr Pro His Ser His Ser Arg Thr Pro Glu Tyr
            850                 855                 860

Tyr Pro Asn Ala Gly Leu Ile Met Asn Tyr Cys Arg Asn Pro Asp Ala
865                 870                 875                 880

Val Ala Ala Pro Tyr Cys Tyr Thr Arg Asp Pro Gly Val Arg Trp Glu
                885                 890                 895

Tyr Cys Asn Leu Thr Gln Cys Ser Asp Ala Glu Gly Thr Ala Val Ala
```

-continued

```
                900             905             910
Pro Pro Thr Val Thr Pro Val Pro Ser Leu Glu Ala Pro Ser Glu Gln
    915                 920                 925

Ala Pro Thr Glu Gln Arg Pro Gly Val Gln Glu Cys Tyr His Gly Asn
    930                 935                 940

Gly Gln Ser Tyr Arg Gly Thr Tyr Ser Thr Thr Val Thr Gly Arg Thr
945                 950                 955                 960

Cys Gln Ala Trp Ser Ser Met Thr Pro His Ser His Ser Arg Thr Pro
                965                 970                 975

Glu Tyr Tyr Pro Asn Ala Gly Leu Ile Met Asn Tyr Cys Arg Asn Pro
                980                 985                 990

Asp Ala Val Ala Ala Pro Tyr Cys Tyr Thr Arg Asp Pro Gly Val Arg
                995                 1000                1005

Trp Glu Tyr Cys Asn Leu Thr Gln Cys Ser Asp Ala Glu Gly Thr Ala
    1010                1015                1020

Val Ala Pro Pro Thr Val Thr Pro Val Pro Ser Leu Glu Ala Pro Ser
1025                1030                1035                1040

Glu Gln Ala Pro Thr Glu Gln Arg Pro Gly Val Gln Glu Cys Tyr His
                1045                1050                1055

Gly Asn Gly Gln Ser Tyr Arg Gly Thr Tyr Ser Thr Thr Val Thr Gly
                1060                1065                1070

Arg Thr Cys Gln Ala Trp Ser Ser Met Thr Pro His Ser His Ser Arg
                1075                1080                1085

Thr Pro Glu Tyr Tyr Pro Asn Ala Gly Leu Ile Met Asn Tyr Cys Arg
                1090                1095                1100

Asn Pro Asp Ala Val Ala Ala Pro Tyr Cys Tyr Thr Arg Asp Pro Gly
1105                1110                1115                1120

Val Arg Trp Glu Tyr Cys Asn Leu Thr Gln Cys Ser Asp Ala Glu Gly
                1125                1130                1135

Thr Ala Val Ala Pro Pro Thr Val Thr Pro Val Pro Ser Leu Glu Ala
                1140                1145                1150

Pro Ser Glu Gln Ala Pro Thr Glu Gln Arg Pro Gly Val Gln Glu Cys
                1155                1160                1165

Tyr His Gly Asn Gly Gln Ser Tyr Arg Gly Thr Tyr Ser Thr Thr Val
    1170                1175                1180

Thr Gly Arg Thr Cys Gln Ala Trp Ser Ser Met Thr Pro His Ser His
1185                1190                1195                1200

Ser Arg Thr Pro Glu Tyr Tyr Pro Asn Ala Gly Leu Ile Met Asn Tyr
                1205                1210                1215

Cys Arg Asn Pro Asp Ala Val Ala Ala Pro Tyr Cys Tyr Thr Arg Asp
                1220                1225                1230

Pro Gly Val Arg Trp Glu Tyr Cys Asn Leu Thr Gln Cys Ser Asp Ala
                1235                1240                1245

Glu Gly Thr Ala Val Ala Pro Pro Thr Val Thr Pro Val Pro Ser Leu
                1250                1255                1260

Glu Ala Pro Ser Glu Gln Ala Pro Thr Glu Gln Arg Pro Gly Val Gln
1265                1270                1275                1280

Glu Cys Tyr His Gly Asn Gly Gln Ser Tyr Arg Gly Thr Tyr Ser Thr
                1285                1290                1295

Thr Val Thr Gly Arg Thr Cys Gln Ala Trp Ser Ser Met Thr Pro His
                1300                1305                1310

Ser His Ser Arg Thr Pro Glu Tyr Tyr Pro Asn Ala Gly Leu Ile Met
                1315                1320                1325
```

-continued

```
Asn Tyr Cys Arg Asn Pro Asp Ala Val Ala Ala Pro Tyr Cys Tyr Thr
        1330                1335                1340

Arg Asp Pro Gly Val Arg Trp Glu Tyr Cys Asn Leu Thr Gln Cys Ser
1345                1350                1355                1360

Asp Ala Glu Gly Thr Ala Val Ala Pro Pro Thr Val Thr Pro Val Pro
            1365                1370                1375

Ser Leu Glu Ala Pro Ser Glu Gln Ala Pro Thr Glu Gln Arg Pro Gly
        1380                1385                1390

Val Gln Glu Cys Tyr His Gly Asn Gly Gln Ser Tyr Arg Gly Thr Tyr
    1395                1400                1405

Ser Thr Thr Val Thr Gly Arg Thr Cys Gln Ala Trp Ser Ser Met Thr
    1410                1415                1420

Pro His Ser His Ser Arg Thr Pro Glu Tyr Tyr Pro Asn Ala Gly Leu
1425                1430                1435                1440

Ile Met Asn Tyr Cys Arg Asn Pro Asp Ala Val Ala Ala Pro Tyr Cys
                1445                1450                1455

Tyr Thr Arg Asp Pro Gly Val Arg Trp Glu Tyr Cys Asn Leu Thr Gln
            1460                1465                1470

Cys Ser Asp Ala Glu Gly Thr Ala Val Ala Pro Pro Thr Val Thr Pro
        1475                1480                1485

Val Pro Ser Leu Glu Ala Pro Ser Glu Gln Ala Pro Thr Glu Gln Arg
    1490                1495                1500

Pro Gly Val Gln Glu Cys Tyr His Gly Asn Gly Gln Ser Tyr Arg Gly
1505                1510                1515                1520

Thr Tyr Ser Thr Thr Val Thr Gly Arg Thr Cys Gln Ala Trp Ser Ser
                1525                1530                1535

Met Thr Pro His Ser His Ser Arg Thr Pro Glu Tyr Tyr Pro Asn Ala
            1540                1545                1550

Gly Leu Ile Met Asn Tyr Cys Arg Asn Pro Asp Ala Val Ala Ala Pro
        1555                1560                1565

Tyr Cys Tyr Thr Arg Asp Pro Gly Val Arg Trp Glu Tyr Cys Asn Leu
    1570                1575                1580

Thr Gln Cys Ser Asp Ala Glu Gly Thr Ala Val Ala Pro Pro Thr Val
1585                1590                1595                1600

Thr Pro Val Pro Ser Leu Glu Ala Pro Ser Glu Gln Ala Pro Thr Glu
                1605                1610                1615

Gln Arg Pro Gly Val Gln Glu Cys Tyr His Gly Asn Gly Gln Ser Tyr
            1620                1625                1630

Arg Gly Thr Tyr Ser Thr Thr Val Thr Gly Arg Thr Cys Gln Ala Trp
        1635                1640                1645

Ser Ser Met Thr Pro His Ser His Ser Arg Thr Pro Glu Tyr Tyr Pro
    1650                1655                1660

Asn Ala Gly Leu Ile Met Asn Tyr Cys Arg Asn Pro Asp Ala Val Ala
1665                1670                1675                1680

Ala Pro Tyr Cys Tyr Thr Arg Asp Pro Gly Val Arg Trp Glu Tyr Cys
                1685                1690                1695

Asn Leu Thr Gln Cys Ser Asp Ala Glu Gly Thr Ala Val Ala Pro Pro
            1700                1705                1710

Thr Val Thr Pro Val Pro Ser Leu Glu Ala Pro Ser Glu Gln Ala Pro
        1715                1720                1725

Thr Glu Gln Arg Pro Gly Val Gln Glu Cys Tyr His Gly Asn Gly Gln
    1730                1735                1740

Ser Tyr Arg Gly Thr Tyr Ser Thr Thr Val Thr Gly Arg Thr Cys Gln
1745                1750                1755                1760
```

-continued

Ala Trp Ser Ser Met Thr Pro His Ser His Ser Arg Thr Pro Glu Tyr
            1765                1770                1775

Tyr Pro Asn Ala Gly Leu Ile Met Asn Tyr Cys Arg Asn Pro Asp Ala
        1780                1785                1790

Val Ala Ala Pro Tyr Cys Tyr Thr Arg Asp Pro Gly Val Arg Trp Glu
    1795                1800                1805

Tyr Cys Asn Leu Thr Gln Cys Ser Asp Ala Glu Gly Thr Ala Val Ala
    1810                1815                1820

Pro Pro Thr Val Thr Pro Val Pro Ser Leu Glu Ala Pro Ser Glu Gln
1825                1830                1835                1840

Ala Pro Thr Glu Gln Arg Pro Gly Val Gln Glu Cys Tyr His Gly Asn
            1845                1850                1855

Gly Gln Ser Tyr Arg Gly Thr Tyr Ser Thr Thr Val Thr Gly Arg Thr
            1860                1865                1870

Cys Gln Ala Trp Ser Ser Met Thr Pro His Ser His Ser Arg Thr Pro
        1875                1880                1885

Glu Tyr Tyr Pro Asn Ala Gly Leu Ile Met Asn Tyr Cys Arg Asn Pro
    1890                1895                1900

Asp Ala Val Ala Ala Pro Tyr Cys Tyr Thr Arg Asp Pro Gly Val Arg
1905                1910                1915                1920

Trp Glu Tyr Cys Asn Leu Thr Gln Cys Ser Asp Ala Glu Gly Thr Ala
            1925                1930                1935

Val Ala Pro Pro Thr Val Thr Pro Val Pro Ser Leu Glu Ala Pro Ser
        1940                1945                1950

Glu Gln Ala Pro Thr Glu Gln Arg Pro Gly Val Gln Glu Cys Tyr His
    1955                1960                1965

Gly Asn Gly Gln Ser Tyr Arg Gly Thr Tyr Ser Thr Thr Val Thr Gly
    1970                1975                1980

Arg Thr Cys Gln Ala Trp Ser Ser Met Thr Pro His Ser His Ser Arg
1985                1990                1995                2000

Thr Pro Glu Tyr Tyr Pro Asn Ala Gly Leu Ile Met Asn Tyr Cys Arg
            2005                2010                2015

Asn Pro Asp Ala Val Ala Ala Pro Tyr Cys Tyr Thr Arg Asp Pro Gly
        2020                2025                2030

Val Arg Trp Glu Tyr Cys Asn Leu Thr Gln Cys Ser Asp Ala Glu Gly
    2035                2040                2045

Thr Ala Val Ala Pro Pro Thr Val Thr Pro Val Pro Ser Leu Glu Ala
    2050                2055                2060

Pro Ser Glu Gln Ala Pro Thr Glu Gln Arg Pro Gly Val Gln Glu Cys
2065                2070                2075                2080

Tyr His Gly Asn Gly Gln Ser Tyr Arg Gly Thr Tyr Ser Thr Thr Val
            2085                2090                2095

Thr Gly Arg Thr Cys Gln Ala Trp Ser Ser Met Thr Pro His Ser His
        2100                2105                2110

Ser Arg Thr Pro Glu Tyr Tyr Pro Asn Ala Gly Leu Ile Met Asn Tyr
    2115                2120                2125

Cys Arg Asn Pro Asp Ala Val Ala Ala Pro Tyr Cys Tyr Thr Arg Asp
    2130                2135                2140

Pro Gly Val Arg Trp Glu Tyr Cys Asn Leu Thr Gln Cys Ser Asp Ala
2145                2150                2155                2160

Glu Gly Thr Ala Val Ala Pro Pro Thr Val Thr Pro Val Pro Ser Leu
            2165                2170                2175

Glu Ala Pro Ser Glu Gln Ala Pro Thr Glu Gln Arg Pro Gly Val Gln

-continued

```
                2180                2185                2190
Glu Cys Tyr His Gly Asn Gly Gln Ser Tyr Arg Gly Thr Tyr Ser Thr
            2195                2200                2205
Thr Val Thr Gly Arg Thr Cys Gln Ala Trp Ser Ser Met Thr Pro His
            2210                2215                2220
Ser His Ser Arg Thr Pro Glu Tyr Tyr Pro Asn Ala Gly Leu Ile Met
2225                2230                2235                2240
Asn Tyr Cys Arg Asn Pro Asp Ala Val Ala Ala Pro Tyr Cys Tyr Thr
            2245                2250                2255
Arg Asp Pro Gly Val Arg Trp Glu Tyr Cys Asn Leu Thr Gln Cys Ser
            2260                2265                2270
Asp Ala Glu Gly Thr Ala Val Ala Pro Pro Thr Val Thr Pro Val Pro
            2275                2280                2285
Ser Leu Glu Ala Pro Ser Glu Gln Ala Pro Thr Glu Gln Arg Pro Gly
            2290                2295                2300
Val Gln Glu Cys Tyr His Gly Asn Gly Gln Ser Tyr Arg Gly Thr Tyr
2305                2310                2315                2320
Ser Thr Thr Val Thr Gly Arg Thr Cys Gln Ala Trp Ser Ser Met Thr
                2325                2330                2335
Pro His Ser His Ser Arg Thr Pro Glu Tyr Tyr Pro Asn Ala Gly Leu
            2340                2345                2350
Ile Met Asn Tyr Cys Arg Asn Pro Asp Ala Val Ala Ala Pro Tyr Cys
            2355                2360                2365
Tyr Thr Arg Asp Pro Gly Val Arg Trp Glu Tyr Cys Asn Leu Thr Gln
            2370                2375                2380
Cys Ser Asp Ala Glu Gly Thr Ala Val Ala Pro Pro Thr Val Thr Pro
2385                2390                2395                2400
Val Pro Ser Leu Glu Ala Pro Ser Glu Gln Ala Pro Thr Glu Gln Arg
            2405                2410                2415
Pro Gly Val Gln Glu Cys Tyr His Gly Asn Gly Gln Ser Tyr Arg Gly
            2420                2425                2430
Thr Tyr Ser Thr Thr Val Thr Gly Arg Thr Cys Gln Ala Trp Ser Ser
            2435                2440                2445
Met Thr Pro His Ser His Ser Arg Thr Pro Glu Tyr Tyr Pro Asn Ala
            2450                2455                2460
Gly Leu Ile Met Asn Tyr Cys Arg Asn Pro Asp Ala Val Ala Ala Pro
2465                2470                2475                2480
Tyr Cys Tyr Thr Arg Asp Pro Gly Val Arg Trp Glu Tyr Cys Asn Leu
            2485                2490                2495
Thr Gln Cys Ser Asp Ala Glu Gly Thr Ala Val Ala Pro Pro Thr Val
            2500                2505                2510
Thr Pro Val Pro Ser Leu Glu Ala Pro Ser Glu Gln Ala Pro Thr Glu
            2515                2520                2525
Gln Arg Pro Gly Val Gln Glu Cys Tyr His Gly Asn Gly Gln Ser Tyr
            2530                2535                2540
Arg Gly Thr Tyr Ser Thr Thr Val Thr Gly Arg Thr Cys Gln Ala Trp
2545                2550                2555                2560
Ser Ser Met Thr Pro His Ser His Ser Arg Thr Pro Glu Tyr Tyr Pro
                2565                2570                2575
Asn Ala Gly Leu Ile Met Asn Tyr Cys Arg Asn Pro Asp Ala Val Ala
            2580                2585                2590
Ala Pro Tyr Cys Tyr Thr Arg Asp Pro Gly Val Arg Trp Glu Tyr Cys
            2595                2600                2605
```

```
Asn Leu Thr Gln Cys Ser Asp Ala Glu Gly Thr Ala Val Ala Pro Pro
    2610                2615                2620

Thr Val Thr Pro Val Pro Ser Leu Glu Ala Pro Ser Glu Gln Ala Pro
2625                2630                2635                2640

Thr Glu Gln Arg Pro Gly Val Gln Glu Cys Tyr His Gly Asn Gly Gln
            2645                2650                2655

Ser Tyr Arg Gly Thr Tyr Ser Thr Thr Val Thr Gly Arg Thr Cys Gln
            2660                2665                2670

Ala Trp Ser Ser Met Thr Pro His Ser His Ser Arg Thr Pro Glu Tyr
            2675                2680                2685

Tyr Pro Asn Ala Gly Leu Ile Met Asn Tyr Cys Arg Asn Pro Asp Ala
    2690                2695                2700

Val Ala Ala Pro Tyr Cys Tyr Thr Arg Asp Pro Gly Val Arg Trp Glu
2705                2710                2715                2720

Tyr Cys Asn Leu Thr Gln Cys Ser Asp Ala Glu Gly Thr Ala Val Ala
            2725                2730                2735

Pro Pro Thr Val Thr Pro Val Pro Ser Leu Glu Ala Pro Ser Glu Gln
            2740                2745                2750

Ala Pro Thr Glu Gln Arg Pro Gly Val Gln Glu Cys Tyr His Gly Asn
            2755                2760                2765

Gly Gln Ser Tyr Arg Gly Thr Tyr Ser Thr Thr Val Thr Gly Arg Thr
    2770                2775                2780

Cys Gln Ala Trp Ser Ser Met Thr Pro His Ser His Ser Arg Thr Pro
2785                2790                2795                2800

Glu Tyr Tyr Pro Asn Ala Gly Leu Ile Met Asn Tyr Cys Arg Asn Pro
            2805                2810                2815

Asp Ala Val Ala Ala Pro Tyr Cys Tyr Thr Arg Asp Pro Gly Val Arg
            2820                2825                2830

Trp Glu Tyr Cys Asn Leu Thr Gln Cys Ser Asp Ala Glu Gly Thr Ala
            2835                2840                2845

Val Ala Pro Pro Thr Val Thr Pro Val Pro Ser Leu Glu Ala Pro Ser
    2850                2855                2860

Glu Gln Ala Pro Thr Glu Gln Arg Pro Gly Val Gln Glu Cys Tyr His
2865                2870                2875                2880

Gly Asn Gly Gln Ser Tyr Arg Gly Thr Tyr Ser Thr Thr Val Thr Gly
            2885                2890                2895

Arg Thr Cys Gln Ala Trp Ser Ser Met Thr Pro His Ser His Ser Arg
            2900                2905                2910

Thr Pro Glu Tyr Tyr Pro Asn Ala Gly Leu Ile Met Asn Tyr Cys Arg
            2915                2920                2925

Asn Pro Asp Ala Val Ala Ala Pro Tyr Cys Tyr Thr Arg Asp Pro Gly
    2930                2935                2940

Val Arg Trp Glu Tyr Cys Asn Leu Thr Gln Cys Ser Asp Ala Glu Gly
2945                2950                2955                2960

Thr Ala Val Ala Pro Pro Thr Val Thr Pro Val Pro Ser Leu Glu Ala
            2965                2970                2975

Pro Ser Glu Gln Ala Pro Thr Glu Gln Arg Pro Gly Val Gln Glu Cys
            2980                2985                2990

Tyr His Gly Asn Gly Gln Ser Tyr Arg Gly Thr Tyr Ser Thr Thr Val
            2995                3000                3005

Thr Gly Arg Thr Cys Gln Ala Trp Ser Ser Met Thr Pro His Ser His
    3010                3015                3020

Ser Arg Thr Pro Glu Tyr Tyr Pro Asn Ala Gly Leu Ile Met Asn Tyr
3025                3030                3035                3040
```

-continued

```
Cys Arg Asn Pro Asp Ala Val Ala Ala Pro Tyr Cys Tyr Thr Arg Asp
            3045                3050                3055

Pro Gly Val Arg Trp Glu Tyr Cys Asn Leu Thr Gln Cys Ser Asp Ala
        3060                3065                3070

Glu Gly Thr Ala Val Ala Pro Pro Thr Val Thr Pro Val Pro Ser Leu
        3075                3080                3085

Glu Ala Pro Ser Glu Gln Ala Pro Thr Glu Gln Arg Pro Gly Val Gln
        3090                3095                3100

Glu Cys Tyr His Gly Asn Gly Gln Ser Tyr Arg Gly Thr Tyr Ser Thr
3105                3110                3115                3120

Thr Val Thr Gly Arg Thr Cys Gln Ala Trp Ser Ser Met Thr Pro His
                3125                3130                3135

Ser His Ser Arg Thr Pro Glu Tyr Tyr Pro Asn Ala Gly Leu Ile Met
            3140                3145                3150

Asn Tyr Cys Arg Asn Pro Asp Ala Val Ala Ala Pro Tyr Cys Tyr Thr
        3155                3160                3165

Arg Asp Pro Gly Val Arg Trp Glu Tyr Cys Asn Leu Thr Gln Cys Ser
    3170                3175                3180

Asp Ala Glu Gly Thr Ala Val Ala Pro Pro Thr Val Thr Pro Val Pro
3185                3190                3195                3200

Ser Leu Glu Ala Pro Ser Glu Gln Ala Pro Thr Glu Gln Arg Pro Gly
            3205                3210                3215

Val Gln Glu Cys Tyr His Gly Asn Gly Gln Ser Tyr Arg Gly Thr Tyr
        3220                3225                3230

Ser Thr Thr Val Thr Gly Arg Thr Cys Gln Ala Trp Ser Ser Met Thr
        3235                3240                3245

Pro His Ser His Ser Arg Thr Pro Glu Tyr Tyr Pro Asn Ala Gly Leu
        3250                3255                3260

Ile Met Asn Tyr Cys Arg Asn Pro Asp Ala Val Ala Ala Pro Tyr Cys
3265                3270                3275                3280

Tyr Thr Arg Asp Pro Gly Val Arg Trp Glu Tyr Cys Asn Leu Thr Gln
            3285                3290                3295

Cys Ser Asp Ala Glu Gly Thr Ala Val Ala Pro Pro Thr Val Thr Pro
        3300                3305                3310

Val Pro Ser Leu Glu Ala Pro Ser Glu Gln Ala Pro Thr Glu Gln Arg
        3315                3320                3325

Pro Gly Val Gln Glu Cys Tyr His Gly Asn Gly Gln Ser Tyr Arg Gly
    3330                3335                3340

Thr Tyr Ser Thr Thr Val Thr Gly Arg Thr Cys Gln Ala Trp Ser Ser
3345                3350                3355                3360

Met Thr Pro His Ser His Ser Arg Thr Pro Glu Tyr Tyr Pro Asn Ala
            3365                3370                3375

Gly Leu Ile Met Asn Tyr Cys Arg Asn Pro Asp Pro Val Ala Ala Pro
        3380                3385                3390

Tyr Cys Tyr Thr Arg Asp Pro Ser Val Arg Trp Glu Tyr Cys Asn Leu
        3395                3400                3405

Thr Gln Cys Ser Asp Ala Glu Gly Thr Ala Val Ala Pro Pro Thr Ile
        3410                3415                3420

Thr Pro Ile Pro Ser Leu Glu Ala Pro Ser Glu Gln Ala Pro Thr Glu
3425                3430                3435                3440

Gln Arg Pro Gly Val Gln Glu Cys Tyr His Gly Asn Gly Gln Ser Tyr
            3445                3450                3455

Gln Gly Thr Tyr Phe Ile Thr Val Thr Gly Arg Thr Cys Gln Ala Trp
```

-continued

```
                    3460                3465                3470
Ser Ser Met Thr Pro His Ser His Ser Arg Thr Pro Ala Tyr Tyr Pro
            3475                3480                3485
Asn Ala Gly Leu Ile Lys Asn Tyr Cys Arg Asn Pro Asp Pro Val Ala
            3490                3495                3500
Ala Pro Trp Cys Tyr Thr Thr Asp Pro Ser Val Arg Trp Glu Tyr Cys
3505                3510                3515                3520
Asn Leu Thr Arg Cys Ser Asp Ala Glu Trp Thr Ala Phe Val Pro Pro
            3525                3530                3535
Asn Val Ile Leu Ala Pro Ser Leu Glu Ala Phe Phe Glu Gln Ala Leu
            3540                3545                3550
Thr Glu Glu Thr Pro Gly Val Gln Asp Cys Tyr Tyr His Tyr Gly Gln
            3555                3560                3565
Ser Tyr Arg Gly Thr Tyr Ser Thr Val Thr Gly Arg Thr Cys Gln
            3570                3575                3580
Ala Trp Ser Ser Met Thr Pro His Gln His Ser Arg Thr Pro Glu Asn
3585                3590                3595                3600
Tyr Pro Asn Ala Gly Leu Thr Arg Asn Tyr Cys Arg Asn Pro Asp Ala
            3605                3610                3615
Glu Ile Arg Pro Trp Cys Tyr Thr Met Asp Pro Ser Val Arg Trp Glu
            3620                3625                3630
Tyr Cys Asn Leu Thr Gln Cys Leu Val Thr Glu Ser Ser Val Leu Ala
            3635                3640                3645
Thr Leu Thr Val Val Pro Asp Pro Ser Thr Glu Ala Ser Ser Glu Glu
            3650                3655                3660
Ala Pro Thr Glu Gln Ser Pro Gly Val Gln Asp Cys Tyr His Gly Asp
3665                3670                3675                3680
Gly Gln Ser Tyr Arg Gly Ser Phe Ser Thr Thr Val Thr Gly Arg Thr
            3685                3690                3695
Cys Gln Ser Trp Ser Ser Met Thr Pro His Trp His Gln Arg Thr Thr
            3700                3705                3710
Glu Tyr Tyr Pro Asn Gly Gly Leu Thr Arg Asn Tyr Cys Arg Asn Pro
            3715                3720                3725
Asp Ala Glu Ile Ser Pro Trp Cys Tyr Thr Met Asp Pro Asn Val Arg
            3730                3735                3740
Trp Glu Tyr Cys Asn Leu Thr Gln Cys Pro Val Thr Glu Ser Ser Val
3745                3750                3755                3760
Leu Ala Thr Ser Thr Ala Val Ser Glu Gln Ala Pro Thr Glu Gln Ser
            3765                3770                3775
Pro Thr Val Gln Asp Cys Tyr His Gly Asp Gly Gln Ser Tyr Arg Gly
            3780                3785                3790
Ser Phe Ser Thr Thr Val Thr Gly Arg Thr Cys Gln Ser Trp Ser Ser
            3795                3800                3805
Met Thr Pro His Trp His Gln Arg Thr Thr Glu Tyr Tyr Pro Asn Gly
            3810                3815                3820
Gly Leu Thr Arg Asn Tyr Cys Arg Asn Pro Asp Ala Glu Ile Arg Pro
3825                3830                3835                3840
Trp Cys Tyr Thr Met Asp Pro Ser Val Arg Trp Glu Tyr Cys Asn Leu
            3845                3850                3855
Thr Gln Cys Pro Val Met Glu Ser Thr Leu Leu Thr Pro Thr Val
            3860                3865                3870
Val Pro Val Pro Ser Thr Glu Leu Pro Ser Glu Glu Ala Pro Thr Glu
            3875                3880                3885
```

```
Asn Ser Thr Gly Val Gln Asp Cys Tyr Arg Gly Asp Gly Gln Ser Tyr
    3890                3895                3900

Arg Gly Thr Leu Ser Thr Thr Ile Thr Gly Arg Thr Cys Gln Ser Trp
3905                3910                3915                3920

Ser Ser Met Thr Pro His Trp His Arg Arg Ile Pro Leu Tyr Tyr Pro
            3925                3930                3935

Asn Ala Gly Leu Thr Arg Asn Tyr Cys Arg Asn Pro Asp Ala Glu Ile
            3940                3945                3950

Arg Pro Trp Cys Tyr Thr Met Asp Pro Ser Val Arg Trp Glu Tyr Cys
        3955                3960                3965

Asn Leu Thr Arg Cys Pro Val Thr Glu Ser Ser Val Leu Thr Thr Pro
        3970                3975                3980

Thr Val Ala Pro Val Pro Ser Thr Glu Ala Pro Ser Glu Gln Ala Pro
3985                3990                3995                4000

Pro Glu Lys Ser Pro Val Val Gln Asp Cys Tyr His Gly Asp Gly Arg
                4005                4010                4015

Ser Tyr Arg Gly Ile Ser Ser Thr Thr Val Thr Gly Arg Thr Cys Gln
            4020                4025                4030

Ser Trp Ser Ser Met Ile Pro His Trp His Gln Arg Thr Pro Glu Asn
        4035                4040                4045

Tyr Pro Asn Ala Gly Leu Thr Glu Asn Tyr Cys Arg Asn Pro Asp Ser
    4050                4055                4060

Gly Lys Gln Pro Trp Cys Tyr Thr Thr Asp Pro Cys Val Arg Trp Glu
4065                4070                4075                4080

Tyr Cys Asn Leu Thr Gln Cys Ser Glu Thr Glu Ser Gly Val Leu Glu
            4085                4090                4095

Thr Pro Thr Val Val Pro Val Pro Ser Met Glu Ala His Ser Glu Ala
            4100                4105                4110

Ala Pro Thr Glu Gln Thr Pro Val Val Arg Gln Cys Tyr His Gly Asn
        4115                4120                4125

Gly Gln Ser Tyr Arg Gly Thr Phe Ser Thr Thr Val Thr Gly Arg Thr
        4130                4135                4140

Cys Gln Ser Trp Ser Ser Met Thr Pro His Arg His Gln Arg Thr Pro
4145                4150                4155                4160

Glu Asn Tyr Pro Asn Asp Gly Leu Thr Met Asn Tyr Cys Arg Asn Pro
                4165                4170                4175

Asp Ala Asp Thr Gly Pro Trp Cys Phe Thr Met Asp Pro Ser Ile Arg
            4180                4185                4190

Trp Glu Tyr Cys Asn Leu Thr Arg Cys Ser Asp Thr Glu Gly Thr Val
        4195                4200                4205

Val Ala Pro Pro Thr Val Ile Gln Val Pro Ser Leu Gly Pro Pro Ser
    4210                4215                4220

Glu Gln Asp Cys Met Phe Gly Asn Gly Lys Gly Tyr Arg Gly Lys Lys
4225                4230                4235                4240

Ala Thr Thr Val Thr Gly Thr Pro Cys Gln Glu Trp Ala Ala Gln Glu
            4245                4250                4255

Pro His Arg His Ser Thr Phe Ile Pro Gly Thr Asn Lys Trp Ala Gly
            4260                4265                4270

Leu Glu Lys Asn Tyr Cys Arg Asn Pro Asp Gly Asp Ile Asn Gly Pro
        4275                4280                4285

Trp Cys Tyr Thr Met Asn Pro Arg Lys Leu Phe Asp Tyr Cys Asp Ile
    4290                4295                4300

Pro Leu Cys Ala Ser Ser Ser Phe Asp Cys Gly Lys Pro Gln Val Glu
4305                4310                4315                4320
```

```
Pro Lys Lys Cys Pro Gly Ser Ile Val Gly Gly Cys Val Ala His Pro
                4325                4330                4335

His Ser Trp Pro Trp Gln Val Ser Leu Arg Thr Arg Phe Gly Lys His
            4340                4345                4350

Phe Cys Gly Gly Thr Leu Ile Ser Pro Glu Trp Val Leu Thr Ala Ala
        4355                4360                4365

His Cys Leu Lys Lys Ser Ser Arg Pro Ser Ser Tyr Lys Val Ile Leu
    4370                4375                4380

Gly Ala His Gln Glu Val Asn Leu Glu Ser His Val Gln Glu Ile Glu
4385                4390                4395                4400

Val Ser Arg Leu Phe Leu Glu Pro Thr Gln Ala Asp Ile Ala Leu Leu
                4405                4410                4415

Lys Leu Ser Arg Pro Ala Val Ile Thr Asp Lys Val Met Pro Ala Cys
            4420                4425                4430

Leu Pro Ser Pro Asp Tyr Met Val Thr Ala Arg Thr Glu Cys Tyr Ile
        4435                4440                4445

Thr Gly Trp Gly Glu Thr Gln Gly Thr Phe Gly Thr Gly Leu Leu Lys
    4450                4455                4460

Glu Ala Gln Leu Leu Val Ile Glu Asn Glu Val Cys Asn His Tyr Lys
4465                4470                4475                4480

Tyr Ile Cys Ala Glu His Leu Ala Arg Gly Thr Asp Ser Cys Gln Gly
                4485                4490                4495

Asp Ser Gly Gly Pro Leu Val Cys Phe Glu Lys Asp Lys Tyr Ile Leu
            4500                4505                4510

Gln Gly Val Thr Ser Trp Gly Leu Gly Cys Ala Arg Pro Asn Lys Pro
        4515                4520                4525

Gly Val Tyr Ala Arg Val Ser Arg Phe Val Thr Trp Ile Glu Gly Met
    4530                4535                4540

Met Arg Asn Asn
4545

<210> SEQ ID NO 14
<211> LENGTH: 654
<212> TYPE: PRT
<213> ORGANISM: Homo sapiens
<220> FEATURE:
<223> OTHER INFORMATION: heat shock 70kDa protein 5  (HSPA5),
      glucose-regulated protein, 70kDa, BiP

<400> SEQUENCE: 14

Met Lys Leu Ser Leu Val Ala Ala Met Leu Leu Leu Leu Ser Ala Ala
 1               5                  10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125
```

```
Gln Val Asp Ile Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ile Ala
            195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
                275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
                355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
    435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
                515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
```

```
                545                 550                 555                 560
Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
                580                 585                 590

Thr Met Glu Lys Ala Val Glu Glu Lys Ile Glu Trp Leu Glu Ser His
                595                 600                 605

Gln Asp Ala Asp Ile Glu Asp Phe Lys Ala Lys Lys Glu Leu Glu
                610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 15
<211> LENGTH: 130
<212> TYPE: PRT
<213> ORGANISM: Homo sapiens
<220> FEATURE:
<223> OTHER INFORMATION: histone H2A, histone cluster 3, H2a (HIST3H2A)

<400> SEQUENCE: 15

Met Ser Gly Arg Gly Lys Gln Gly Gly Lys Ala Arg Ala Lys Ala Lys
1               5                   10                  15

Ser Arg Ser Ser Arg Ala Gly Leu Gln Phe Pro Val Gly Arg Val His
                20                  25                  30

Arg Leu Leu Arg Lys Gly Asn Tyr Ser Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
                100                 105                 110

Gln Ala Val Leu Leu Pro Lys Lys Thr Glu Ser His His Lys Ala Lys
            115                 120                 125

Gly Lys
    130

<210> SEQ ID NO 16
<211> LENGTH: 126
<212> TYPE: PRT
<213> ORGANISM: Homo sapiens
<220> FEATURE:
<223> OTHER INFORMATION: histone H2B, histone cluster 3, H2bb
      (HIST3H2BB)

<400> SEQUENCE: 16

Met Pro Asp Pro Ser Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Gly Arg Lys Glu Ser Tyr Ser Ile Tyr Val Tyr Lys Val Leu Lys Gln
            35                  40                  45

Val His Pro Asp Thr Gly Ile Ser Ser Lys Ala Met Gly Ile Met Asn
        50                  55                  60
```

```
Ser Phe Val Asn Asp Ile Phe Glu Arg Ile Ala Ser Glu Ala Ser Arg
 65                  70                  75                  80

Leu Ala His Tyr Asn Lys Arg Ser Thr Ile Thr Ser Arg Glu Val Gln
                 85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 17
<211> LENGTH: 136
<212> TYPE: PRT
<213> ORGANISM: Homo sapiens
<220> FEATURE:
<223> OTHER INFORMATION: histone H3.1, histone cluster 1, H3c (HIST1H3C)

<400> SEQUENCE: 17

```
Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ala
             20                  25                  30

Thr Gly Gly Val Lys Lys Pro His Arg Tyr Arg Pro Gly Thr Val Ala
         35                  40                  45

Leu Arg Glu Ile Arg Arg Tyr Gln Lys Ser Thr Glu Leu Leu Ile Arg
 50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ser Ala Val Met Ala Leu Gln Glu Ala
                 85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
130                 135
```

<210> SEQ ID NO 18
<211> LENGTH: 136
<212> TYPE: PRT
<213> ORGANISM: Homo sapiens
<220> FEATURE:
<223> OTHER INFORMATION: histone H3.2, histone cluster 2, H3c (HIST2H3C)

<400> SEQUENCE: 18

```
Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ala
             20                  25                  30

Thr Gly Gly Val Lys Lys Pro His Arg Tyr Arg Pro Gly Thr Val Ala
         35                  40                  45

Leu Arg Glu Ile Arg Arg Tyr Gln Lys Ser Thr Glu Leu Leu Ile Arg
 50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ser Ala Val Met Ala Leu Gln Glu Ala
                 85                  90                  95

Ser Glu Ala Tyr Leu Val Gly Leu Phe Glu Asp Thr Asn Leu Cys Ala
            100                 105                 110
```

```
Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 19
<211> LENGTH: 136
<212> TYPE: PRT
<213> ORGANISM: Homo sapiens
<220> FEATURE:
<223> OTHER INFORMATION: histone H3.3, H3 histone, family 3A (H3F3A)

<400> SEQUENCE: 19

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 20
<211> LENGTH: 136
<212> TYPE: PRT
<213> ORGANISM: Homo sapiens
<220> FEATURE:
<223> OTHER INFORMATION: histone H3.4, histone cluster 3, H3 (HIST3H3)

<400> SEQUENCE: 20

Met Ala Arg Thr Lys Gln Thr Ala Arg Lys Ser Thr Gly Gly Lys Ala
1               5                   10                  15

Pro Arg Lys Gln Leu Ala Thr Lys Val Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Met Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ser Tyr Leu Val Gly Leu Phe Glu Asp Thr Asn Leu Cys Val
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135
```

```
<210> SEQ ID NO 21
<211> LENGTH: 103
<212> TYPE: PRT
<213> ORGANISM: Homo sapiens
<220> FEATURE:
<223> OTHER INFORMATION: histone H4, histone cluster 2, H4a (HIST2H4A)

<400> SEQUENCE: 21

Met Ser Gly Arg Gly Lys Gly Gly Lys Gly Leu Gly Lys Gly Gly Ala
 1               5                  10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 22
<211> LENGTH: 1487
<212> TYPE: PRT
<213> ORGANISM: Homo sapiens
<220> FEATURE:
<223> OTHER INFORMATION: collagen, type II, alpha 1 (COL2A1),
      Coll.T2alpha1

<400> SEQUENCE: 22

Met Ile Arg Leu Gly Ala Pro Gln Thr Leu Val Leu Leu Thr Leu Leu
 1               5                  10                  15

Val Ala Ala Val Leu Arg Cys Gln Gly Gln Asp Val Gln Glu Ala Gly
                20                  25                  30

Ser Cys Val Gln Asp Gly Gln Arg Tyr Asn Asp Lys Asp Val Trp Lys
            35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
            115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
    195                 200                 205
```

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
        275                 280                 285

His Arg Gly Tyr Pro Gly Leu Asp Gly Ala Lys Gly Glu Ala Gly Ala
    290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
        355                 360                 365

Gly Ala Pro Gly Ala Lys Gly Glu Ala Gly Pro Thr Gly Ala Arg Gly
    370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
        435                 440                 445

Leu Gly Pro Lys Gly Gln Thr Gly Glu Pro Gly Ile Ala Gly Phe Lys
    450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
        515                 520                 525

Ala Pro Gly Glu Arg Gly Pro Ser Gly Leu Ala Gly Pro Lys Gly Ala
    530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
                565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
        595                 600                 605

Gly Ala Asn Gly Glu Pro Gly Lys Ala Gly Glu Lys Gly Leu Pro Gly
    610                 615                 620

Ala Pro Gly Leu Arg Gly Leu Pro Gly Lys Asp Gly Glu Thr Gly Ala

```
                    625                 630                 635                 640
Ala Gly Pro Pro Gly Pro Ala Gly Pro Ala Gly Glu Arg Gly Glu Gln
                    645                 650                 655
Gly Ala Pro Gly Pro Ser Gly Phe Gln Gly Leu Pro Gly Pro Pro Gly
                    660                 665                 670
Pro Pro Gly Glu Gly Gly Lys Pro Gly Asp Gln Gly Val Pro Gly Glu
                    675                 680                 685
Ala Gly Ala Pro Gly Leu Val Gly Pro Arg Gly Glu Arg Gly Phe Pro
                    690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
                    725                 730                 735
Ala Gly Pro Pro Gly Ala Gln Gly Pro Pro Gly Leu Gln Gly Met Pro
                    740                 745                 750
Gly Glu Arg Gly Ala Ala Gly Ile Ala Gly Pro Lys Gly Asp Arg Gly
                    755                 760                 765
Asp Val Gly Glu Lys Gly Pro Glu Gly Ala Pro Gly Lys Asp Gly Gly
                    770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                    805                 810                 815
Ala Arg Gly Ala Pro Gly Glu Arg Gly Glu Thr Gly Pro Pro Gly Pro
                    820                 825                 830
Ala Gly Phe Ala Gly Pro Pro Gly Ala Asp Gly Gln Pro Gly Ala Lys
                    835                 840                 845
Gly Glu Gln Gly Glu Ala Gly Gln Lys Gly Asp Ala Gly Ala Pro Gly
                    850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
                    885                 890                 895
Gly Phe Pro Gly Ala Ala Gly Arg Val Gly Pro Pro Gly Ser Asn Gly
                    900                 905                 910
Asn Pro Gly Pro Pro Gly Pro Pro Gly Pro Ser Gly Lys Asp Gly Pro
                    915                 920                 925
Lys Gly Ala Arg Gly Asp Ser Gly Pro Pro Gly Arg Ala Gly Glu Pro
                    930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
                    965                 970                 975
Ala Gly Gln Arg Gly Ile Val Gly Leu Pro Gly Gln Arg Gly Glu Arg
                    980                 985                 990
Gly Phe Pro Gly Leu Pro Gly Pro Ser Gly Glu Pro Gly Lys Gln Gly
                    995                 1000                1005
Ala Pro Gly Ala Ser Gly Asp Arg Gly Pro Pro Gly Pro Val Gly Pro
                    1010                1015                1020
Pro Gly Leu Thr Gly Pro Ala Gly Glu Pro Gly Arg Glu Gly Ser Pro
1025                1030                1035                1040
Gly Ala Asp Gly Pro Pro Gly Arg Asp Gly Ala Ala Gly Val Lys Gly
                    1045                1050                1055
```

-continued

Asp Arg Gly Glu Thr Gly Ala Val Gly Ala Pro Gly Ala Pro Gly Pro
        1060                1065                1070

Pro Gly Ser Pro Gly Pro Ala Gly Pro Thr Gly Lys Gln Gly Asp Arg
        1075                1080                1085

Gly Glu Ala Gly Ala Gln Gly Pro Met Gly Pro Ser Gly Pro Ala Gly
        1090                1095                1100

Ala Arg Gly Ile Gln Gly Pro Gln Gly Pro Arg Gly Asp Lys Gly Glu
1105                1110                1115                1120

Ala Gly Glu Pro Gly Glu Arg Gly Leu Lys Gly His Arg Gly Phe Thr
        1125                1130                1135

Gly Leu Gln Gly Leu Pro Gly Pro Gly Pro Ser Gly Asp Gln Gly
        1140                1145                1150

Ala Ser Gly Pro Ala Gly Pro Ser Gly Pro Arg Gly Pro Pro Gly Pro
        1155                1160                1165

Val Gly Pro Ser Gly Lys Asp Gly Ala Asn Gly Ile Pro Gly Pro Ile
        1170                1175                1180

Gly Pro Pro Gly Pro Arg Gly Arg Ser Gly Glu Thr Gly Pro Ala Gly
1185                1190                1195                1200

Pro Pro Gly Asn Pro Gly Pro Pro Gly Pro Pro Gly Pro Pro Gly Pro
        1205                1210                1215

Gly Ile Asp Met Ser Ala Phe Ala Gly Leu Gly Pro Arg Glu Lys Gly
        1220                1225                1230

Pro Asp Pro Leu Gln Tyr Met Arg Ala Asp Gln Ala Ala Gly Gly Leu
        1235                1240                1245

Arg Gln His Asp Ala Glu Val Asp Ala Thr Leu Lys Ser Leu Asn Asn
        1250                1255                1260

Gln Ile Glu Ser Ile Arg Ser Pro Glu Gly Ser Arg Lys Asn Pro Ala
1265                1270                1275                1280

Arg Thr Cys Arg Asp Leu Lys Leu Cys His Pro Glu Trp Lys Ser Gly
        1285                1290                1295

Asp Tyr Trp Ile Asp Pro Asn Gln Gly Cys Thr Leu Asp Ala Met Lys
        1300                1305                1310

Val Phe Cys Asn Met Glu Thr Gly Glu Thr Cys Val Tyr Pro Asn Pro
        1315                1320                1325

Ala Asn Val Pro Lys Lys Asn Trp Trp Ser Ser Lys Ser Lys Glu Lys
        1330                1335                1340

Lys His Ile Trp Phe Gly Glu Thr Ile Asn Gly Gly Phe His Phe Ser
1345                1350                1355                1360

Tyr Gly Asp Asp Asn Leu Ala Pro Asn Thr Ala Asn Val Gln Met Thr
        1365                1370                1375

Phe Leu Arg Leu Leu Ser Thr Glu Gly Ser Gln Asn Ile Thr Tyr His
        1380                1385                1390

Cys Lys Asn Ser Ile Ala Tyr Leu Asp Glu Ala Ala Gly Asn Leu Lys
        1395                1400                1405

Lys Ala Leu Leu Ile Gln Gly Ser Asn Asp Val Glu Ile Arg Ala Glu
        1410                1415                1420

Gly Asn Ser Arg Phe Thr Tyr Thr Ala Leu Lys Asp Gly Cys Thr Lys
1425                1430                1435                1440

His Thr Gly Lys Trp Gly Lys Thr Val Ile Glu Tyr Arg Ser Gln Lys
        1445                1450                1455

Thr Ser Arg Leu Pro Ile Ile Asp Ile Ala Pro Met Asp Ile Gly Gly
        1460                1465                1470

Pro Glu Gln Glu Phe Gly Val Asp Ile Gly Pro Val Cys Phe Leu
        1475                1480                1485

```
<210> SEQ ID NO 23
<211> LENGTH: 921
<212> TYPE: PRT
<213> ORGANISM: Homo sapiens
<220> FEATURE:
<223> OTHER INFORMATION: collagen, type IX, alpha 1 (COL9A1),
      Coll.T9alpha1

<400> SEQUENCE: 23

Met Lys Thr Cys Trp Lys Ile Pro Val Phe Phe Val Cys Ser Phe
  1               5                  10                  15

Leu Glu Pro Trp Ala Ser Ala Ala Val Lys Arg Arg Pro Arg Phe Pro
                 20                  25                  30

Val Asn Ser Asn Ser Asn Gly Gly Asn Glu Leu Cys Pro Lys Ile Arg
         35                  40                  45

Ile Gly Gln Asp Asp Leu Pro Gly Phe Asp Leu Ile Ser Gln Phe Gln
     50                  55                  60

Val Asp Lys Ala Ala Ser Arg Arg Ala Ile Gln Arg Val Val Gly Ser
 65                  70                  75                  80

Ala Thr Leu Gln Val Ala Tyr Lys Leu Gly Asn Asn Val Asp Phe Arg
                 85                  90                  95

Ile Pro Thr Arg Asn Leu Tyr Pro Ser Gly Leu Pro Glu Glu Tyr Ser
                100                 105                 110

Phe Leu Thr Thr Phe Arg Met Thr Gly Ser Thr Leu Lys Lys Asn Trp
            115                 120                 125

Asn Ile Trp Gln Ile Gln Asp Ser Ser Gly Lys Glu Gln Val Gly Ile
        130                 135                 140

Lys Ile Asn Gly Gln Thr Gln Ser Val Val Phe Ser Tyr Lys Gly Leu
145                 150                 155                 160

Asp Gly Ser Leu Gln Thr Ala Ala Phe Ser Asn Leu Ser Ser Leu Phe
                165                 170                 175

Asp Ser Gln Trp His Lys Ile Met Ile Gly Val Glu Arg Ser Ser Ala
                180                 185                 190

Thr Leu Phe Val Asp Cys Asn Arg Ile Glu Ser Leu Pro Ile Lys Pro
            195                 200                 205

Arg Gly Pro Ile Asp Ile Asp Gly Phe Ala Val Leu Gly Lys Leu Ala
        210                 215                 220

Asp Asn Pro Gln Val Ser Val Pro Phe Glu Leu Gln Trp Met Leu Ile
225                 230                 235                 240

His Cys Asp Pro Leu Arg Pro Arg Arg Glu Thr Cys His Glu Leu Pro
                245                 250                 255

Ala Arg Ile Thr Pro Ser Gln Thr Thr Asp Glu Arg Gly Pro Pro Gly
            260                 265                 270

Glu Gln Gly Pro Pro Gly Pro Pro Gly Pro Pro Gly Val Pro Gly Ile
        275                 280                 285

Asp Gly Ile Asp Gly Asp Arg Gly Pro Lys Gly Pro Pro Gly Pro Pro
    290                 295                 300

Gly Pro Ala Gly Glu Pro Gly Lys Pro Gly Ala Pro Gly Lys Pro Gly
305                 310                 315                 320

Thr Pro Gly Ala Asp Gly Leu Thr Gly Pro Asp Gly Ser Pro Gly Ser
                325                 330                 335

Ile Gly Ser Lys Gly Gln Lys Gly Glu Pro Gly Val Pro Gly Ser Arg
                340                 345                 350

Gly Phe Pro Gly Arg Gly Ile Pro Gly Pro Pro Gly Pro Pro Gly Thr
            355                 360                 365
```

```
Ala Gly Leu Pro Gly Glu Leu Gly Arg Val Gly Pro Val Gly Asp Pro
        370                 375                 380

Gly Arg Arg Gly Pro Pro Gly Pro Pro Gly Pro Pro Gly Pro Arg Gly
385                 390                 395                 400

Thr Ile Gly Phe His Asp Gly Asp Pro Leu Cys Pro Asn Ala Cys Pro
                405                 410                 415

Pro Gly Arg Ser Gly Tyr Pro Gly Leu Pro Gly Met Arg Gly His Lys
            420                 425                 430

Gly Ala Lys Gly Glu Ile Gly Glu Pro Gly Arg Gln Gly His Lys Gly
        435                 440                 445

Glu Glu Gly Asp Gln Gly Glu Leu Gly Glu Val Gly Ala Gln Gly Pro
        450                 455                 460

Pro Gly Ala Gln Gly Leu Arg Gly Ile Thr Gly Ile Val Gly Asp Lys
465                 470                 475                 480

Gly Glu Lys Gly Ala Arg Gly Leu Asp Gly Glu Pro Gly Pro Gln Gly
                485                 490                 495

Leu Pro Gly Ala Pro Gly Asp Gln Gly Gln Arg Gly Pro Pro Gly Glu
            500                 505                 510

Ala Gly Pro Lys Gly Asp Arg Gly Ala Glu Gly Ala Arg Gly Ile Pro
        515                 520                 525

Gly Leu Pro Gly Pro Lys Gly Asp Thr Gly Leu Pro Gly Val Asp Gly
        530                 535                 540

Arg Asp Gly Ile Pro Gly Met Pro Gly Thr Lys Gly Glu Pro Gly Lys
545                 550                 555                 560

Pro Gly Pro Pro Gly Asp Ala Gly Leu Gln Gly Leu Pro Gly Val Pro
                565                 570                 575

Gly Ile Pro Gly Ala Lys Gly Val Ala Gly Glu Lys Gly Ser Thr Gly
            580                 585                 590

Ala Pro Gly Lys Pro Gly Gln Met Gly Asn Ser Gly Lys Pro Gly Gln
        595                 600                 605

Gln Gly Pro Pro Gly Glu Val Gly Pro Arg Gly Pro Gln Gly Leu Pro
        610                 615                 620

Gly Ser Arg Gly Glu Leu Gly Pro Val Gly Ser Pro Gly Leu Pro Gly
625                 630                 635                 640

Lys Leu Gly Ser Leu Gly Ser Pro Gly Leu Pro Gly Leu Pro Gly Pro
                645                 650                 655

Pro Gly Leu Pro Gly Met Lys Gly Asp Arg Gly Val Val Gly Glu Pro
            660                 665                 670

Gly Pro Lys Gly Glu Gln Gly Ala Ser Gly Glu Glu Gly Glu Ala Gly
        675                 680                 685

Glu Arg Gly Glu Leu Gly Asp Ile Gly Leu Pro Gly Pro Lys Gly Ser
        690                 695                 700

Ala Gly Asn Pro Gly Glu Pro Gly Leu Arg Gly Pro Glu Gly Ser Arg
705                 710                 715                 720

Gly Leu Pro Gly Val Glu Gly Pro Arg Gly Pro Pro Gly Pro Arg Gly
                725                 730                 735

Val Gln Gly Glu Gln Gly Ala Thr Gly Leu Pro Gly Val Gln Gly Pro
            740                 745                 750

Pro Gly Arg Ala Pro Thr Asp Gln His Ile Lys Gln Val Cys Met Arg
        755                 760                 765

Val Ile Gln Glu His Phe Ala Glu Met Ala Ala Ser Leu Lys Arg Pro
        770                 775                 780

Asp Ser Gly Ala Thr Gly Leu Pro Gly Arg Pro Gly Pro Pro Gly Pro
```

```
                785                 790                 795                 800
Pro Gly Pro Pro Gly Glu Asn Gly Phe Pro Gly Gln Met Gly Ile Arg
                    805                 810                 815
Gly Leu Pro Gly Ile Lys Gly Pro Pro Gly Ala Leu Gly Leu Arg Gly
                    820                 825                 830
Pro Lys Gly Asp Leu Gly Glu Lys Gly Glu Arg Gly Pro Pro Gly Arg
                    835                 840                 845
Gly Pro Asn Gly Leu Pro Gly Ala Ile Gly Leu Pro Gly Asp Pro Gly
                    850                 855                 860
Pro Ala Ser Tyr Gly Arg Asn Gly Arg Asp Gly Glu Arg Gly Pro Pro
865                 870                 875                 880
Gly Val Ala Gly Ile Pro Gly Val Pro Gly Pro Pro Gly Pro Pro Gly
                    885                 890                 895
Leu Pro Gly Phe Cys Glu Pro Ala Ser Cys Thr Met Gln Ala Gly Gln
                    900                 905                 910
Arg Ala Phe Asn Lys Gly Pro Asp Pro
                    915                 920

<210> SEQ ID NO 24
<211> LENGTH: 680
<212> TYPE: PRT
<213> ORGANISM: Homo sapiens
<220> FEATURE:
<223> OTHER INFORMATION: collagen, type X, alpha 1 (COL10A1),
      Coll.T10alpha1

<400> SEQUENCE: 24

Met Leu Pro Gln Ile Pro Phe Leu Leu Leu Val Ser Leu Asn Leu Val
1               5                   10                  15
His Gly Val Phe Tyr Ala Glu Arg Tyr Gln Met Pro Thr Gly Ile Lys
                20                  25                  30
Gly Pro Leu Pro Asn Thr Lys Thr Gln Phe Phe Ile Pro Tyr Thr Ile
                35                  40                  45
Lys Ser Lys Gly Ile Ala Val Arg Gly Glu Gln Gly Thr Pro Gly Pro
                50                  55                  60
Pro Gly Pro Ala Gly Pro Arg Gly His Pro Gly Pro Ser Gly Pro Pro
65                  70                  75                  80
Gly Lys Pro Gly Tyr Gly Ser Pro Gly Leu Gln Gly Glu Pro Gly Leu
                85                  90                  95
Pro Gly Pro Pro Gly Pro Ser Ala Val Gly Lys Pro Gly Val Pro Gly
                100                 105                 110
Leu Pro Gly Lys Pro Gly Glu Arg Gly Pro Tyr Gly Pro Lys Gly Asp
                115                 120                 125
Val Gly Pro Ala Gly Leu Pro Gly Pro Arg Gly Pro Pro Gly Pro Pro
                130                 135                 140
Gly Ile Pro Gly Pro Ala Gly Ile Ser Val Pro Gly Lys Pro Gly Gln
145                 150                 155                 160
Gln Gly Pro Thr Gly Ala Pro Gly Pro Arg Gly Phe Pro Gly Glu Lys
                165                 170                 175
Gly Ala Pro Gly Val Pro Gly Met Asn Gly Gln Lys Gly Glu Met Gly
                180                 185                 190
Tyr Gly Ala Pro Gly Arg Pro Gly Glu Arg Gly Leu Pro Gly Pro Gln
                195                 200                 205
Gly Pro Thr Gly Pro Ser Gly Pro Pro Gly Val Gly Lys Arg Gly Glu
                210                 215                 220
Asn Gly Val Pro Gly Gln Pro Gly Ile Lys Gly Asp Arg Gly Phe Pro
```

```
                225                 230                 235                 240
Gly Glu Met Gly Pro Ile Gly Pro Pro Gly Pro Gln Gly Pro Pro Gly
                    245                 250                 255
Glu Arg Gly Pro Glu Gly Ile Gly Lys Pro Gly Ala Ala Gly Ala Pro
                260                 265                 270
Gly Gln Pro Gly Ile Pro Gly Thr Lys Gly Leu Pro Gly Ala Pro Gly
                275                 280                 285
Ile Ala Gly Pro Pro Gly Pro Pro Gly Phe Gly Lys Pro Gly Leu Pro
                290                 295                 300
Gly Leu Lys Gly Glu Arg Gly Pro Ala Gly Leu Pro Gly Gly Pro Gly
305                 310                 315                 320
Ala Lys Gly Glu Gln Gly Pro Ala Gly Leu Pro Gly Lys Pro Gly Leu
                    325                 330                 335
Thr Gly Pro Pro Gly Asn Met Gly Pro Gln Gly Pro Lys Gly Ile Pro
                340                 345                 350
Gly Ser His Gly Leu Pro Gly Pro Lys Gly Glu Thr Gly Pro Ala Gly
                355                 360                 365
Pro Ala Gly Tyr Pro Gly Ala Lys Gly Glu Arg Gly Ser Pro Gly Ser
                370                 375                 380
Asp Gly Lys Pro Gly Tyr Pro Gly Lys Pro Gly Leu Asp Gly Pro Lys
385                 390                 395                 400
Gly Asn Pro Gly Leu Pro Gly Pro Lys Gly Asp Pro Gly Val Gly Gly
                    405                 410                 415
Pro Pro Gly Leu Pro Gly Pro Val Gly Pro Ala Gly Ala Lys Gly Met
                420                 425                 430
Pro Gly His Asn Gly Glu Ala Gly Pro Arg Gly Ala Pro Gly Ile Pro
                435                 440                 445
Gly Thr Arg Gly Pro Ile Gly Pro Pro Gly Ile Pro Gly Phe Pro Gly
                450                 455                 460
Ser Lys Gly Asp Pro Gly Ser Pro Gly Pro Pro Gly Pro Ala Gly Ile
465                 470                 475                 480
Ala Thr Lys Gly Leu Asn Gly Pro Thr Gly Pro Pro Gly Pro Pro Gly
                    485                 490                 495
Pro Arg Gly His Ser Gly Glu Pro Gly Leu Pro Gly Pro Pro Gly Pro
                500                 505                 510
Pro Gly Pro Pro Gly Gln Ala Val Met Pro Glu Gly Phe Ile Lys Ala
                515                 520                 525
Gly Gln Arg Pro Ser Leu Ser Gly Thr Pro Leu Val Ser Ala Asn Gln
530                 535                 540
Gly Val Thr Gly Met Pro Val Ser Ala Phe Thr Val Ile Leu Ser Lys
545                 550                 555                 560
Ala Tyr Pro Ala Ile Gly Thr Pro Ile Pro Phe Asp Lys Ile Leu Tyr
                    565                 570                 575
Asn Arg Gln Gln His Tyr Asp Pro Arg Thr Gly Ile Phe Thr Cys Gln
                580                 585                 590
Ile Pro Gly Ile Tyr Tyr Phe Ser Tyr His Val His Val Lys Gly Thr
                595                 600                 605
His Val Trp Val Gly Leu Tyr Lys Asn Gly Thr Pro Val Met Tyr Thr
                610                 615                 620
Tyr Asp Glu Tyr Thr Lys Gly Tyr Leu Asp Gln Ala Ser Gly Ser Ala
625                 630                 635                 640
Ile Ile Asp Leu Thr Glu Asn Asp Gln Val Trp Leu Gln Leu Pro Asn
                    645                 650                 655
```

```
Ala Glu Ser Asn Gly Leu Tyr Ser Ser Glu Tyr Val His Ser Ser Phe
            660                 665                 670

Ser Gly Phe Leu Val Ala Pro Met
            675                 680

<210> SEQ ID NO 25
<211> LENGTH: 1806
<212> TYPE: PRT
<213> ORGANISM: Homo sapiens
<220> FEATURE:
<223> OTHER INFORMATION: collagen, type XI, alpha 1, isoform A
      (COL11A1), Coll.T11alpha1

<400> SEQUENCE: 25

Met Glu Pro Trp Ser Ser Arg Trp Lys Thr Lys Arg Trp Leu Trp Asp
 1               5                  10                  15

Phe Thr Val Thr Thr Leu Ala Leu Thr Phe Leu Phe Gln Ala Arg Glu
            20                  25                  30

Val Arg Gly Ala Ala Pro Val Asp Val Leu Lys Ala Leu Asp Phe His
            35                  40                  45

Asn Ser Pro Glu Gly Ile Ser Lys Thr Thr Gly Phe Cys Thr Asn Arg
 50                  55                  60

Lys Asn Ser Lys Gly Ser Asp Thr Ala Tyr Arg Val Ser Lys Gln Ala
 65                  70                  75                  80

Gln Leu Ser Ala Pro Thr Lys Gln Leu Phe Pro Gly Gly Thr Phe Pro
                 85                  90                  95

Glu Asp Phe Ser Ile Leu Phe Thr Val Lys Pro Lys Lys Gly Ile Gln
            100                 105                 110

Ser Phe Leu Leu Ser Ile Tyr Asn Glu His Gly Ile Gln Gln Ile Gly
            115                 120                 125

Val Glu Val Gly Arg Ser Pro Val Phe Leu Phe Glu Asp His Thr Gly
    130                 135                 140

Lys Pro Ala Pro Glu Asp Tyr Pro Leu Phe Arg Thr Val Asn Ile Ala
145                 150                 155                 160

Asp Gly Lys Trp His Arg Val Ala Ile Ser Val Glu Lys Lys Thr Val
                165                 170                 175

Thr Met Ile Val Asp Cys Lys Lys Lys Thr Thr Lys Pro Leu Asp Arg
            180                 185                 190

Ser Glu Arg Ala Ile Val Asp Thr Asn Gly Ile Thr Val Phe Gly Thr
            195                 200                 205

Arg Ile Leu Asp Glu Glu Val Phe Glu Gly Asp Ile Gln Gln Phe Leu
    210                 215                 220

Ile Thr Gly Asp Pro Lys Ala Ala Tyr Asp Tyr Cys Glu His Tyr Ser
225                 230                 235                 240

Pro Asp Cys Asp Ser Ser Ala Pro Lys Ala Ala Gln Ala Gln Glu Pro
                245                 250                 255

Gln Ile Asp Glu Tyr Ala Pro Glu Asp Ile Ile Glu Tyr Asp Tyr Glu
            260                 265                 270

Tyr Gly Glu Ala Glu Tyr Lys Glu Ala Glu Ser Val Thr Glu Gly Pro
            275                 280                 285

Thr Val Thr Glu Glu Thr Ile Ala Gln Thr Glu Ala Asn Ile Val Asp
    290                 295                 300

Asp Phe Gln Glu Tyr Asn Tyr Gly Thr Met Glu Ser Tyr Gln Thr Glu
305                 310                 315                 320

Ala Pro Arg His Val Ser Gly Thr Asn Glu Pro Asn Pro Val Glu Glu
                325                 330                 335
```

-continued

```
Ile Phe Thr Glu Glu Tyr Leu Thr Gly Glu Asp Tyr Asp Ser Gln Arg
            340                 345                 350

Lys Asn Ser Glu Asp Thr Leu Tyr Glu Asn Lys Glu Ile Asp Gly Arg
        355                 360                 365

Asp Ser Asp Leu Leu Val Asp Gly Asp Leu Gly Glu Tyr Asp Phe Tyr
        370                 375                 380

Glu Tyr Lys Glu Tyr Glu Asp Lys Pro Thr Ser Pro Pro Asn Glu Glu
385                 390                 395                 400

Phe Gly Pro Gly Val Pro Ala Glu Thr Asp Ile Thr Glu Thr Ser Ile
                405                 410                 415

Asn Gly His Gly Ala Tyr Gly Glu Lys Gly Gln Lys Gly Glu Pro Ala
            420                 425                 430

Val Val Glu Pro Gly Met Leu Val Glu Gly Pro Pro Gly Pro Ala Gly
        435                 440                 445

Pro Ala Gly Ile Met Gly Pro Pro Gly Leu Gln Gly Pro Thr Gly Pro
    450                 455                 460

Pro Gly Asp Pro Gly Asp Arg Gly Pro Pro Gly Arg Pro Gly Leu Pro
465                 470                 475                 480

Gly Ala Asp Gly Leu Pro Gly Pro Pro Gly Thr Met Leu Met Leu Pro
                485                 490                 495

Phe Arg Tyr Gly Gly Asp Gly Ser Lys Gly Pro Thr Ile Ser Ala Gln
            500                 505                 510

Glu Ala Gln Ala Gln Ala Ile Leu Gln Gln Ala Arg Ile Ala Leu Arg
        515                 520                 525

Gly Pro Pro Gly Pro Met Gly Leu Thr Gly Arg Pro Gly Pro Val Gly
    530                 535                 540

Gly Pro Gly Ser Ser Gly Ala Lys Gly Glu Ser Gly Asp Pro Gly Pro
545                 550                 555                 560

Gln Gly Pro Arg Gly Val Gln Gly Pro Pro Gly Pro Thr Gly Lys Pro
                565                 570                 575

Gly Lys Arg Gly Arg Pro Gly Ala Asp Gly Gly Arg Gly Met Pro Gly
            580                 585                 590

Glu Pro Gly Ala Lys Gly Asp Arg Gly Phe Asp Gly Leu Pro Gly Leu
        595                 600                 605

Pro Gly Asp Lys Gly His Arg Gly Glu Arg Gly Pro Gln Gly Pro Pro
    610                 615                 620

Gly Pro Pro Gly Asp Asp Gly Met Arg Gly Glu Asp Gly Glu Ile Gly
625                 630                 635                 640

Pro Arg Gly Leu Pro Gly Glu Ala Gly Pro Arg Gly Leu Leu Gly Pro
                645                 650                 655

Arg Gly Thr Pro Gly Ala Pro Gly Gln Pro Gly Met Ala Gly Val Asp
            660                 665                 670

Gly Pro Pro Gly Pro Lys Gly Asn Met Gly Pro Gln Gly Glu Pro Gly
        675                 680                 685

Pro Pro Gly Gln Gln Gly Asn Pro Gly Pro Gln Gly Leu Pro Gly Pro
    690                 695                 700

Gln Gly Pro Ile Gly Pro Pro Gly Glu Lys Gly Pro Gln Gly Lys Pro
705                 710                 715                 720

Gly Leu Ala Gly Leu Pro Gly Ala Asp Gly Pro Pro Gly His Pro Gly
                725                 730                 735

Lys Glu Gly Gln Ser Gly Glu Lys Gly Ala Leu Gly Pro Pro Gly Pro
            740                 745                 750

Gln Gly Pro Ile Gly Tyr Pro Gly Pro Arg Gly Val Lys Gly Ala Asp
        755                 760                 765
```

Gly Val Arg Gly Leu Lys Gly Ser Lys Gly Glu Lys Gly Glu Asp Gly
            770                 775                 780

Phe Pro Gly Phe Lys Gly Asp Met Gly Leu Lys Gly Asp Arg Gly Glu
785                 790                 795                 800

Val Gly Gln Ile Gly Pro Arg Gly Glu Asp Gly Pro Glu Gly Pro Lys
            805                 810                 815

Gly Arg Ala Gly Pro Thr Gly Asp Pro Gly Pro Ser Gly Gln Ala Gly
            820                 825                 830

Glu Lys Gly Lys Leu Gly Val Pro Gly Leu Pro Gly Tyr Pro Gly Arg
            835                 840                 845

Gln Gly Pro Lys Gly Ser Thr Gly Phe Pro Gly Phe Pro Gly Ala Asn
            850                 855                 860

Gly Glu Lys Gly Ala Arg Gly Val Ala Gly Lys Pro Gly Pro Arg Gly
865                 870                 875                 880

Gln Arg Gly Pro Thr Gly Pro Arg Gly Ser Arg Gly Ala Arg Gly Pro
            885                 890                 895

Thr Gly Lys Pro Gly Pro Lys Gly Thr Ser Gly Gly Asp Gly Pro Pro
            900                 905                 910

Gly Pro Pro Gly Glu Arg Gly Pro Gln Gly Pro Gln Gly Pro Val Gly
            915                 920                 925

Phe Pro Gly Pro Lys Gly Pro Pro Gly Pro Pro Gly Lys Asp Gly Leu
930                 935                 940

Pro Gly His Pro Gly Gln Arg Gly Glu Thr Gly Phe Gln Gly Lys Thr
945                 950                 955                 960

Gly Pro Pro Gly Pro Gly Gly Val Val Gly Pro Gln Gly Pro Thr Gly
            965                 970                 975

Glu Thr Gly Pro Ile Gly Glu Arg Gly His Pro Gly Pro Pro Gly Pro
            980                 985                 990

Pro Gly Glu Gln Gly Leu Pro Gly Ala Ala Gly Lys Glu Gly Ala Lys
            995                 1000                1005

Gly Asp Pro Gly Pro Gln Gly Ile Ser Gly Lys Asp Gly Pro Ala Gly
            1010                1015                1020

Leu Arg Gly Phe Pro Gly Glu Arg Gly Leu Pro Gly Ala Gln Gly Ala
1025                1030                1035                1040

Pro Gly Leu Lys Gly Gly Glu Gly Pro Gln Gly Pro Pro Gly Pro Val
            1045                1050                1055

Gly Ser Pro Gly Glu Arg Gly Ser Ala Gly Thr Ala Gly Pro Ile Gly
            1060                1065                1070

Leu Pro Gly Arg Pro Gly Pro Gln Gly Pro Pro Gly Pro Ala Gly Glu
            1075                1080                1085

Lys Gly Ala Pro Gly Glu Lys Gly Pro Gln Gly Pro Ala Gly Arg Asp
            1090                1095                1100

Gly Val Gln Gly Pro Val Gly Leu Pro Gly Pro Ala Gly Pro Ala Gly
1105                1110                1115                1120

Ser Pro Gly Glu Asp Gly Asp Lys Gly Glu Ile Gly Glu Pro Gly Gln
            1125                1130                1135

Lys Gly Ser Lys Gly Asp Lys Gly Glu Asn Gly Pro Pro Gly Pro Pro
            1140                1145                1150

Gly Leu Gln Gly Pro Val Gly Ala Pro Gly Ile Ala Gly Gly Asp Gly
            1155                1160                1165

Glu Pro Gly Pro Arg Gly Gln Gln Gly Met Phe Gly Gln Lys Gly Asp
            1170                1175                1180

Glu Gly Ala Arg Gly Phe Pro Gly Pro Pro Gly Pro Ile Gly Leu Gln

```
                        1185                1190                1195                1200
Gly Leu Pro Gly Pro Pro Gly Glu Lys Gly Glu Asn Gly Asp Val Gly
                1205                1210                1215
Pro Met Gly Pro Pro Gly Pro Pro Gly Pro Arg Gly Pro Gln Gly Pro
                1220                1225                1230
Asn Gly Ala Asp Gly Pro Gln Gly Pro Pro Gly Ser Val Gly Ser Val
                1235                1240                1245
Gly Gly Val Gly Glu Lys Gly Glu Pro Gly Glu Ala Gly Asn Pro Gly
                1250                1255                1260
Pro Pro Gly Glu Ala Gly Val Gly Gly Pro Lys Gly Glu Arg Gly Glu
1265                1270                1275                1280
Lys Gly Glu Ala Gly Pro Pro Gly Ala Ala Gly Pro Pro Gly Ala Lys
                1285                1290                1295
Gly Pro Pro Gly Asp Asp Gly Pro Lys Gly Asn Pro Gly Pro Val Gly
                1300                1305                1310
Phe Pro Gly Asp Pro Gly Pro Pro Gly Glu Pro Gly Pro Ala Gly Gln
                1315                1320                1325
Asp Gly Val Gly Gly Asp Lys Gly Glu Asp Gly Asp Pro Gly Gln Pro
                1330                1335                1340
Gly Pro Pro Gly Pro Ser Gly Glu Ala Gly Pro Pro Gly Pro Pro Gly
1345                1350                1355                1360
Lys Arg Gly Pro Pro Gly Ala Ala Gly Ala Glu Gly Arg Gln Gly Glu
                1365                1370                1375
Lys Gly Ala Lys Gly Glu Ala Gly Ala Glu Gly Pro Pro Gly Lys Thr
                1380                1385                1390
Gly Pro Val Gly Pro Gln Gly Pro Ala Gly Lys Pro Gly Pro Glu Gly
                1395                1400                1405
Leu Arg Gly Ile Pro Gly Pro Val Gly Glu Gln Gly Leu Pro Gly Ala
                1410                1415                1420
Ala Gly Gln Asp Gly Pro Pro Gly Pro Met Gly Pro Pro Gly Leu Pro
1425                1430                1435                1440
Gly Leu Lys Gly Asp Pro Gly Ser Lys Gly Glu Lys Gly His Pro Gly
                1445                1450                1455
Leu Ile Gly Leu Ile Gly Pro Pro Gly Glu Gln Gly Glu Lys Gly Asp
                1460                1465                1470
Arg Gly Leu Pro Gly Thr Gln Gly Ser Pro Gly Ala Lys Gly Asp Gly
                1475                1480                1485
Gly Ile Pro Gly Pro Ala Gly Pro Leu Gly Pro Pro Gly Pro Pro Gly
                1490                1495                1500
Leu Pro Gly Pro Gln Gly Pro Lys Gly Asn Lys Gly Ser Thr Gly Pro
1505                1510                1515                1520
Ala Gly Gln Lys Gly Asp Ser Gly Leu Pro Gly Pro Pro Gly Ser Pro
                1525                1530                1535
Gly Pro Pro Gly Glu Val Ile Gln Pro Leu Pro Ile Leu Ser Ser Lys
                1540                1545                1550
Lys Thr Arg Arg His Thr Glu Gly Met Gln Ala Asp Ala Asp Asp Asn
                1555                1560                1565
Ile Leu Asp Tyr Ser Asp Gly Met Glu Glu Ile Phe Gly Ser Leu Asn
                1570                1575                1580
Ser Leu Lys Gln Asp Ile Glu His Met Lys Phe Pro Met Gly Thr Gln
1585                1590                1595                1600
Thr Asn Pro Ala Arg Thr Cys Lys Asp Leu Gln Leu Ser His Pro Asp
                1605                1610                1615
```

-continued

```
Phe Pro Asp Gly Glu Tyr Trp Ile Asp Pro Asn Gln Gly Cys Ser Gly
        1620                1625                1630

Asp Ser Phe Lys Val Tyr Cys Asn Phe Thr Ser Gly Gly Glu Thr Cys
        1635                1640                1645

Ile Tyr Pro Asp Lys Lys Ser Glu Gly Val Arg Ile Ser Ser Trp Pro
        1650                1655                1660

Lys Glu Lys Pro Gly Ser Trp Phe Ser Glu Phe Lys Arg Gly Lys Leu
1665                1670                1675                1680

Leu Ser Tyr Leu Asp Val Glu Gly Asn Ser Ile Asn Met Val Gln Met
                1685                1690                1695

Thr Phe Leu Lys Leu Leu Thr Ala Ser Ala Arg Gln Asn Phe Thr Tyr
            1700                1705                1710

His Cys His Gln Ser Ala Ala Trp Tyr Asp Val Ser Ser Gly Ser Tyr
        1715                1720                1725

Asp Lys Ala Leu Arg Phe Leu Gly Ser Asn Asp Glu Glu Met Ser Tyr
        1730                1735                1740

Asp Asn Asn Pro Phe Ile Lys Thr Leu Tyr Asp Gly Cys Ala Ser Arg
1745                1750                1755                1760

Lys Gly Tyr Glu Lys Thr Val Ile Glu Ile Asn Thr Pro Lys Ile Asp
                1765                1770                1775

Gln Val Pro Ile Val Asp Val Met Ile Asn Asp Phe Gly Asp Gln Asn
            1780                1785                1790

Gln Lys Phe Gly Phe Glu Val Gly Pro Val Cys Phe Leu Gly
        1795                1800                1805

<210> SEQ ID NO 26
<211> LENGTH: 1818
<212> TYPE: PRT
<213> ORGANISM: Homo sapiens
<220> FEATURE:
<223> OTHER INFORMATION: collagen, type XI, alpha 1, isoform B
      (COL11A1), Coll.T11alpha1

<400> SEQUENCE: 26

Met Glu Pro Trp Ser Ser Arg Trp Lys Thr Lys Arg Trp Leu Trp Asp
1               5                   10                  15

Phe Thr Val Thr Thr Leu Ala Leu Thr Phe Leu Phe Gln Ala Arg Glu
                20                  25                  30

Val Arg Gly Ala Ala Pro Val Asp Val Leu Lys Ala Leu Asp Phe His
            35                  40                  45

Asn Ser Pro Glu Gly Ile Ser Lys Thr Thr Gly Phe Cys Thr Asn Arg
        50                  55                  60

Lys Asn Ser Lys Gly Ser Asp Thr Ala Tyr Arg Val Ser Lys Gln Ala
65                  70                  75                  80

Gln Leu Ser Ala Pro Thr Lys Gln Leu Phe Pro Gly Gly Thr Phe Pro
                85                  90                  95

Glu Asp Phe Ser Ile Leu Phe Thr Val Lys Pro Lys Lys Gly Ile Gln
            100                 105                 110

Ser Phe Leu Leu Ser Ile Tyr Asn Glu His Gly Ile Gln Gln Ile Gly
        115                 120                 125

Val Glu Val Gly Arg Ser Pro Val Phe Leu Phe Glu Asp His Thr Gly
    130                 135                 140

Lys Pro Ala Pro Glu Asp Tyr Pro Leu Phe Arg Thr Val Asn Ile Ala
145                 150                 155                 160

Asp Gly Lys Trp His Arg Val Ala Ile Ser Val Glu Lys Lys Thr Val
                165                 170                 175
```

-continued

```
Thr Met Ile Val Asp Cys Lys Lys Thr Lys Pro Leu Asp Arg
            180                 185                 190

Ser Glu Arg Ala Ile Val Asp Thr Asn Gly Ile Thr Val Phe Gly Thr
        195                 200                 205

Arg Ile Leu Asp Glu Glu Val Phe Glu Gly Asp Ile Gln Gln Phe Leu
    210                 215                 220

Ile Thr Gly Asp Pro Lys Ala Ala Tyr Asp Tyr Cys Glu His Tyr Ser
225                 230                 235                 240

Pro Asp Cys Asp Ser Ser Ala Pro Lys Ala Ala Gln Ala Gln Glu Pro
                245                 250                 255

Gln Ile Asp Glu Lys Lys Ser Asn Phe Lys Lys Met Arg Thr
            260                 265                 270

Val Ala Thr Lys Ser Lys Glu Lys Ser Lys Lys Phe Thr Pro Pro Lys
    275                 280                 285

Ser Glu Lys Phe Ser Ser Lys Lys Lys Ser Tyr Gln Ala Ser Ala
        290                 295                 300

Lys Ala Lys Leu Gly Val Lys Ala Asn Ile Val Asp Asp Phe Gln Glu
305                 310                 315                 320

Tyr Asn Tyr Gly Thr Met Glu Ser Tyr Gln Thr Glu Ala Pro Arg His
                325                 330                 335

Val Ser Gly Thr Asn Glu Pro Asn Pro Val Glu Glu Ile Phe Thr Glu
            340                 345                 350

Glu Tyr Leu Thr Gly Glu Asp Tyr Asp Ser Gln Arg Lys Asn Ser Glu
        355                 360                 365

Asp Thr Leu Tyr Glu Asn Lys Glu Ile Asp Gly Arg Asp Ser Asp Leu
    370                 375                 380

Leu Val Asp Gly Asp Leu Gly Glu Tyr Asp Phe Tyr Glu Tyr Lys Glu
385                 390                 395                 400

Tyr Glu Asp Lys Pro Thr Ser Pro Pro Asn Glu Glu Phe Gly Pro Gly
                405                 410                 415

Val Pro Ala Glu Thr Asp Ile Thr Glu Thr Ser Ile Asn Gly His Gly
            420                 425                 430

Ala Tyr Gly Glu Lys Gly Gln Lys Gly Glu Pro Ala Val Val Glu Pro
        435                 440                 445

Gly Met Leu Val Glu Gly Pro Pro Gly Pro Ala Gly Pro Ala Gly Ile
    450                 455                 460

Met Gly Pro Pro Gly Leu Gln Gly Pro Thr Gly Pro Pro Gly Asp Pro
465                 470                 475                 480

Gly Asp Arg Gly Pro Pro Gly Arg Pro Gly Leu Pro Gly Ala Asp Gly
                485                 490                 495

Leu Pro Gly Pro Pro Gly Thr Met Leu Met Leu Pro Phe Arg Tyr Gly
            500                 505                 510

Gly Asp Gly Ser Lys Gly Pro Thr Ile Ser Ala Gln Glu Ala Gln Ala
        515                 520                 525

Gln Ala Ile Leu Gln Gln Ala Arg Ile Ala Leu Arg Gly Pro Pro Gly
    530                 535                 540

Pro Met Gly Leu Thr Gly Arg Pro Gly Pro Val Gly Pro Pro Gly Ser
545                 550                 555                 560

Ser Gly Ala Lys Gly Glu Ser Gly Asp Pro Gly Pro Gln Gly Pro Arg
                565                 570                 575

Gly Val Gln Gly Pro Pro Gly Pro Thr Gly Lys Pro Gly Lys Arg Gly
            580                 585                 590

Arg Pro Gly Ala Asp Gly Gly Arg Gly Met Pro Gly Glu Pro Gly Ala
        595                 600                 605
```

Lys Gly Asp Arg Gly Phe Asp Gly Leu Pro Gly Leu Pro Gly Asp Lys
    610                 615                 620

Gly His Arg Gly Glu Arg Gly Pro Gln Gly Pro Pro Gly Pro Pro Gly
625                 630                 635                 640

Asp Asp Gly Met Arg Gly Glu Asp Gly Glu Ile Gly Pro Arg Gly Leu
                645                 650                 655

Pro Gly Glu Ala Gly Pro Arg Gly Leu Leu Gly Pro Arg Gly Thr Pro
            660                 665                 670

Gly Ala Pro Gly Gln Pro Gly Met Ala Gly Val Asp Gly Pro Pro Gly
        675                 680                 685

Pro Lys Gly Asn Met Gly Pro Gln Gly Glu Pro Gly Pro Pro Gly Gln
    690                 695                 700

Gln Gly Asn Pro Gly Pro Gln Gly Leu Pro Gly Pro Gln Gly Pro Ile
705                 710                 715                 720

Gly Pro Pro Gly Glu Lys Gly Pro Gln Gly Lys Pro Gly Leu Ala Gly
                725                 730                 735

Leu Pro Gly Ala Asp Gly Pro Pro Gly His Pro Gly Lys Glu Gly Gln
            740                 745                 750

Ser Gly Glu Lys Gly Ala Leu Gly Pro Pro Gly Pro Gln Gly Pro Ile
        755                 760                 765

Gly Tyr Pro Gly Pro Arg Gly Val Lys Gly Ala Asp Gly Val Arg Gly
    770                 775                 780

Leu Lys Gly Ser Lys Gly Glu Lys Gly Glu Asp Gly Phe Pro Gly Phe
785                 790                 795                 800

Lys Gly Asp Met Gly Leu Lys Gly Asp Arg Gly Glu Val Gly Gln Ile
                805                 810                 815

Gly Pro Arg Gly Glu Asp Gly Pro Glu Gly Pro Lys Gly Arg Ala Gly
            820                 825                 830

Pro Thr Gly Asp Pro Gly Pro Ser Gly Gln Ala Gly Glu Lys Gly Lys
        835                 840                 845

Leu Gly Val Pro Gly Leu Pro Gly Tyr Pro Gly Arg Gln Gly Pro Lys
    850                 855                 860

Gly Ser Thr Gly Phe Pro Gly Phe Pro Gly Ala Asn Gly Glu Lys Gly
865                 870                 875                 880

Ala Arg Gly Val Ala Gly Lys Pro Gly Pro Arg Gly Gln Arg Gly Pro
                885                 890                 895

Thr Gly Pro Arg Gly Ser Arg Gly Ala Arg Gly Pro Thr Gly Lys Pro
            900                 905                 910

Gly Pro Lys Gly Thr Ser Gly Asp Gly Pro Pro Gly Pro Pro Gly
        915                 920                 925

Glu Arg Gly Pro Gln Gly Pro Gln Gly Pro Val Gly Phe Pro Gly Pro
    930                 935                 940

Lys Gly Pro Pro Gly Pro Pro Gly Lys Asp Gly Leu Pro Gly His Pro
945                 950                 955                 960

Gly Gln Arg Gly Glu Thr Gly Phe Gln Gly Lys Thr Gly Pro Pro Gly
                965                 970                 975

Pro Gly Gly Val Val Gly Pro Gln Gly Pro Thr Gly Glu Thr Gly Pro
            980                 985                 990

Ile Gly Glu Arg Gly His Pro Gly Pro Pro Gly Pro Pro Gly Glu Gln
        995                 1000                1005

Gly Leu Pro Gly Ala Ala Gly Lys Glu Gly Ala Lys Gly Asp Pro Gly
    1010                1015                1020

Pro Gln Gly Ile Ser Gly Lys Asp Gly Pro Ala Gly Leu Arg Gly Phe

```
                1025                1030                1035                1040
Pro Gly Glu Arg Gly Leu Pro Gly Ala Gln Gly Ala Pro Gly Leu Lys
                1045                1050                1055
Gly Gly Glu Gly Pro Gln Gly Pro Pro Gly Pro Val Gly Ser Pro Gly
                1060                1065                1070
Glu Arg Gly Ser Ala Gly Thr Ala Gly Pro Ile Gly Leu Pro Gly Arg
                1075                1080                1085
Pro Gly Pro Gln Gly Pro Pro Gly Pro Ala Gly Glu Lys Gly Ala Pro
                1090                1095                1100
Gly Glu Lys Gly Pro Gln Gly Pro Ala Gly Arg Asp Gly Val Gln Gly
1105                1110                1115                1120
Pro Val Gly Leu Pro Gly Pro Ala Gly Pro Ala Gly Ser Pro Gly Glu
                1125                1130                1135
Asp Gly Asp Lys Gly Glu Ile Gly Glu Pro Gly Gln Lys Gly Ser Lys
                1140                1145                1150
Gly Asp Lys Gly Glu Asn Gly Pro Pro Gly Pro Pro Gly Leu Gln Gly
                1155                1160                1165
Pro Val Gly Ala Pro Gly Ile Ala Gly Asp Gly Glu Pro Gly Pro
                1170                1175                1180
Arg Gly Gln Gln Gly Met Phe Gly Gln Lys Gly Asp Glu Gly Ala Arg
1185                1190                1195                1200
Gly Phe Pro Gly Pro Pro Gly Pro Ile Gly Leu Gln Gly Leu Pro Gly
                1205                1210                1215
Pro Pro Gly Glu Lys Gly Glu Asn Gly Asp Val Gly Pro Met Gly Pro
                1220                1225                1230
Pro Gly Pro Pro Gly Pro Arg Gly Pro Gln Gly Pro Asn Gly Ala Asp
                1235                1240                1245
Gly Pro Gln Gly Pro Pro Gly Ser Val Gly Ser Val Gly Gly Val Gly
                1250                1255                1260
Glu Lys Gly Glu Pro Gly Glu Ala Gly Asn Pro Gly Pro Pro Gly Glu
1265                1270                1275                1280
Ala Gly Val Gly Gly Pro Lys Gly Glu Arg Gly Glu Lys Gly Glu Ala
                1285                1290                1295
Gly Pro Pro Gly Ala Ala Gly Pro Pro Gly Ala Lys Gly Pro Pro Gly
                1300                1305                1310
Asp Asp Gly Pro Lys Gly Asn Pro Gly Pro Val Gly Phe Pro Gly Asp
                1315                1320                1325
Pro Gly Pro Pro Gly Glu Pro Gly Pro Ala Gly Gln Asp Gly Val Gly
                1330                1335                1340
Gly Asp Lys Gly Glu Asp Gly Asp Pro Gly Gln Pro Gly Pro Pro Gly
1345                1350                1355                1360
Pro Ser Gly Glu Ala Gly Pro Pro Gly Pro Pro Gly Lys Arg Gly Pro
                1365                1370                1375
Pro Gly Ala Ala Gly Ala Glu Gly Arg Gln Gly Glu Lys Gly Ala Lys
                1380                1385                1390
Gly Glu Ala Gly Ala Glu Gly Pro Pro Gly Lys Thr Gly Pro Val Gly
                1395                1400                1405
Pro Gln Gly Pro Ala Gly Lys Pro Gly Pro Glu Gly Leu Arg Gly Ile
                1410                1415                1420
Pro Gly Pro Val Gly Glu Gln Gly Leu Pro Gly Ala Ala Gly Gln Asp
1425                1430                1435                1440
Gly Pro Pro Gly Pro Met Gly Pro Pro Gly Leu Pro Gly Leu Lys Gly
                1445                1450                1455
```

```
Asp Pro Gly Ser Lys Gly Glu Lys Gly His Pro Gly Leu Ile Gly Leu
            1460                1465                1470

Ile Gly Pro Pro Gly Glu Gln Gly Glu Lys Gly Asp Arg Gly Leu Pro
        1475                1480                1485

Gly Thr Gln Gly Ser Pro Gly Ala Lys Gly Asp Gly Gly Ile Pro Gly
    1490                1495                1500

Pro Ala Gly Pro Leu Gly Pro Pro Gly Pro Pro Gly Leu Pro Gly Pro
1505                1510                1515                1520

Gln Gly Pro Lys Gly Asn Lys Gly Ser Thr Gly Pro Ala Gly Gln Lys
        1525                1530                1535

Gly Asp Ser Gly Leu Pro Gly Pro Pro Gly Ser Gly Pro Pro Gly
    1540                1545                1550

Glu Val Ile Gln Pro Leu Pro Ile Leu Ser Ser Lys Lys Thr Arg Arg
        1555                1560                1565

His Thr Glu Gly Met Gln Ala Asp Ala Asp Asp Asn Ile Leu Asp Tyr
    1570                1575                1580

Ser Asp Gly Met Glu Glu Ile Phe Gly Ser Leu Asn Ser Leu Lys Gln
1585                1590                1595                1600

Asp Ile Glu His Met Lys Phe Pro Met Gly Thr Gln Thr Asn Pro Ala
        1605                1610                1615

Arg Thr Cys Lys Asp Leu Gln Leu Ser His Pro Asp Phe Pro Asp Gly
        1620                1625                1630

Glu Tyr Trp Ile Asp Pro Asn Gln Gly Cys Ser Gly Asp Ser Phe Lys
    1635                1640                1645

Val Tyr Cys Asn Phe Thr Ser Gly Gly Glu Thr Cys Ile Tyr Pro Asp
        1650                1655                1660

Lys Lys Ser Glu Gly Val Arg Ile Ser Ser Trp Pro Lys Glu Lys Pro
1665                1670                1675                1680

Gly Ser Trp Phe Ser Glu Phe Lys Arg Gly Lys Leu Leu Ser Tyr Leu
        1685                1690                1695

Asp Val Glu Gly Asn Ser Ile Asn Met Val Gln Met Thr Phe Leu Lys
        1700                1705                1710

Leu Leu Thr Ala Ser Ala Arg Gln Asn Phe Thr Tyr His Cys His Gln
    1715                1720                1725

Ser Ala Ala Trp Tyr Asp Val Ser Ser Gly Ser Tyr Asp Lys Ala Leu
    1730                1735                1740

Arg Phe Leu Gly Ser Asn Asp Glu Glu Met Ser Tyr Asp Asn Asn Pro
1745                1750                1755                1760

Phe Ile Lys Thr Leu Tyr Asp Gly Cys Ala Ser Arg Lys Gly Tyr Glu
                1765                1770                1775

Lys Thr Val Ile Glu Ile Asn Thr Pro Lys Ile Asp Gln Val Pro Ile
            1780                1785                1790

Val Asp Val Met Ile Asn Asp Phe Gly Asp Gln Asn Gln Lys Phe Gly
        1795                1800                1805

Phe Glu Val Gly Pro Val Cys Phe Leu Gly
    1810                1815

<210> SEQ ID NO 27
<211> LENGTH: 1736
<212> TYPE: PRT
<213> ORGANISM: Homo sapiens
<220> FEATURE:
<223> OTHER INFORMATION: collagen, type XI, alpha 2, isoform 1
      (COL11A2), Coll.T11alpha2

<400> SEQUENCE: 27
```

-continued

```
Met Glu Arg Cys Ser Arg Cys His Arg Leu Leu Leu Leu Pro Leu
 1               5                  10                  15
Val Leu Gly Leu Ser Ala Ala Pro Gly Trp Ala Gly Ala Pro Pro Val
             20                  25                  30
Asp Val Leu Arg Ala Leu Arg Phe Pro Ser Leu Pro Asp Gly Val Arg
                 35                  40                  45
Arg Ala Lys Gly Ile Cys Pro Ala Asp Val Ala Tyr Arg Val Ala Arg
         50                  55                  60
Pro Ala Gln Leu Ser Ala Pro Thr Arg Gln Leu Phe Pro Gly Gly Phe
 65                  70                  75                  80
Pro Lys Asp Phe Ser Leu Leu Thr Val Val Arg Thr Arg Pro Gly Leu
                 85                  90                  95
Gln Ala Pro Leu Leu Thr Leu Tyr Ser Ala Gln Gly Val Arg Gln Leu
                100                 105                 110
Gly Leu Glu Leu Gly Arg Pro Val Arg Phe Leu Tyr Glu Asp Gln Thr
                115                 120                 125
Gly Arg Pro Gln Pro Ser Gln Pro Val Phe Arg Gly Leu Ser Leu
                130                 135                 140
Ala Asp Gly Lys Trp His Arg Val Ala Val Ala Val Lys Gly Gln Ser
145                 150                 155                 160
Val Thr Leu Ile Val Asp Cys Lys Lys Arg Val Thr Arg Pro Leu Pro
                165                 170                 175
Arg Ser Ala Arg Pro Val Leu Asp Thr His Gly Val Ile Ile Phe Gly
                180                 185                 190
Ala Arg Ile Leu Asp Glu Glu Val Phe Glu Gly Asp Val Gln Glu Leu
            195                 200                 205
Ala Ile Val Pro Gly Val Gln Ala Ala Tyr Glu Ser Cys Glu Gln Lys
210                 215                 220
Glu Leu Glu Cys Glu Gly Gly Gln Arg Glu Arg Pro Gln Asn Gln Gln
225                 230                 235                 240
Pro His Arg Ala Gln Arg Ser Pro Gln Gln Pro Ser Arg Leu His
                245                 250                 255
Arg Pro Gln Asn Gln Glu Pro Gln Ser Gln Pro Thr Glu Ser Leu Tyr
                260                 265                 270
Tyr Asp Tyr Glu Pro Pro Tyr Tyr Asp Val Met Thr Thr Gly Thr Thr
            275                 280                 285
Pro Asp Tyr Gln Asp Pro Thr Pro Gly Glu Glu Glu Ile Leu Glu
            290                 295                 300
Ser Ser Leu Leu Pro Pro Leu Glu Glu Glu Thr Asp Leu Gln Val
305                 310                 315                 320
Pro Pro Thr Ala Asp Arg Phe Gln Ala Glu Tyr Gly Glu Gly Gly
                325                 330                 335
Thr Asp Pro Pro Glu Gly Pro Tyr Asp Tyr Thr Tyr Gly Tyr Gly Asp
            340                 345                 350
Asp Tyr Arg Glu Glu Thr Glu Leu Gly Pro Ala Leu Ser Ala Glu Thr
                355                 360                 365
Ala His Ser Gly Ala Ala His Gly Pro Arg Gly Leu Lys Gly Glu
        370                 375                 380
Lys Gly Glu Pro Ala Val Leu Glu Pro Gly Met Leu Val Glu Gly Pro
385                 390                 395                 400
Pro Gly Pro Glu Gly Pro Ala Gly Leu Ile Gly Pro Pro Gly Ile Gln
                405                 410                 415
Gly Asn Pro Gly Pro Val Gly Asp Pro Gly Glu Arg Gly Pro Pro Gly
                420                 425                 430
```

```
Arg Ala Gly Leu Pro Gly Ser Asp Gly Ala Pro Gly Pro Pro Gly Thr
            435                 440                 445

Ser Leu Met Leu Pro Phe Arg Phe Gly Ser Gly Gly Asp Lys Gly
    450                 455                 460

Pro Val Val Ala Ala Gln Glu Ala Gln Ala Gln Ala Ile Leu Gln Gln
465                 470                 475                 480

Ala Arg Leu Ala Leu Arg Gly Pro Pro Gly Pro Met Gly Tyr Thr Gly
                485                 490                 495

Arg Pro Gly Pro Leu Gly Gln Pro Gly Ser Pro Gly Leu Lys Gly Glu
            500                 505                 510

Ser Gly Asp Leu Gly Pro Gln Gly Pro Arg Gly Pro Gln Gly Leu Thr
            515                 520                 525

Gly Pro Pro Gly Lys Ala Gly Arg Arg Gly Arg Ala Gly Ala Asp Gly
            530                 535                 540

Ala Arg Gly Met Pro Gly Asp Pro Gly Val Lys Gly Asp Arg Gly Phe
545                 550                 555                 560

Asp Gly Leu Pro Gly Leu Pro Gly Glu Lys Gly His Arg Gly Asp Thr
                565                 570                 575

Gly Ala Gln Gly Leu Pro Gly Pro Gly Glu Asp Gly Glu Arg Gly
                580                 585                 590

Asp Asp Gly Glu Ile Gly Pro Arg Gly Leu Pro Gly Glu Ser Gly Pro
            595                 600                 605

Arg Gly Leu Leu Gly Pro Lys Gly Pro Pro Gly Ile Pro Gly Pro Pro
            610                 615                 620

Gly Val Arg Gly Met Asp Gly Pro Gln Gly Pro Lys Gly Ser Leu Gly
625                 630                 635                 640

Pro Gln Gly Glu Pro Gly Pro Pro Gly Gln Gln Gly Thr Pro Gly Thr
                645                 650                 655

Gln Gly Leu Pro Gly Pro Gln Gly Ala Ile Gly Pro His Gly Glu Lys
                660                 665                 670

Gly Pro Gln Gly Lys Pro Gly Leu Pro Gly Met Pro Gly Ser Asp Gly
            675                 680                 685

Pro Pro Gly His Pro Gly Lys Glu Gly Pro Pro Gly Thr Lys Gly Asn
            690                 695                 700

Gln Gly Pro Ser Gly Pro Gln Gly Pro Leu Gly Tyr Pro Gly Pro Arg
705                 710                 715                 720

Gly Val Lys Gly Val Asp Gly Ile Arg Gly Leu Lys Gly His Lys Gly
                725                 730                 735

Glu Lys Gly Glu Asp Gly Phe Pro Gly Phe Lys Gly Asp Ile Gly Val
                740                 745                 750

Lys Gly Asp Arg Gly Glu Val Gly Val Pro Gly Ser Arg Gly Glu Asp
            755                 760                 765

Gly Pro Glu Gly Pro Lys Gly Arg Thr Gly Pro Thr Gly Asp Pro Gly
            770                 775                 780

Pro Pro Gly Leu Met Gly Glu Lys Gly Lys Leu Gly Val Pro Gly Leu
785                 790                 795                 800

Pro Gly Tyr Pro Gly Arg Gln Gly Pro Lys Gly Ser Leu Gly Phe Pro
                805                 810                 815

Gly Phe Pro Gly Ala Ser Gly Glu Lys Gly Ala Arg Gly Leu Ser Gly
                820                 825                 830

Lys Ser Gly Pro Arg Gly Glu Arg Gly Pro Thr Gly Pro Arg Gly Gln
            835                 840                 845

Arg Gly Pro Arg Gly Ala Thr Gly Lys Ser Gly Ala Lys Gly Thr Ser
```

```
                    850                 855                 860
Gly Gly Asp Gly Pro His Gly Pro Pro Gly Glu Arg Gly Leu Pro Gly
865                 870                 875                 880

Pro Gln Gly Pro Asn Gly Phe Pro Gly Pro Lys Gly Pro Pro Gly Pro
                885                 890                 895

Pro Gly Lys Asp Gly Leu Pro Gly His Pro Gly Gln Arg Gly Glu Val
                900                 905                 910

Gly Phe Gln Gly Lys Thr Gly Pro Pro Gly Pro Pro Gly Val Val Gly
                915                 920                 925

Pro Gln Gly Ala Ala Gly Glu Thr Gly Pro Met Gly Glu Arg Gly His
930                 935                 940

Pro Gly Pro Pro Gly Pro Pro Gly Glu Gln Gly Leu Pro Gly Thr Ala
945                 950                 955                 960

Gly Lys Glu Gly Thr Lys Gly Asp Pro Gly Pro Pro Gly Ala Pro Gly
                965                 970                 975

Lys Asp Gly Pro Ala Gly Leu Arg Gly Phe Pro Gly Glu Arg Gly Leu
                980                 985                 990

Pro Gly Thr Ala Gly Gly Pro Gly Leu Lys Gly Asn Glu Gly Pro Ser
                995                 1000                1005

Gly Pro Pro Gly Pro Ala Gly Ser Pro Gly Glu Arg Gly Ala Ala Gly
        1010                1015                1020

Ser Gly Gly Pro Ile Gly Pro Pro Gly Arg Pro Gly Pro Gln Gly Pro
1025                1030                1035                1040

Pro Gly Ala Ala Gly Glu Lys Gly Val Pro Gly Glu Lys Gly Pro Ile
                1045                1050                1055

Gly Pro Thr Gly Arg Asp Gly Val Gln Gly Pro Val Gly Leu Pro Gly
                1060                1065                1070

Pro Ala Gly Pro Pro Gly Val Ala Gly Glu Asp Gly Asp Lys Gly Glu
        1075                1080                1085

Val Gly Asp Pro Gly Gln Lys Gly Thr Lys Gly Asn Lys Gly Glu His
        1090                1095                1100

Gly Pro Pro Gly Pro Pro Gly Pro Ile Gly Pro Val Gly Gln Pro Gly
1105                1110                1115                1120

Ala Ala Gly Ala Asp Gly Glu Pro Gly Ala Arg Gly Pro Gln Gly His
                1125                1130                1135

Phe Gly Ala Lys Gly Asp Glu Gly Thr Arg Gly Phe Asn Gly Pro Pro
                1140                1145                1150

Gly Pro Ile Gly Leu Gln Gly Leu Pro Gly Pro Ser Gly Glu Lys Gly
                1155                1160                1165

Glu Thr Gly Asp Val Gly Pro Met Gly Pro Pro Gly Pro Pro Gly Pro
                1170                1175                1180

Arg Gly Pro Ala Gly Pro Asn Gly Ala Asp Gly Pro Gln Gly Pro Pro
1185                1190                1195                1200

Gly Gly Val Gly Asn Leu Gly Pro Pro Gly Glu Lys Gly Glu Pro Gly
                1205                1210                1215

Glu Ser Gly Ser Pro Gly Ile Gln Gly Glu Pro Gly Val Lys Gly Pro
                1220                1225                1230

Arg Gly Glu Arg Gly Glu Lys Gly Glu Ser Gly Gln Pro Gly Glu Pro
        1235                1240                1245

Gly Pro Pro Gly Pro Lys Gly Pro Thr Gly Asp Asp Gly Pro Lys Gly
                1250                1255                1260

Asn Pro Gly Pro Val Gly Phe Pro Gly Asp Pro Gly Pro Pro Gly Glu
1265                1270                1275                1280
```

```
Gly Gly Pro Arg Gly Gln Asp Gly Ala Lys Gly Asp Arg Gly Glu Asp
            1285                1290                1295

Gly Glu Pro Gly Gln Pro Gly Ser Pro Gly Pro Thr Gly Glu Asn Gly
        1300                1305                1310

Pro Pro Gly Pro Leu Gly Lys Arg Gly Pro Ala Gly Ser Pro Gly Ser
        1315                1320                1325

Glu Gly Arg Gln Gly Gly Lys Gly Ala Lys Gly Asp Pro Gly Ala Ile
        1330                1335                1340

Gly Ala Pro Gly Lys Thr Gly Pro Val Gly Pro Ala Gly Pro Ala Gly
1345                1350                1355                1360

Lys Pro Gly Pro Asp Gly Leu Arg Gly Leu Pro Gly Ser Val Gly Gln
        1365                1370                1375

Gln Gly Arg Pro Gly Ala Thr Gly Gln Ala Gly Pro Pro Gly Pro Val
        1380                1385                1390

Gly Pro Pro Gly Leu Pro Gly Leu Arg Gly Asp Ala Gly Ala Lys Gly
        1395                1400                1405

Glu Lys Gly His Pro Gly Leu Ile Gly Leu Ile Gly Pro Pro Gly Glu
        1410                1415                1420

Gln Gly Glu Lys Gly Asp Arg Gly Leu Pro Gly Pro Gln Gly Ser Pro
1425                1430                1435                1440

Gly Gln Lys Gly Glu Met Gly Ile Pro Gly Ala Ser Gly Pro Ile Gly
        1445                1450                1455

Pro Gly Gly Pro Pro Gly Leu Pro Gly Pro Ala Gly Pro Lys Gly Ala
        1460                1465                1470

Lys Gly Ala Thr Gly Pro Gly Gly Pro Lys Gly Glu Lys Gly Val Gln
        1475                1480                1485

Gly Pro Pro Gly His Pro Gly Pro Pro Gly Glu Val Ile Gln Pro Leu
        1490                1495                1500

Pro Ile Gln Met Pro Lys Lys Thr Arg Arg Ser Val Asp Gly Ser Arg
1505                1510                1515                1520

Leu Met Gln Glu Asp Glu Ala Ile Pro Thr Gly Gly Ala Pro Gly Ser
        1525                1530                1535

Pro Gly Gly Leu Glu Glu Ile Phe Gly Ser Leu Asp Ser Leu Arg Glu
        1540                1545                1550

Glu Ile Glu Gln Met Arg Arg Pro Thr Gly Thr Gln Asp Ser Pro Ala
        1555                1560                1565

Arg Thr Cys Gln Asp Leu Lys Leu Cys His Pro Glu Leu Pro Asp Gly
        1570                1575                1580

Glu Tyr Trp Val Asp Pro Asn Gln Gly Cys Ala Arg Asp Ala Phe Arg
1585                1590                1595                1600

Val Phe Cys Asn Phe Thr Ala Gly Gly Glu Thr Cys Val Thr Pro Arg
        1605                1610                1615

Asp Asp Val Thr Gln Phe Ser Tyr Val Asp Ser Glu Gly Ser Pro Val
        1620                1625                1630

Gly Val Val Gln Leu Thr Phe Leu Arg Leu Leu Ser Val Ser Ala His
        1635                1640                1645

Gln Asp Val Ser Tyr Pro Cys Ser Gly Ala Ala Arg Asp Gly Pro Leu
        1650                1655                1660

Arg Leu Arg Gly Ala Asn Glu Asp Glu Leu Ser Pro Glu Thr Ser Pro
1665                1670                1675                1680

Tyr Val Lys Glu Phe Arg Asp Gly Cys Gln Thr Gln Gln Gly Arg Thr
        1685                1690                1695

Val Leu Glu Val Arg Thr Pro Val Leu Glu Gln Leu Pro Val Leu Asp
        1700                1705                1710
```

```
Ala Ser Phe Ser Asp Leu Gly Ala Pro Pro Arg Arg Gly Gly Val Leu
        1715                1720                1725

Leu Gly Pro Val Cys Phe Met Gly
    1730            1735

<210> SEQ ID NO 28
<211> LENGTH: 310
<212> TYPE: PRT
<213> ORGANISM: Homo sapiens
<220> FEATURE:
<223> OTHER INFORMATION: syndecan-1 (SDC1)

<400> SEQUENCE: 28

Met Arg Arg Ala Ala Leu Trp Leu Trp Leu Cys Ala Leu Ala Leu Ser
 1               5                  10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 29
<211> LENGTH: 442
```

-continued

```
<212> TYPE: PRT
<213> ORGANISM: Homo sapiens
<220> FEATURE:
<223> OTHER INFORMATION: syndecan-3 (SDC3)

<400> SEQUENCE: 29

Met Lys Pro Gly Pro Pro His Arg Ala Gly Ala His Gly Ala Gly
 1               5                  10                  15

Ala Gly Ala Gly Ala Ala Ala Gly Pro Gly Ala Arg Gly Leu Leu Leu
                20                  25                  30

Pro Pro Leu Leu Leu Leu Leu Leu Ala Gly Arg Ala Ala Gly Ala Gln
                35                  40                  45

Arg Trp Arg Ser Glu Asn Phe Glu Arg Pro Val Asp Leu Glu Gly Ser
    50                  55                  60

Gly Asp Asp Ser Phe Pro Asp Asp Glu Leu Asp Asp Leu Tyr Ser
 65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
                100                 105                 110

Val Leu Pro Thr Thr Asn Ile Gln Pro Val Gly Thr Pro Phe Glu Glu
                115                 120                 125

Leu Pro Ser Glu Arg Pro Thr Leu Glu Pro Ala Thr Ser Pro Leu Val
    130                 135                 140

Val Thr Glu Val Pro Glu Pro Ser Gln Arg Ala Thr Thr Val Ser
 145                 150                 155                 160

Thr Thr Met Ala Thr Ala Ala Thr Ser Thr Gly Asp Pro Thr Val
                165                 170                 175

Ala Thr Val Pro Ala Thr Val Ala Thr Ala Pro Ser Thr Pro Ala
                180                 185                 190

Ala Pro Pro Phe Thr Ala Thr Ala Val Ile Arg Thr Thr Gly Val
                195                 200                 205

Arg Arg Leu Leu Pro Leu Pro Leu Thr Thr Val Ala Thr Ala Arg Ala
    210                 215                 220

Thr Thr Pro Glu Ala Pro Ser Pro Pro Thr Thr Ala Ala Val Leu Asp
 225                 230                 235                 240

Thr Glu Ala Pro Thr Pro Arg Leu Val Ser Thr Ala Thr Ser Arg Pro
                245                 250                 255

Arg Ala Leu Pro Arg Pro Ala Thr Thr Gln Glu Pro Asp Ile Pro Glu
                260                 265                 270

Arg Ser Thr Leu Pro Leu Gly Thr Thr Ala Pro Gly Pro Thr Glu Val
    275                 280                 285

Ala Gln Thr Pro Thr Pro Glu Thr Phe Leu Thr Thr Ile Arg Asp Glu
 290                 295                 300

Pro Glu Val Pro Val Ser Gly Gly Pro Ser Gly Asp Phe Glu Leu Pro
305                 310                 315                 320

Glu Glu Glu Thr Thr Gln Pro Asp Thr Ala Asn Glu Val Val Ala Val
                325                 330                 335

Gly Gly Ala Ala Ala Lys Ala Ser Ser Pro Pro Gly Thr Leu Pro Lys
                340                 345                 350

Gly Ala Arg Pro Gly Pro Gly Leu Leu Asp Asn Ala Ile Asp Ser Gly
                355                 360                 365

Ser Ser Ala Ala Gln Leu Pro Gln Lys Ser Ile Leu Glu Arg Lys Glu
    370                 375                 380

Val Leu Val Ala Val Ile Val Gly Gly Val Val Gly Ala Leu Phe Ala
```

```
                385                 390                 395                 400
Ala Phe Leu Val Thr Leu Leu Ile Tyr Arg Met Lys Lys Lys Asp Glu
                    405                 410                 415

Gly Ser Tyr Thr Leu Glu Glu Pro Lys Gln Ala Ser Val Thr Tyr Gln
                    420                 425                 430

Lys Pro Asp Lys Gln Glu Glu Phe Tyr Ala
                    435                 440

<210> SEQ ID NO 30
<211> LENGTH: 742
<212> TYPE: PRT
<213> ORGANISM: Homo sapiens
<220> FEATURE:
<223> OTHER INFORMATION: CD44, Indian blood group

<400> SEQUENCE: 30

Met Asp Lys Phe Trp Trp His Ala Ala Trp Gly Leu Cys Leu Val Pro
  1               5                  10                  15

Leu Ser Leu Ala Gln Ile Asp Leu Asn Ile Thr Cys Arg Phe Ala Gly
                 20                  25                  30

Val Phe His Val Glu Lys Asn Gly Arg Tyr Ser Ile Ser Arg Thr Glu
             35                  40                  45

Ala Ala Asp Leu Cys Lys Ala Phe Asn Ser Thr Leu Pro Thr Met Ala
         50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320
```

```
Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
            405                 410                 415

Lys Glu Asp Ser His Ser Thr Thr Gly Thr Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
        450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
        530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
        690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
```

-continued

```
                740

<210> SEQ ID NO 31
<211> LENGTH: 532
<212> TYPE: PRT
<213> ORGANISM: Homo sapiens
<220> FEATURE:
<223> OTHER INFORMATION: intercellular adhesion molecule 1 (ICAM1)

<400> SEQUENCE: 31

Met Ala Pro Ser Ser Pro Arg Pro Ala Leu Pro Ala Leu Leu Val Leu
  1               5                  10                  15

Leu Gly Ala Leu Phe Pro Gly Pro Gly Asn Ala Gln Thr Ser Val Ser
             20                  25                  30

Pro Ser Lys Val Ile Leu Pro Arg Gly Gly Ser Val Leu Val Thr Cys
         35                  40                  45

Ser Thr Ser Cys Asp Gln Pro Lys Leu Leu Gly Ile Glu Thr Pro Leu
     50                  55                  60

Pro Lys Lys Glu Leu Leu Leu Pro Gly Asn Asn Arg Lys Val Tyr Glu
 65                  70                  75                  80

Leu Ser Asn Val Gln Glu Asp Ser Gln Pro Met Cys Tyr Ser Asn Cys
                 85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365
```

Phe Ser Cys Ser Ala Thr Leu Glu Val Ala Gly Gln Leu Ile His Lys
370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
                420                 425                 430

Lys Asp Gly Thr Phe Pro Leu Pro Ile Gly Glu Ser Val Thr Val Thr
            435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
    515                 520                 525

Ala Thr Pro Pro
    530

<210> SEQ ID NO 32
<211> LENGTH: 739
<212> TYPE: PRT
<213> ORGANISM: Homo sapiens
<220> FEATURE:
<223> OTHER INFORMATION: vascular cell adhesion molecule 1 (VCAM1)

<400> SEQUENCE: 32

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

-continued

```
Leu Val Cys Arg Ala Lys Leu His Ile Asp Glu Met Asp Ser Val Pro
            195                 200                 205

Thr Val Arg Gln Ala Val Lys Glu Leu Gln Val Tyr Ile Ser Pro Lys
210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
                260                 265                 270

Asn Ala Thr Leu Thr Leu Ile Ala Met Arg Met Glu Asp Ser Gly Ile
            275                 280                 285

Tyr Val Cys Glu Gly Val Asn Leu Ile Gly Lys Asn Arg Lys Glu Val
            290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
                340                 345                 350

Ser Pro Leu Ser Gly Lys Val Arg Ser Glu Gly Thr Asn Ser Thr Leu
            355                 360                 365

Thr Leu Ser Pro Val Ser Phe Glu Asn Glu His Ser Tyr Leu Cys Thr
370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
            435                 440                 445

Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
                500                 505                 510

Asp Thr Thr Val Leu Val Ser Pro Ser Ser Ile Leu Glu Glu Gly Ser
            515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
                580                 585                 590

Glu Leu Ile Ile Gln Val Thr Pro Lys Asp Ile Lys Leu Thr Ala Phe
            595                 600                 605

Pro Ser Glu Ser Val Lys Glu Gly Asp Thr Val Ile Ile Ser Cys Thr
610                 615                 620
```

```
Cys Gly Asn Val Pro Glu Thr Trp Ile Ile Leu Lys Lys Ala Glu
625                 630                 635                 640

Thr Gly Asp Thr Val Leu Lys Ser Ile Asp Gly Ala Tyr Thr Ile Arg
            645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
        690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
            725                 730                 735

Ser Lys Val

<210> SEQ ID NO 33
<211> LENGTH: 558
<212> TYPE: PRT
<213> ORGANISM: Homo sapiens
<220> FEATURE:
<223> OTHER INFORMATION: glypican 1 (GPC1)

<400> SEQUENCE: 33

Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
```

```
                        245                 250                 255
Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Gly Lys Leu Ala Pro Arg Glu
        355                 360                 365

Arg Pro Pro Ser Gly Thr Leu Glu Lys Leu Val Ser Glu Ala Lys Ala
    370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
        435                 440                 445

Pro Asp Met Thr Ile Arg Gln Gln Ile Met Gln Leu Lys Ile Met Thr
    450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Ser Gly Asp Gly Cys Leu Asp
                485                 490                 495

Asp Leu Cys Ser Arg Lys Val Ser Arg Lys Ser Ser Ser Arg Thr
            500                 505                 510

Pro Leu Thr His Ala Leu Pro Gly Leu Ser Glu Gln Glu Gly Gln Lys
        515                 520                 525

Thr Ser Ala Ala Ser Cys Pro Gln Pro Pro Thr Phe Leu Leu Pro Leu
    530                 535                 540

Leu Leu Phe Leu Ala Leu Thr Val Ala Arg Pro Arg Trp Arg
545                 550                 555

<210> SEQ ID NO 34
<211> LENGTH: 579
<212> TYPE: PRT
<213> ORGANISM: Homo sapiens
<220> FEATURE:
<223> OTHER INFORMATION: glypican 2 (GPC2)

<400> SEQUENCE: 34

Met Ser Ala Leu Arg Pro Leu Leu Leu Leu Leu Pro Leu Cys Pro
  1               5                  10                  15

Gly Pro Gly Pro Gly Pro Gly Ser Glu Ala Lys Val Thr Arg Ser Cys
            20                  25                  30

Ala Glu Thr Arg Gln Val Leu Gly Ala Arg Gly Tyr Ser Leu Asn Leu
        35                  40                  45

Ile Pro Pro Ala Leu Ile Ser Gly Glu His Leu Arg Val Cys Pro Gln
    50                  55                  60
```

-continued

```
Glu Tyr Thr Cys Cys Ser Ser Glu Thr Glu Gln Arg Leu Ile Arg Glu
 65                  70                  75                  80

Thr Glu Ala Thr Phe Arg Gly Leu Val Glu Asp Ser Gly Ser Phe Leu
                 85                  90                  95

Val His Thr Leu Ala Ala Arg His Arg Lys Phe Asp Glu Phe Phe Leu
            100                 105                 110

Glu Met Leu Ser Val Ala Gln His Ser Leu Thr Gln Leu Phe Ser His
        115                 120                 125

Ser Tyr Gly Arg Leu Tyr Ala Gln His Ala Leu Ile Phe Asn Gly Leu
    130                 135                 140

Phe Ser Arg Leu Arg Asp Phe Tyr Gly Glu Ser Gly Glu Gly Leu Asp
145                 150                 155                 160

Asp Thr Leu Ala Asp Phe Trp Ala Gln Leu Leu Glu Arg Val Phe Pro
                165                 170                 175

Leu Leu His Pro Gln Tyr Ser Phe Pro Pro Asp Tyr Leu Leu Cys Leu
            180                 185                 190

Ser Arg Leu Ala Ser Ser Thr Asp Gly Ser Leu Gln Pro Phe Gly Asp
        195                 200                 205

Ser Pro Arg Arg Leu Arg Leu Gln Ile Thr Arg Thr Leu Val Ala Ala
    210                 215                 220

Arg Ala Phe Val Gln Gly Leu Glu Thr Gly Arg Asn Val Val Ser Glu
225                 230                 235                 240

Ala Leu Lys Val Pro Val Ser Glu Gly Cys Ser Gln Ala Leu Met Arg
                245                 250                 255

Leu Ile Gly Cys Pro Leu Cys Arg Gly Val Pro Ser Leu Met Pro Cys
            260                 265                 270

Gln Gly Phe Cys Leu Asn Val Val Arg Gly Cys Leu Ser Ser Arg Gly
        275                 280                 285

Leu Glu Pro Asp Trp Gly Asn Tyr Leu Asp Gly Leu Leu Ile Leu Ala
    290                 295                 300

Asp Lys Leu Gln Gly Pro Phe Ser Phe Glu Leu Thr Ala Glu Ser Ile
305                 310                 315                 320

Gly Val Lys Ile Ser Glu Gly Leu Met Tyr Leu Gln Glu Asn Ser Ala
                325                 330                 335

Lys Val Ser Ala Gln Val Phe Gln Glu Cys Gly Pro Pro Asp Pro Val
            340                 345                 350

Pro Ala Arg Asn Arg Arg Ala Pro Pro Arg Glu Glu Ala Gly Arg
        355                 360                 365

Leu Trp Ser Met Val Thr Glu Glu Arg Pro Thr Thr Ala Ala Gly
    370                 375                 380

Thr Asn Leu His Arg Leu Val Trp Glu Leu Arg Glu Arg Leu Ala Arg
385                 390                 395                 400

Met Arg Gly Phe Trp Ala Arg Leu Ser Leu Thr Val Cys Gly Asp Ser
                405                 410                 415

Arg Met Ala Ala Asp Ala Ser Leu Glu Ala Ala Pro Cys Trp Thr Gly
            420                 425                 430

Ala Gly Arg Gly Arg Tyr Leu Pro Pro Val Val Gly Ser Pro Ala
        435                 440                 445

Glu Gln Val Asn Asn Pro Glu Leu Lys Val Asp Ala Ser Gly Pro Asp
    450                 455                 460

Val Pro Thr Arg Arg Arg Leu Gln Leu Arg Ala Ala Thr Ala Arg
465                 470                 475                 480

Met Lys Thr Ala Ala Leu Gly His Asp Leu Asp Gly Gln Asp Ala Asp
```

```
                       485                 490                 495
Glu Asp Ala Ser Gly Ser Gly Gly Gln Gln Tyr Ala Asp Asp Trp
                500                 505                 510

Met Ala Gly Ala Val Ala Pro Pro Ala Arg Pro Pro Arg Pro Tyr
                515                 520                 525

Pro Pro Arg Arg Asp Gly Ser Gly Gly Lys Gly Gly Gly Ser Ala
                530                 535                 540

Arg Tyr Asn Gln Gly Arg Ser Arg Ser Gly Gly Ala Ser Ile Gly Phe
545                 550                 555                 560

His Thr Gln Thr Ile Leu Ile Leu Ser Leu Ser Ala Leu Ala Leu Leu
                565                 570                 575

Gly Pro Arg

<210> SEQ ID NO 35
<211> LENGTH: 556
<212> TYPE: PRT
<213> ORGANISM: Homo sapiens
<220> FEATURE:
<223> OTHER INFORMATION: glypican 4 (GPC4)

<400> SEQUENCE: 35

Met Ala Arg Phe Gly Leu Pro Ala Leu Leu Cys Thr Leu Ala Val Leu
1               5                   10                  15

Ser Ala Ala Leu Leu Ala Ala Glu Leu Lys Ser Lys Ser Cys Ser Glu
                20                  25                  30

Val Arg Arg Leu Tyr Val Ser Lys Gly Phe Asn Lys Asn Asp Ala Pro
                35                  40                  45

Leu His Glu Ile Asn Gly Asp His Leu Lys Ile Cys Pro Gln Gly Ser
        50                  55                  60

Thr Cys Cys Ser Gln Glu Met Glu Glu Lys Tyr Ser Leu Gln Ser Lys
65                  70                  75                  80

Asp Asp Phe Lys Ser Val Val Ser Glu Gln Cys Asn His Leu Gln Ala
                85                  90                  95

Val Phe Ala Ser Arg Tyr Lys Lys Phe Asp Glu Phe Phe Lys Glu Leu
                100                 105                 110

Leu Glu Asn Ala Glu Lys Ser Leu Asn Asp Met Phe Val Lys Thr Tyr
        115                 120                 125

Gly His Leu Tyr Met Gln Asn Ser Glu Leu Phe Lys Asp Leu Phe Val
        130                 135                 140

Glu Leu Lys Arg Tyr Tyr Val Val Gly Asn Val Asn Leu Glu Glu Met
145                 150                 155                 160

Leu Asn Asp Phe Trp Ala Arg Leu Leu Glu Arg Met Phe Arg Leu Val
                165                 170                 175

Asn Ser Gln Tyr His Phe Thr Asp Glu Tyr Leu Glu Cys Val Ser Lys
                180                 185                 190

Tyr Thr Glu Gln Leu Lys Pro Phe Gly Asp Val Pro Arg Lys Leu Lys
        195                 200                 205

Leu Gln Val Thr Arg Ala Phe Val Ala Ala Arg Thr Phe Ala Gln Gly
        210                 215                 220

Leu Ala Val Ala Gly Asp Val Val Ser Lys Val Ser Val Val Asn Pro
225                 230                 235                 240

Thr Ala Gln Cys Thr His Ala Leu Leu Lys Met Ile Tyr Cys Ser His
                245                 250                 255

Cys Arg Gly Leu Val Thr Val Lys Pro Cys Tyr Asn Tyr Cys Ser Asn
                260                 265                 270
```

```
Ile Met Arg Gly Cys Leu Ala Asn Gln Gly Asp Leu Asp Phe Glu Trp
         275                 280                 285

Asn Asn Phe Ile Asp Ala Met Leu Met Val Ala Glu Arg Leu Glu Gly
         290                 295                 300

Pro Phe Asn Ile Glu Ser Val Met Asp Pro Ile Asp Val Lys Ile Ser
305                 310                 315                 320

Asp Ala Ile Met Asn Met Gln Asp Asn Ser Val Gln Val Ser Gln Lys
                325                 330                 335

Val Phe Gln Gly Cys Gly Pro Pro Lys Pro Leu Pro Ala Gly Arg Ile
                340                 345                 350

Ser Arg Ser Ile Ser Glu Ser Ala Phe Ser Ala Arg Phe Arg Pro His
                355                 360                 365

His Pro Glu Glu Arg Pro Thr Thr Ala Ala Gly Thr Ser Leu Asp Arg
         370                 375                 380

Leu Val Thr Asp Val Lys Glu Lys Leu Lys Gln Ala Lys Lys Phe Trp
385                 390                 395                 400

Ser Ser Leu Pro Ser Asn Val Cys Asn Asp Glu Arg Met Ala Ala Gly
                405                 410                 415

Asn Gly Asn Glu Asp Asp Cys Trp Asn Gly Lys Gly Lys Ser Arg Tyr
                420                 425                 430

Leu Phe Ala Val Thr Gly Asn Gly Leu Ala Asn Gln Gly Asn Asn Pro
         435                 440                 445

Glu Val Gln Val Asp Thr Ser Lys Pro Asp Ile Leu Ile Leu Arg Gln
         450                 455                 460

Ile Met Ala Leu Arg Val Met Thr Ser Lys Met Lys Asn Ala Tyr Asn
465                 470                 475                 480

Gly Asn Asp Val Asp Phe Phe Asp Ile Ser Asp Glu Ser Ser Gly Glu
                485                 490                 495

Gly Ser Gly Ser Gly Cys Glu Tyr Gln Gln Cys Pro Ser Glu Phe Asp
                500                 505                 510

Tyr Asn Ala Thr Asp His Ala Gly Lys Ser Ala Asn Glu Lys Ala Asp
         515                 520                 525

Ser Ala Gly Val Arg Pro Gly Ala Gln Ala Tyr Leu Leu Thr Val Phe
         530                 535                 540

Cys Ile Leu Phe Leu Val Met Gln Arg Glu Trp Arg
545                 550                 555

<210> SEQ ID NO 36
<211> LENGTH: 572
<212> TYPE: PRT
<213> ORGANISM: Homo sapiens
<220> FEATURE:
<223> OTHER INFORMATION: glypican 5 (GPC5)

<400> SEQUENCE: 36

Met Asp Ala Gln Thr Trp Pro Val Gly Phe Arg Cys Leu Leu Leu Leu
  1               5                  10                  15

Ala Leu Val Gly Ser Ala Arg Ser Glu Gly Val Gln Thr Cys Glu Glu
              20                  25                  30

Val Arg Lys Leu Phe Gln Trp Arg Leu Leu Gly Ala Val Arg Gly Leu
          35                  40                  45

Pro Asp Ser Pro Arg Ala Gly Pro Asp Leu Gln Val Cys Ile Ser Lys
      50                  55                  60

Lys Pro Thr Cys Cys Thr Arg Lys Met Glu Glu Arg Tyr Gln Ile Ala
65                  70                  75                  80

Ala Arg Gln Asp Met Gln Gln Phe Leu Gln Thr Ser Ser Ser Thr Leu
```

```
                85                  90                  95
Lys Phe Leu Ile Ser Arg Asn Ala Ala Phe Gln Glu Thr Leu Glu
            100                 105                 110

Thr Leu Ile Lys Gln Ala Glu Asn Tyr Thr Ser Ile Leu Phe Cys Ser
            115                 120                 125

Thr Tyr Arg Asn Met Ala Leu Glu Ala Ala Ser Val Gln Glu Phe
            130                 135                 140

Phe Thr Asp Val Gly Leu Tyr Leu Phe Gly Ala Asp Val Asn Pro Glu
145                         150                 155                 160

Glu Phe Val Asn Arg Phe Phe Asp Ser Leu Phe Pro Leu Val Tyr Asn
                165                 170                 175

His Leu Ile Asn Pro Gly Val Thr Asp Ser Ser Leu Glu Tyr Ser Glu
            180                 185                 190

Cys Ile Arg Met Ala Arg Arg Asp Val Ser Pro Phe Gly Asn Ile Pro
            195                 200                 205

Gln Arg Val Met Gly Gln Met Gly Arg Ser Leu Leu Pro Ser Arg Thr
            210                 215                 220

Phe Leu Gln Ala Leu Asn Leu Gly Ile Glu Val Ile Asn Thr Thr Asp
225                 230                 235                 240

Tyr Leu His Phe Ser Lys Glu Cys Ser Arg Ala Leu Leu Lys Met Gln
                245                 250                 255

Tyr Cys Pro His Cys Gln Gly Leu Ala Leu Thr Lys Pro Cys Met Gly
            260                 265                 270

Tyr Cys Leu Asn Val Met Arg Gly Cys Leu Ala His Met Ala Glu Leu
            275                 280                 285

Asn Pro His Trp His Ala Tyr Ile Arg Ser Leu Glu Glu Leu Ser Asp
            290                 295                 300

Ala Met His Gly Thr Tyr Asp Ile Gly His Val Leu Leu Asn Phe His
305                 310                 315                 320

Leu Leu Val Asn Asp Ala Val Leu Gln Ala His Leu Asn Gly Gln Lys
                325                 330                 335

Leu Leu Glu Gln Val Asn Arg Ile Cys Gly Arg Pro Val Arg Thr Pro
            340                 345                 350

Thr Gln Ser Pro Arg Cys Ser Phe Asp Gln Ser Lys Glu Lys His Gly
            355                 360                 365

Met Lys Thr Thr Thr Arg Asn Ser Glu Glu Thr Leu Ala Asn Arg Arg
            370                 375                 380

Lys Glu Phe Ile Asn Ser Leu Arg Leu Tyr Arg Ser Phe Tyr Gly Gly
385                 390                 395                 400

Leu Ala Asp Gln Leu Cys Ala Asn Glu Leu Ala Ala Ala Asp Gly Leu
                405                 410                 415

Pro Cys Trp Asn Gly Glu Asp Ile Val Lys Ser Tyr Thr Gln Arg Val
            420                 425                 430

Val Gly Asn Gly Ile Lys Ala Gln Ser Gly Asn Pro Glu Val Lys Val
            435                 440                 445

Lys Gly Ile Asp Pro Val Ile Asn Gln Ile Ile Asp Lys Leu Lys His
            450                 455                 460

Val Val Gln Leu Leu Gln Gly Arg Ser Pro Lys Pro Asp Lys Trp Glu
465                 470                 475                 480

Leu Leu Gln Leu Gly Ser Gly Gly Met Val Glu Val Ser Gly
                485                 490                 495                     Gly

Asp Cys Asp Asp Glu Asp Gly Cys Gly Gly Ser Gly Ser Gly Glu Val
            500                 505                 510
```

```
Lys Arg Thr Leu Lys Ile Thr Asp Trp Met Pro Asp Met Asn Phe
            515                 520                 525

Ser Asp Val Lys Gln Ile His Gln Thr Asp Thr Gly Ser Thr Leu Asp
530                 535                 540

Thr Thr Gly Ala Gly Cys Ala Val Ala Thr Glu Ser Met Thr Phe Thr
545                 550                 555                 560

Leu Ile Ser Val Val Met Leu Leu Pro Gly Ile Trp
                565                 570

<210> SEQ ID NO 37
<211> LENGTH: 555
<212> TYPE: PRT
<213> ORGANISM: Homo sapiens
<220> FEATURE:
<223> OTHER INFORMATION: glypican 6 (GPC6)

<400> SEQUENCE: 37

Met Pro Ser Trp Ile Gly Ala Val Ile Leu Pro Leu Leu Gly Leu Leu
1               5                   10                  15

Leu Ser Leu Pro Ala Gly Ala Asp Val Lys Ala Arg Ser Cys Gly Glu
                20                  25                  30

Val Arg Gln Ala Tyr Gly Ala Lys Gly Phe Ser Leu Ala Asp Ile Pro
            35                  40                  45

Tyr Gln Glu Ile Ala Gly Glu His Leu Arg Ile Cys Pro Gln Glu Tyr
        50                  55                  60

Thr Cys Cys Thr Thr Glu Met Glu Asp Lys Leu Ser Gln Gln Ser Lys
65                  70                  75                  80

Leu Glu Phe Glu Asn Leu Val Glu Glu Thr Ser His Phe Val Arg Thr
                85                  90                  95

Thr Phe Val Ser Arg His Lys Lys Phe Asp Glu Phe Phe Arg Glu Leu
            100                 105                 110

Leu Glu Asn Ala Glu Lys Ser Leu Asn Asp Met Phe Val Arg Thr Tyr
        115                 120                 125

Gly Met Leu Tyr Met Gln Asn Ser Glu Val Phe Gln Asp Leu Phe Thr
130                 135                 140

Glu Leu Lys Arg Tyr Tyr Thr Gly Gly Asn Val Asn Leu Glu Glu Met
145                 150                 155                 160

Leu Asn Asp Phe Trp Ala Arg Leu Leu Glu Arg Met Phe Gln Leu Ile
                165                 170                 175

Asn Pro Gln Tyr His Phe Ser Glu Asp Tyr Leu Glu Cys Val Ser Lys
            180                 185                 190

Tyr Thr Asp Gln Leu Lys Pro Phe Gly Asp Val Pro Arg Lys Leu Lys
        195                 200                 205

Ile Gln Val Thr Arg Ala Phe Ile Ala Ala Arg Thr Phe Val Gln Gly
210                 215                 220

Leu Thr Val Gly Arg Glu Val Ala Asn Arg Val Ser Lys Val Ser Pro
225                 230                 235                 240

Thr Pro Gly Cys Ile Arg Ala Leu Met Lys Met Leu Tyr Cys Pro Tyr
                245                 250                 255

Cys Arg Gly Leu Pro Thr Val Arg Pro Cys Asn Asn Tyr Cys Leu Asn
            260                 265                 270

Val Met Lys Gly Cys Leu Ala Asn Gln Ala Asp Leu Asp Thr Glu Trp
        275                 280                 285

Asn Leu Phe Ile Asp Ala Met Leu Leu Val Ala Glu Arg Leu Glu Gly
290                 295                 300

Pro Phe Asn Ile Glu Ser Val Met Asp Pro Ile Asp Val Lys Ile Ser
```

```
                305                 310                 315                 320
Glu Ala Ile Met Asn Met Gln Glu Asn Ser Met Gln Val Ser Ala Lys
                325                 330                 335

Val Phe Gln Gly Cys Gly Gln Pro Lys Pro Ala Pro Ala Leu Arg Ser
                340                 345                 350

Ala Arg Ser Ala Pro Glu Asn Phe Asn Thr Arg Phe Arg Pro Tyr Asn
                355                 360                 365

Pro Glu Glu Arg Pro Thr Thr Ala Ala Gly Thr Ser Leu Asp Arg Leu
                370                 375                 380

Val Thr Asp Ile Lys Glu Lys Leu Lys Leu Ser Lys Lys Val Trp Ser
385                 390                 395                 400

Ala Leu Pro Tyr Thr Ile Cys Lys Asp Glu Ser Val Thr Ala Gly Thr
                405                 410                 415

Ser Asn Glu Glu Glu Cys Trp Asn Gly His Ser Lys Ala Arg Tyr Leu
                420                 425                 430

Pro Glu Ile Met Asn Asp Gly Leu Thr Asn Gln Ile Asn Asn Pro Glu
                435                 440                 445

Val Asp Val Asp Ile Thr Arg Pro Asp Thr Phe Ile Arg Gln Gln Ile
                450                 455                 460

Met Ala Leu Arg Val Met Thr Asn Lys Leu Lys Asn Ala Tyr Asn Gly
465                 470                 475                 480

Asn Asp Val Asn Phe Gln Asp Thr Ser Asp Glu Ser Ser Gly Ser Gly
                485                 490                 495

Ser Gly Ser Gly Cys Met Asp Asp Val Cys Pro Thr Glu Phe Glu Phe
                500                 505                 510

Val Thr Thr Glu Ala Pro Ala Val Asp Pro Asp Arg Arg Glu Val Asp
                515                 520                 525

Ser Ser Ala Ala Gln Arg Gly His Ser Leu Leu Ser Trp Ser Leu Thr
                530                 535                 540

Cys Ile Val Leu Ala Leu Gln Arg Leu Cys Arg
545                 550                 555

<210> SEQ ID NO 38
<211> LENGTH: 478
<212> TYPE: PRT
<213> ORGANISM: Homo sapiens
<220> FEATURE:
<223> OTHER INFORMATION: vitronectin precursor

<400> SEQUENCE: 38

Met Ala Pro Leu Arg Pro Leu Leu Ile Leu Ala Leu Leu Ala Trp Val
 1               5                  10                  15

Ala Leu Ala Asp Gln Glu Ser Cys Lys Gly Arg Cys Thr Glu Gly Phe
                20                  25                  30

Asn Val Asp Lys Lys Cys Gln Cys Asp Glu Leu Cys Ser Tyr Tyr Gln
                35                  40                  45

Ser Cys Cys Thr Asp Tyr Thr Ala Glu Cys Lys Pro Gln Val Thr Arg
        50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
                100                 105                 110

Thr Pro Val Leu Lys Pro Glu Glu Glu Ala Pro Ala Pro Glu Val Gly
                115                 120                 125
```

```
Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Arg Ser Gln Arg Gly
    370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Ser Gly Asp Lys Tyr Tyr Arg Val Asn
        435                 440                 445

Leu Arg Thr Arg Arg Val Asp Thr Val Asp Pro Pro Tyr Pro Arg Ser
    450                 455                 460

Ile Ala Gln Tyr Trp Leu Gly Cys Pro Ala Pro Gly His Leu
465                 470                 475

<210> SEQ ID NO 39
<211> LENGTH: 1247
<212> TYPE: PRT
<213> ORGANISM: Homo sapiens
<220> FEATURE:
<223> OTHER INFORMATION: nidogen 1 precursor

<400> SEQUENCE: 39

Met Leu Ala Ser Ser Ser Arg Ile Arg Ala Ala Trp Thr Arg Ala Leu
 1               5                  10                  15
```

```
Leu Leu Pro Leu Leu Ala Gly Pro Val Gly Cys Leu Ser Arg Gln
            20              25              30

Glu Leu Phe Pro Phe Gly Pro Gln Gly Asp Leu Glu Leu Glu Asp
        35              40              45

Gly Asp Asp Phe Val Ser Pro Ala Leu Glu Leu Ser Gly Ala Leu Arg
50              55              60

Phe Tyr Asp Arg Ser Asp Ile Asp Ala Val Tyr Val Thr Thr Asn Gly
65              70              75              80

Ile Ile Ala Thr Ser Glu Pro Ala Lys Glu Ser His Pro Gly Leu
            85              90              95

Phe Pro Pro Thr Phe Gly Ala Val Ala Pro Phe Leu Ala Asp Leu Asp
                100             105             110

Thr Thr Asp Gly Leu Gly Lys Val Tyr Tyr Arg Glu Asp Leu Ser Pro
        115             120             125

Ser Ile Thr Gln Arg Ala Ala Glu Cys Val His Arg Gly Phe Pro Glu
        130             135             140

Ile Ser Phe Gln Pro Ser Ser Ala Val Val Thr Trp Glu Ser Val
145             150             155             160

Ala Pro Tyr Gln Gly Pro Ser Arg Asp Pro Asp Gln Lys Gly Lys Arg
                165             170             175

Asn Thr Phe Gln Ala Val Leu Ala Ser Ser Asp Ser Ser Tyr Ala
            180             185             190

Ile Phe Leu Tyr Pro Glu Asp Gly Leu Gln Phe His Thr Thr Phe Ser
        195             200             205

Lys Lys Glu Asn Asn Gln Val Pro Ala Val Val Ala Phe Ser Gln Gly
        210             215             220

Ser Val Gly Phe Leu Trp Lys Ser Asn Gly Ala Tyr Asn Ile Phe Ala
225             230             235             240

Asn Asp Arg Glu Ser Val Glu Asn Leu Ala Lys Ser Ser Asn Ser Gly
                245             250             255

Gln Gln Gly Val Trp Val Phe Glu Ile Gly Ser Pro Ala Thr Thr Asn
                260             265             270

Gly Val Val Pro Ala Asp Val Ile Leu Gly Thr Glu Asp Gly Ala Glu
            275             280             285

Tyr Asp Asp Glu Asp Glu Asp Tyr Asp Leu Ala Thr Thr Arg Leu Gly
290             295             300

Leu Glu Asp Val Gly Thr Thr Pro Phe Ser Tyr Lys Ala Leu Arg Arg
305             310             315             320

Gly Gly Ala Asp Thr Tyr Ser Val Pro Ser Val Leu Ser Pro Arg Arg
            325             330             335

Ala Ala Thr Glu Arg Pro Leu Gly Pro Pro Thr Glu Arg Thr Arg Ser
            340             345             350

Phe Gln Leu Ala Val Glu Thr Phe His Gln His Pro Gln Val Ile
        355             360             365

Asp Val Asp Glu Val Glu Glu Thr Gly Val Val Phe Ser Tyr Asn Thr
        370             375             380

Asp Ser Arg Gln Thr Cys Ala Asn Asn Arg His Gln Cys Ser Val His
385             390             395             400

Ala Glu Cys Arg Asp Tyr Ala Thr Gly Phe Cys Cys Ser Cys Val Ala
                405             410             415

Gly Tyr Thr Gly Asn Gly Arg Gln Cys Val Ala Glu Gly Ser Pro Gln
            420             425             430

Arg Val Asn Gly Lys Val Lys Gly Arg Ile Phe Val Gly Ser Ser Gln
        435             440             445
```

-continued

Val Pro Ile Val Phe Glu Asn Thr Asp Leu His Ser Tyr Val Val Met
450                     455                 460

Asn His Gly Arg Ser Tyr Thr Ala Ile Ser Thr Ile Pro Glu Thr Val
465                 470                  475                  480

Gly Tyr Ser Leu Leu Pro Leu Ala Pro Val Gly Ile Ile Gly Trp
                485                 490                 495

Met Phe Ala Val Glu Gln Asp Gly Phe Lys Asn Gly Phe Ser Ile Thr
            500                 505                 510

Gly Gly Glu Phe Thr Arg Gln Ala Glu Val Thr Phe Val Gly His Pro
        515                 520                 525

Gly Asn Leu Val Ile Lys Gln Arg Phe Ser Gly Ile Asp Glu His Gly
    530                 535                 540

His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Thr Arg Glu Tyr Thr Val Thr
            580                 585                 590

Glu Pro Glu Arg Asp Gly Ala Ser Pro Ser Arg Ile Tyr Thr Tyr Gln
        595                 600                 605

Trp Arg Gln Thr Ile Thr Phe Gln Glu Cys Val His Asp Asp Ser Arg
610                 615                 620

Pro Ala Leu Pro Ser Thr Gln Gln Leu Ser Val Asp Ser Val Phe Val
625                 630                 635                 640

Leu Tyr Asn Gln Glu Glu Lys Ile Leu Arg Tyr Ala Leu Ser Asn Ser
                645                 650                 655

Ile Gly Pro Val Arg Glu Gly Ser Pro Asp Ala Leu Gln Asn Pro Cys
            660                 665                 670

Tyr Ile Gly Thr His Gly Cys Asp Thr Asn Ala Ala Cys Arg Pro Gly
        675                 680                 685

Pro Arg Thr Gln Phe Thr Cys Glu Cys Ser Ile Gly Phe Arg Gly Asp
    690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                725                 730                 735

Glu Cys Val Glu Gly Tyr Gln Phe Ser Asp Glu Gly Thr Cys Val Ala
            740                 745                 750

Val Val Asp Gln Arg Pro Ile Asn Tyr Cys Glu Thr Gly Leu His Asn
    755                 760                 765

Cys Asp Ile Pro Gln Arg Ala Gln Cys Ile Tyr Thr Gly Gly Ser Ser
770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                805                 810                 815

Cys Tyr Asn Thr Pro Gly Ser Phe Thr Cys Gln Cys Lys Pro Gly Tyr
            820                 825                 830

Gln Gly Asp Gly Phe Arg Cys Val Pro Gly Glu Val Glu Lys Thr Arg
        835                 840                 845

Cys Gln His Glu Arg Glu His Ile Leu Gly Ala Ala Gly Ala Thr Asp
    850                 855                 860

Pro Gln Arg Pro Ile Pro Pro Gly Leu Phe Val Pro Glu Cys Asp Ala

|   |   |   |   |   |   |   |   |   |   |   |   |   |   |   |
|---|---|---|---|---|---|---|---|---|---|---|---|---|---|---|
| 865 |   |   |   |   | 870 |   |   |   |   | 875 |   |   |   | 880 |

His Gly His Tyr Ala Pro Thr Gln Cys His Gly Ser Thr Gly Tyr Cys
                885                     890                 895

Trp Cys Val Asp Arg Asp Gly Arg Glu Val Glu Gly Thr Arg Thr Arg
                900                     905                 910

Pro Gly Met Thr Pro Pro Cys Leu Ser Thr Val Ala Pro Ile His
            915                 920                 925

Gln Gly Pro Ala Val Pro Thr Ala Val Ile Pro Leu Pro Pro Gly Thr
        930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
                965                 970                 975

Ala Lys Val Ile Ile Gly Leu Ala Phe Asp Cys Val Asp Lys Met Val
            980                 985                 990

Tyr Trp Thr Asp Ile Thr Glu Pro Ser Ile Gly Arg Ala Ser Leu His
        995                 1000                1005

Gly Gly Glu Pro Thr Thr Ile Ile Arg Gln Asp Leu Gly Ser Pro Glu
    1010                1015                1020

Gly Ile Ala Val Asp His Leu Gly Arg Asn Ile Phe Trp Thr Asp Ser
1025                1030                1035                1040

Asn Leu Asp Arg Ile Glu Val Ala Lys Leu Asp Gly Thr Gln Arg Arg
                1045                1050                1055

Val Leu Phe Glu Thr Asp Leu Val Asn Pro Arg Gly Ile Val Thr Asp
                1060                1065                1070

Ser Val Arg Gly Asn Leu Tyr Trp Thr Asp Trp Asn Arg Asp Asn Pro
            1075                1080                1085

Lys Ile Glu Thr Ser Tyr Met Asp Gly Thr Asn Arg Arg Ile Leu Val
        1090                1095                1100

Gln Asp Asp Leu Gly Leu Pro Asn Gly Leu Thr Phe Asp Ala Phe Ser
1105                1110                1115                1120

Ser Gln Leu Cys Trp Val Asp Ala Gly Thr Asn Arg Ala Glu Cys Leu
                1125                1130                1135

Asn Pro Ser Gln Pro Ser Arg Arg Lys Ala Leu Glu Gly Leu Gln Tyr
            1140                1145                1150

Pro Phe Ala Val Thr Ser Tyr Gly Lys Asn Leu Tyr Phe Thr Asp Trp
        1155                1160                1165

Lys Met Asn Ser Val Val Ala Leu Asp Leu Ala Ile Ser Lys Glu Thr
    1170                1175                1180

Asp Ala Phe Gln Pro His Lys Gln Thr Arg Leu Tyr Gly Ile Thr Thr
1185                1190                1195                1200

Ala Leu Ser Gln Cys Pro Gln Gly His Asn Tyr Cys Ser Val Asn Asn
            1205                1210                1215

Gly Gly Cys Thr His Leu Cys Leu Ala Thr Pro Gly Ser Arg Thr Cys
        1220                1225                1230

Arg Cys Pro Asp Asn Thr Leu Gly Val Asp Cys Ile Glu Gln Lys
    1235                1240                1245

<210> SEQ ID NO 40
<211> LENGTH: 25
<212> TYPE: PRT
<213> ORGANISM: Artificial Sequence
<220> FEATURE:
<223> OTHER INFORMATION: synthetic citrullinated vimentin peptide VMT1
<220> FEATURE:
<221> NAME/KEY: MOD_RES

```
<222> LOCATION: (1)...(1)
<223> OTHER INFORMATION: Gly modified by biotin
<220> FEATURE:
<221> NAME/KEY: MOD_RES
<222> LOCATION: (6)...(6)
<223> OTHER INFORMATION: Xaa = citrulline
<220> FEATURE:
<221> NAME/KEY: AMIDATION
<222> LOCATION: (25)...(25)
<223> OTHER INFORMATION: serinamide

<400> SEQUENCE: 40

Gly Gly Gly Ala Thr Xaa Ser Ser Ala Val Arg Leu Arg Ser Ser Val
1               5                   10                  15

Pro Gly Val Arg Leu Leu Gln Asp Ser
            20                  25

<210> SEQ ID NO 41
<211> LENGTH: 22
<212> TYPE: PRT
<213> ORGANISM: Artificial Sequence
<220> FEATURE:
<223> OTHER INFORMATION: synthetic vimentin peptide VMT1 core sequence
<220> FEATURE:
<221> NAME/KEY: MOD_RES
<222> LOCATION: (3)...(3)
<223> OTHER INFORMATION: Xaa = citrulline

<400> SEQUENCE: 41

Ala Thr Xaa Ser Ser Ala Val Arg Leu Arg Ser Ser Val Pro Gly Val
1               5                   10                  15

Arg Leu Leu Gln Asp Ser
            20

<210> SEQ ID NO 42
<211> LENGTH: 25
<212> TYPE: PRT
<213> ORGANISM: Artificial Sequence
<220> FEATURE:
<223> OTHER INFORMATION: synthetic citrullinated vimentin peptide VMT2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (11)...(11)
<223> OTHER INFORMATION: Xaa = citrulline
<220> FEATURE:
<221> NAME/KEY: AMIDATION
<222> LOCATION: (25)...(25)
<223> OTHER INFORMATION: serinamide

<400> SEQUENCE: 42

Gly Gly Gly Ala Thr Arg Ser Ser Ala Val Xaa Leu Arg Ser Ser Val
1               5                   10                  15

Pro Gly Val Arg Leu Leu Gln Asp Ser
            20                  25

<210> SEQ ID NO 43
<211> LENGTH: 22
<212> TYPE: PRT
<213> ORGANISM: Artificial Sequence
<220> FEATURE:
<223> OTHER INFORMATION: synthetic vimentin peptide VMT2 core sequence
<220> FEATURE:
<221> NAME/KEY: MOD_RES
<222> LOCATION: (8)...(8)
<223> OTHER INFORMATION: Xaa = citrulline

<400> SEQUENCE: 43
```

```
Ala Thr Arg Ser Ser Ala Val Xaa Leu Arg Ser Ser Val Pro Gly Val
1               5                   10                  15

Arg Leu Leu Gln Asp Ser
            20
```

<210> SEQ ID NO 44
<211> LENGTH: 25
<212> TYPE: PRT
<213> ORGANISM: Artificial Sequence
<220> FEATURE:
<223> OTHER INFORMATION: synthetic citrullinated vimentin peptide VMT3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (13)...(13)
<223> OTHER INFORMATION: Xaa = citrulline
<220> FEATURE:
<221> NAME/KEY: AMIDATION
<222> LOCATION: (25)...(25)
<223> OTHER INFORMATION: serinamide

<400> SEQUENCE: 44

```
Gly Gly Gly Ala Thr Arg Ser Ser Ala Val Arg Leu Xaa Ser Ser Val
1               5                   10                  15

Pro Gly Val Arg Leu Leu Gln Asp Ser
            20                  25
```

<210> SEQ ID NO 45
<211> LENGTH: 22
<212> TYPE: PRT
<213> ORGANISM: Artificial Sequence
<220> FEATURE:
<223> OTHER INFORMATION: synthetic vimentin peptide VMT3 core sequence
<220> FEATURE:
<221> NAME/KEY: MOD_RES
<222> LOCATION: (10)...(10)
<223> OTHER INFORMATION: Xaa = citrulline

<400> SEQUENCE: 45

```
Ala Thr Arg Ser Ser Ala Val Arg Leu Xaa Ser Ser Val Pro Gly Val
1               5                   10                  15

Arg Leu Leu Gln Asp Ser
            20
```

<210> SEQ ID NO 46
<211> LENGTH: 25
<212> TYPE: PRT
<213> ORGANISM: Artificial Sequence
<220> FEATURE:
<223> OTHER INFORMATION: synthetic citrullinated vimentin peptide VMT4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (20)...(20)
<223> OTHER INFORMATION: Xaa = citrulline
<220> FEATURE:
<221> NAME/KEY: AMIDATION
<222> LOCATION: (25)...(25)
<223> OTHER INFORMATION: serinamide

<400> SEQUENCE: 46

```
Gly Gly Gly Ala Thr Arg Ser Ser Ala Val Arg Leu Arg Ser Ser Val
1               5                   10                  15
```

Pro Gly Val Xaa Leu Leu Gln Asp Ser
            20                  25

<210> SEQ ID NO 47
<211> LENGTH: 22
<212> TYPE: PRT
<213> ORGANISM: Artificial Sequence
<220> FEATURE:
<223> OTHER INFORMATION: synthetic vimentin peptide VMT4 core sequence
<220> FEATURE:
<221> NAME/KEY: MOD_RES
<222> LOCATION: (17)...(17)
<223> OTHER INFORMATION: Xaa = citrulline

<400> SEQUENCE: 47

Ala Thr Arg Ser Ser Ala Val Arg Leu Arg Ser Ser Val Pro Gly Val
1               5                   10                  15

Xaa Leu Leu Gln Asp Ser
            20

<210> SEQ ID NO 48
<211> LENGTH: 25
<212> TYPE: PRT
<213> ORGANISM: Artificial Sequence
<220> FEATURE:
<223> OTHER INFORMATION: synthetic citrullinated vimentin peptide VMT5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(20)
<223> OTHER INFORMATION: Xaa = citrulline
<220> FEATURE:
<221> NAME/KEY: AMIDATION
<222> LOCATION: (25)...(25)
<223> OTHER INFORMATION: serinamide

<400> SEQUENCE: 48

Gly Gly Gly Ala Thr Xaa Ser Ser Ala Val Xaa Leu Xaa Ser Ser Val
1               5                   10                  15

Pro Gly Val Xaa Leu Leu Gln Asp Ser
            20                  25

<210> SEQ ID NO 49
<211> LENGTH: 22
<212> TYPE: PRT
<213> ORGANISM: Artificial Sequence
<220> FEATURE:
<223> OTHER INFORMATION: synthetic vimentin peptide VMT5 core sequence
<220> FEATURE:
<221> NAME/KEY: MOD_RES
<222> LOCATION: (3)...(17)
<223> OTHER INFORMATION: Xaa = citrulline

<400> SEQUENCE: 49

Ala Thr Xaa Ser Ser Ala Val Xaa Leu Xaa Ser Ser Val Pro Gly Val
1               5                   10                  15

Xaa Leu Leu Gln Asp Ser
            20

<210> SEQ ID NO 50
<211> LENGTH: 32
<212> TYPE: PRT
<213> ORGANISM: Artificial Sequence
<220> FEATURE:
<223> OTHER INFORMATION: synthetic citrullinated vimentin peptide VMT6
<220> FEATURE:
<221> NAME/KEY: MOD_RES

```
<222> LOCATION: (1)...(1)
<223> OTHER INFORMATION: Gly modified by biotin
<220> FEATURE:
<221> NAME/KEY: MOD_RES
<222> LOCATION: (4)...(29)
<223> OTHER INFORMATION: Xaa = citrulline
<220> FEATURE:
<221> NAME/KEY: AMIDATION
<222> LOCATION: (32)...(32)
<223> OTHER INFORMATION: valinamide

<400> SEQUENCE: 50

Gly Ser Thr Xaa Ser Val Ser Ser Ser Tyr Arg Xaa Arg Ser Val
1               5                   10                  15

Ser Ser Ser Ser Tyr Xaa Ser Arg Pro Ser Ser Ser Xaa Ser Tyr Val
                20                  25                  30

<210> SEQ ID NO 51
<211> LENGTH: 31
<212> TYPE: PRT
<213> ORGANISM: Artificial Sequence
<220> FEATURE:
<223> OTHER INFORMATION: synthetic vimentin peptide VMT6 core sequence,
      vimentin composite sequence of synthetic fragments, synthetic
      composite sequence
<220> FEATURE:
<221> NAME/KEY: MOD_RES
<222> LOCATION: (3)...(28)
<223> OTHER INFORMATION: Xaa = citrulline

<400> SEQUENCE: 51

Ser Thr Xaa Ser Val Ser Ser Ser Ser Tyr Arg Xaa Arg Ser Val Ser
1               5                   10                  15

Ser Ser Ser Tyr Xaa Ser Arg Pro Ser Ser Ser Xaa Ser Tyr Val
                20                  25                  30

<210> SEQ ID NO 52
<211> LENGTH: 33
<212> TYPE: PRT
<213> ORGANISM: Artificial Sequence
<220> FEATURE:
<223> OTHER INFORMATION: synthetic citrullinated vimentin peptide VMT7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(27)
<223> OTHER INFORMATION: Xaa = citrulline
<220> FEATURE:
<221> NAME/KEY: AMIDATION
<222> LOCATION: (33)...(33)
<223> OTHER INFORMATION: leucinamide

<400> SEQUENCE: 52

Gly Arg Ser Tyr Val Thr Thr Ser Thr Xaa Thr Tyr Ser Ala Leu Arg
1               5                   10                  15

Pro Ser Thr Ser Xaa Ser Leu Tyr Ala Thr Xaa Ser Ser Ala Val Arg
                20                  25                  30

Leu

<210> SEQ ID NO 53
<211> LENGTH: 32
<212> TYPE: PRT
<213> ORGANISM: Artificial Sequence
<220> FEATURE:
<223> OTHER INFORMATION: synthetic vimentin peptide VMT7 core sequence
<220> FEATURE:
<221> NAME/KEY: MOD_RES
```

```
<222> LOCATION: (9)...(26)
<223> OTHER INFORMATION: Xaa = citrulline

<400> SEQUENCE: 53

Arg Ser Tyr Val Thr Thr Ser Thr Xaa Thr Tyr Ser Ala Leu Arg Pro
1               5                   10                  15

Ser Thr Ser Xaa Ser Leu Tyr Ala Thr Xaa Ser Ser Ala Val Arg Leu
            20                  25                  30

<210> SEQ ID NO 54
<211> LENGTH: 26
<212> TYPE: PRT
<213> ORGANISM: Artificial Sequence
<220> FEATURE:
<223> OTHER INFORMATION: synthetic citrullinated vimentin peptide VMT8
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(21)
<223> OTHER INFORMATION: Xaa = citrulline
<220> FEATURE:
<221> NAME/KEY: AMIDATION
<222> LOCATION: (26)...(26)
<223> OTHER INFORMATION: glycinamide

<400> SEQUENCE: 54

Gly Thr Arg Ser Ser Ala Val Xaa Leu Arg Ser Ser Val Pro Gly Val
1               5                   10                  15

Xaa Val Arg Leu Xaa Ser Ser Val Pro Gly
            20                  25

<210> SEQ ID NO 55
<211> LENGTH: 25
<212> TYPE: PRT
<213> ORGANISM: Artificial Sequence
<220> FEATURE:
<223> OTHER INFORMATION: synthetic vimentin peptide VMT8 core sequence
<220> FEATURE:
<221> NAME/KEY: MOD_RES
<222> LOCATION: (7)...(20)
<223> OTHER INFORMATION: Xaa = citrulline

<400> SEQUENCE: 55

Thr Arg Ser Ser Ala Val Xaa Leu Arg Ser Ser Val Pro Gly Val Xaa
1               5                   10                  15

Val Arg Leu Xaa Ser Ser Val Pro Gly
            20                  25

<210> SEQ ID NO 56
<211> LENGTH: 27
<212> TYPE: PRT
<213> ORGANISM: Artificial Sequence
<220> FEATURE:
<223> OTHER INFORMATION: synthetic citrullinated vimentin peptide VMT9
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(20)
<223> OTHER INFORMATION: Xaa = citrulline
<220> FEATURE:
<221> NAME/KEY: AMIDATION
<222> LOCATION: (27)...(27)
<223> OTHER INFORMATION: threoninamide

<400> SEQUENCE: 56
```

```
Gly Phe Lys Asn Thr Xaa Thr Asn Glu Lys Asn Tyr Ile Asp Lys Val
 1               5                  10                  15

Xaa Phe Leu Xaa Arg Gln Val Asp Gln Leu Thr
            20                  25
```

<210> SEQ ID NO 57
<211> LENGTH: 26
<212> TYPE: PRT
<213> ORGANISM: Artificial Sequence
<220> FEATURE:
<223> OTHER INFORMATION: synthetic vimentin peptide VMT9 core sequence
<220> FEATURE:
<221> NAME/KEY: MOD_RES
<222> LOCATION: (5)...(19)
<223> OTHER INFORMATION: Xaa = citrulline

<400> SEQUENCE: 57

```
Phe Lys Asn Thr Xaa Thr Asn Glu Lys Asn Tyr Ile Asp Lys Val Xaa
 1               5                  10                  15

Phe Leu Xaa Arg Gln Val Asp Gln Leu Thr
            20                  25
```

<210> SEQ ID NO 58
<211> LENGTH: 32
<212> TYPE: PRT
<213> ORGANISM: Artificial Sequence
<220> FEATURE:
<223> OTHER INFORMATION: synthetic citrullinated vimentin peptide VMT10
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline
<220> FEATURE:
<221> NAME/KEY: AMIDATION
<222> LOCATION: (32)...(32)
<223> OTHER INFORMATION: valinamide

<400> SEQUENCE: 58

```
Gly Leu Arg Xaa Gln Val Asp Gln Leu Thr Ser Phe Xaa Gln Asp Val
 1               5                  10                  15

Asp Asn Ala Ser Leu Ala Xaa Ala Arg Leu Asp Leu Glu Xaa Lys Val
            20                  25                  30
```

<210> SEQ ID NO 59
<211> LENGTH: 31
<212> TYPE: PRT
<213> ORGANISM: Artificial Sequence
<220> FEATURE:
<223> OTHER INFORMATION: synthetic vimentin peptide VMT10 core sequence
<220> FEATURE:
<221> NAME/KEY: MOD_RES
<222> LOCATION: (3)...(29)
<223> OTHER INFORMATION: Xaa = citrulline

<400> SEQUENCE: 59

```
Leu Arg Xaa Gln Val Asp Gln Leu Thr Ser Phe Xaa Gln Asp Val Asp
 1               5                  10                  15

Asn Ala Ser Leu Ala Xaa Ala Arg Leu Asp Leu Glu Xaa Lys Val
            20                  25                  30
```

<210> SEQ ID NO 60
<211> LENGTH: 21
<212> TYPE: PRT
<213> ORGANISM: Artificial Sequence

```
<220> FEATURE:
<223> OTHER INFORMATION: synthetic citrullinated vimentin peptide VMT11
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(14)
<223> OTHER INFORMATION: Xaa = citrulline
<220> FEATURE:
<221> NAME/KEY: AMIDATION
<222> LOCATION: (21)...(21)
<223> OTHER INFORMATION: serinamide

<400> SEQUENCE: 60

Gly Thr Ala Ala Leu Xaa Asp Val Arg Gln Gln Tyr Arg Xaa Gln Val
1               5                   10                  15

Gln Ser Leu Thr Ser
            20

<210> SEQ ID NO 61
<211> LENGTH: 20
<212> TYPE: PRT
<213> ORGANISM: Artificial Sequence
<220> FEATURE:
<223> OTHER INFORMATION: synthetic vimentin peptide VMT11 core sequence
<220> FEATURE:
<221> NAME/KEY: MOD_RES
<222> LOCATION: (5)...(13)
<223> OTHER INFORMATION: Xaa = citrulline

<400> SEQUENCE: 61

Thr Ala Ala Leu Xaa Asp Val Arg Gln Gln Tyr Arg Xaa Gln Val Gln
1               5                   10                  15

Ser Leu Thr Ser
            20

<210> SEQ ID NO 62
<211> LENGTH: 27
<212> TYPE: PRT
<213> ORGANISM: Artificial Sequence
<220> FEATURE:
<223> OTHER INFORMATION: synthetic citrullinated vimentin peptide VMT12
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (27)...(27)
<223> OTHER INFORMATION: threoninamide

<400> SEQUENCE: 62

Gly Ala Asn Arg Asn Asn Asp Ala Leu Xaa Gln Ala Lys Gln Glu Ser
1               5                   10                  15

Thr Glu Tyr Xaa Arg Gln Val Gln Ser Leu Thr
            20                  25

<210> SEQ ID NO 63
<211> LENGTH: 26
<212> TYPE: PRT
<213> ORGANISM: Artificial Sequence
<220> FEATURE:
<223> OTHER INFORMATION: synthetic vimentin peptide VMT12 core sequence
<220> FEATURE:
<221> NAME/KEY: MOD_RES
```

```
<222> LOCATION: (9)...(19)
<223> OTHER INFORMATION: Xaa = citrulline

<400> SEQUENCE: 63

Ala Asn Arg Asn Asn Asp Ala Leu Xaa Gln Ala Lys Gln Glu Ser Thr
1               5                   10                  15

Glu Tyr Xaa Arg Gln Val Gln Ser Leu Thr
            20                  25

<210> SEQ ID NO 64
<211> LENGTH: 32
<212> TYPE: PRT
<213> ORGANISM: Artificial Sequence
<220> FEATURE:
<223> OTHER INFORMATION: synthetic citrullinated vimentin peptide VMT13
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (11)...(29)
<223> OTHER INFORMATION: Xaa = citrulline
<220> FEATURE:
<221> NAME/KEY: AMIDATION
<222> LOCATION: (32)...(32)
<223> OTHER INFORMATION: argininamide

<400> SEQUENCE: 64

Gly Arg Ala Asn Tyr Gln Asp Thr Ile Gly Xaa Leu Asp Ile Glu Ile
1               5                   10                  15

Ala Thr Tyr Xaa Lys Leu Leu Glu Gly Glu Glu Ser Xaa Ile Ser Arg
            20                  25                  30

<210> SEQ ID NO 65
<211> LENGTH: 29
<212> TYPE: PRT
<213> ORGANISM: Artificial Sequence
<220> FEATURE:
<223> OTHER INFORMATION: synthetic vimentin peptide VMT13 core sequence
<220> FEATURE:
<221> NAME/KEY: MOD_RES
<222> LOCATION: (9)...(27)
<223> OTHER INFORMATION: Xaa = citrulline

<400> SEQUENCE: 65

Ala Asn Tyr Gln Asp Thr Ile Gly Xaa Leu Asp Ile Glu Ile Ala Thr
1               5                   10                  15

Tyr Xaa Lys Leu Leu Glu Gly Glu Glu Ser Xaa Ile Ser
            20                  25

<210> SEQ ID NO 66
<211> LENGTH: 37
<212> TYPE: PRT
<213> ORGANISM: Artificial Sequence
<220> FEATURE:
<223> OTHER INFORMATION: synthetic citrullinated vimentin peptide VMT14
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(35)
<223> OTHER INFORMATION: Xaa = citrulline
<220> FEATURE:
<221> NAME/KEY: AMIDATION
<222> LOCATION: (37)...(37)
<223> OTHER INFORMATION: glycinamide

<400> SEQUENCE: 66
```

```
Gly Asn Phe Ser Ser Leu Asn Leu Xaa Glu Thr Asn Leu Asp Ser Leu
 1               5                  10                  15

Pro Leu Val Asp Thr His Ser Lys Xaa Thr Leu Leu Ile Lys Thr Val
            20                  25                  30

Glu Thr Xaa Asp Gly
        35

<210> SEQ ID NO 67
<211> LENGTH: 36
<212> TYPE: PRT
<213> ORGANISM: Artificial Sequence
<220> FEATURE:
<223> OTHER INFORMATION: synthetic vimentin peptide VMT14 core sequence
<220> FEATURE:
<221> NAME/KEY: MOD_RES
<222> LOCATION: (8)...(34)
<223> OTHER INFORMATION: Xaa = citrulline

<400> SEQUENCE: 67

Asn Phe Ser Ser Leu Asn Leu Xaa Glu Thr Asn Leu Asp Ser Leu Pro
 1               5                  10                  15

Leu Val Asp Thr His Ser Lys Xaa Thr Leu Leu Ile Lys Thr Val Glu
            20                  25                  30

Thr Xaa Asp Gly
        35

<210> SEQ ID NO 68
<211> LENGTH: 19
<212> TYPE: PRT
<213> ORGANISM: Artificial Sequence
<220> FEATURE:
<223> OTHER INFORMATION: synthetic citrullinated alpha enolase peptide
      H-Enls-1
<220> FEATURE:
<221> NAME/KEY: MOD_RES
<222> LOCATION: (1)...(1)
<223> OTHER INFORMATION: Cys modified by biotin
<220> FEATURE:
<221> NAME/KEY: DISULFID
<222> LOCATION: (1)..(19)
<220> FEATURE:
<221> NAME/KEY: MOD_RES
<222> LOCATION: (6)...(12)
<223> OTHER INFORMATION: Xaa = citrulline
<220> FEATURE:
<221> NAME/KEY: AMIDATION
<222> LOCATION: (19)...(19)
<223> OTHER INFORMATION: cysteinamide

<400> SEQUENCE: 68

Cys Lys Ile His Ala Xaa Glu Ile Phe Asp Ser Xaa Gly Asn Pro Thr
 1               5                  10                  15

Val Glu Cys

<210> SEQ ID NO 69
<211> LENGTH: 17
<212> TYPE: PRT
<213> ORGANISM: Artificial Sequence
<220> FEATURE:
<223> OTHER INFORMATION: synthetic alpha enolase peptide H-Enls-1 core
      sequence
<220> FEATURE:
<221> NAME/KEY: MOD_RES
<222> LOCATION: (5)...(11)
<223> OTHER INFORMATION: Xaa = citrulline

<400> SEQUENCE: 69

Lys Ile His Ala Xaa Glu Ile Phe Asp Ser Xaa Gly Asn Pro Thr Val
```

Glu

```
<210> SEQ ID NO 70
<211> LENGTH: 19
<212> TYPE: PRT
<213> ORGANISM: Artificial Sequence
<220> FEATURE:
<223> OTHER INFORMATION: synthetic citrullinated alpha enolase peptide
      H-Enls-2
<220> FEATURE:
<221> NAME/KEY: MOD_RES
<222> LOCATION: (1)...(1)
<223> OTHER INFORMATION: Cys modified by biotin
<220> FEATURE:
<221> NAME/KEY: DISULFID
<222> LOCATION: (1)..(19)
<220> FEATURE:
<221> NAME/KEY: MOD_RES
<222> LOCATION: (12)...(12)
<223> OTHER INFORMATION: Xaa = citrulline
<220> FEATURE:
<221> NAME/KEY: AMIDATION
<222> LOCATION: (19)...(19)
<223> OTHER INFORMATION: cysteinamide

<400> SEQUENCE: 70

Cys Lys Ile His Ala Arg Glu Ile Phe Asp Ser Xaa Gly Asn Pro Thr
1               5                   10                  15

Val Glu Cys

<210> SEQ ID NO 71
<211> LENGTH: 17
<212> TYPE: PRT
<213> ORGANISM: Artificial Sequence
<220> FEATURE:
<223> OTHER INFORMATION: synthetic alpha enolase peptide H-Enls-2 core
      sequence
<220> FEATURE:
<221> NAME/KEY: MOD_RES
<222> LOCATION: (11)...(11)
<223> OTHER INFORMATION: Xaa = citrulline

<400> SEQUENCE: 71

Lys Ile His Ala Arg Glu Ile Phe Asp Ser Xaa Gly Asn Pro Thr Val
1               5                   10                  15

Glu

<210> SEQ ID NO 72
<211> LENGTH: 19
<212> TYPE: PRT
<213> ORGANISM: Artificial Sequence
<220> FEATURE:
<223> OTHER INFORMATION: synthetic citrullinated alpha enolase peptide
      H-Enls-3
<220> FEATURE:
<221> NAME/KEY: MOD_RES
<222> LOCATION: (1)...(1)
<223> OTHER INFORMATION: Ala modified by biotin
<220> FEATURE:
<221> NAME/KEY: MOD_RES
<222> LOCATION: (12)...(12)
<223> OTHER INFORMATION: Xaa = citrulline
<220> FEATURE:
<221> NAME/KEY: AMIDATION
<222> LOCATION: (19)...(19)
<223> OTHER INFORMATION: alaninamide

<400> SEQUENCE: 72

Ala Lys Ile His Ala Arg Glu Ile Phe Asp Ser Xaa Gly Asn Pro Thr
1               5                   10                  15
```

Val Glu Ala

<210> SEQ ID NO 73
<211> LENGTH: 17
<212> TYPE: PRT
<213> ORGANISM: Artificial Sequence
<220> FEATURE:
<223> OTHER INFORMATION: synthetic alpha enolase peptide H-Enls-3 core
      sequence
<220> FEATURE:
<221> NAME/KEY: MOD_RES
<222> LOCATION: (11)...(11)
<223> OTHER INFORMATION: Xaa = citrulline

<400> SEQUENCE: 73

Lys Ile His Ala Arg Glu Ile Phe Asp Ser Xaa Gly Asn Pro Thr Val
 1               5                  10                  15

Glu

<210> SEQ ID NO 74
<211> LENGTH: 34
<212> TYPE: PRT
<213> ORGANISM: Artificial Sequence
<220> FEATURE:
<223> OTHER INFORMATION: synthetic citrullinated alpha enolase peptide
      H-Enls-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline
<220> FEATURE:
<221> NAME/KEY: AMIDATION
<222> LOCATION: (34)...(34)
<223> OTHER INFORMATION: argininamide

<400> SEQUENCE: 74

Gly Phe Asp Ser Xaa Gly Asn Pro Thr Val Glu Val Gly Leu Phe Xaa
 1               5                  10                  15

Ala Ala Val Pro Ser Gly Ala Ser Leu Glu Leu Xaa Asp Asn Asp Lys
            20                  25                  30

Thr Arg

<210> SEQ ID NO 75
<211> LENGTH: 33
<212> TYPE: PRT
<213> ORGANISM: Artificial Sequence
<220> FEATURE:
<223> OTHER INFORMATION: synthetic alpha enolase peptide H-Enls-4 core
      sequence
<220> FEATURE:
<221> NAME/KEY: MOD_RES
<222> LOCATION: (4)...(27)
<223> OTHER INFORMATION: Xaa = citrulline

<400> SEQUENCE: 75

Phe Asp Ser Xaa Gly Asn Pro Thr Val Glu Val Gly Leu Phe Xaa Ala
 1               5                  10                  15

Ala Val Pro Ser Gly Ala Ser Leu Glu Leu Xaa Asp Asn Asp Lys Thr
            20                  25                  30

Arg

<210> SEQ ID NO 76
<211> LENGTH: 33

```
<212> TYPE: PRT
<213> ORGANISM: Artificial Sequence
<220> FEATURE:
<223> OTHER INFORMATION: synthetic citrullinated alpha enolase
      peptide H-Enls-5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline
<220> FEATURE:
<221> NAME/KEY: AMIDATION
<222> LOCATION: (33)...(33)
<223> OTHER INFORMATION: lysinamide

<400> SEQUENCE: 76

Gly Leu Tyr Xaa His Ile Ala Asp Leu Ala Gly Ser Xaa Tyr Ile Ser
1               5                   10                  15

Pro Asp Gln Leu Ala Asp Leu Thr Val Thr Asn Pro Lys Xaa Ile Ala
            20                  25                  30

Lys

<210> SEQ ID NO 77
<211> LENGTH: 32
<212> TYPE: PRT
<213> ORGANISM: Artificial Sequence
<220> FEATURE:
<223> OTHER INFORMATION: synthetic alpha enolase peptide H-Enls-5 core
      sequence
<220> FEATURE:
<221> NAME/KEY: MOD_RES
<222> LOCATION: (3)...(29)
<223> OTHER INFORMATION: Xaa = citrulline

<400> SEQUENCE: 77

Leu Tyr Xaa His Ile Ala Asp Leu Ala Gly Ser Xaa Tyr Ile Ser Pro
1               5                   10                  15

Asp Gln Leu Ala Asp Leu Thr Val Thr Asn Pro Lys Xaa Ile Ala Lys
            20                  25                  30

<210> SEQ ID NO 78
<211> LENGTH: 33
<212> TYPE: PRT
<213> ORGANISM: Artificial Sequence
<220> FEATURE:
<223> OTHER INFORMATION: synthetic citrullinated alpha enolase peptide
      H-Enls-6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(28)
<223> OTHER INFORMATION: Xaa = citrulline
<220> FEATURE:
<221> NAME/KEY: AMIDATION
<222> LOCATION: (33)...(33)
<223> OTHER INFORMATION: lysinamide

<400> SEQUENCE: 78

Gly Gly Trp Gly Val Met Val Ser His Xaa Ser Gly Glu Thr Leu Xaa
1               5                   10                  15

Ile Glu Glu Glu Leu Gly Ser Gly Arg Asn Phe Xaa Asn Pro Leu Ala
            20                  25                  30

Lys
```

```
<210> SEQ ID NO 79
<211> LENGTH: 32
<212> TYPE: PRT
<213> ORGANISM: Artificial Sequence
<220> FEATURE:
<223> OTHER INFORMATION: synthetic alpha enolase peptide H-Enls-6 core
      sequence
<220> FEATURE:
<221> NAME/KEY: MOD_RES
<222> LOCATION: (9)...(27)
<223> OTHER INFORMATION: Xaa = citrulline

<400> SEQUENCE: 79

Gly Trp Gly Val Met Val Ser His Xaa Ser Gly Glu Thr Leu Xaa Ile
 1               5                  10                  15

Glu Glu Glu Leu Gly Ser Gly Arg Asn Phe Xaa Asn Pro Leu Ala Lys
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: synthetic fibrin alpha-chain peptide alpha32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: AMIDATION
<222> LOCATION: (32)...(32)
<223> OTHER INFORMATION: threoninamide

<400> SEQUENCE: 80

Gly Gly Gly Pro Arg Val Val Glu Arg His Gln Ser Ala Gly Gly Gly
 1               5                  10                  15

Thr Lys Arg Gly His Ala Lys Ser Arg Pro Val Arg Gly Ile His Thr
            20                  25                  30

<210> SEQ ID NO 81
<211> LENGTH: 28
<212> TYPE: PRT
<213> ORGANISM: Artificial Sequence
<220> FEATURE:
<223> OTHER INFORMATION: synthetic fibrin alpha-chain peptide alpha32
      core sequence
<220> FEATURE:
<221> NAME/KEY: MOD_RES
<222> LOCATION: (12)...(12)
<223> OTHER INFORMATION: Xaa = any amino acid

<400> SEQUENCE: 81

Gly Pro Arg Val Val Glu Arg His Gln Ser Ala Xaa Thr Lys Arg Gly
 1               5                  10                  15

His Ala Lys Ser Arg Pro Val Arg Gly Ile His Thr
            20                  25

<210> SEQ ID NO 82
<211> LENGTH: 32
<212> TYPE: PRT
<213> ORGANISM: Artificial Sequence
<220> FEATURE:
<223> OTHER INFORMATION: synthetic citrullinated fibrin alpha-chain
      peptide Cit-alpha32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
```

```
<222> LOCATION: (5)...(28)
<223> OTHER INFORMATION: Xaa = citrulline
<220> FEATURE:
<221> NAME/KEY: AMIDATION
<222> LOCATION: (32)...(32)
<223> OTHER INFORMATION: threoninamide

<400> SEQUENCE: 82

Gly Gly Gly Pro Xaa Val Val Glu Xaa His Gln Ser Ala Gly Gly Gly
 1               5                  10                  15

Thr Lys Xaa Gly His Ala Lys Ser Xaa Pro Val Xaa Gly Ile His Thr
            20                  25                  30

<210> SEQ ID NO 83
<211> LENGTH: 28
<212> TYPE: PRT
<213> ORGANISM: Artificial Sequence
<220> FEATURE:
<223> OTHER INFORMATION: synthetic fibrin alpha-chain peptide
      Cit-alpha32 core sequence
<220> FEATURE:
<221> NAME/KEY: MOD_RES
<222> LOCATION: (3)...(7)
<223> OTHER INFORMATION: Xaa = citrulline
<220> FEATURE:
<221> NAME/KEY: MOD_RES
<222> LOCATION: (12)...(12)
<223> OTHER INFORMATION: Xaa = any amino acid
<220> FEATURE:
<221> NAME/KEY: MOD_RES
<222> LOCATION: (15)...(24)
<223> OTHER INFORMATION: Xaa = citrulline

<400> SEQUENCE: 83

Gly Pro Xaa Val Val Glu Xaa His Gln Ser Ala Xaa Thr Lys Xaa Gly
 1               5                  10                  15

His Ala Lys Ser Xaa Pro Val Xaa Gly Ile His Thr
            20                  25

<210> SEQ ID NO 84
<211> LENGTH: 32
<212> TYPE: PRT
<213> ORGANISM: Artificial Sequence
<220> FEATURE:
<223> OTHER INFORMATION: synthetic citrullinated fibrin alpha-chain
      peptide [627-Arg]Cit-alpha32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline
<220> FEATURE:
<221> NAME/KEY: AMIDATION
<222> LOCATION: (32)...(32)
<223> OTHER INFORMATION: threoninamide

<400> SEQUENCE: 84

Gly Gly Gly Pro Xaa Val Val Glu Xaa His Gln Ser Ala Gly Gly Gly
 1               5                  10                  15

Thr Lys Xaa Gly His Ala Lys Ser Arg Pro Val Xaa Gly Ile His Thr
            20                  25                  30

<210> SEQ ID NO 85
<211> LENGTH: 28
<212> TYPE: PRT
<213> ORGANISM: Artificial Sequence
<220> FEATURE:
<223> OTHER INFORMATION: synthetic fibrin alpha-chain peptide
```

```
                      [627-Arg]Cit-alpha32 core sequence
<220> FEATURE:
<221> NAME/KEY: MOD_RES
<222> LOCATION: (3)...(7)
<223> OTHER INFORMATION: Xaa = citrulline
<220> FEATURE:
<221> NAME/KEY: MOD_RES
<222> LOCATION: (12)...(12)
<223> OTHER INFORMATION: Xaa = any amino acid
<220> FEATURE:
<221> NAME/KEY: MOD_RES
<222> LOCATION: (15)...(24)
<223> OTHER INFORMATION: Xaa = citrulline

<400> SEQUENCE: 85

Gly Pro Xaa Val Val Glu Xaa His Gln Ser Ala Xaa Thr Lys Xaa Gly
1               5                   10                  15

His Ala Lys Ser Arg Pro Val Xaa Gly Ile His Thr
            20                  25

<210> SEQ ID NO 86
<211> LENGTH: 15
<212> TYPE: PRT
<213> ORGANISM: Artificial Sequence
<220> FEATURE:
<223> OTHER INFORMATION: synthetic citrullinated fibrin alpha-chain
      peptide [38,42-Cit]FB2-alpha(36-50)
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (3)...(7)
<223> OTHER INFORMATION: Xaa = citrulline
<220> FEATURE:
<221> NAME/KEY: AMIDATION
<222> LOCATION: (15)...(15)
<223> OTHER INFORMATION: serinamide

<400> SEQUENCE: 86

Gly Pro Xaa Val Val Glu Xaa His Gln Ser Ala Ser Lys Asp Ser
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: synthetic fibrin alpha-chain peptide
      [38,42-Cit]FB2-alpha(36-50) core sequence
<220> FEATURE:
<221> NAME/KEY: MOD_RES
<222> LOCATION: (3)...(7)
<223> OTHER INFORMATION: Xaa = citrulline

<400> SEQUENCE: 87

Gly Pro Xaa Val Val Glu Xaa His Gln Ser Ala Ser Lys Asp Ser
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: synthetic citrullinated fibrin alpha-chain
      peptide [621,630-Cit]FB4-alpha(617-631)
<220> FEATURE:
<221> NAME/KEY: MOD_RES
<222> LOCATION: (1)...(1)
<223> OTHER INFORMATION: His modified by biotin
<220> FEATURE:
<221> NAME/KEY: MOD_RES
```

```
<222> LOCATION: (5)...(14)
<223> OTHER INFORMATION: Xaa = citrulline
<220> FEATURE:
<221> NAME/KEY: AMIDATION
<222> LOCATION: (15)...(15)
<223> OTHER INFORMATION: glycinamide

<400> SEQUENCE: 88

His Ser Thr Lys Xaa Gly His Ala Lys Ser Arg Pro Val Xaa Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: synthetic fibrin alpha-chain peptide
      [621,630-Cit]FB4-alpha(617-631) core sequence
<220> FEATURE:
<221> NAME/KEY: MOD_RES
<222> LOCATION: (5)...(14)
<223> OTHER INFORMATION: Xaa = citrulline

<400> SEQUENCE: 89

His Ser Thr Lys Xaa Gly His Ala Lys Ser Arg Pro Val Xaa Gly
1               5                   10                  15

<210> SEQ ID NO 90
<211> LENGTH: 31
<212> TYPE: PRT
<213> ORGANISM: Artificial Sequence
<220> FEATURE:
<223> OTHER INFORMATION: synthetic citrullinated fibrin alpha-chain
      peptide Fib-A1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(29)
<223> OTHER INFORMATION: Xaa = citrulline
<220> FEATURE:
<221> NAME/KEY: AMIDATION
<222> LOCATION: (31)...(31)
<223> OTHER INFORMATION: serinamide

<400> SEQUENCE: 90

Gly Arg Gly Pro Arg Val Val Glu Xaa His Glu Val Asn Gln Asp Phe
1               5                   10                  15

Thr Asn Xaa Ile Asn Lys Leu Lys Ile Arg Ser Ser Xaa Gly Ser
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: synthetic fibrin alpha-chain peptide Fib-A1
      core sequence
<220> FEATURE:
<221> NAME/KEY: MOD_RES
<222> LOCATION: (8)...(28)
<223> OTHER INFORMATION: Xaa = citrulline

<400> SEQUENCE: 91

Arg Gly Pro Arg Val Val Glu Xaa His Glu Val Asn Gln Asp Phe Thr
1               5                   10                  15

Asn Xaa Ile Asn Lys Leu Lys Ile Arg Ser Ser Xaa Gly Ser
            20                  25                  30
```

```
<210> SEQ ID NO 92
<211> LENGTH: 31
<212> TYPE: PRT
<213> ORGANISM: Artificial Sequence
<220> FEATURE:
<223> OTHER INFORMATION: synthetic citrullinated fibrin alpha-chain
      peptide Fib-A2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(24)
<223> OTHER INFORMATION: Xaa = citrulline
<220> FEATURE:
<221> NAME/KEY: AMIDATION
<222> LOCATION: (31)...(31)
<223> OTHER INFORMATION: serinamide

<400> SEQUENCE: 92

Gly Thr Asn Ile Met Glu Ile Leu Xaa Gly Asp Phe Ser Ser Ala Asn
 1               5                  10                  15

Asn Arg Asp Asn Thr Tyr Asn Xaa Val Ser Glu Asp Leu Arg Ser
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: synthetic fibrin alpha-chain peptide Fib-A2
      core sequence
<220> FEATURE:
<221> NAME/KEY: MOD_RES
<222> LOCATION: (8)...(23)
<223> OTHER INFORMATION: Xaa = citrulline

<400> SEQUENCE: 93

Thr Asn Ile Met Glu Ile Leu Xaa Gly Asp Phe Ser Ser Ala Asn Asn
 1               5                  10                  15

Arg Asp Asn Thr Tyr Asn Xaa Val Ser Glu Asp Leu Arg Ser
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: synthetic citrullinated fibrin alpha-chain
      peptide Fib-A3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(31)
<223> OTHER INFORMATION: Xaa = citrulline
<220> FEATURE:
<221> NAME/KEY: AMIDATION
<222> LOCATION: (32)...(32)
<223> OTHER INFORMATION: alaninamide

<400> SEQUENCE: 94

Gly Tyr Asn Arg Val Ser Glu Asp Leu Xaa Ser Arg Ile Glu Val Leu
 1               5                  10                  15

Lys Xaa Lys Val Ile Glu Lys Gln Leu Leu Gln Lys Asn Val Xaa Ala
            20                  25                  30
```

```
<210> SEQ ID NO 95
<211> LENGTH: 31
<212> TYPE: PRT
<213> ORGANISM: Artificial Sequence
<220> FEATURE:
<223> OTHER INFORMATION: synthetic fibrin alpha-chain peptide Fib-A3
      core sequence
<220> FEATURE:
<221> NAME/KEY: MOD_RES
<222> LOCATION: (9)...(30)
<223> OTHER INFORMATION: Xaa = citrulline

<400> SEQUENCE: 95

Tyr Asn Arg Val Ser Glu Asp Leu Xaa Ser Arg Ile Glu Val Leu Lys
 1               5                  10                  15

Xaa Lys Val Ile Glu Lys Gln Leu Leu Gln Lys Asn Val Xaa Ala
            20                  25                  30

<210> SEQ ID NO 96
<211> LENGTH: 33
<212> TYPE: PRT
<213> ORGANISM: Artificial Sequence
<220> FEATURE:
<223> OTHER INFORMATION: synthetic citrullinated fibrin alpha-chain
      peptide Fib-A4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(31)
<223> OTHER INFORMATION: Xaa = citrulline
<220> FEATURE:
<221> NAME/KEY: AMIDATION
<222> LOCATION: (33)...(33)
<223> OTHER INFORMATION: histidinamide

<400> SEQUENCE: 96

Gly Asp Ile Lys Ile Xaa Ser Ser Arg Gly Ser Ser Xaa Ala Leu
 1               5                  10                  15

Leu Pro Ser Xaa Asp Arg Gln His Leu Leu Pro Ser Arg Asp Xaa Gln
            20                  25                  30

His

<210> SEQ ID NO 97
<211> LENGTH: 32
<212> TYPE: PRT
<213> ORGANISM: Artificial Sequence
<220> FEATURE:
<223> OTHER INFORMATION: synthetic fibrin alpha-chain peptide Fib-A4
      core sequence
<220> FEATURE:
<221> NAME/KEY: MOD_RES
<222> LOCATION: (5)...(30)
<223> OTHER INFORMATION: Xaa = citrulline

<400> SEQUENCE: 97

Asp Ile Lys Ile Xaa Ser Ser Arg Gly Ser Ser Ser Xaa Ala Leu Leu
 1               5                  10                  15

Pro Ser Xaa Asp Arg Gln His Leu Leu Pro Ser Arg Asp Xaa Gln His
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: synthetic citrullinated fibrin alpha-chain
      peptide Fib-A5
```

```
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline
<220> FEATURE:
<221> NAME/KEY: AMIDATION
<222> LOCATION: (32)...(32)
<223> OTHER INFORMATION: serinamide

<400> SEQUENCE: 98

Gly Arg Phe Xaa Pro Asp Ser Pro Gly Ser Gly Thr Trp Asn Pro Gly
1               5                   10                  15

Ser Ser Glu Xaa Gly Thr Ser Gly Ser Thr Thr Thr Thr Xaa Arg Ser
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: synthetic fibrin alpha-chain peptide Fib-A5
      core sequence
<220> FEATURE:
<221> NAME/KEY: MOD_RES
<222> LOCATION: (2)...(28)
<223> OTHER INFORMATION: Xaa = citrulline

<400> SEQUENCE: 99

Phe Xaa Pro Asp Ser Pro Gly Ser Gly Thr Trp Asn Pro Gly Ser Ser
1               5                   10                  15

Glu Xaa Gly Thr Ser Gly Ser Thr Thr Thr Thr Xaa Arg Ser
            20                  25                  30

<210> SEQ ID NO 100
<211> LENGTH: 25
<212> TYPE: PRT
<213> ORGANISM: Artificial Sequence
<220> FEATURE:
<223> OTHER INFORMATION: synthetic citrullinated fibrin alpha-chain
      peptide Fib-A6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (25)...(25)
<223> OTHER INFORMATION: alaninamide

<400> SEQUENCE: 100

Gly Ser Gly Ser Thr Thr Thr Thr Arg Xaa Ser Ser Ser Lys Thr Val
1               5                   10                  15

Phe Arg His Xaa His Pro Asp Glu Ala
            20                  25

<210> SEQ ID NO 101
<211> LENGTH: 24
<212> TYPE: PRT
<213> ORGANISM: Artificial Sequence
<220> FEATURE:
<223> OTHER INFORMATION: synthetic fibrin alpha-chain peptide Fib-A6
      core sequence
<220> FEATURE:
```

```
<221> NAME/KEY: MOD_RES
<222> LOCATION: (9)...(19)
<223> OTHER INFORMATION: Xaa = citrulline

<400> SEQUENCE: 101

Ser Gly Ser Thr Thr Thr Thr Arg Xaa Ser Ser Ser Lys Thr Val Phe
 1               5                  10                  15

Arg His Xaa His Pro Asp Glu Ala
            20

<210> SEQ ID NO 102
<211> LENGTH: 30
<212> TYPE: PRT
<213> ORGANISM: Artificial Sequence
<220> FEATURE:
<223> OTHER INFORMATION: synthetic citrullinated fibrin alpha-chain
      peptide Fib-A7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (11)...(22)
<223> OTHER INFORMATION: Xaa = citrulline
<220> FEATURE:
<221> NAME/KEY: AMIDATION
<222> LOCATION: (30)...(30)
<223> OTHER INFORMATION: lysinamide

<400> SEQUENCE: 102

Gly Arg Glu Phe Val Ser Glu Thr Glu Ser Xaa Gly Ser Phe Thr Ser
 1               5                  10                  15

Ser Thr Ser Tyr Asn Xaa Gly Asp Ser Thr Phe Glu Ser Lys
            20                  25                  30

<210> SEQ ID NO 103
<211> LENGTH: 28
<212> TYPE: PRT
<213> ORGANISM: Artificial Sequence
<220> FEATURE:
<223> OTHER INFORMATION: synthetic fibrin alpha-chain peptide Fib-A7
      core sequence
<220> FEATURE:
<221> NAME/KEY: MOD_RES
<222> LOCATION: (9)...(20)
<223> OTHER INFORMATION: Xaa = citrulline

<400> SEQUENCE: 103

Glu Phe Val Ser Glu Thr Glu Ser Xaa Gly Ser Phe Thr Ser Ser Thr
 1               5                  10                  15

Ser Tyr Asn Xaa Gly Asp Ser Thr Phe Glu Ser Lys
            20                  25

<210> SEQ ID NO 104
<211> LENGTH: 28
<212> TYPE: PRT
<213> ORGANISM: Artificial Sequence
<220> FEATURE:
<223> OTHER INFORMATION: synthetic citrullinated fibrin alpha-chain
      peptide Fib-A8
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(19)
<223> OTHER INFORMATION: Xaa = citrulline
<220> FEATURE:
<221> NAME/KEY: AMIDATION
```

```
<222> LOCATION: (28)...(28)
<223> OTHER INFORMATION: lysinamide

<400> SEQUENCE: 104

Gly His Glu Gly Thr His Ser Thr Lys Xaa Gly His Ala Lys Ser Arg
1               5                   10                  15

Pro Val Xaa Gly Ile His Thr Ser Pro Leu Gly Lys
            20                  25

<210> SEQ ID NO 105
<211> LENGTH: 27
<212> TYPE: PRT
<213> ORGANISM: Artificial Sequence
<220> FEATURE:
<223> OTHER INFORMATION: synthetic fibrin alpha-chain peptide Fib-A8
      core sequence
<220> FEATURE:
<221> NAME/KEY: MOD_RES
<222> LOCATION: (9)...(18)
<223> OTHER INFORMATION: Xaa = citrulline

<400> SEQUENCE: 105

His Glu Gly Thr His Ser Thr Lys Xaa Gly His Ala Lys Ser Arg Pro
1               5                   10                  15

Val Xaa Gly Ile His Thr Ser Pro Leu Gly Lys
            20                  25

<210> SEQ ID NO 106
<211> LENGTH: 32
<212> TYPE: PRT
<213> ORGANISM: Artificial Sequence
<220> FEATURE:
<223> OTHER INFORMATION: synthetic citrullinated fibrin beta-chain
      peptide beta32
<220> FEATURE:
<221> NAME/KEY: MOD_RES
<222> LOCATION: (1)...(1)
<223> OTHER INFORMATION: Gly modified by biotin

<400> SEQUENCE: 106

Gly Gly Gly His Arg Pro Leu Asp Lys Lys Arg Glu Glu Ala Pro Ser
1               5                   10                  15

Leu Arg Pro Ala Pro Pro Pro Ile Ser Gly Gly Gly Tyr Arg Ala Arg
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: synthetic fibrin beta-chain peptide beta32
      core sequence

<400> SEQUENCE: 107

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: synthetic citrullinated fibrin beta-chain
      peptide Cit-beta32
<220> FEATURE:
<221> NAME/KEY: MOD_RES
```

```
<222> LOCATION: (1)...(1)
<223> OTHER INFORMATION: Gly modified by biotin
<220> FEATURE:
<221> NAME/KEY: MOD_RES
<222> LOCATION: (5)...(32)
<223> OTHER INFORMATION: Xaa = citrulline

<400> SEQUENCE: 108

Gly Gly Gly His Xaa Pro Leu Asp Lys Lys Xaa Glu Glu Ala Pro Ser
1               5                   10                  15

Leu Xaa Pro Ala Pro Pro Pro Ile Ser Gly Gly Gly Tyr Xaa Ala Xaa
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: synthetic fibrin beta-chain peptide Cit-beta32
      core sequence
<220> FEATURE:
<221> NAME/KEY: MOD_RES
<222> LOCATION: (3)...(30)
<223> OTHER INFORMATION: Xaa = citrulline

<400> SEQUENCE: 109

Gly His Xaa Pro Leu Asp Lys Lys Xaa Glu Glu Ala Pro Ser Leu Xaa
1               5                   10                  15

Pro Ala Pro Pro Pro Ile Ser Gly Gly Gly Tyr Xaa Ala Xaa
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: synthetic citrullinated fibrin beta-chain
      peptide [53-Arg]Cit-beta32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(32)
<223> OTHER INFORMATION: Xaa = citrulline

<400> SEQUENCE: 110

Gly Gly Gly His Xaa Pro Leu Asp Lys Lys Arg Glu Glu Ala Pro Ser
1               5                   10                  15

Leu Xaa Pro Ala Pro Pro Pro Ile Ser Gly Gly Gly Tyr Xaa Ala Xaa
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: synthetic fibrin beta-chain peptide
      [53-Arg]Cit-beta32 core sequence
<220> FEATURE:
<221> NAME/KEY: MOD_RES
<222> LOCATION: (3)...(30)
<223> OTHER INFORMATION: Xaa = citrulline

<400> SEQUENCE: 111

Gly His Xaa Pro Leu Asp Lys Lys Arg Glu Glu Ala Pro Ser Leu Xaa
1               5                   10                  15

Pro Ala Pro Pro Pro Ile Ser Gly Gly Gly Tyr Xaa Ala Xaa
            20                  25                  30
```

<210> SEQ ID NO 112
<211> LENGTH: 15
<212> TYPE: PRT
<213> ORGANISM: Artificial Sequence
<220> FEATURE:
<223> OTHER INFORMATION: synthetic citrullinated fibrin beta-chain
      peptide [60,72,74-Cit]FB3-beta(60-74)
<220> FEATURE:
<221> NAME/KEY: MOD_RES
<222> LOCATION: (1)...(1)
<223> OTHER INFORMATION: Xaa = citrulline modified by biotin
<220> FEATURE:
<221> NAME/KEY: MOD_RES
<222> LOCATION: (13)...(13)
<223> OTHER INFORMATION: Xaa = citrulline
<220> FEATURE:
<221> NAME/KEY: AMIDATION
<222> LOCATION: (15)...(15)
<223> OTHER INFORMATION: citrullinamide

<400> SEQUENCE: 112

Xaa Pro Ala Pro Pro Pro Ile Ser Gly Gly Gly Tyr Xaa Ala Xaa
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: synthetic fibrin beta-chain peptide
      [60,72,74-Cit]FB3-beta(60-74) core sequence
<220> FEATURE:
<221> NAME/KEY: MOD_RES
<222> LOCATION: (1)...(15)
<223> OTHER INFORMATION: Xaa = citrulline

<400> SEQUENCE: 113

Xaa Pro Ala Pro Pro Pro Ile Ser Gly Gly Gly Tyr Xaa Ala Xaa
1               5                   10                  15

<210> SEQ ID NO 114
<211> LENGTH: 20
<212> TYPE: PRT
<213> ORGANISM: Artificial Sequence
<220> FEATURE:
<223> OTHER INFORMATION: synthetic citrullinated fibrin beta-chain
      peptide [47,60-Cit]FB5-beta(43-62)
<220> FEATURE:
<221> NAME/KEY: MOD_RES
<222> LOCATION: (1)...(1)
<223> OTHER INFORMATION: Ala modified by biotin
<220> FEATURE:
<221> NAME/KEY: MOD_RES
<222> LOCATION: (5)...(18)
<223> OTHER INFORMATION: Xaa = citrulline
<220> FEATURE:
<221> NAME/KEY: AMIDATION
<222> LOCATION: (20)...(20)
<223> OTHER INFORMATION: alaninamide

<400> SEQUENCE: 114

Ala Arg Gly His Xaa Pro Leu Asp Lys Lys Arg Glu Glu Ala Pro Ser
1               5                   10                  15

Leu Xaa Pro Ala
            20

<210> SEQ ID NO 115
<211> LENGTH: 20
<212> TYPE: PRT
<213> ORGANISM: Artificial Sequence

```
<220> FEATURE:
<223> OTHER INFORMATION: synthetic fibrin beta-chain peptide
      [47,60-Cit]FB5-beta(43-62) core sequence
<220> FEATURE:
<221> NAME/KEY: MOD_RES
<222> LOCATION: (5)...(18)
<223> OTHER INFORMATION: Xaa = citrulline

<400> SEQUENCE: 115

Ala Arg Gly His Xaa Pro Leu Asp Lys Lys Arg Glu Glu Ala Pro Ser
 1               5                  10                  15

Leu Xaa Pro Ala
         20

<210> SEQ ID NO 116
<211> LENGTH: 32
<212> TYPE: PRT
<213> ORGANISM: Artificial Sequence
<220> FEATURE:
<223> OTHER INFORMATION: synthetic citrullinated fibrin beta-chain
      peptide Fib-B1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline
<220> FEATURE:
<221> NAME/KEY: AMIDATION
<222> LOCATION: (32)...(32)
<223> OTHER INFORMATION: serinamide

<400> SEQUENCE: 116

Gly Tyr Arg Ala Xaa Pro Ala Lys Ala Ala Leu Leu Lys Asp Leu Trp
 1               5                  10                  15

Gln Lys Xaa Asn Ser Asn Ile Pro Thr Asn Leu Xaa Val Leu Arg Ser
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: synthetic fibrin beta-chain peptide Fib-B1 core
      sequence
<220> FEATURE:
<221> NAME/KEY: MOD_RES
<222> LOCATION: (5)...(28)
<223> OTHER INFORMATION: Xaa = citrulline

<400> SEQUENCE: 117

Gly Tyr Arg Ala Xaa Pro Ala Lys Ala Ala Leu Leu Lys Asp Leu Trp
 1               5                  10                  15

Gln Lys Xaa Asn Ser Asn Ile Pro Thr Asn Leu Xaa Val Leu Arg Ser
            20                  25                  30

<210> SEQ ID NO 118
<211> LENGTH: 35
<212> TYPE: PRT
<213> ORGANISM: Artificial Sequence
<220> FEATURE:
<223> OTHER INFORMATION: synthetic citrullinated fibrin beta-chain
      peptide Fib-B2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
```

```
<222> LOCATION: (9)...(29)
<223> OTHER INFORMATION: Xaa = citrulline
<220> FEATURE:
<221> NAME/KEY: AMIDATION
<222> LOCATION: (35)...(35)
<223> OTHER INFORMATION: serinamide

<400> SEQUENCE: 118

Gly Pro Thr Asn Leu Arg Val Leu Xaa Ser Ile Leu Glu Asn Leu Arg
1               5                   10                  15

Ser Ile Leu Glu Asn Leu Xaa Ser Met Glu Tyr Ser Xaa Thr Pro Ser
            20                  25                  30

Thr Val Ser
        35

<210> SEQ ID NO 119
<211> LENGTH: 34
<212> TYPE: PRT
<213> ORGANISM: Artificial Sequence
<220> FEATURE:
<223> OTHER INFORMATION: synthetic fibrin beta-chain peptide Fib-B2
      core sequence
<220> FEATURE:
<221> NAME/KEY: MOD_RES
<222> LOCATION: (8)...(28)
<223> OTHER INFORMATION: Xaa = citrulline

<400> SEQUENCE: 119

Pro Thr Asn Leu Arg Val Leu Xaa Ser Ile Leu Glu Asn Leu Arg Ser
1               5                   10                  15

Ile Leu Glu Asn Leu Xaa Ser Met Glu Tyr Ser Xaa Thr Pro Ser Thr
            20                  25                  30

Val Ser

<210> SEQ ID NO 120
<211> LENGTH: 29
<212> TYPE: PRT
<213> ORGANISM: Artificial Sequence
<220> FEATURE:
<223> OTHER INFORMATION: synthetic citrullinated fibrin beta-chain
      peptide Fib-B3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(27)
<223> OTHER INFORMATION: Xaa = citrulline
<220> FEATURE:
<221> NAME/KEY: AMIDATION
<222> LOCATION: (29)...(29)
<223> OTHER INFORMATION: glutaminamide

<400> SEQUENCE: 120

Gly Asp Lys Ile Ser Gln Leu Thr Xaa Met Gly Tyr Gln Ile Ser Val
1               5                   10                  15

Asn Lys Tyr Xaa Trp Leu Thr Ser Asp Pro Xaa Lys Gln
            20                  25

<210> SEQ ID NO 121
<211> LENGTH: 28
<212> TYPE: PRT
<213> ORGANISM: Artificial Sequence
<220> FEATURE:
<223> OTHER INFORMATION: synthetic fibrin beta-chain peptide Fib-B3 core
      sequence
<220> FEATURE:
<221> NAME/KEY: MOD_RES
```

```
<222> LOCATION: (8)...(26)
<223> OTHER INFORMATION: Xaa = citrulline

<400> SEQUENCE: 121

Asp Lys Ile Ser Gln Leu Thr Xaa Met Gly Tyr Gln Ile Ser Val Asn
1               5                   10                  15

Lys Tyr Xaa Trp Leu Thr Ser Asp Pro Xaa Lys Gln
            20                  25

<210> SEQ ID NO 122
<211> LENGTH: 30
<212> TYPE: PRT
<213> ORGANISM: Artificial Sequence
<220> FEATURE:
<223> OTHER INFORMATION: synthetic citrullinated fibrin gamma-chain
      peptide Fib-G1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(28)
<223> OTHER INFORMATION: Xaa = citrulline
<220> FEATURE:
<221> NAME/KEY: AMIDATION
<222> LOCATION: (30)...(30)
<223> OTHER INFORMATION: argininamide

<400> SEQUENCE: 122

Gly Tyr Val Ala Thr Xaa Asp Asn Ser Ser Ile Leu Asp Glu Xaa Phe
1               5                   10                  15

Gly Ser Arg Ile Leu Thr His Asp Ser Ser Ile Xaa Tyr Arg
            20                  25                  30

<210> SEQ ID NO 123
<211> LENGTH: 28
<212> TYPE: PRT
<213> ORGANISM: Artificial Sequence
<220> FEATURE:
<223> OTHER INFORMATION: synthetic fibrin gamma-chain peptide Fib-G1
      core sequence
<220> FEATURE:
<221> NAME/KEY: MOD_RES
<222> LOCATION: (5)...(14)
<223> OTHER INFORMATION: Xaa = citrulline
<220> FEATURE:
<221> NAME/KEY: MOD_RES
<222> LOCATION: (18)...(18)
<223> OTHER INFORMATION: Xaa = any amino acid
<220> FEATURE:
<221> NAME/KEY: MOD_RES
<222> LOCATION: (27)...(27)
<223> OTHER INFORMATION: Xaa = citrulline

<400> SEQUENCE: 123

Tyr Val Ala Thr Xaa Asp Asn Ser Ser Ile Leu Asp Glu Xaa Phe Gly
1               5                   10                  15

Ser Xaa Ile Leu Thr His Asp Ser Ser Ile Xaa Tyr
            20                  25

<210> SEQ ID NO 124
<211> LENGTH: 34
<212> TYPE: PRT
<213> ORGANISM: Artificial Sequence
<220> FEATURE:
<223> OTHER INFORMATION: synthetic citrullinated fibrin gamma-chain
      peptide Fib-G2
<220> FEATURE:
<221> NAME/KEY: MOD_RES
<222> LOCATION: (1)...(1)
```

<223> OTHER INFORMATION: Gly modified by biotin
<220> FEATURE:
<221> NAME/KEY: MOD_RES
<222> LOCATION: (6)...(31)
<223> OTHER INFORMATION: Xaa = citrulline
<220> FEATURE:
<221> NAME/KEY: AMIDATION
<222> LOCATION: (34)...(34)
<223> OTHER INFORMATION: argininamide

<400> SEQUENCE: 124

Gly Val Phe Gln Lys Xaa Leu Asp Gly Ser Val Asp Phe Tyr Xaa Leu
1               5                   10                  15

Thr Tyr Ala Tyr Phe Ala Thr Met Lys Ile Ile Pro Phe Asn Xaa Leu
            20                  25                  30

Thr Arg

<210> SEQ ID NO 125
<211> LENGTH: 32
<212> TYPE: PRT
<213> ORGANISM: Artificial Sequence
<220> FEATURE:
<223> OTHER INFORMATION: synthetic fibrin gamma-chain peptide Fib-G2
      core sequence
<220> FEATURE:
<221> NAME/KEY: MOD_RES
<222> LOCATION: (5)...(30)
<223> OTHER INFORMATION: Xaa = citrulline

<400> SEQUENCE: 125

Val Phe Gln Lys Xaa Leu Asp Gly Ser Val Asp Phe Tyr Xaa Leu Thr
1               5                   10                  15

Tyr Ala Tyr Phe Ala Thr Met Lys Ile Ile Pro Phe Asn Xaa Leu Thr
            20                  25                  30

<210> SEQ ID NO 126
<211> LENGTH: 26
<212> TYPE: PRT
<213> ORGANISM: Artificial Sequence
<220> FEATURE:
<223> OTHER INFORMATION: synthetic citrullinated fibronectin peptide
      Fibronectin-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(24)
<223> OTHER INFORMATION: Xaa = citrulline
<220> FEATURE:
<221> NAME/KEY: AMIDATION
<222> LOCATION: (26)...(26)
<223> OTHER INFORMATION: glycinamide

<400> SEQUENCE: 126

Gly Ser Leu Gly Glu Gly Ser Gly Xaa Ile Thr Ser Thr Ser Arg Asn
1               5                   10                  15

Gly Arg Ile Thr Ser Thr Ser Xaa Asn Gly
            20                  25

<210> SEQ ID NO 127
<211> LENGTH: 24
<212> TYPE: PRT
<213> ORGANISM: Artificial Sequence
<220> FEATURE:
<223> OTHER INFORMATION: synthetic fibronectin peptide Fibronectin-1
      core sequence
<220> FEATURE:
<221> NAME/KEY: MOD_RES

```
<222> LOCATION: (8)...(23)
<223> OTHER INFORMATION: Xaa = citrulline

<400> SEQUENCE: 127

Ser Leu Gly Glu Gly Ser Gly Xaa Ile Thr Ser Thr Ser Arg Asn Gly
1               5                   10                  15

Arg Ile Thr Ser Thr Ser Xaa Asn
            20

<210> SEQ ID NO 128
<211> LENGTH: 29
<212> TYPE: PRT
<213> ORGANISM: Artificial Sequence
<220> FEATURE:
<223> OTHER INFORMATION: synthetic citrullinated fibronectin peptide
      Fibronectin-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(26)
<223> OTHER INFORMATION: Xaa = citrulline
<220> FEATURE:
<221> NAME/KEY: AMIDATION
<222> LOCATION: (29)...(29)
<223> OTHER INFORMATION: glycinamide

<400> SEQUENCE: 128

Gly Arg Ile Thr Ser Thr Ser Arg Asn Xaa Asp Gln Asp Thr Arg Thr
1               5                   10                  15

Ser Tyr Xaa Ser Asn Asp Gln Asp Thr Xaa Thr Ser Gly
            20                  25

<210> SEQ ID NO 129
<211> LENGTH: 28
<212> TYPE: PRT
<213> ORGANISM: Artificial Sequence
<220> FEATURE:
<223> OTHER INFORMATION: synthetic fibronectin peptide Fibronectin-2
      core sequence
<220> FEATURE:
<221> NAME/KEY: MOD_RES
<222> LOCATION: (10)...(26)
<223> OTHER INFORMATION: Xaa = citrulline

<400> SEQUENCE: 129

Gly Arg Ile Thr Ser Thr Ser Arg Asn Xaa Asp Gln Asp Thr Arg Thr
1               5                   10                  15

Ser Tyr Xaa Ser Asn Asp Gln Asp Thr Xaa Thr Ser
            20                  25

<210> SEQ ID NO 130
<211> LENGTH: 21
<212> TYPE: PRT
<213> ORGANISM: Artificial Sequence
<220> FEATURE:
<223> OTHER INFORMATION: synthetic citrullinated fibronectin peptide
      Fibronectin-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(18)
<223> OTHER INFORMATION: Xaa = citrulline
<220> FEATURE:
<221> NAME/KEY: AMIDATION
<222> LOCATION: (21)...(21)
```

<223> OTHER INFORMATION: glycinamide

<400> SEQUENCE: 130

Gly Val Leu Val Xaa Trp Thr Pro Pro Arg Leu Val Arg Trp Thr Pro
1               5                   10                  15

Pro Xaa Ala Gln Gly
            20

<210> SEQ ID NO 131
<211> LENGTH: 19
<212> TYPE: PRT
<213> ORGANISM: Artificial Sequence
<220> FEATURE:
<223> OTHER INFORMATION: synthetic fibronectin peptide Fibronectin-3
      core sequence
<220> FEATURE:
<221> NAME/KEY: MOD_RES
<222> LOCATION: (4)...(17)
<223> OTHER INFORMATION: Xaa = citrulline

<400> SEQUENCE: 131

Val Leu Val Xaa Trp Thr Pro Pro Arg Leu Val Arg Trp Thr Pro Pro
1               5                   10                  15

Xaa Ala Gln

<210> SEQ ID NO 132
<211> LENGTH: 27
<212> TYPE: PRT
<213> ORGANISM: Artificial Sequence
<220> FEATURE:
<223> OTHER INFORMATION: synthetic citrullinated fibronectin peptide
      Fibronectin-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(19)
<223> OTHER INFORMATION: Xaa = citrulline
<220> FEATURE:
<221> NAME/KEY: AMIDATION
<222> LOCATION: (27)...(27)
<223> OTHER INFORMATION: glycinamide

<400> SEQUENCE: 132

Gly Tyr Arg Leu Thr Val Gly Leu Thr Xaa Pro Arg Ala Gln Ile Thr
1               5                   10                  15

Gly Tyr Xaa Leu Thr Val Gly Leu Thr Arg Gly
            20                  25

<210> SEQ ID NO 133
<211> LENGTH: 25
<212> TYPE: PRT
<213> ORGANISM: Artificial Sequence
<220> FEATURE:
<223> OTHER INFORMATION: synthetic fibronectin peptide Fibronectin-4
      core sequence
<220> FEATURE:
<221> NAME/KEY: MOD_RES
<222> LOCATION: (9)...(18)
<223> OTHER INFORMATION: Xaa = citrulline

<400> SEQUENCE: 133

Tyr Arg Leu Thr Val Gly Leu Thr Xaa Pro Arg Ala Gln Ile Thr Gly
1               5                   10                  15

Tyr Xaa Leu Thr Val Gly Leu Thr Arg
            20                  25

<210> SEQ ID NO 134
<211> LENGTH: 28
<212> TYPE: PRT
<213> ORGANISM: Artificial Sequence
<220> FEATURE:
<223> OTHER INFORMATION: synthetic citrullinated fibronectin peptide
      Fibronectin-5
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (28)...(28)
<223> OTHER INFORMATION: argininamide

<400> SEQUENCE: 134

Arg Gly Val Leu Thr Val Ser Trp Glu Xaa Ser Thr Thr Pro Asp Ile
1               5                   10                  15

Thr Gly Tyr Xaa Ile Thr Thr Thr Pro Thr Asn Arg
            20                  25

<210> SEQ ID NO 135
<211> LENGTH: 26
<212> TYPE: PRT
<213> ORGANISM: Artificial Sequence
<220> FEATURE:
<223> OTHER INFORMATION: synthetic fibronectin peptide Fibronectin-5
      core sequence
<220> FEATURE:
<221> NAME/KEY: MOD_RES
<222> LOCATION: (9)...(19)
<223> OTHER INFORMATION: Xaa = citrulline

<400> SEQUENCE: 135

Gly Val Leu Thr Val Ser Trp Glu Xaa Ser Thr Thr Pro Asp Ile Thr
1               5                   10                  15

Gly Tyr Xaa Ile Thr Thr Thr Pro Thr Asn
            20                  25

<210> SEQ ID NO 136
<211> LENGTH: 29
<212> TYPE: PRT
<213> ORGANISM: Artificial Sequence
<220> FEATURE:
<223> OTHER INFORMATION: synthetic citrullinated fibronectin peptide
      Fibronectin-6
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (5)...(23)
<223> OTHER INFORMATION: Xaa = citrulline
<220> FEATURE:
<221> NAME/KEY: AMIDATION
<222> LOCATION: (29)...(29)
<223> OTHER INFORMATION: glycinamide

<400> SEQUENCE: 136

Arg Ile Ala Pro Xaa Ala Thr Ile Thr Gly Pro Arg Ala Thr Ile Thr
1               5                   10                  15

Gly Tyr Xaa Tyr Arg Ile Xaa His His Pro Glu His Gly
            20                  25

```
<210> SEQ ID NO 137
<211> LENGTH: 27
<212> TYPE: PRT
<213> ORGANISM: Artificial Sequence
<220> FEATURE:
<223> OTHER INFORMATION: synthetic fibronectin peptide Fibronectin-6
      core sequence
<220> FEATURE:
<221> NAME/KEY: MOD_RES
<222> LOCATION: (4)...(22)
<223> OTHER INFORMATION: Xaa = citrulline

<400> SEQUENCE: 137

Ile Ala Pro Xaa Ala Thr Ile Thr Gly Pro Arg Ala Thr Ile Thr Gly
 1               5                  10                  15

Tyr Xaa Tyr Arg Ile Xaa His His Pro Glu His
            20                  25

<210> SEQ ID NO 138
<211> LENGTH: 28
<212> TYPE: PRT
<213> ORGANISM: Artificial Sequence
<220> FEATURE:
<223> OTHER INFORMATION: synthetic citrullinated fibronectin peptide
      Fibronectin-7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (3)...(20)
<223> OTHER INFORMATION: Xaa = citrulline
<220> FEATURE:
<221> NAME/KEY: AMIDATION
<222> LOCATION: (28)...(28)
<223> OTHER INFORMATION: glycinamide

<400> SEQUENCE: 138

Gly Pro Xaa Glu Asp Arg Val Pro His Ser Pro Arg Glu Asp Xaa Val
 1               5                  10                  15

Pro His Ser Xaa Asn Ser Ile Thr Leu Thr Asn Gly
            20                  25

<210> SEQ ID NO 139
<211> LENGTH: 26
<212> TYPE: PRT
<213> ORGANISM: Artificial Sequence
<220> FEATURE:
<223> OTHER INFORMATION: synthetic fibronectin peptide Fibronectin-7
      core sequence
<220> FEATURE:
<221> NAME/KEY: MOD_RES
<222> LOCATION: (2)...(19)
<223> OTHER INFORMATION: Xaa = citrulline

<400> SEQUENCE: 139

Pro Xaa Glu Asp Arg Val Pro His Ser Pro Arg Glu Asp Xaa Val Pro
 1               5                  10                  15

His Ser Xaa Asn Ser Ile Thr Leu Thr Asn
            20                  25

<210> SEQ ID NO 140
<211> LENGTH: 32
<212> TYPE: PRT
<213> ORGANISM: Artificial Sequence
<220> FEATURE:
<223> OTHER INFORMATION: synthetic citrullinated fibronectin peptide
      Fibronectin-8
<220> FEATURE:
<221> NAME/KEY: MOD_RES
```

```
<222> LOCATION: (1)...(1)
<223> OTHER INFORMATION: Arg modified by biotin
<220> FEATURE:
<221> NAME/KEY: MOD_RES
<222> LOCATION: (9)...(24)
<223> OTHER INFORMATION: Xaa = citrulline
<220> FEATURE:
<221> NAME/KEY: AMIDATION
<222> LOCATION: (32)...(32)
<223> OTHER INFORMATION: glycinamide

<400> SEQUENCE: 140

Arg Thr Val Tyr Ala Val Thr Gly Xaa Gly Asp Ser Pro Ala Ser Ser
1               5                   10                  15

Lys Pro Ile Ser Ile Asn Tyr Xaa Thr Glu Ile Asp Lys Pro Ser Gly
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: synthetic fibronectin peptide Fibronectin-8
      core sequence
<220> FEATURE:
<221> NAME/KEY: MOD_RES
<222> LOCATION: (8)...(23)
<223> OTHER INFORMATION: Xaa = citrulline

<400> SEQUENCE: 141

Thr Val Tyr Ala Val Thr Gly Xaa Gly Asp Ser Pro Ala Ser Ser Lys
1               5                   10                  15

Pro Ile Ser Ile Asn Tyr Xaa Thr Glu Ile Asp Lys Pro Ser
            20                  25                  30

<210> SEQ ID NO 142
<211> LENGTH: 30
<212> TYPE: PRT
<213> ORGANISM: Artificial Sequence
<220> FEATURE:
<223> OTHER INFORMATION: synthetic citrullinated fibronectin peptide
      Fibronectin-9
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (8)...(24)
<223> OTHER INFORMATION: Xaa = citrulline
<220> FEATURE:
<221> NAME/KEY: AMIDATION
<222> LOCATION: (30)...(30)
<223> OTHER INFORMATION: glycinamide

<400> SEQUENCE: 142

Arg Pro Gln Gly Gln Val Ser Xaa Tyr Arg Val Thr Tyr Ser Ser Pro
1               5                   10                  15

Gln Gly Gln Val Ser Arg Tyr Xaa Val Thr Tyr Ser Ser Gly
            20                  25                  30

<210> SEQ ID NO 143
<211> LENGTH: 28
<212> TYPE: PRT
<213> ORGANISM: Artificial Sequence
<220> FEATURE:
<223> OTHER INFORMATION: synthetic fibronectin peptide Fibronectin-9
      core sequence
<220> FEATURE:
<221> NAME/KEY: MOD_RES
<222> LOCATION: (7)...(23)
```

```
<223> OTHER INFORMATION: Xaa = citrulline

<400> SEQUENCE: 143

Pro Gln Gly Gln Val Ser Xaa Tyr Arg Val Thr Tyr Ser Ser Pro Gln
1               5                   10                  15

Gly Gln Val Ser Arg Tyr Xaa Val Thr Tyr Ser Ser
            20                  25

<210> SEQ ID NO 144
<211> LENGTH: 22
<212> TYPE: PRT
<213> ORGANISM: Artificial Sequence
<220> FEATURE:
<223> OTHER INFORMATION: synthetic citrullinated fibronectin peptide
      Fibronectin-10
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(13)
<223> OTHER INFORMATION: Xaa = citrulline
<220> FEATURE:
<221> NAME/KEY: AMIDATION
<222> LOCATION: (22)...(22)
<223> OTHER INFORMATION: argininamide

<400> SEQUENCE: 144

Gly Gly Phe Arg Xaa Thr Thr Pro Pro Thr Thr Phe Xaa Arg Thr Thr
1               5                   10                  15

Pro Pro Thr Thr Ala Arg
            20

<210> SEQ ID NO 145
<211> LENGTH: 20
<212> TYPE: PRT
<213> ORGANISM: Artificial Sequence
<220> FEATURE:
<223> OTHER INFORMATION: synthetic fibronectin peptide Fibronectin-10
      core sequence
<220> FEATURE:
<221> NAME/KEY: MOD_RES
<222> LOCATION: (4)...(12)
<223> OTHER INFORMATION: Xaa = citrulline

<400> SEQUENCE: 145

Gly Phe Arg Xaa Thr Thr Pro Pro Thr Thr Phe Xaa Arg Thr Thr Pro
1               5                   10                  15

Pro Thr Thr Ala
            20

<210> SEQ ID NO 146
<211> LENGTH: 21
<212> TYPE: PRT
<213> ORGANISM: Artificial Sequence
<220> FEATURE:
<223> OTHER INFORMATION: synthetic citrullinated fibronectin peptide
      Fibronectin-11
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(19)
<223> OTHER INFORMATION: Xaa = citrulline
<220> FEATURE:
<221> NAME/KEY: AMIDATION
<222> LOCATION: (21)...(21)
<223> OTHER INFORMATION: lysinamide
```

```
<400> SEQUENCE: 146

Gly Arg Arg Ala Xaa Val Thr Asp Ala Thr Glu Thr Thr Ile Thr Ile
 1               5                  10                  15

Ser Trp Xaa Thr Lys
            20

<210> SEQ ID NO 147
<211> LENGTH: 20
<212> TYPE: PRT
<213> ORGANISM: Artificial Sequence
<220> FEATURE:
<223> OTHER INFORMATION: synthetic fibronectin peptide Fibronectin-11
      core sequence
<220> FEATURE:
<221> NAME/KEY: MOD_RES
<222> LOCATION: (4)...(18)
<223> OTHER INFORMATION: Xaa = citrulline

<400> SEQUENCE: 147

Arg Arg Ala Xaa Val Thr Asp Ala Thr Glu Thr Thr Ile Thr Ile Ser
 1               5                  10                  15

Trp Xaa Thr Lys
            20

<210> SEQ ID NO 148
<211> LENGTH: 24
<212> TYPE: PRT
<213> ORGANISM: Artificial Sequence
<220> FEATURE:
<223> OTHER INFORMATION: synthetic citrullinated fibronectin peptide
      Fibronectin-12
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(17)
<223> OTHER INFORMATION: Xaa = citrulline
<220> FEATURE:
<221> NAME/KEY: AMIDATION
<222> LOCATION: (24)...(24)
<223> OTHER INFORMATION: argininamide

<400> SEQUENCE: 148

Arg Ala Asn Gly Gln Thr Pro Ile Gln Xaa Thr Ile Lys Pro Asp Val
 1               5                  10                  15

Xaa Ser Tyr Thr Ile Thr Gly Arg
            20

<210> SEQ ID NO 149
<211> LENGTH: 22
<212> TYPE: PRT
<213> ORGANISM: Artificial Sequence
<220> FEATURE:
<223> OTHER INFORMATION: synthetic fibronectin peptide Fibronectin-12
      core sequence
<220> FEATURE:
<221> NAME/KEY: MOD_RES
<222> LOCATION: (9)...(16)
<223> OTHER INFORMATION: Xaa = citrulline

<400> SEQUENCE: 149

Ala Asn Gly Gln Thr Pro Ile Gln Xaa Thr Ile Lys Pro Asp Val Xaa
 1               5                  10                  15

Ser Tyr Thr Ile Thr Gly
            20
```

```
<210> SEQ ID NO 150
<211> LENGTH: 26
<212> TYPE: PRT
<213> ORGANISM: Artificial Sequence
<220> FEATURE:
<223> OTHER INFORMATION: synthetic citrullinated lamin B1 peptide
      Lamin-B1-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(17)
<223> OTHER INFORMATION: Xaa = citrulline
<220> FEATURE:
<221> NAME/KEY: AMIDATION
<222> LOCATION: (26)...(26)
<223> OTHER INFORMATION: glutamic acid amide

<400> SEQUENCE: 150

Gly Leu Glu Phe Xaa Lys Ser Met Tyr Glu Glu Glu Ile Asn Glu Thr
1               5                   10                  15

Xaa Arg Lys His Glu Thr Arg Leu Val Glu
            20                  25

<210> SEQ ID NO 151
<211> LENGTH: 25
<212> TYPE: PRT
<213> ORGANISM: Artificial Sequence
<220> FEATURE:
<223> OTHER INFORMATION: synthetic lamin B1 peptide Lamin-B1-1 core
      sequence
<220> FEATURE:
<221> NAME/KEY: MOD_RES
<222> LOCATION: (4)...(16)
<223> OTHER INFORMATION: Xaa = citrulline

<400> SEQUENCE: 151

Leu Glu Phe Xaa Lys Ser Met Tyr Glu Glu Glu Ile Asn Glu Thr Xaa
1               5                   10                  15

Arg Lys His Glu Thr Arg Leu Val Glu
            20                  25

<210> SEQ ID NO 152
<211> LENGTH: 18
<212> TYPE: PRT
<213> ORGANISM: Artificial Sequence
<220> FEATURE:
<223> OTHER INFORMATION: synthetic citrullinated lamin B1 peptide
      Lamin-B1-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(16)
<223> OTHER INFORMATION: Xaa = citrulline
<220> FEATURE:
<221> NAME/KEY: AMIDATION
<222> LOCATION: (18)...(18)
<223> OTHER INFORMATION: glycinamide

<400> SEQUENCE: 152

Gly Arg Arg Lys His Glu Thr Xaa Leu Val Glu Val Asp Ser Gly Xaa
1               5                   10                  15

Gln Gly

<210> SEQ ID NO 153
```

```
<211> LENGTH: 16
<212> TYPE: PRT
<213> ORGANISM: Artificial Sequence
<220> FEATURE:
<223> OTHER INFORMATION: synthetic lamin B1 peptide Lamin-B1-2 core
      sequence
<220> FEATURE:
<221> NAME/KEY: MOD_RES
<222> LOCATION: (7)...(15)
<223> OTHER INFORMATION: Xaa = citrulline

<400> SEQUENCE: 153

Arg Arg Lys His Glu Thr Xaa Leu Val Glu Val Asp Ser Gly Xaa Gln
 1               5                  10                  15

<210> SEQ ID NO 154
<211> LENGTH: 35
<212> TYPE: PRT
<213> ORGANISM: Artificial Sequence
<220> FEATURE:
<223> OTHER INFORMATION: synthetic citrullinated lamin B1 peptide
      Lamin-B1-3
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (3)...(26)
<223> OTHER INFORMATION: Xaa = citrulline
<220> FEATURE:
<221> NAME/KEY: AMIDATION
<222> LOCATION: (35)...(35)
<223> OTHER INFORMATION: glutamic acid amide

<400> SEQUENCE: 154

Ser Ser Xaa Val Thr Val Ser Arg Ala Ser Ser Xaa Ser Val Ser
 1               5                  10                  15

Arg Ser Val Arg Thr Thr Xaa Gly Lys Xaa Lys Arg Val Asp Val Glu
                20                  25                  30

Glu Ser Glu
        35

<210> SEQ ID NO 155
<211> LENGTH: 35
<212> TYPE: PRT
<213> ORGANISM: Artificial Sequence
<220> FEATURE:
<223> OTHER INFORMATION: synthetic lamin B1 peptide Lamin-B1-3 core
      sequence
<220> FEATURE:
<221> NAME/KEY: MOD_RES
<222> LOCATION: (3)...(26)
<223> OTHER INFORMATION: Xaa = citrulline

<400> SEQUENCE: 155

Ser Ser Xaa Val Thr Val Ser Arg Ala Ser Ser Xaa Ser Val Ser
 1               5                  10                  15

Arg Ser Val Arg Thr Thr Xaa Gly Lys Xaa Lys Arg Val Asp Val Glu
                20                  25                  30

Glu Ser Glu
        35

<210> SEQ ID NO 156
<211> LENGTH: 22
<212> TYPE: PRT
<213> ORGANISM: Artificial Sequence
<220> FEATURE:
<223> OTHER INFORMATION: synthetic citrullinated lamin B1 peptide
      Lamin-B1-4
```

```
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(17)
<223> OTHER INFORMATION: Xaa = citrulline
<220> FEATURE:
<221> NAME/KEY: AMIDATION
<222> LOCATION: (22)...(22)
<223> OTHER INFORMATION: lysinamide

<400> SEQUENCE: 156

Gly Ser Ser Arg Val Thr Val Ser Xaa Ala Ser Ser Arg Ser Val
 1               5                  10                  15

Xaa Thr Thr Arg Gly Lys
            20

<210> SEQ ID NO 157
<211> LENGTH: 21
<212> TYPE: PRT
<213> ORGANISM: Artificial Sequence
<220> FEATURE:
<223> OTHER INFORMATION: synthetic lamin B1 peptide Lamin-B1-4 core
      sequence
<220> FEATURE:
<221> NAME/KEY: MOD_RES
<222> LOCATION: (8)...(16)
<223> OTHER INFORMATION: Xaa = citrulline

<400> SEQUENCE: 157

Ser Ser Arg Val Thr Val Ser Xaa Ala Ser Ser Arg Ser Val Xaa
 1               5                  10                  15

Thr Thr Arg Gly Lys
            20

<210> SEQ ID NO 158
<211> LENGTH: 30
<212> TYPE: PRT
<213> ORGANISM: Artificial Sequence
<220> FEATURE:
<223> OTHER INFORMATION: synthetic citrullinated lamin B1 peptide
      Lamin-B1-5
<220> FEATURE:
<221> NAME/KEY: MOD_RES
<222> LOCATION: (1)...(1)
<223> OTHER INFORMATION: Asn modified by biotin
<220> FEATURE:
<221> NAME/KEY: MOD_RES
<222> LOCATION: (10)...(24)
<223> OTHER INFORMATION: Xaa = citrulline
<220> FEATURE:
<221> NAME/KEY: AMIDATION
<222> LOCATION: (30)...(30)
<223> OTHER INFORMATION: glycinamide

<400> SEQUENCE: 158

Asn Ser Gln Gly Glu Glu Val Ala Gln Xaa Ser Thr Val Phe Lys Thr
 1               5                  10                  15

Phe His Gln Gln Gly Thr Pro Xaa Ala Ser Asn Arg Ser Gly
            20                  25                  30

<210> SEQ ID NO 159
<211> LENGTH: 29
<212> TYPE: PRT
<213> ORGANISM: Artificial Sequence
<220> FEATURE:
<223> OTHER INFORMATION: synthetic lamin B1 peptide Lamin-B1-5 core
      sequence
<220> FEATURE:
```

```
<221> NAME/KEY: MOD_RES
<222> LOCATION: (10)...(24)
<223> OTHER INFORMATION: Xaa = citrulline

<400> SEQUENCE: 159

Asn Ser Gln Gly Glu Glu Val Ala Gln Xaa Ser Thr Val Phe Lys Thr
1               5                   10                  15

Phe His Gln Gln Gly Thr Pro Xaa Ala Ser Asn Arg Ser
            20                  25

<210> SEQ ID NO 160
<211> LENGTH: 26
<212> TYPE: PRT
<213> ORGANISM: Artificial Sequence
<220> FEATURE:
<223> OTHER INFORMATION: synthetic citrullinated lamin B2 peptide
      Lamin-B2-1
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (9)...(24)
<223> OTHER INFORMATION: Xaa = citrulline
<220> FEATURE:
<221> NAME/KEY: AMIDATION
<222> LOCATION: (26)...(26)
<223> OTHER INFORMATION: glutaminamide

<400> SEQUENCE: 160

Lys Leu Glu Lys Glu Thr Leu Met Xaa Val Asp Leu Glu Asn Arg Ser
1               5                   10                  15

Met Arg Val Asp Leu Glu Asn Xaa Ser Gln
            20                  25

<210> SEQ ID NO 161
<211> LENGTH: 25
<212> TYPE: PRT
<213> ORGANISM: Artificial Sequence
<220> FEATURE:
<223> OTHER INFORMATION: synthetic lamin B2 peptide Lamin-B2-1 core
      sequence
<220> FEATURE:
<221> NAME/KEY: MOD_RES
<222> LOCATION: (8)...(23)
<223> OTHER INFORMATION: Xaa = citrulline

<400> SEQUENCE: 161

Leu Glu Lys Glu Thr Leu Met Xaa Val Asp Leu Glu Asn Arg Ser Met
1               5                   10                  15

Arg Val Asp Leu Glu Asn Xaa Ser Gln
            20                  25

<210> SEQ ID NO 162
<211> LENGTH: 23
<212> TYPE: PRT
<213> ORGANISM: Artificial Sequence
<220> FEATURE:
<223> OTHER INFORMATION: synthetic citrullinated lamin B2 peptide
      Lamin-B2-2
<220> FEATURE:
<221> NAME/KEY: MOD_RES
<222> LOCATION: (1)...(1)
<223> OTHER INFORMATION: Glu modified by biotin
<220> FEATURE:
<221> NAME/KEY: MOD_RES
<222> LOCATION: (2)...(20)
<223> OTHER INFORMATION: Xaa = citrulline
<220> FEATURE:
<221> NAME/KEY: AMIDATION
```

```
<222> LOCATION: (23)...(23)
<223> OTHER INFORMATION: glutamic acid amide

<400> SEQUENCE: 162

Glu Xaa Arg Leu Val Glu Val Asp Ser Ser Arg Xaa Leu Val Glu Val
1               5                   10                  15

Asp Ser Ser Xaa Gln Gln Glu
            20

<210> SEQ ID NO 163
<211> LENGTH: 23
<212> TYPE: PRT
<213> ORGANISM: Artificial Sequence
<220> FEATURE:
<223> OTHER INFORMATION: synthetic lamin B2 peptide Lamin-B2-2 core
      sequence
<220> FEATURE:
<221> NAME/KEY: MOD_RES
<222> LOCATION: (2)...(20)
<223> OTHER INFORMATION: Xaa = citrulline

<400> SEQUENCE: 163

Glu Xaa Arg Leu Val Glu Val Asp Ser Ser Arg Xaa Leu Val Glu Val
1               5                   10                  15

Asp Ser Ser Xaa Gln Gln Glu
            20

<210> SEQ ID NO 164
<211> LENGTH: 26
<212> TYPE: PRT
<213> ORGANISM: Artificial Sequence
<220> FEATURE:
<223> OTHER INFORMATION: synthetic citrullinated lamin B2 peptide
      Lamin-B2-3
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (9)...(18)
<223> OTHER INFORMATION: Xaa = citrulline
<220> FEATURE:
<221> NAME/KEY: AMIDATION
<222> LOCATION: (26)...(26)
<223> OTHER INFORMATION: serinamide

<400> SEQUENCE: 164

Lys Leu Ser Pro Ser Pro Ser Ser Xaa Val Ser Ser Arg Val Thr Val
1               5                   10                  15

Ser Xaa Ala Thr Ser Ser Ser Ser Gly Ser
            20                  25

<210> SEQ ID NO 165
<211> LENGTH: 26
<212> TYPE: PRT
<213> ORGANISM: Artificial Sequence
<220> FEATURE:
<223> OTHER INFORMATION: synthetic lamin B2 peptide Lamin-B2-3 core
      sequence
<220> FEATURE:
<221> NAME/KEY: MOD_RES
<222> LOCATION: (9)...(18)
<223> OTHER INFORMATION: Xaa = citrulline

<400> SEQUENCE: 165

Lys Leu Ser Pro Ser Pro Ser Ser Xaa Val Ser Ser Arg Val Thr Val
1               5                   10                  15

Ser Xaa Ala Thr Ser Ser Ser Ser Gly Ser
```

-continued

```
                20                  25

<210> SEQ ID NO 166
<211> LENGTH: 32
<212> TYPE: PRT
<213> ORGANISM: Artificial Sequence
<220> FEATURE:
<223> OTHER INFORMATION: synthetic citrullinated lamin B2 peptide
      Lamin-B2-4
<220> FEATURE:
<221> NAME/KEY: MOD_RES
<222> LOCATION: (1)...(1)
<223> OTHER INFORMATION: Glu modified by biotin
<220> FEATURE:
<221> NAME/KEY: MOD_RES
<222> LOCATION: (6)...(28)
<223> OTHER INFORMATION: Xaa = citrulline
<220> FEATURE:
<221> NAME/KEY: AMIDATION
<222> LOCATION: (32)...(32)
<223> OTHER INFORMATION: argininamide

<400> SEQUENCE: 166

Glu Glu Val Ala Met Xaa Thr Val Lys Lys Ser Ser Val Met Xaa Glu
 1               5                  10                  15

Asn Glu Asn Gly Phe His Gln Gln Gly Asp Pro Xaa Thr Thr Ser Arg
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: synthetic lamin B2 peptide Lamin-B2-4 core
      sequence
<220> FEATURE:
<221> NAME/KEY: MOD_RES
<222> LOCATION: (6)...(28)
<223> OTHER INFORMATION: Xaa = citrulline

<400> SEQUENCE: 167

Glu Glu Val Ala Met Xaa Thr Val Lys Lys Ser Ser Val Met Xaa Glu
 1               5                  10                  15

Asn Glu Asn Gly Phe His Gln Gln Gly Asp Pro Xaa Thr Thr Ser Arg
            20                  25                  30

<210> SEQ ID NO 168
<211> LENGTH: 29
<212> TYPE: PRT
<213> ORGANISM: Artificial Sequence
<220> FEATURE:
<223> OTHER INFORMATION: synthetic citrullinated lamin A/C peptide
      Lamin-A/C-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(24)
<223> OTHER INFORMATION: Xaa = citrulline
<220> FEATURE:
<221> NAME/KEY: AMIDATION
<222> LOCATION: (29)...(29)
<223> OTHER INFORMATION: alaninamide

<400> SEQUENCE: 168

Gly Ser Gln Arg Xaa Ala Thr Arg Ser Gly Xaa Arg Ala Thr Arg Ser
 1               5                  10                  15

Gly Ala Gln Arg Arg Ala Thr Xaa Ser Gly Ala Gln Ala
            20                  25
```

```
<210> SEQ ID NO 169
<211> LENGTH: 28
<212> TYPE: PRT
<213> ORGANISM: Artificial Sequence
<220> FEATURE:
<223> OTHER INFORMATION: synthetic lamin A/C peptide Lamin-A/C-1 core
      sequence
<220> FEATURE:
<221> NAME/KEY: MOD_RES
<222> LOCATION: (4)...(23)
<223> OTHER INFORMATION: Xaa = citrulline

<400> SEQUENCE: 169

Ser Gln Arg Xaa Ala Thr Arg Ser Gly Xaa Arg Ala Thr Arg Ser Gly
1               5                   10                  15

Ala Gln Arg Arg Ala Thr Xaa Ser Gly Ala Gln Ala
            20                  25

<210> SEQ ID NO 170
<211> LENGTH: 27
<212> TYPE: PRT
<213> ORGANISM: Artificial Sequence
<220> FEATURE:
<223> OTHER INFORMATION: synthetic citrullinated lamin A/C peptide
      Lamin-A/C-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (7)...(19)
<223> OTHER INFORMATION: Xaa = citrulline
<220> FEATURE:
<221> NAME/KEY: AMIDATION
<222> LOCATION: (27)...(27)
<223> OTHER INFORMATION: glycinamide

<400> SEQUENCE: 170

Gly Ala Val Tyr Ile Asp Xaa Val Arg Ser Leu Ala Val Tyr Ile Asp
1               5                   10                  15

Arg Val Xaa Ser Leu Glu Thr Glu Asn Ala Gly
            20                  25

<210> SEQ ID NO 171
<211> LENGTH: 26
<212> TYPE: PRT
<213> ORGANISM: Artificial Sequence
<220> FEATURE:
<223> OTHER INFORMATION: synthetic lamin A/C peptide Lamin-A/C-2 core
      sequence
<220> FEATURE:
<221> NAME/KEY: MOD_RES
<222> LOCATION: (6)...(18)
<223> OTHER INFORMATION: Xaa = citrulline

<400> SEQUENCE: 171

Ala Val Tyr Ile Asp Xaa Val Arg Ser Leu Ala Val Tyr Ile Asp Arg
1               5                   10                  15

Val Xaa Ser Leu Glu Thr Glu Asn Ala Gly
            20                  25

<210> SEQ ID NO 172
<211> LENGTH: 21
<212> TYPE: PRT
<213> ORGANISM: Artificial Sequence
<220> FEATURE:
<223> OTHER INFORMATION: synthetic citrullinated lamin A/C peptide
      Lamin-A/C-3
```

```
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(15)
<223> OTHER INFORMATION: Xaa = citrulline
<220> FEATURE:
<221> NAME/KEY: AMIDATION
<222> LOCATION: (21)...(21)
<223> OTHER INFORMATION: lysinamide

<400> SEQUENCE: 172

Gly Leu Arg Leu Xaa Ile Thr Glu Ser Glu Glu Val Val Ser Xaa Glu
 1               5                  10                  15

Val Ser Gly Ile Lys
            20

<210> SEQ ID NO 173
<211> LENGTH: 21
<212> TYPE: PRT
<213> ORGANISM: Artificial Sequence
<220> FEATURE:
<223> OTHER INFORMATION: synthetic lamin A/C peptide Lamin-A/C-3 core
      sequence
<220> FEATURE:
<221> NAME/KEY: MOD_RES
<222> LOCATION: (5)...(15)
<223> OTHER INFORMATION: Xaa = citrulline

<400> SEQUENCE: 173

Gly Leu Arg Leu Xaa Ile Thr Glu Ser Glu Glu Val Val Ser Xaa Glu
 1               5                  10                  15

Val Ser Gly Ile Lys
            20

<210> SEQ ID NO 174
<211> LENGTH: 37
<212> TYPE: PRT
<213> ORGANISM: Artificial Sequence
<220> FEATURE:
<223> OTHER INFORMATION: synthetic citrullinated lamin A/C peptide
      Lamin-A/C-4
<220> FEATURE:
<221> NAME/KEY: MOD_RES
<222> LOCATION: (1)...(1)
<223> OTHER INFORMATION: Thr modified by biotin
<220> FEATURE:
<221> NAME/KEY: MOD_RES
<222> LOCATION: (3)...(36)
<223> OTHER INFORMATION: Xaa = citrulline
<220> FEATURE:
<221> NAME/KEY: AMIDATION
<222> LOCATION: (37)...(37)
<223> OTHER INFORMATION: glutamic acid amide

<400> SEQUENCE: 174

Thr Lys Xaa Arg His Glu Thr Arg Leu Val Lys Arg Xaa His Glu Thr
 1               5                  10                  15

Arg Leu Val Lys Arg Arg His Glu Thr Xaa Leu Val Glu Ile Asp Asn
            20                  25                  30

Gly Lys Gln Xaa Glu
        35

<210> SEQ ID NO 175
<211> LENGTH: 37
<212> TYPE: PRT
<213> ORGANISM: Artificial Sequence
<220> FEATURE:
```

```
<223> OTHER INFORMATION: synthetic lamin A/C peptide Lamin-A/C-4 core
      sequence
<220> FEATURE:
<221> NAME/KEY: MOD_RES
<222> LOCATION: (3)...(36)
<223> OTHER INFORMATION: Xaa = citrulline

<400> SEQUENCE: 175

Thr Lys Xaa Arg His Glu Thr Arg Leu Val Lys Arg Xaa His Glu Thr
 1               5                  10                  15

Arg Leu Val Lys Arg Arg His Glu Thr Xaa Leu Val Glu Ile Asp Asn
            20                  25                  30

Gly Lys Gln Xaa Glu
        35

<210> SEQ ID NO 176
<211> LENGTH: 23
<212> TYPE: PRT
<213> ORGANISM: Artificial Sequence
<220> FEATURE:
<223> OTHER INFORMATION: synthetic citrullinated lamin A/C peptide
      Lamin-A/C-5
<220> FEATURE:
<221> NAME/KEY: MOD_RES
<222> LOCATION: (1)...(1)
<223> OTHER INFORMATION: Gln modified by biotin
<220> FEATURE:
<221> NAME/KEY: MOD_RES
<222> LOCATION: (5)...(13)
<223> OTHER INFORMATION: Xaa = citrulline
<220> FEATURE:
<221> NAME/KEY: AMIDATION
<222> LOCATION: (23)...(23)
<223> OTHER INFORMATION: glycinamide

<400> SEQUENCE: 176

Gln Ser Arg Ile Xaa Ile Asp Ser Leu Ser Ala Gln Xaa Ile Arg Ile
 1               5                  10                  15

Asp Ser Leu Ser Ala Gln Gly
            20

<210> SEQ ID NO 177
<211> LENGTH: 22
<212> TYPE: PRT
<213> ORGANISM: Artificial Sequence
<220> FEATURE:
<223> OTHER INFORMATION: synthetic lamin A/C peptide Lamin-A/C-5 core
      sequence
<220> FEATURE:
<221> NAME/KEY: MOD_RES
<222> LOCATION: (5)...(13)
<223> OTHER INFORMATION: Xaa = citrulline

<400> SEQUENCE: 177

Gln Ser Arg Ile Xaa Ile Asp Ser Leu Ser Ala Gln Xaa Ile Arg Ile
 1               5                  10                  15

Asp Ser Leu Ser Ala Gln
            20

<210> SEQ ID NO 178
<211> LENGTH: 31
<212> TYPE: PRT
<213> ORGANISM: Artificial Sequence
<220> FEATURE:
<223> OTHER INFORMATION: synthetic citrullinated lamin A/C peptide
      Lamin-A/C-6
<220> FEATURE:
<221> NAME/KEY: MOD_RES
<222> LOCATION: (1)...(1)
<223> OTHER INFORMATION: Glu modified by biotin
```

```
<220> FEATURE:
<221> NAME/KEY: MOD_RES
<222> LOCATION: (5)...(25)
<223> OTHER INFORMATION: Xaa = citrulline
<220> FEATURE:
<221> NAME/KEY: AMIDATION
<222> LOCATION: (31)...(31)
<223> OTHER INFORMATION: serinamide

<400> SEQUENCE: 178

Glu Glu Arg Leu Xaa Leu Ser Pro Ser Pro Thr Ser Gln Xaa Gly Arg
  1               5                   10                  15

Ala Ser Ser His Ser Ser Arg Gly Xaa Ala Ser Ser His Ser Ser
             20                  25                  30

<210> SEQ ID NO 179
<211> LENGTH: 31
<212> TYPE: PRT
<213> ORGANISM: Artificial Sequence
<220> FEATURE:
<223> OTHER INFORMATION: synthetic lamin A/C peptide Lamin-A/C-6 core
      sequence
<220> FEATURE:
<221> NAME/KEY: MOD_RES
<222> LOCATION: (5)...(25)
<223> OTHER INFORMATION: Xaa = citrulline

<400> SEQUENCE: 179

Glu Glu Arg Leu Xaa Leu Ser Pro Ser Pro Thr Ser Gln Xaa Gly Arg
  1               5                   10                  15

Ala Ser Ser His Ser Ser Arg Gly Xaa Ala Ser Ser His Ser Ser
             20                  25                  30

<210> SEQ ID NO 180
<211> LENGTH: 19
<212> TYPE: PRT
<213> ORGANISM: Artificial Sequence
<220> FEATURE:
<223> OTHER INFORMATION: synthetic citrullinated lamin A/C peptide
      Lamin-A/C-7
<220> FEATURE:
<221> NAME/KEY: MOD_RES
<222> LOCATION: (1)...(1)
<223> OTHER INFORMATION: Gln modified by biotin
<220> FEATURE:
<221> NAME/KEY: MOD_RES
<222> LOCATION: (10)...(10)
<223> OTHER INFORMATION: Xaa = citrulline
<220> FEATURE:
<221> NAME/KEY: AMIDATION
<222> LOCATION: (19)...(19)
<223> OTHER INFORMATION: serinamide

<400> SEQUENCE: 180

Gln Gly Gly Gly Ser Val Thr Lys Lys Xaa Lys Leu Glu Ser Thr Glu
  1               5                   10                  15

Ser Arg Ser

<210> SEQ ID NO 181
<211> LENGTH: 19
<212> TYPE: PRT
<213> ORGANISM: Artificial Sequence
<220> FEATURE:
<223> OTHER INFORMATION: synthetic lamin A/C peptide Lamin-A/C-7 core
      sequence
<220> FEATURE:
<221> NAME/KEY: MOD_RES
<222> LOCATION: (10)...(10)
<223> OTHER INFORMATION: Xaa = citrulline

<400> SEQUENCE: 181
```

```
Gln Gly Gly Gly Ser Val Thr Lys Lys Xaa Lys Leu Glu Ser Thr Glu
1               5                   10                  15

Ser Arg Ser
```

<210> SEQ ID NO 182
<211> LENGTH: 24
<212> TYPE: PRT
<213> ORGANISM: Artificial Sequence
<220> FEATURE:
<223> OTHER INFORMATION: synthetic citrullinated lamin A/C peptide
      Lamin-A/C-8
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (10)...(18)
<223> OTHER INFORMATION: Xaa = citrulline
<220> FEATURE:
<221> NAME/KEY: AMIDATION
<222> LOCATION: (24)...(24)
<223> OTHER INFORMATION: alaninamide

<400> SEQUENCE: 182

```
Lys Arg Lys Leu Glu Ser Thr Glu Ser Xaa Ser Ser Phe Ser Gln His
1               5                   10                  15

Ala Xaa Thr Ser Gly Arg Val Ala
            20
```

<210> SEQ ID NO 183
<211> LENGTH: 24
<212> TYPE: PRT
<213> ORGANISM: Artificial Sequence
<220> FEATURE:
<223> OTHER INFORMATION: synthetic lamin A/C peptide Lamin-A/C-8 core
      sequence
<220> FEATURE:
<221> NAME/KEY: MOD_RES
<222> LOCATION: (10)...(18)
<223> OTHER INFORMATION: Xaa = citrulline

<400> SEQUENCE: 183

```
Lys Arg Lys Leu Glu Ser Thr Glu Ser Xaa Ser Ser Phe Ser Gln His
1               5                   10                  15

Ala Xaa Thr Ser Gly Arg Val Ala
            20
```

<210> SEQ ID NO 184
<211> LENGTH: 25
<212> TYPE: PRT
<213> ORGANISM: Artificial Sequence
<220> FEATURE:
<223> OTHER INFORMATION: synthetic citrullinated lamin A/C peptide
      Lamin-A/C-9
<220> FEATURE:
<221> NAME/KEY: MOD_RES
<222> LOCATION: (1)...(1)
<223> OTHER INFORMATION: Glu modified by biotin
<220> FEATURE:
<221> NAME/KEY: MOD_RES
<222> LOCATION: (5)...(18)
<223> OTHER INFORMATION: Xaa = citrulline
<220> FEATURE:
<221> NAME/KEY: AMIDATION
<222> LOCATION: (25)...(25)
<223> OTHER INFORMATION: aspartic acid amide

<400> SEQUENCE: 184

Glu Val Ala Met Xaa Lys Leu Val Arg Ser Val Thr Val Arg Lys Leu

```
                1               5                  10                  15
Val Xaa Ser Val Thr Val Val Glu Asp
            20                  25

<210> SEQ ID NO 185
<211> LENGTH: 25
<212> TYPE: PRT
<213> ORGANISM: Artificial Sequence
<220> FEATURE:
<223> OTHER INFORMATION: synthetic lamin A/C peptide Lamin-A/C-9 core
      sequence
<220> FEATURE:
<221> NAME/KEY: MOD_RES
<222> LOCATION: (5)...(18)
<223> OTHER INFORMATION: Xaa = citrulline

<400> SEQUENCE: 185

Glu Val Ala Met Xaa Lys Leu Val Arg Ser Val Thr Val Arg Lys Leu
1               5                  10                  15

Val Xaa Ser Val Thr Val Val Glu Asp
            20                  25

<210> SEQ ID NO 186
<211> LENGTH: 26
<212> TYPE: PRT
<213> ORGANISM: Artificial Sequence
<220> FEATURE:
<223> OTHER INFORMATION: synthetic citrullinated lamin A/C peptide
      Lamin-A/C-10
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(20)
<223> OTHER INFORMATION: Xaa = citrulline
<220> FEATURE:
<221> NAME/KEY: AMIDATION
<222> LOCATION: (26)...(26)
<223> OTHER INFORMATION: threoninamide

<400> SEQUENCE: 186

Gly Asp Pro Ala Glu Tyr Asn Leu Xaa Ser Arg Thr Val Leu Ser Asn
1               5                  10                  15

Leu Arg Ser Xaa Thr Val Leu Ser Gly Thr
            20                  25

<210> SEQ ID NO 187
<211> LENGTH: 26
<212> TYPE: PRT
<213> ORGANISM: Artificial Sequence
<220> FEATURE:
<223> OTHER INFORMATION: synthetic lamin A/C peptide Lamin-A/C-10 core
      sequence
<220> FEATURE:
<221> NAME/KEY: MOD_RES
<222> LOCATION: (9)...(20)
<223> OTHER INFORMATION: Xaa = citrulline

<400> SEQUENCE: 187

Gly Asp Pro Ala Glu Tyr Asn Leu Xaa Ser Arg Thr Val Leu Ser Asn
1               5                  10                  15

Leu Arg Ser Xaa Thr Val Leu Ser Gly Thr
            20                  25

<210> SEQ ID NO 188
<211> LENGTH: 23
<212> TYPE: PRT
```

```
<213> ORGANISM: Artificial Sequence
<220> FEATURE:
<223> OTHER INFORMATION: synthetic citrullinated lamin A/C peptide
      Lamin-A/C-11
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (9)...(18)
<223> OTHER INFORMATION: Xaa = citrulline
<220> FEATURE:
<221> NAME/KEY: AMIDATION
<222> LOCATION: (23)...(23)
<223> OTHER INFORMATION: valinamide

<400> SEQUENCE: 188

Ser Val Thr Val Thr Arg Ser Tyr Xaa Ser Ala Ser Ser Val Thr Val
 1               5                  10                  15

Thr Xaa Ser Tyr Arg Ser Val
            20

<210> SEQ ID NO 189
<211> LENGTH: 23
<212> TYPE: PRT
<213> ORGANISM: Artificial Sequence
<220> FEATURE:
<223> OTHER INFORMATION: synthetic lamin A/C peptide Lamin-A/C-11 core
      sequence
<220> FEATURE:
<221> NAME/KEY: MOD_RES
<222> LOCATION: (9)...(18)
<223> OTHER INFORMATION: Xaa = citrulline

<400> SEQUENCE: 189

Ser Val Thr Val Thr Arg Ser Tyr Xaa Ser Ala Ser Ser Val Thr Val
 1               5                  10                  15

Thr Xaa Ser Tyr Arg Ser Val
            20

<210> SEQ ID NO 190
<211> LENGTH: 23
<212> TYPE: PRT
<213> ORGANISM: Artificial Sequence
<220> FEATURE:
<223> OTHER INFORMATION: synthetic citrullinated lamin A/C peptide
      Lamin-A/C-12
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (9)...(19)
<223> OTHER INFORMATION: Xaa = citrulline
<220> FEATURE:
<221> NAME/KEY: AMIDATION
<222> LOCATION: (23)...(23)
<223> OTHER INFORMATION: glycinamide

<400> SEQUENCE: 190

Ser Phe Gly Asp Asn Leu Val Thr Xaa Ser Tyr Leu Leu Gly Asn Ser
 1               5                  10                  15

Ser Pro Xaa Thr Gln Ser Gly
            20

<210> SEQ ID NO 191
<211> LENGTH: 22
<212> TYPE: PRT
<213> ORGANISM: Artificial Sequence
```

```
<220> FEATURE:
<223> OTHER INFORMATION: synthetic lamin A/C peptide Lamin-A/C-12 core
      sequence
<220> FEATURE:
<221> NAME/KEY: MOD_RES
<222> LOCATION: (9)...(19)
<223> OTHER INFORMATION: Xaa = citrulline

<400> SEQUENCE: 191

Ser Phe Gly Asp Asn Leu Val Thr Xaa Ser Tyr Leu Leu Gly Asn Ser
 1               5                  10                  15

Ser Pro Xaa Thr Gln Ser
            20

<210> SEQ ID NO 192
<211> LENGTH: 20
<212> TYPE: PRT
<213> ORGANISM: Artificial Sequence
<220> FEATURE:
<223> OTHER INFORMATION: synthetic citrullinated beta-actin peptide
      beta-actin-1
<220> FEATURE:
<221> NAME/KEY: MOD_RES
<222> LOCATION: (1)...(1)
<223> OTHER INFORMATION: Tyr modified by biotin
<220> FEATURE:
<221> NAME/KEY: MOD_RES
<222> LOCATION: (9)...(19)
<223> OTHER INFORMATION: Xaa = citrulline
<220> FEATURE:
<221> NAME/KEY: AMIDATION
<222> LOCATION: (20)...(20)
<223> OTHER INFORMATION: glutamic acid amide

<400> SEQUENCE: 192

Tyr Leu Met Lys Ile Leu Thr Glu Xaa Gly Tyr Ser Phe Thr Thr Thr
 1               5                  10                  15

Ala Glu Xaa Glu
            20

<210> SEQ ID NO 193
<211> LENGTH: 20
<212> TYPE: PRT
<213> ORGANISM: Artificial Sequence
<220> FEATURE:
<223> OTHER INFORMATION: synthetic beta-actin peptide beta-actin-1 core
      sequence
<220> FEATURE:
<221> NAME/KEY: MOD_RES
<222> LOCATION: (9)...(19)
<223> OTHER INFORMATION: Xaa = citrulline

<400> SEQUENCE: 193

Tyr Leu Met Lys Ile Leu Thr Glu Xaa Gly Tyr Ser Phe Thr Thr Thr
 1               5                  10                  15

Ala Glu Xaa Glu
            20

<210> SEQ ID NO 194
<211> LENGTH: 18
<212> TYPE: PRT
<213> ORGANISM: Artificial Sequence
<220> FEATURE:
<223> OTHER INFORMATION: synthetic citrullinated myeloblastin peptide
      myeloblastin-1
<220> FEATURE:
<221> NAME/KEY: MOD_RES
<222> LOCATION: (1)...(1)
<223> OTHER INFORMATION: His modified by biotin
<220> FEATURE:
<221> NAME/KEY: MOD_RES
```

```
<222> LOCATION: (3)...(12)
<223> OTHER INFORMATION: Xaa = citrulline
<220> FEATURE:
<221> NAME/KEY: AMIDATION
<222> LOCATION: (18)...(18)
<223> OTHER INFORMATION: histidinamide

<400> SEQUENCE: 194

His Ser Xaa Pro Tyr Met Ala Ser Leu Gln Met Xaa Gly Asn Pro Gly
 1               5                  10                  15

Ser His

<210> SEQ ID NO 195
<211> LENGTH: 18
<212> TYPE: PRT
<213> ORGANISM: Artificial Sequence
<220> FEATURE:
<223> OTHER INFORMATION: synthetic myeloblastin peptide myeloblastin-1
      core sequence
<220> FEATURE:
<221> NAME/KEY: MOD_RES
<222> LOCATION: (3)...(12)
<223> OTHER INFORMATION: Xaa = citrulline

<400> SEQUENCE: 195

His Ser Xaa Pro Tyr Met Ala Ser Leu Gln Met Xaa Gly Asn Pro Gly
 1               5                  10                  15

Ser His

<210> SEQ ID NO 196
<211> LENGTH: 30
<212> TYPE: PRT
<213> ORGANISM: Artificial Sequence
<220> FEATURE:
<223> OTHER INFORMATION: synthetic citrullinated myeloblastin peptide
      myeloblastin-2
<220> FEATURE:
<221> NAME/KEY: MOD_RES
<222> LOCATION: (1)...(1)
<223> OTHER INFORMATION: His modified by biotin
<220> FEATURE:
<221> NAME/KEY: MOD_RES
<222> LOCATION: (9)...(21)
<223> OTHER INFORMATION: Xaa = citrulline
<220> FEATURE:
<221> NAME/KEY: AMIDATION
<222> LOCATION: (30)...(30)
<223> OTHER INFORMATION: glycinamide

<400> SEQUENCE: 196

His Ser Leu Arg Asp Ile Pro Gln Xaa Leu Val Asn Val Val Leu Gly
 1               5                  10                  15

Ala His Asn Val Xaa Thr Gln Glu Pro Thr Gln Gln His Gly
            20                  25                  30

<210> SEQ ID NO 197
<211> LENGTH: 29
<212> TYPE: PRT
<213> ORGANISM: Artificial Sequence
<220> FEATURE:
<223> OTHER INFORMATION: synthetic myeloblastin peptide myeloblastin-2
      core sequence
<220> FEATURE:
<221> NAME/KEY: MOD_RES
<222> LOCATION: (9)...(21)
<223> OTHER INFORMATION: Xaa = citrulline

<400> SEQUENCE: 197

His Ser Leu Arg Asp Ile Pro Gln Xaa Leu Val Asn Val Val Leu Gly
 1               5                  10                  15
```

```
Ala His Asn Val Xaa Thr Gln Glu Pro Thr Gln Gln His
            20                  25
```

<210> SEQ ID NO 198
<211> LENGTH: 24
<212> TYPE: PRT
<213> ORGANISM: Artificial Sequence
<220> FEATURE:
<223> OTHER INFORMATION: synthetic citrullinated myeloblastin peptide
      myeloblastin-3
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (10)...(18)
<223> OTHER INFORMATION: Xaa = citrulline
<220> FEATURE:
<221> NAME/KEY: AMIDATION
<222> LOCATION: (24)...(24)
<223> OTHER INFORMATION: aspartic acid amide

<400> SEQUENCE: 198

```
Ser Phe Val Ile Trp Gly Ser Ala Thr Xaa Leu Phe Pro Asp Phe Phe
1               5                   10                  15

Thr Xaa Val Ala Leu Tyr Val Asp
            20
```

<210> SEQ ID NO 199
<211> LENGTH: 24
<212> TYPE: PRT
<213> ORGANISM: Artificial Sequence
<220> FEATURE:
<223> OTHER INFORMATION: synthetic myeloblastin peptide myeloblastin-3
      core sequence
<220> FEATURE:
<221> NAME/KEY: MOD_RES
<222> LOCATION: (10)...(18)
<223> OTHER INFORMATION: Xaa = citrulline

<400> SEQUENCE: 199

```
Ser Phe Val Ile Trp Gly Ser Ala Thr Xaa Leu Phe Pro Asp Phe Phe
1               5                   10                  15

Thr Xaa Val Ala Leu Tyr Val Asp
            20
```

<210> SEQ ID NO 200
<211> LENGTH: 30
<212> TYPE: PRT
<213> ORGANISM: Artificial Sequence
<220> FEATURE:
<223> OTHER INFORMATION: synthetic citrullinated myeloblastin peptide
      myeloblastin-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(27)
<223> OTHER INFORMATION: Xaa = citrulline
<220> FEATURE:
<221> NAME/KEY: AMIDATION
<222> LOCATION: (30)...(30)
<223> OTHER INFORMATION: glutamic acid amide

<400> SEQUENCE: 200

```
Gly Asp Trp Ile Xaa Ser Thr Leu Arg Arg Asp Trp Ile Arg Ser Thr
1               5                   10                  15
```

```
Leu Arg Xaa Val Trp Ile Arg Ser Thr Leu Xaa Arg Val Glu
            20                  25                  30

<210> SEQ ID NO 201
<211> LENGTH: 29
<212> TYPE: PRT
<213> ORGANISM: Artificial Sequence
<220> FEATURE:
<223> OTHER INFORMATION: synthetic myeloblastin peptide myeloblastin-4
      core sequence
<220> FEATURE:
<221> NAME/KEY: MOD_RES
<222> LOCATION: (4)...(26)
<223> OTHER INFORMATION: Xaa = citrulline

<400> SEQUENCE: 201

Asp Trp Ile Xaa Ser Thr Leu Arg Arg Asp Trp Ile Arg Ser Thr Leu
1               5                   10                  15

Arg Xaa Val Trp Ile Arg Ser Thr Leu Xaa Arg Val Glu
            20                  25

<210> SEQ ID NO 202
<211> LENGTH: 31
<212> TYPE: PRT
<213> ORGANISM: Artificial Sequence
<220> FEATURE:
<223> OTHER INFORMATION: synthetic citrullinated phospholipid scramblase
      peptide PL Scramblase-1
<220> FEATURE:
<221> NAME/KEY: MOD_RES
<222> LOCATION: (1)...(1)
<223> OTHER INFORMATION: Thr modified by biotin
<220> FEATURE:
<221> NAME/KEY: MOD_RES
<222> LOCATION: (3)...(29)
<223> OTHER INFORMATION: Xaa = citrulline
<220> FEATURE:
<221> NAME/KEY: AMIDATION
<222> LOCATION: (31)...(31)
<223> OTHER INFORMATION: serinamide

<400> SEQUENCE: 202

Thr Leu Xaa Ile Ile Asp Asn Met Gly Gln Glu Val Ile Thr Leu Glu
1               5                   10                  15

Xaa Pro Leu Arg Ser Ile Thr Leu Glu Arg Pro Leu Xaa Ser Ser
            20                  25                  30

<210> SEQ ID NO 203
<211> LENGTH: 31
<212> TYPE: PRT
<213> ORGANISM: Artificial Sequence
<220> FEATURE:
<223> OTHER INFORMATION: synthetic phospholipid scramblase peptide PL
      Scramblase-1 core sequence
<220> FEATURE:
<221> NAME/KEY: MOD_RES
<222> LOCATION: (3)...(29)
<223> OTHER INFORMATION: Xaa = citrulline

<400> SEQUENCE: 203

Thr Leu Xaa Ile Ile Asp Asn Met Gly Gln Glu Val Ile Thr Leu Glu
1               5                   10                  15

Xaa Pro Leu Arg Ser Ile Thr Leu Glu Arg Pro Leu Xaa Ser Ser
            20                  25                  30

<210> SEQ ID NO 204
<211> LENGTH: 25
<212> TYPE: PRT
<213> ORGANISM: Artificial Sequence
<220> FEATURE:
```

```
<223> OTHER INFORMATION: synthetic citrullinated apolipoprotein (a)
      peptide Apolipo(a)-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (25)...(25)
<223> OTHER INFORMATION: argininamide

<400> SEQUENCE: 204

Gly Tyr His Gly Asp Gly Gln Ser Tyr Xaa Gly Thr Tyr Ser Thr Thr
1               5                   10                  15

Val Thr Gly Xaa Thr Ser Gln Ala Arg
            20                  25

<210> SEQ ID NO 205
<211> LENGTH: 23
<212> TYPE: PRT
<213> ORGANISM: Artificial Sequence
<220> FEATURE:
<223> OTHER INFORMATION: synthetic apolipoprotein (a) peptide
      Apolipo(a)-1 core sequence
<220> FEATURE:
<221> NAME/KEY: MOD_RES
<222> LOCATION: (9)...(19)
<223> OTHER INFORMATION: Xaa = citrulline

<400> SEQUENCE: 205

Tyr His Gly Asp Gly Gln Ser Tyr Xaa Gly Thr Tyr Ser Thr Thr Val
1               5                   10                  15

Thr Gly Xaa Thr Ser Gln Ala
            20

<210> SEQ ID NO 206
<211> LENGTH: 29
<212> TYPE: PRT
<213> ORGANISM: Artificial Sequence
<220> FEATURE:
<223> OTHER INFORMATION: synthetic citrullinated apolipoprotein (a)
      peptide Apolipo(a)-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(28)
<223> OTHER INFORMATION: Xaa = citrulline
<220> FEATURE:
<221> NAME/KEY: AMIDATION
<222> LOCATION: (29)...(29)
<223> OTHER INFORMATION: glycinamide

<400> SEQUENCE: 206

Gly Tyr Thr Xaa Asp Pro Gly Val Arg Trp Tyr Thr Arg Asp Pro Gly
1               5                   10                  15

Val Xaa Trp Ser Glu Gln Ala Pro Thr Glu Gln Xaa Gly
            20                  25

<210> SEQ ID NO 207
<211> LENGTH: 27
<212> TYPE: PRT
<213> ORGANISM: Artificial Sequence
<220> FEATURE:
<223> OTHER INFORMATION: synthetic apolipoprotein (a) peptide
```

```
         Apolipo(a)-2 core sequence
<220> FEATURE:
<221> NAME/KEY: MOD_RES
<222> LOCATION: (3)...(27)
<223> OTHER INFORMATION: Xaa = citrulline

<400> SEQUENCE: 207

Tyr Thr Xaa Asp Pro Gly Val Arg Trp Tyr Thr Arg Asp Pro Gly Val
1               5                   10                  15

Xaa Trp Ser Glu Gln Ala Pro Thr Glu Gln Xaa
            20                  25

<210> SEQ ID NO 208
<211> LENGTH: 24
<212> TYPE: PRT
<213> ORGANISM: Artificial Sequence
<220> FEATURE:
<223> OTHER INFORMATION: synthetic citrullinated apolipoprotein (a)
      peptide Apolipo(a)-3
<220> FEATURE:
<221> NAME/KEY: MOD_RES
<222> LOCATION: (1)...(1)
<223> OTHER INFORMATION: Tyr modified by biotin
<220> FEATURE:
<221> NAME/KEY: MOD_RES
<222> LOCATION: (9)...(19)
<223> OTHER INFORMATION: Xaa = citrulline
<220> FEATURE:
<221> NAME/KEY: AMIDATION
<222> LOCATION: (24)...(24)
<223> OTHER INFORMATION: argininamide

<400> SEQUENCE: 208

Tyr Tyr His Tyr Gly Gln Ser Tyr Xaa Gly Ser Phe Ser Thr Thr Val
1               5                   10                  15

Thr Gly Xaa Thr Ser Gln Ser Arg
            20

<210> SEQ ID NO 209
<211> LENGTH: 23
<212> TYPE: PRT
<213> ORGANISM: Artificial Sequence
<220> FEATURE:
<223> OTHER INFORMATION: synthetic apolipoprotein (a) peptide
      Apolipo(a)-3 core sequence
<220> FEATURE:
<221> NAME/KEY: MOD_RES
<222> LOCATION: (9)...(19)
<223> OTHER INFORMATION: Xaa = citrulline

<400> SEQUENCE: 209

Tyr Tyr His Tyr Gly Gln Ser Tyr Xaa Gly Ser Phe Ser Thr Thr Val
1               5                   10                  15

Thr Gly Xaa Thr Ser Gln Ser
            20

<210> SEQ ID NO 210
<211> LENGTH: 27
<212> TYPE: PRT
<213> ORGANISM: Artificial Sequence
<220> FEATURE:
<223> OTHER INFORMATION: synthetic citrullinated apolipoprotein (a)
      peptide Apolipo(a)-4
<220> FEATURE:
<221> NAME/KEY: MOD_RES
<222> LOCATION: (1)...(1)
<223> OTHER INFORMATION: His modified by biotin
<220> FEATURE:
<221> NAME/KEY: MOD_RES
<222> LOCATION: (5)...(26)
<223> OTHER INFORMATION: Xaa = citrulline
```

```
<220> FEATURE:
<221> NAME/KEY: AMIDATION
<222> LOCATION: (27)...(27)
<223> OTHER INFORMATION: asparaginamide

<400> SEQUENCE: 210

His Trp His Gln Xaa Thr Thr Glu Tyr Tyr Pro Asn Gly Gly Leu Thr
1               5                   10                  15

Xaa Gly Gly Leu Thr Arg Asn Tyr Ser Xaa Asn
            20                  25

<210> SEQ ID NO 211
<211> LENGTH: 27
<212> TYPE: PRT
<213> ORGANISM: Artificial Sequence
<220> FEATURE:
<223> OTHER INFORMATION: synthetic apolipoprotein (a) peptide
      Apolipo(a)-4 core sequence
<220> FEATURE:
<221> NAME/KEY: MOD_RES
<222> LOCATION: (5)...(26)
<223> OTHER INFORMATION: Xaa = citrulline

<400> SEQUENCE: 211

His Trp His Gln Xaa Thr Thr Glu Tyr Tyr Pro Asn Gly Gly Leu Thr
1               5                   10                  15

Xaa Gly Gly Leu Thr Arg Asn Tyr Ser Xaa Asn
            20                  25

<210> SEQ ID NO 212
<211> LENGTH: 25
<212> TYPE: PRT
<213> ORGANISM: Artificial Sequence
<220> FEATURE:
<223> OTHER INFORMATION: synthetic citrullinated apolipoprotein (a)
      peptide Apolipo(a)-5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (25)...(25)
<223> OTHER INFORMATION: argininamide

<400> SEQUENCE: 212

Gly Tyr Arg Gly Asp Gly Gln Ser Tyr Xaa Gly Thr Leu Ser Thr Thr
1               5                   10                  15

Ile Thr Gly Xaa Thr Ser Gln Ser Arg
            20                  25

<210> SEQ ID NO 213
<211> LENGTH: 23
<212> TYPE: PRT
<213> ORGANISM: Artificial Sequence
<220> FEATURE:
<223> OTHER INFORMATION: synthetic apolipoprotein (a) peptide
      Apolipo(a)-5 core sequence
<220> FEATURE:
<221> NAME/KEY: MOD_RES
<222> LOCATION: (9)...(19)
<223> OTHER INFORMATION: Xaa = citrulline

<400> SEQUENCE: 213

Tyr Arg Gly Asp Gly Gln Ser Tyr Xaa Gly Thr Leu Ser Thr Thr Ile
1               5                   10                  15
```

```
Thr Gly Xaa Thr Ser Gln Ser
            20

<210> SEQ ID NO 214
<211> LENGTH: 27
<212> TYPE: PRT
<213> ORGANISM: Artificial Sequence
<220> FEATURE:
<223> OTHER INFORMATION: synthetic citrullinated apolipoprotein (a)
      peptide Apolipo(a)-6
<220> FEATURE:
<221> NAME/KEY: MOD_RES
<222> LOCATION: (1)...(1)
<223> OTHER INFORMATION: His modified by biotin
<220> FEATURE:
<221> NAME/KEY: MOD_RES
<222> LOCATION: (5)...(26)
<223> OTHER INFORMATION: Xaa = citrulline
<220> FEATURE:
<221> NAME/KEY: AMIDATION
<222> LOCATION: (27)...(27)
<223> OTHER INFORMATION: asparaginamide

<400> SEQUENCE: 214

His Trp His Arg Xaa Ile Pro Leu Tyr Tyr Pro Asn Ala Gly Leu Thr
1               5                   10                  15

Xaa Ala Gly Leu Thr Arg Asn Tyr Ser Xaa Asn
            20                  25

<210> SEQ ID NO 215
<211> LENGTH: 27
<212> TYPE: PRT
<213> ORGANISM: Artificial Sequence
<220> FEATURE:
<223> OTHER INFORMATION: synthetic apolipoprotein (a) peptide
      Apolipo(a)-6 core sequence
<220> FEATURE:
<221> NAME/KEY: MOD_RES
<222> LOCATION: (5)...(26)
<223> OTHER INFORMATION: Xaa = citrulline

<400> SEQUENCE: 215

His Trp His Arg Xaa Ile Pro Leu Tyr Tyr Pro Asn Ala Gly Leu Thr
1               5                   10                  15

Xaa Ala Gly Leu Thr Arg Asn Tyr Ser Xaa Asn
            20                  25

<210> SEQ ID NO 216
<211> LENGTH: 25
<212> TYPE: PRT
<213> ORGANISM: Artificial Sequence
<220> FEATURE:
<223> OTHER INFORMATION: synthetic citrullinated apolipoprotein (a)
      peptide Apolipo(a)-7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (25)...(25)
<223> OTHER INFORMATION: argininamide

<400> SEQUENCE: 216

Gly Tyr His Gly Asp Gly Arg Ser Tyr Xaa Gly Ile Ser Ser Thr Thr
1               5                   10                  15
```

```
Val Thr Gly Xaa Thr Ser Gln Ser Arg
            20                  25
```

```
<210> SEQ ID NO 217
<211> LENGTH: 23
<212> TYPE: PRT
<213> ORGANISM: Artificial Sequence
<220> FEATURE:
<223> OTHER INFORMATION: synthetic apolipoprotein (a) peptide
      Apolipo(a)-7 core sequence
<220> FEATURE:
<221> NAME/KEY: MOD_RES
<222> LOCATION: (9)...(19)
<223> OTHER INFORMATION: Xaa = citrulline

<400> SEQUENCE: 217

Tyr His Gly Asp Gly Arg Ser Tyr Xaa Gly Ile Ser Ser Thr Thr Val
1               5                   10                  15

Thr Gly Xaa Thr Ser Gln Ser
            20
```

```
<210> SEQ ID NO 218
<211> LENGTH: 35
<212> TYPE: PRT
<213> ORGANISM: Artificial Sequence
<220> FEATURE:
<223> OTHER INFORMATION: synthetic citrullinated apolipoprotein (a)
      peptide Apolipo(a)-8
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (3)...(30)
<223> OTHER INFORMATION: Xaa = citrulline
<220> FEATURE:
<221> NAME/KEY: AMIDATION
<222> LOCATION: (35)...(35)
<223> OTHER INFORMATION: glycinamide

<400> SEQUENCE: 218

Ser Tyr Xaa Gly Thr Phe Ser Thr Thr Val Thr Gly Xaa Thr Ser Gln
1               5                   10                  15

Ser Trp Ser Ser Met Thr Pro His Xaa His Arg His Gln Xaa Thr Pro
            20                  25                  30

Glu Asn Gly
        35
```

```
<210> SEQ ID NO 219
<211> LENGTH: 34
<212> TYPE: PRT
<213> ORGANISM: Artificial Sequence
<220> FEATURE:
<223> OTHER INFORMATION: synthetic apolipoprotein (a) peptide
      Apolipo(a)-8 core sequence
<220> FEATURE:
<221> NAME/KEY: MOD_RES
<222> LOCATION: (3)...(30)
<223> OTHER INFORMATION: Xaa = citrulline

<400> SEQUENCE: 219

Ser Tyr Xaa Gly Thr Phe Ser Thr Thr Val Thr Gly Xaa Thr Ser Gln
1               5                   10                  15

Ser Trp Ser Ser Met Thr Pro His Xaa His Arg His Gln Xaa Thr Pro
            20                  25                  30

Glu Asn
```

```
<210> SEQ ID NO 220
<211> LENGTH: 24
<212> TYPE: PRT
<213> ORGANISM: Artificial Sequence
<220> FEATURE:
<223> OTHER INFORMATION: synthetic citrullinated apolipoprotein (a)
      peptide Apolipo(a)-9
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(18)
<223> OTHER INFORMATION: Xaa = citrulline
<220> FEATURE:
<221> NAME/KEY: AMIDATION
<222> LOCATION: (24)...(24)
<223> OTHER INFORMATION: threoninamide

<400> SEQUENCE: 220

Gly Gly Val Tyr Ala Arg Val Ser Xaa Phe Val Thr Trp Ile Val Tyr
 1               5                  10                  15

Ala Xaa Val Ser Arg Phe Val Thr
            20

<210> SEQ ID NO 221
<211> LENGTH: 23
<212> TYPE: PRT
<213> ORGANISM: Artificial Sequence
<220> FEATURE:
<223> OTHER INFORMATION: synthetic apolipoprotein (a) peptide
      Apolipo(a)-9 core sequence
<220> FEATURE:
<221> NAME/KEY: MOD_RES
<222> LOCATION: (8)...(17)
<223> OTHER INFORMATION: Xaa = citrulline

<400> SEQUENCE: 221

Gly Val Tyr Ala Arg Val Ser Xaa Phe Val Thr Trp Ile Val Tyr Ala
 1               5                  10                  15

Xaa Val Ser Arg Phe Val Thr
            20

<210> SEQ ID NO 222
<211> LENGTH: 25
<212> TYPE: PRT
<213> ORGANISM: Artificial Sequence
<220> FEATURE:
<223> OTHER INFORMATION: synthetic citrullinated heat shock 70kDa
      protein 5 peptide BiP-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (8)...(18)
<223> OTHER INFORMATION: Xaa = citrulline
 <220> FEATURE:
<221> NAME/KEY: AMIDATION
<222> LOCATION: (25)...(25)
<223> OTHER INFORMATION: argininamide

<400> SEQUENCE: 222

Arg Tyr Phe Asn Asp Ala Gln Xaa Gln Ala Ile Ala Gly Leu Asn Val
 1               5                  10                  15

Met Xaa Ile Ile Asn Glu Pro Thr Arg
            20                  25

<210> SEQ ID NO 223
```

```
<211> LENGTH: 23
<212> TYPE: PRT
<213> ORGANISM: Artificial Sequence
<220> FEATURE:
<223> OTHER INFORMATION: synthetic heat shock 70kDa protein 5 peptide
      BiP-1 core sequence
<220> FEATURE:
<221> NAME/KEY: MOD_RES
<222> LOCATION: (7)...(17)
<223> OTHER INFORMATION: Xaa = citrulline

<400> SEQUENCE: 223

Tyr Phe Asn Asp Ala Gln Xaa Gln Ala Ile Ala Gly Leu Asn Val Met
1               5                   10                  15

Xaa Ile Ile Asn Glu Pro Thr
            20

<210> SEQ ID NO 224
<211> LENGTH: 28
<212> TYPE: PRT
<213> ORGANISM: Artificial Sequence
<220> FEATURE:
<223> OTHER INFORMATION: synthetic citrullinated heat shock 70kDa
      protein 5 peptide BiP-2
<220> FEATURE:
<221> NAME/KEY: MOD_RES
<222> LOCATION: (1)...(1)
<223> OTHER INFORMATION: Asp modified by biotin
<220> FEATURE:
<221> NAME/KEY: MOD_RES
<222> LOCATION: (7)...(21)
<223> OTHER INFORMATION: Xaa = citrulline
<220> FEATURE:
<221> NAME/KEY: AMIDATION
<222> LOCATION: (28)...(28)
<223> OTHER INFORMATION: glutaminamide

<400> SEQUENCE: 224

Asp Val Arg Lys Asp Asn Xaa Ala Val Gln Lys Leu Arg Xaa Glu Val
1               5                   10                  15

Glu Lys Ala Lys Xaa Ala Leu Ser Ser Gln His Gln
            20                  25

<210> SEQ ID NO 225
<211> LENGTH: 28
<212> TYPE: PRT
<213> ORGANISM: Artificial Sequence
<220> FEATURE:
<223> OTHER INFORMATION: synthetic heat shock 70kDa protein 5 peptide
      BiP-2 core sequence
<220> FEATURE:
<221> NAME/KEY: MOD_RES
<222> LOCATION: (7)...(21)
<223> OTHER INFORMATION: Xaa = citrulline

<400> SEQUENCE: 225

Asp Val Arg Lys Asp Asn Xaa Ala Val Gln Lys Leu Arg Xaa Glu Val
1               5                   10                  15

Glu Lys Ala Lys Xaa Ala Leu Ser Ser Gln His Gln
            20                  25

<210> SEQ ID NO 226
<211> LENGTH: 29
<212> TYPE: PRT
<213> ORGANISM: Artificial Sequence
<220> FEATURE:
<223> OTHER INFORMATION: synthetic citrullinated heat shock 70kDa
      protein 5 peptide BiP-3
<220> FEATURE:
<221> NAME/KEY: MOD_RES
<222> LOCATION: (1)...(1)
```

```
<223> OTHER INFORMATION: Gly modified by biotin
<220> FEATURE:
<221> NAME/KEY: MOD_RES
<222> LOCATION: (10)...(28)
<223> OTHER INFORMATION: Xaa = citrulline
<220> FEATURE:
<221> NAME/KEY: AMIDATION
<222> LOCATION: (29)...(29)
<223> OTHER INFORMATION: argininamide

<400> SEQUENCE: 226

Gly Glu Asp Phe Ser Glu Thr Leu Thr Xaa Asp Leu Phe Xaa Ser Thr
 1               5                  10                  15

Met Lys Pro Ile Val Leu Val Gly Gly Ser Thr Xaa Arg
             20                  25

<210> SEQ ID NO 227
<211> LENGTH: 28
<212> TYPE: PRT
<213> ORGANISM: Artificial Sequence
<220> FEATURE:
<223> OTHER INFORMATION: synthetic heat shock 70kDa protein 5 peptide
      BiP-3 core sequence
<220> FEATURE:
<221> NAME/KEY: MOD_RES
<222> LOCATION: (10)...(28)
<223> OTHER INFORMATION: Xaa = citrulline

<400> SEQUENCE: 227

Gly Glu Asp Phe Ser Glu Thr Leu Thr Xaa Asp Leu Phe Xaa Ser Thr
 1               5                  10                  15

Met Lys Pro Ile Val Leu Val Gly Gly Ser Thr Xaa
             20                  25

<210> SEQ ID NO 228
<211> LENGTH: 22
<212> TYPE: PRT
<213> ORGANISM: Artificial Sequence
<220> FEATURE:
<223> OTHER INFORMATION: synthetic citrullinated heat shock 70kDa
      protein 5 peptide BiP-4
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (5)...(19)
<223> OTHER INFORMATION: Xaa = citrulline
<220> FEATURE:
<221> NAME/KEY: AMIDATION
<222> LOCATION: (22)...(22)
<223> OTHER INFORMATION: argininamide

<400> SEQUENCE: 228

Lys Leu Ile Pro Xaa Asn Thr Val Val Pro Ile Thr Ile Thr Asn Asp
 1               5                  10                  15

Gln Asn Xaa Leu Thr Arg
             20

<210> SEQ ID NO 229
<211> LENGTH: 21
<212> TYPE: PRT
<213> ORGANISM: Artificial Sequence
<220> FEATURE:
<223> OTHER INFORMATION: synthetic heat shock 70kDa protein 5 peptide
      BiP-4 core sequence
<220> FEATURE:
<221> NAME/KEY: MOD_RES
<222> LOCATION: (5)...(19)
<223> OTHER INFORMATION: Xaa = citrulline
```

-continued

```
<400> SEQUENCE: 229

Lys Leu Ile Pro Xaa Asn Thr Val Val Pro Ile Thr Ile Thr Asn Asp
1               5                   10                  15

Gln Asn Xaa Leu Thr
            20

<210> SEQ ID NO 230
<211> LENGTH: 24
<212> TYPE: PRT
<213> ORGANISM: Artificial Sequence
<220> FEATURE:
<223> OTHER INFORMATION: synthetic citrullinated histone peptide
      Histone H2A-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 230

Gly Leu Glu Leu Ala Gly Asn Ala Ala Xaa Asp Asn Lys Lys Thr Arg
1               5                   10                  15

Ile Ile Pro Xaa His Leu Gln Gly
            20

<210> SEQ ID NO 231
<211> LENGTH: 22
<212> TYPE: PRT
<213> ORGANISM: Artificial Sequence
<220> FEATURE:
<223> OTHER INFORMATION: synthetic histone peptide Histone H2A-1 core
      sequence
<220> FEATURE:
<221> NAME/KEY: MOD_RES
<222> LOCATION: (9)...(19)
<223> OTHER INFORMATION: Xaa = citrulline

<400> SEQUENCE: 231

Leu Glu Leu Ala Gly Asn Ala Ala Xaa Asp Asn Lys Lys Thr Arg Ile
1               5                   10                  15

Ile Pro Xaa His Leu Gln
            20

<210> SEQ ID NO 232
<211> LENGTH: 15
<212> TYPE: PRT
<213> ORGANISM: Artificial Sequence
<220> FEATURE:
<223> OTHER INFORMATION: synthetic citrullinated histone peptide Histone
      H2B-1
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (5)...(5)
<223> OTHER INFORMATION: Xaa = citrulline
<220> FEATURE:
<221> NAME/KEY: AMIDATION
<222> LOCATION: (15)...(15)
<223> OTHER INFORMATION: lysinamide
```

```
<400> SEQUENCE: 232

Ser Lys Arg Ser Xaa Lys Glu Ser Tyr Ser Val Tyr Val Tyr Lys
1               5                   10                  15

<210> SEQ ID NO 233
<211> LENGTH: 14
<212> TYPE: PRT
<213> ORGANISM: Artificial Sequence
<220> FEATURE:
<223> OTHER INFORMATION: synthetic histone peptide Histone H2B-1 core
      sequence
<220> FEATURE:
<221> NAME/KEY: MOD_RES
<222> LOCATION: (4)...(4)
<223> OTHER INFORMATION: Xaa = citrulline

<400> SEQUENCE: 233

Lys Arg Ser Xaa Lys Glu Ser Tyr Ser Val Tyr Val Tyr Lys
1               5                   10

<210> SEQ ID NO 234
<211> LENGTH: 31
<212> TYPE: PRT
<213> ORGANISM: Artificial Sequence
<220> FEATURE:
<223> OTHER INFORMATION: synthetic citrullinated histone peptide Histone
      H2B-2
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (9)...(29)
<223> OTHER INFORMATION: Xaa = citrulline
<220> FEATURE:
<221> NAME/KEY: AMIDATION
<222> LOCATION: (31)...(31)
<223> OTHER INFORMATION: glycinamide

<400> SEQUENCE: 234

Ser Phe Val Asn Asp Ile Phe Glu Xaa Ile Ala Gly Glu Ala Ser Xaa
1               5                   10                  15

Leu Ala His Tyr Asn Lys Arg Ser Thr Ile Thr Ser Xaa Glu Gly
            20                  25                  30

<210> SEQ ID NO 235
<211> LENGTH: 30
<212> TYPE: PRT
<213> ORGANISM: Artificial Sequence
<220> FEATURE:
<223> OTHER INFORMATION: synthetic histone peptide Histone H2B-2 core
      sequence
<220> FEATURE:
<221> NAME/KEY: MOD_RES
<222> LOCATION: (9)...(29)
<223> OTHER INFORMATION: Xaa = citrulline

<400> SEQUENCE: 235

Ser Phe Val Asn Asp Ile Phe Glu Xaa Ile Ala Gly Glu Ala Ser Xaa
1               5                   10                  15

Leu Ala His Tyr Asn Lys Arg Ser Thr Ile Thr Ser Xaa Glu
            20                  25                  30

<210> SEQ ID NO 236
<211> LENGTH: 24
<212> TYPE: PRT
<213> ORGANISM: Artificial Sequence
<220> FEATURE:
<223> OTHER INFORMATION: synthetic citrullinated histone peptide
```

```
                          Histone H2B-3
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: MOD_RES
<222> LOCATION: (9)...(22)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 236

Ser Arg Leu Ala His Tyr Asn Lys Xaa Ser Thr Ile Thr Ser Arg Glu
1               5                   10                  15

Ile Gln Thr Ala Val Xaa Leu Gly
            20

<210> SEQ ID NO 237
<211> LENGTH: 23
<212> TYPE: PRT
<213> ORGANISM: Artificial Sequence
<220> FEATURE:
<223> OTHER INFORMATION: synthetic histone peptide Histone H2B-3 core
      sequence
<220> FEATURE:
<221> NAME/KEY: MOD_RES
<222> LOCATION: (9)...(22)
<223> OTHER INFORMATION: Xaa = citrulline

<400> SEQUENCE: 237

Ser Arg Leu Ala His Tyr Asn Lys Xaa Ser Thr Ile Thr Ser Arg Glu
1               5                   10                  15

Ile Gln Thr Ala Val Xaa Leu
            20

<210> SEQ ID NO 238
<211> LENGTH: 30
<212> TYPE: PRT
<213> ORGANISM: Artificial Sequence
<220> FEATURE:
<223> OTHER INFORMATION: synthetic citrullinated histone peptide
      Histone H3-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(24)
<223> OTHER INFORMATION: Xaa = citrulline
<220> FEATURE:
<221> NAME/KEY: AMIDATION
<222> LOCATION: (30)...(30)
<223> OTHER INFORMATION: argininamide

<400> SEQUENCE: 238

Arg Tyr Arg Pro Gly Thr Val Ala Leu Xaa Glu Ile Xaa Arg Tyr Gln
1               5                   10                  15

Lys Ser Thr Glu Leu Leu Ile Xaa Lys Leu Pro Phe Gln Arg
            20                  25                  30

<210> SEQ ID NO 239
<211> LENGTH: 30
<212> TYPE: PRT
<213> ORGANISM: Artificial Sequence
<220> FEATURE:
<223> OTHER INFORMATION: synthetic histone peptide Histone H3-1 core
      sequence
```

```
<220> FEATURE:
<221> NAME/KEY: MOD_RES
<222> LOCATION: (10)...(24)
<223> OTHER INFORMATION: Xaa = citrulline

<400> SEQUENCE: 239

Arg Tyr Arg Pro Gly Thr Val Ala Leu Xaa Glu Ile Xaa Arg Tyr Gln
 1               5                  10                  15

Lys Ser Thr Glu Leu Leu Ile Xaa Lys Leu Pro Phe Gln Arg
            20                  25                  30

<210> SEQ ID NO 240
<211> LENGTH: 24
<212> TYPE: PRT
<213> ORGANISM: Artificial Sequence
<220> FEATURE:
<223> OTHER INFORMATION: synthetic citrullinated histone peptide
      Histone H3-2
<220> FEATURE:
<221> NAME/KEY: MOD_RES
<222> LOCATION: (1)...(1)
<223> OTHER INFORMATION: Asp modified by biotin
<220> FEATURE:
<221> NAME/KEY: MOD_RES
<222> LOCATION: (7)...(22)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 240

Asp Phe Lys Thr Asp Leu Xaa Phe Gln Ser Ser Ala Val Met Ala Arg
 1               5                  10                  15

Arg Ile Arg Gly Glu Xaa Ala Gly
            20

<210> SEQ ID NO 241
<211> LENGTH: 23
<212> TYPE: PRT
<213> ORGANISM: Artificial Sequence
<220> FEATURE:
<223> OTHER INFORMATION: synthetic histone peptide Histone H3-2 core
      sequence
<220> FEATURE:
<221> NAME/KEY: MOD_RES
<222> LOCATION: (7)...(22)
<223> OTHER INFORMATION: Xaa = citrulline

<400> SEQUENCE: 241

Asp Phe Lys Thr Asp Leu Xaa Phe Gln Ser Ser Ala Val Met Ala Arg
 1               5                  10                  15

Arg Ile Arg Gly Glu Xaa Ala
            20

<210> SEQ ID NO 242
<211> LENGTH: 20
<212> TYPE: PRT
<213> ORGANISM: Artificial Sequence
<220> FEATURE:
<223> OTHER INFORMATION: synthetic citrullinated histone peptide
      Histone H4-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (5)...(15)
<223> OTHER INFORMATION: Xaa = citrulline
<220> FEATURE:
```

```
<221> NAME/KEY: AMIDATION
<222> LOCATION: (20)...(20)
<223> OTHER INFORMATION: glycinamide

<400> SEQUENCE: 242

Arg Lys Val Leu Xaa Asp Asn Ile Gln Gly Lys Arg Gln Gly Xaa Thr
1               5                   10                  15

Leu Tyr Gly Gly
            20

<210> SEQ ID NO 243
<211> LENGTH: 19
<212> TYPE: PRT
<213> ORGANISM: Artificial Sequence
<220> FEATURE:
<223> OTHER INFORMATION: synthetic histone peptide Histone H4-1 core
      sequence
<220> FEATURE:
<221> NAME/KEY: MOD_RES
<222> LOCATION: (5)...(15)
<223> OTHER INFORMATION: Xaa = citrulline

<400> SEQUENCE: 243

Arg Lys Val Leu Xaa Asp Asn Ile Gln Gly Lys Arg Gln Gly Xaa Thr
1               5                   10                  15

Leu Tyr Gly

<210> SEQ ID NO 244
<211> LENGTH: 37
<212> TYPE: PRT
<213> ORGANISM: Artificial Sequence
<220> FEATURE:
<223> OTHER INFORMATION: synthetic citrullinated histone peptide
      Histone H4-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(31)
<223> OTHER INFORMATION: Xaa = citrulline
<220> FEATURE:
<221> NAME/KEY: AMIDATION
<222> LOCATION: (37)...(37)
<223> OTHER INFORMATION: glycinamide

<400> SEQUENCE: 244

Gly Leu Ile Tyr Glu Glu Thr Xaa Gly Val Leu Lys Val Phe Leu Glu
1               5                   10                  15

Asn Val Ile Xaa Asp Ala Val Thr Tyr Thr Glu His Ala Lys Xaa Lys
                20                  25                  30

Thr Val Thr Ala Gly
        35

<210> SEQ ID NO 245
<211> LENGTH: 36
<212> TYPE: PRT
<213> ORGANISM: Artificial Sequence
<220> FEATURE:
<223> OTHER INFORMATION: synthetic histone peptide Histone H4-2 core
      sequence
<220> FEATURE:
<221> NAME/KEY: MOD_RES
<222> LOCATION: (8)...(31)
<223> OTHER INFORMATION: Xaa = citrulline

<400> SEQUENCE: 245

Gly Leu Ile Tyr Glu Glu Thr Xaa Gly Val Leu Lys Val Phe Leu Glu
```

```
                1               5                   10                  15
Asn Val Ile Xaa Asp Ala Val Thr Tyr Thr Glu His Ala Lys Xaa Lys
                20                  25                  30

Thr Val Thr Ala
        35

<210> SEQ ID NO 246
<211> LENGTH: 27
<212> TYPE: PRT
<213> ORGANISM: Artificial Sequence
<220> FEATURE:
<223> OTHER INFORMATION: synthetic citrullinated collagen peptide Coll.
      T2alpha1-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(19)
<223> OTHER INFORMATION: Xaa = citrulline
<220> FEATURE:
<221> NAME/KEY: AMIDATION
<222> LOCATION: (27)...(27)
<223> OTHER INFORMATION: lysinamide

<400> SEQUENCE: 246

Arg Asn Asn Gln Ile Glu Ser Ile Xaa Ser Ala Asn Val Gln Met Thr
1               5                   10                  15

Phe Leu Xaa Leu Leu Ser Thr Glu Gly Ser Lys
                20                  25

<210> SEQ ID NO 247
<211> LENGTH: 25
<212> TYPE: PRT
<213> ORGANISM: Artificial Sequence
<220> FEATURE:
<223> OTHER INFORMATION: synthetic collagen peptide Coll. T2alpha1-1
      core sequence
<220> FEATURE:
<221> NAME/KEY: MOD_RES
<222> LOCATION: (8)...(18)
<223> OTHER INFORMATION: Xaa = citrulline

<400> SEQUENCE: 247

Asn Asn Gln Ile Glu Ser Ile Xaa Ser Ala Asn Val Gln Met Thr Phe
1               5                   10                  15

Leu Xaa Leu Leu Ser Thr Glu Gly Ser
                20                  25

<210> SEQ ID NO 248
<211> LENGTH: 26
<212> TYPE: PRT
<213> ORGANISM: Artificial Sequence
<220> FEATURE:
<223> OTHER INFORMATION: synthetic citrullinated collagen peptide Coll.
      T2alpha1-2
<220> FEATURE:
<221> NAME/KEY: MOD_RES
<222> LOCATION: (1)...(1)
<223> OTHER INFORMATION: Glu modified by biotin
<220> FEATURE:
<221> NAME/KEY: MOD_RES
<222> LOCATION: (3)...(18)
<223> OTHER INFORMATION: Xaa = citrulline
<220> FEATURE:
<221> NAME/KEY: AMIDATION
<222> LOCATION: (26)...(26)
<223> OTHER INFORMATION: aspartic acid amide

<400> SEQUENCE: 248
```

```
Glu Ile Xaa Ala Glu Gly Asn Ser Arg Phe Ile Arg Ala Glu Gly Asn
1               5                   10                  15

Ser Xaa Phe Thr Tyr Thr Ala Leu Lys Asp
            20                  25
```

<210> SEQ ID NO 249
<211> LENGTH: 26
<212> TYPE: PRT
<213> ORGANISM: Artificial Sequence
<220> FEATURE:
<223> OTHER INFORMATION: synthetic collagen peptide Coll. T2alpha1-2
      core sequence
<220> FEATURE:
<221> NAME/KEY: MOD_RES
<222> LOCATION: (3)...(18)
<223> OTHER INFORMATION: Xaa = citrulline

<400> SEQUENCE: 249

```
Glu Ile Xaa Ala Glu Gly Asn Ser Arg Phe Ile Arg Ala Glu Gly Asn
1               5                   10                  15

Ser Xaa Phe Thr Tyr Thr Ala Leu Lys Asp
            20                  25
```

<210> SEQ ID NO 250
<211> LENGTH: 27
<212> TYPE: PRT
<213> ORGANISM: Artificial Sequence
<220> FEATURE:
<223> OTHER INFORMATION: synthetic citrullinated collagen peptide Coll.
      T2alpha1-3
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (10)...(25)
<223> OTHER INFORMATION: Xaa = citrulline
<220> FEATURE:
<221> NAME/KEY: AMIDATION
<222> LOCATION: (27)...(27)
<223> OTHER INFORMATION: glycinamide

<400> SEQUENCE: 250

```
Lys Trp Gly Lys Thr Val Ile Glu Tyr Xaa Ser Gln Lys Thr Ser Arg
1               5                   10                  15

Leu Tyr Arg Ser Gln Lys Thr Ser Xaa Leu Gly
            20                  25
```

<210> SEQ ID NO 251
<211> LENGTH: 26
<212> TYPE: PRT
<213> ORGANISM: Artificial Sequence
<220> FEATURE:
<223> OTHER INFORMATION: synthetic collagen peptide Coll. T2alpha1-3
      core sequence
<220> FEATURE:
<221> NAME/KEY: MOD_RES
<222> LOCATION: (10)...(25)
<223> OTHER INFORMATION: Xaa = citrulline

<400> SEQUENCE: 251

```
Lys Trp Gly Lys Thr Val Ile Glu Tyr Xaa Ser Gln Lys Thr Ser Arg
1               5                   10                  15

Leu Tyr Arg Ser Gln Lys Thr Ser Xaa Leu
            20                  25
```

<210> SEQ ID NO 252

```
<211> LENGTH: 37
<212> TYPE: PRT
<213> ORGANISM: Artificial Sequence
<220> FEATURE:
<223> OTHER INFORMATION: synthetic citrullinated collagen peptide Coll.
      T9alpha1-1
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (5)...(32)
<223> OTHER INFORMATION: Xaa = citrulline
<220> FEATURE:
<221> NAME/KEY: AMIDATION
<222> LOCATION: (37)...(37)
<223> OTHER INFORMATION: alaninamide

<400> SEQUENCE: 252

Lys Arg Arg Pro Xaa Phe Pro Val Asn Ser Phe Gln Val Asp Lys Ala
 1               5                  10                  15

Ala Ser Xaa Ala Ile Gln Arg Val Val Gly Ser Arg Ala Ile Gln Xaa
            20                  25                  30

Val Val Gly Ser Ala
        35

<210> SEQ ID NO 253
<211> LENGTH: 37
<212> TYPE: PRT
<213> ORGANISM: Artificial Sequence
<220> FEATURE:
<223> OTHER INFORMATION: synthetic collagen peptide Coll. T9alpha1-1
      core sequence
<220> FEATURE:
<221> NAME/KEY: MOD_RES
<222> LOCATION: (5)...(32)
<223> OTHER INFORMATION: Xaa = citrulline

<400> SEQUENCE: 253

Lys Arg Arg Pro Xaa Phe Pro Val Asn Ser Phe Gln Val Asp Lys Ala
 1               5                  10                  15

Ala Ser Xaa Ala Ile Gln Arg Val Val Gly Ser Arg Ala Ile Gln Xaa
            20                  25                  30

Val Val Gly Ser Ala
        35

<210> SEQ ID NO 254
<211> LENGTH: 26
<212> TYPE: PRT
<213> ORGANISM: Artificial Sequence
<220> FEATURE:
<223> OTHER INFORMATION: synthetic citrullinated collagen peptide Coll.
      T9alpha1-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(18)
<223> OTHER INFORMATION: Xaa = citrulline
<220> FEATURE:
<221> NAME/KEY: AMIDATION
<222> LOCATION: (26)...(26)
<223> OTHER INFORMATION: lysinamide

<400> SEQUENCE: 254

Gly Arg Ile Pro Thr Xaa Asn Leu Tyr Pro Tyr Ser Phe Leu Thr Thr
 1               5                  10                  15
```

```
Phe Xaa Met Thr Gly Ser Thr Leu Lys Lys
            20                  25

<210> SEQ ID NO 255
<211> LENGTH: 25
<212> TYPE: PRT
<213> ORGANISM: Artificial Sequence
<220> FEATURE:
<223> OTHER INFORMATION: synthetic collagen peptide Coll. T9alpha1-2
      core sequence
<220> FEATURE:
<221> NAME/KEY: MOD_RES
<222> LOCATION: (5)...(17)
<223> OTHER INFORMATION: Xaa = citrulline

<400> SEQUENCE: 255

Arg Ile Pro Thr Xaa Asn Leu Tyr Pro Tyr Ser Phe Leu Thr Thr Phe
1               5                   10                  15

Xaa Met Thr Gly Ser Thr Leu Lys Lys
            20                  25

<210> SEQ ID NO 256
<211> LENGTH: 28
<212> TYPE: PRT
<213> ORGANISM: Artificial Sequence
<220> FEATURE:
<223> OTHER INFORMATION: synthetic citrullinated collagen peptide Coll.
      T9alpha1-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(21)
<223> OTHER INFORMATION: Xaa = citrulline
<220> FEATURE:
<221> NAME/KEY: AMIDATION
<222> LOCATION: (28)...(28)
<223> OTHER INFORMATION: lysinamide

<400> SEQUENCE: 256

Gly His Lys Ile Met Ile Gly Val Glu Xaa Ser Ser Ala Thr Leu Phe
1               5                   10                  15

Val Asp Ser Asn Xaa Ile Glu Ser Leu Pro Ile Lys
            20                  25

<210> SEQ ID NO 257
<211> LENGTH: 27
<212> TYPE: PRT
<213> ORGANISM: Artificial Sequence
<220> FEATURE:
<223> OTHER INFORMATION: synthetic collagen peptide Coll. T9alpha1-3
      core sequence
<220> FEATURE:
<221> NAME/KEY: MOD_RES
<222> LOCATION: (9)...(20)
<223> OTHER INFORMATION: Xaa = citrulline

<400> SEQUENCE: 257

His Lys Ile Met Ile Gly Val Glu Xaa Ser Ser Ala Thr Leu Phe Val
1               5                   10                  15

Asp Ser Asn Xaa Ile Glu Ser Leu Pro Ile Lys
            20                  25

<210> SEQ ID NO 258
<211> LENGTH: 25
<212> TYPE: PRT
<213> ORGANISM: Artificial Sequence
<220> FEATURE:
```

```
<223> OTHER INFORMATION: synthetic citrullinated collagen peptide Coll.
      T9alpha1-4
<220> FEATURE:
<221> NAME/KEY: MOD_RES
<222> LOCATION: (1)...(1)
<223> OTHER INFORMATION: Gln modified by biotin
<220> FEATURE:
<221> NAME/KEY: MOD_RES
<222> LOCATION: (9)...(24)
<223> OTHER INFORMATION: Xaa = citrulline
<220> FEATURE:
<221> NAME/KEY: AMIDATION
<222> LOCATION: (25)...(25)
<223> OTHER INFORMATION: glycinamide

<400> SEQUENCE: 258

Gln His Ile Lys Gln Val Ser Met Xaa Val Ile Gln Glu His Phe Ala
1               5                   10                  15

Glu Met Ala Ala Ser Leu Lys Xaa Gly
            20                  25

<210> SEQ ID NO 259
<211> LENGTH: 24
<212> TYPE: PRT
<213> ORGANISM: Artificial Sequence
<220> FEATURE:
<223> OTHER INFORMATION: synthetic collagen peptide Coll. T9alpha1-4
      core sequence
<220> FEATURE:
<221> NAME/KEY: MOD_RES
<222> LOCATION: (9)...(24)
<223> OTHER INFORMATION: Xaa = citrulline

<400> SEQUENCE: 259

Gln His Ile Lys Gln Val Ser Met Xaa Val Ile Gln Glu His Phe Ala
1               5                   10                  15

Glu Met Ala Ala Ser Leu Lys Xaa
            20

<210> SEQ ID NO 260
<211> LENGTH: 29
<212> TYPE: PRT
<213> ORGANISM: Artificial Sequence
<220> FEATURE:
<223> OTHER INFORMATION: synthetic citrullinated collagen peptide Coll.
      T10alpha1-1
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (5)...(20)
<223> OTHER INFORMATION: Xaa = citrulline
<220> FEATURE:
<221> NAME/KEY: AMIDATION
<222> LOCATION: (24)...(24)
<223> OTHER INFORMATION: argininamide

<400> SEQUENCE: 260

Lys Ala Gly Gln Xaa Pro Ser Leu Ser Gly Asp Lys Ile Leu Tyr Asn
1               5                   10                  15

Xaa Gln Gln Xaa Thr Gly Ile Phe Thr Ser Gln Ile Arg
            20                  25

<210> SEQ ID NO 261
<211> LENGTH: 28
<212> TYPE: PRT
<213> ORGANISM: Artificial Sequence
<220> FEATURE:
<223> OTHER INFORMATION: synthetic collagen peptide Coll. T10alpha1-1
```

```
                        core sequence
<220> FEATURE:
<221> NAME/KEY: MOD_RES
<222> LOCATION: (5)...(20)
<223> OTHER INFORMATION: Xaa = citrulline

<400> SEQUENCE: 261

Lys Ala Gly Gln Xaa Pro Ser Leu Ser Gly Asp Lys Ile Leu Tyr Asn
 1               5                  10                  15

Xaa Gln Gln Xaa Thr Gly Ile Phe Thr Ser Gln Ile
             20                  25

<210> SEQ ID NO 262
<211> LENGTH: 24
<212> TYPE: PRT
<213> ORGANISM: Artificial Sequence
<220> FEATURE:
<223> OTHER INFORMATION: synthetic citrullinated collagen peptide Coll.
      T11alpha1-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(16)
<223> OTHER INFORMATION: Xaa = citrulline
<220> FEATURE:
<221> NAME/KEY: AMIDATION
<222> LOCATION: (24)...(24)
<223> OTHER INFORMATION: serinamide

<400> SEQUENCE: 262

Gly Ser Thr Asn Xaa Lys Asn Ser Lys Gly Ser Asp Thr Ala Tyr Xaa
 1               5                  10                  15

Val Ser Lys Gln Ala Gln Leu Ser
             20

<210> SEQ ID NO 263
<211> LENGTH: 23
<212> TYPE: PRT
<213> ORGANISM: Artificial Sequence
<220> FEATURE:
<223> OTHER INFORMATION: synthetic collagen peptide Coll. T11alpha1-1
      core sequence
<220> FEATURE:
<221> NAME/KEY: MOD_RES
<222> LOCATION: (4)...(15)
<223> OTHER INFORMATION: Xaa = citrulline

<400> SEQUENCE: 263

Ser Thr Asn Xaa Lys Asn Ser Lys Gly Ser Asp Thr Ala Tyr Xaa Val
 1               5                  10                  15

Ser Lys Gln Ala Gln Leu Ser
             20

<210> SEQ ID NO 264
<211> LENGTH: 26
<212> TYPE: PRT
<213> ORGANISM: Artificial Sequence
<220> FEATURE:
<223> OTHER INFORMATION: synthetic citrullinated collagen peptide Coll.
      T11alpha1-2
<220> FEATURE:
<221> NAME/KEY: MOD_RES
<222> LOCATION: (1)...(1)
<223> OTHER INFORMATION: Asp modified by biotin
<220> FEATURE:
<221> NAME/KEY: MOD_RES
<222> LOCATION: (6)...(17)
<223> OTHER INFORMATION: Xaa = citrulline
```

```
<220> FEATURE:
<221> NAME/KEY: AMIDATION
<222> LOCATION: (26)...(26)
<223> OTHER INFORMATION: glycinamide

<400> SEQUENCE: 264

Asp Tyr Pro Leu Phe Xaa Thr Val Asn Ile Ala Asp Gly Lys Trp His
1               5                   10                  15

Xaa Val Ala Ile Ser Val Glu Lys Lys Gly
            20                  25

<210> SEQ ID NO 265
<211> LENGTH: 25
<212> TYPE: PRT
<213> ORGANISM: Artificial Sequence
<220> FEATURE:
<223> OTHER INFORMATION: synthetic collagen peptide Coll. T11alpha1-2
      core sequence
<220> FEATURE:
<221> NAME/KEY: MOD_RES
<222> LOCATION: (6)...(17)
<223> OTHER INFORMATION: Xaa = citrulline

<400> SEQUENCE: 265

Asp Tyr Pro Leu Phe Xaa Thr Val Asn Ile Ala Asp Gly Lys Trp His
1               5                   10                  15

Xaa Val Ala Ile Ser Val Glu Lys Lys
            20                  25

<210> SEQ ID NO 266
<211> LENGTH: 29
<212> TYPE: PRT
<213> ORGANISM: Artificial Sequence
<220> FEATURE:
<223> OTHER INFORMATION: synthetic citrullinated collagen peptide Coll.
      T11alpha1-3
<220> FEATURE:
<221> NAME/KEY: MOD_RES
<222> LOCATION: (1)...(1)
<223> OTHER INFORMATION: Thr modified by biotin
<220> FEATURE:
<221> NAME/KEY: MOD_RES
<222> LOCATION: (6)...(20)
<223> OTHER INFORMATION: Xaa = citrulline
<220> FEATURE:
<221> NAME/KEY: AMIDATION
<222> LOCATION: (29)...(29)
<223> OTHER INFORMATION: aspartic acid amide

<400> SEQUENCE: 266

Thr Lys Pro Leu Asp Xaa Ser Glu Arg Ala Lys Pro Leu Asp Arg Ser
1               5                   10                  15

Glu Xaa Ala Xaa Arg His Thr Glu Gly Met Gln Ala Asp
            20                  25

<210> SEQ ID NO 267
<211> LENGTH: 29
<212> TYPE: PRT
<213> ORGANISM: Artificial Sequence
<220> FEATURE:
<223> OTHER INFORMATION: synthetic collagen peptide Coll. T11alpha1-3
      core sequence
<220> FEATURE:
<221> NAME/KEY: MOD_RES
<222> LOCATION: (6)...(20)
<223> OTHER INFORMATION: Xaa = citrulline

<400> SEQUENCE: 267

Thr Lys Pro Leu Asp Xaa Ser Glu Arg Ala Lys Pro Leu Asp Arg Ser
1               5                   10                  15
```

```
Glu Xaa Ala Xaa Arg His Thr Glu Gly Met Gln Ala Asp
            20                  25

<210> SEQ ID NO 268
<211> LENGTH: 33
<212> TYPE: PRT
<213> ORGANISM: Artificial Sequence
<220> FEATURE:
<223> OTHER INFORMATION: synthetic citrullinated collagen peptide Coll.
      T11alpha2-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(31)
<223> OTHER INFORMATION: Xaa = citrulline
<220> FEATURE:
<221> NAME/KEY: AMIDATION
<222> LOCATION: (33)...(33)
<223> OTHER INFORMATION: argininamide

<400> SEQUENCE: 268

Gly Ile Ser Pro Ala Asp Val Ala Tyr Xaa Val Ala Arg Pro Ala Gln
1               5                   10                  15

Leu Tyr Arg Val Ala Xaa Pro Ala Gln Leu Ser Ala Pro Thr Xaa Gln
            20                  25                  30

Arg

<210> SEQ ID NO 269
<211> LENGTH: 32
<212> TYPE: PRT
<213> ORGANISM: Artificial Sequence
<220> FEATURE:
<223> OTHER INFORMATION: synthetic collagen peptide Coll. T11alpha2-1
      core sequence
<220> FEATURE:
<221> NAME/KEY: MOD_RES
<222> LOCATION: (10)...(31)
<223> OTHER INFORMATION: Xaa = citrulline

<400> SEQUENCE: 269

Gly Ile Ser Pro Ala Asp Val Ala Tyr Xaa Val Ala Arg Pro Ala Gln
1               5                   10                  15

Leu Tyr Arg Val Ala Xaa Pro Ala Gln Leu Ser Ala Pro Thr Xaa Gln
            20                  25                  30

<210> SEQ ID NO 270
<211> LENGTH: 26
<212> TYPE: PRT
<213> ORGANISM: Artificial Sequence
<220> FEATURE:
<223> OTHER INFORMATION: synthetic citrullinated collagen peptide Coll.
      T11alpha2-2
<220> FEATURE:
<221> NAME/KEY: MOD_RES
<222> LOCATION: (1)...(1)
<223> OTHER INFORMATION: Lys modified by biotin
<220> FEATURE:
<221> NAME/KEY: MOD_RES
<222> LOCATION: (10)...(20)
<223> OTHER INFORMATION: Xaa = citrulline
<220> FEATURE:
<221> NAME/KEY: AMIDATION
<222> LOCATION: (26)...(26)
<223> OTHER INFORMATION: glycinamide

<400> SEQUENCE: 270

Lys Asp Phe Ser Leu Leu Thr Val Val Xaa Thr Ser Leu Leu Thr Val
```

Val Arg Thr Xaa Pro Gly Leu Gln Ala Gly
            20                  25

<210> SEQ ID NO 271
<211> LENGTH: 25
<212> TYPE: PRT
<213> ORGANISM: Artificial Sequence
<220> FEATURE:
<223> OTHER INFORMATION: synthetic collagen peptide Coll. T11alpha2-2
      core sequence
<220> FEATURE:
<221> NAME/KEY: MOD_RES
<222> LOCATION: (10)...(20)
<223> OTHER INFORMATION: Xaa = citrulline

<400> SEQUENCE: 271

Lys Asp Phe Ser Leu Leu Thr Val Val Xaa Thr Ser Leu Leu Thr Val
1               5                   10                  15

Val Arg Thr Xaa Pro Gly Leu Gln Ala
            20                  25

<210> SEQ ID NO 272
<211> LENGTH: 25
<212> TYPE: PRT
<213> ORGANISM: Artificial Sequence
<220> FEATURE:
<223> OTHER INFORMATION: synthetic citrullinated collagen peptide
      Coll. T11alpha2-3
<220> FEATURE:
<221> NAME/KEY: MOD_RES
<222> LOCATION: (1)...(1)
<223> OTHER INFORMATION: Asn modified by biotin
<220> FEATURE:
<221> NAME/KEY: MOD_RES
<222> LOCATION: (9)...(20)
<223> OTHER INFORMATION: Xaa = citrulline
<220> FEATURE:
<221> NAME/KEY: AMIDATION
<222> LOCATION: (25)...(25)
<223> OTHER INFORMATION: glutamic acid amide

<400> SEQUENCE: 272

Asn Gln Gln Pro His Arg Ala Gln Xaa Ser Pro Gln Gln Gln Pro Ser
1               5                   10                  15

Arg Leu His Xaa Pro Gln Asn Gln Glu
            20                  25

<210> SEQ ID NO 273
<211> LENGTH: 25
<212> TYPE: PRT
<213> ORGANISM: Artificial Sequence
<220> FEATURE:
<223> OTHER INFORMATION: synthetic collagen peptide Coll. T11alpha2-3
      core sequence
<220> FEATURE:
<221> NAME/KEY: MOD_RES
<222> LOCATION: (9)...(20)
<223> OTHER INFORMATION: Xaa = citrulline

<400> SEQUENCE: 273

Asn Gln Gln Pro His Arg Ala Gln Xaa Ser Pro Gln Gln Gln Pro Ser
1               5                   10                  15

Arg Leu His Xaa Pro Gln Asn Gln Glu
            20                  25

<210> SEQ ID NO 274
<211> LENGTH: 22
<212> TYPE: PRT

```
<213> ORGANISM: Artificial Sequence
<220> FEATURE:
<223> OTHER INFORMATION: synthetic citrullinated collagen peptide Coll.
      T11alpha2-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (3)...(14)
<223> OTHER INFORMATION: Xaa = citrulline
<220> FEATURE:
<221> NAME/KEY: AMIDATION
<222> LOCATION: (22)...(22)
<223> OTHER INFORMATION: glutamic acid amide

<400> SEQUENCE: 274

Gly His Xaa Ala Gln Arg Ser Pro Gln Gln Gln Pro Ser Xaa Leu His
 1               5                  10                  15

Arg Pro Gln Asn Gln Glu
            20

<210> SEQ ID NO 275
<211> LENGTH: 21
<212> TYPE: PRT
<213> ORGANISM: Artificial Sequence
<220> FEATURE:
<223> OTHER INFORMATION: synthetic collagen peptide Coll. T11alpha2-4
      core sequence
<220> FEATURE:
<221> NAME/KEY: MOD_RES
<222> LOCATION: (2)...(13)
<223> OTHER INFORMATION: Xaa = citrulline

<400> SEQUENCE: 275

His Xaa Ala Gln Arg Ser Pro Gln Gln Gln Pro Ser Xaa Leu His Arg
 1               5                  10                  15

Pro Gln Asn Gln Glu
            20

<210> SEQ ID NO 276
<211> LENGTH: 20
<212> TYPE: PRT
<213> ORGANISM: Artificial Sequence
<220> FEATURE:
<223> OTHER INFORMATION: synthetic citrullinated syndecan peptide
      Syndecan-I-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(18)
<223> OTHER INFORMATION: Xaa = citrulline
<220> FEATURE:
<221> NAME/KEY: AMIDATION
<222> LOCATION: (20)...(20)
<223> OTHER INFORMATION: glycinamide

<400> SEQUENCE: 276

Gly Pro Arg Pro Xaa Glu Thr Thr Gln Leu Gly Gly Pro Ser Ala Thr
 1               5                  10                  15

Glu Xaa Ala Gly
            20

<210> SEQ ID NO 277
<211> LENGTH: 18
<212> TYPE: PRT
<213> ORGANISM: Artificial Sequence
```

```
<220> FEATURE:
<223> OTHER INFORMATION: synthetic syndecan peptide Syndecan-I-1 core
      sequence
<220> FEATURE:
<221> NAME/KEY: MOD_RES
<222> LOCATION: (4)...(17)
<223> OTHER INFORMATION: Xaa = citrulline

<400> SEQUENCE: 277

Pro Arg Pro Xaa Glu Thr Thr Gln Leu Gly Gly Pro Ser Ala Thr Glu
1               5                   10                  15

Xaa Ala

<210> SEQ ID NO 278
<211> LENGTH: 25
<212> TYPE: PRT
<213> ORGANISM: Artificial Sequence
<220> FEATURE:
<223> OTHER INFORMATION: synthetic citrullinated syndecan peptide
      Syndecan-I-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (7)...(16)
<223> OTHER INFORMATION: Xaa = citrulline
<220> FEATURE:
<221> NAME/KEY: AMIDATION
<222> LOCATION: (25)...(25)
<223> OTHER INFORMATION: glycinamide

<400> SEQUENCE: 278

Gly Val Glu Pro Asp Arg Xaa Asn Gln Ser Pro Val Asp Gln Gly Xaa
1               5                   10                  15

Arg Asn Gln Ser Pro Val Asp Gln Gly
                20                  25

<210> SEQ ID NO 279
<211> LENGTH: 24
<212> TYPE: PRT
<213> ORGANISM: Artificial Sequence
<220> FEATURE:
<223> OTHER INFORMATION: synthetic syndecan peptide Syndecan-I-2 core
      sequence
<220> FEATURE:
<221> NAME/KEY: MOD_RES
<222> LOCATION: (6)...(15)
<223> OTHER INFORMATION: Xaa = citrulline

<400> SEQUENCE: 279

Val Glu Pro Asp Arg Xaa Asn Gln Ser Pro Val Asp Gln Gly Xaa Arg
1               5                   10                  15

Asn Gln Ser Pro Val Asp Gln Gly
                20

<210> SEQ ID NO 280
<211> LENGTH: 29
<212> TYPE: PRT
<213> ORGANISM: Artificial Sequence
<220> FEATURE:
<223> OTHER INFORMATION: synthetic citrullinated syndecan peptide
      Syndecan-III-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(27)
```

<223> OTHER INFORMATION: Xaa = citrulline
<220> FEATURE:
<221> NAME/KEY: AMIDATION
<222> LOCATION: (29)...(29)
<223> OTHER INFORMATION: argininamide

<400> SEQUENCE: 280

Arg Ser Gly Ile Glu Thr Ala Met Xaa Phe Glu Val Pro Glu Glu Pro
1               5                   10                  15

Ser Gln Xaa Ala Thr Thr Val Ser Thr Ala Xaa Ala Arg
            20                  25

<210> SEQ ID NO 281
<211> LENGTH: 27
<212> TYPE: PRT
<213> ORGANISM: Artificial Sequence
<220> FEATURE:
<223> OTHER INFORMATION: synthetic syndecan peptide Syndecan-III-1
      core sequence
<220> FEATURE:
<221> NAME/KEY: MOD_RES
<222> LOCATION: (8)...(26)
<223> OTHER INFORMATION: Xaa = citrulline

<400> SEQUENCE: 281

Ser Gly Ile Glu Thr Ala Met Xaa Phe Glu Val Pro Glu Glu Pro Ser
1               5                   10                  15

Gln Xaa Ala Thr Thr Val Ser Thr Ala Xaa Ala
            20                  25

<210> SEQ ID NO 282
<211> LENGTH: 37
<212> TYPE: PRT
<213> ORGANISM: Artificial Sequence
<220> FEATURE:
<223> OTHER INFORMATION: synthetic citrullinated syndecan peptide
      Syndecan-III-2
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(35)
<223> OTHER INFORMATION: Xaa = citrulline
<220> FEATURE:
<221> NAME/KEY: AMIDATION
<222> LOCATION: (37)...(37)
<223> OTHER INFORMATION: glycinamide

<400> SEQUENCE: 282

Arg Phe Thr Ala Thr Thr Ala Val Ile Xaa Thr Thr Gly Val Arg Ala
1               5                   10                  15

Val Ile Arg Thr Thr Gly Val Xaa Arg Leu Val Ile Arg Thr Thr Gly
            20                  25                  30

Val Arg Xaa Leu Gly
        35

<210> SEQ ID NO 283
<211> LENGTH: 35
<212> TYPE: PRT
<213> ORGANISM: Artificial Sequence
<220> FEATURE:
<223> OTHER INFORMATION: synthetic syndecan peptide Syndecan-III-2 core
      sequence
<220> FEATURE:
<221> NAME/KEY: MOD_RES
<222> LOCATION: (9)...(34)
<223> OTHER INFORMATION: Xaa = citrulline

```
<400> SEQUENCE: 283

Phe Thr Ala Thr Thr Ala Val Ile Xaa Thr Thr Gly Val Arg Ala Val
1               5                   10                  15

Ile Arg Thr Thr Gly Val Xaa Arg Leu Val Ile Arg Thr Thr Gly Val
                20                  25                  30

Arg Xaa Leu
        35

<210> SEQ ID NO 284
<211> LENGTH: 31
<212> TYPE: PRT
<213> ORGANISM: Artificial Sequence
<220> FEATURE:
<223> OTHER INFORMATION: synthetic citrullinated syndecan peptide
      Syndecan-III-3
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (3)...(29)
<223> OTHER INFORMATION: Xaa = citrulline
<220> FEATURE:
<221> NAME/KEY: AMIDATION
<222> LOCATION: (31)...(31)
<223> OTHER INFORMATION: glycinamide

<400> SEQUENCE: 284

Arg Pro Xaa Leu Val Ser Thr Ala Thr Ser Xaa Pro Arg Ala Leu Pro
1               5                   10                  15

Xaa Pro Ala Thr Thr Gln Glu Pro Asp Ile Pro Glu Xaa Ser Gly
                20                  25                  30

<210> SEQ ID NO 285
<211> LENGTH: 29
<212> TYPE: PRT
<213> ORGANISM: Artificial Sequence
<220> FEATURE:
<223> OTHER INFORMATION: synthetic syndecan peptide Syndecan-III-3 core
      sequence
<220> FEATURE:
<221> NAME/KEY: MOD_RES
<222> LOCATION: (2)...(28)
<223> OTHER INFORMATION: Xaa = citrulline

<400> SEQUENCE: 285

Pro Xaa Leu Val Ser Thr Ala Thr Ser Xaa Pro Arg Ala Leu Pro Xaa
1               5                   10                  15

Pro Ala Thr Thr Gln Glu Pro Asp Ile Pro Glu Xaa Ser
                20                  25

<210> SEQ ID NO 286
<211> LENGTH: 34
<212> TYPE: PRT
<213> ORGANISM: Artificial Sequence
<220> FEATURE:
<223> OTHER INFORMATION: synthetic citrullinated CD44 peptide CD44-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(29)
<223> OTHER INFORMATION: Xaa = citrulline
<220> FEATURE:
<221> NAME/KEY: AMIDATION
<222> LOCATION: (34)...(34)
<223> OTHER INFORMATION: glycinamide
```

```
<400> SEQUENCE: 286

Arg Ile Asp Leu Asn Ile Thr Ser Xaa Phe Ala Gly Val Phe His Val
 1               5                  10                  15

Glu Lys Asn Gly Xaa Tyr Gly Arg Tyr Ser Ile Ser Xaa Thr Glu Ala
             20                  25                  30

Ala Gly

<210> SEQ ID NO 287
<211> LENGTH: 32
<212> TYPE: PRT
<213> ORGANISM: Artificial Sequence
<220> FEATURE:
<223> OTHER INFORMATION: synthetic CD44 peptide CD44-1 core sequence
<220> FEATURE:
<221> NAME/KEY: MOD_RES
<222> LOCATION: (8)...(28)
<223> OTHER INFORMATION: Xaa = citrulline

<400> SEQUENCE: 287

Ile Asp Leu Asn Ile Thr Ser Xaa Phe Ala Gly Val Phe His Val Glu
 1               5                  10                  15

Lys Asn Gly Xaa Tyr Gly Arg Tyr Ser Ile Ser Xaa Thr Glu Ala Ala
             20                  25                  30

<210> SEQ ID NO 288
<211> LENGTH: 28
<212> TYPE: PRT
<213> ORGANISM: Artificial Sequence
<220> FEATURE:
<223> OTHER INFORMATION: synthetic citrullinated CD44 peptide CD44-2
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (8)...(20)
<223> OTHER INFORMATION: Xaa = citrulline
<220> FEATURE:
<221> NAME/KEY: AMIDATION
<222> LOCATION: (28)...(28)
<223> OTHER INFORMATION: argininamide

<400> SEQUENCE: 288

Arg Ile Gly Phe Glu Thr Ser Xaa Tyr Gly Phe Ile Glu Gly His Val
 1               5                  10                  15

Val Ile Pro Xaa Ile His Pro Asn Ser Ile Ser Arg
             20                  25

<210> SEQ ID NO 289
<211> LENGTH: 26
<212> TYPE: PRT
<213> ORGANISM: Artificial Sequence
<220> FEATURE:
<223> OTHER INFORMATION: synthetic CD44 peptide CD44-2 core sequence
<220> FEATURE:
<221> NAME/KEY: MOD_RES
<222> LOCATION: (7)...(19)
<223> OTHER INFORMATION: Xaa = citrulline

<400> SEQUENCE: 289

Ile Gly Phe Glu Thr Ser Xaa Tyr Gly Phe Ile Glu Gly His Val Val
 1               5                  10                  15

Ile Pro Xaa Ile His Pro Asn Ser Ile Ser
             20                  25
```

```
<210> SEQ ID NO 290
<211> LENGTH: 25
<212> TYPE: PRT
<213> ORGANISM: Artificial Sequence
<220> FEATURE:
<223> OTHER INFORMATION: synthetic citrullinated CD44 peptide CD44-3
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(22)
<223> OTHER INFORMATION: Xaa = citrulline
<220> FEATURE:
<221> NAME/KEY: AMIDATION
<222> LOCATION: (25)...(25)
<223> OTHER INFORMATION: glycinamide

<400> SEQUENCE: 290

Arg Pro Ile Thr Ile Thr Ile Val Asn Xaa Asp Gly Thr Arg Tyr Val
1               5                   10                  15

Asn Arg Asp Gly Thr Xaa Tyr Val Gly
            20                  25

<210> SEQ ID NO 291
<211> LENGTH: 23
<212> TYPE: PRT
<213> ORGANISM: Artificial Sequence
<220> FEATURE:
<223> OTHER INFORMATION: synthetic CD44 peptide CD44-3 core sequence
<220> FEATURE:
<221> NAME/KEY: MOD_RES
<222> LOCATION: (9)...(21)
<223> OTHER INFORMATION: Xaa = citrulline

<400> SEQUENCE: 291

Pro Ile Thr Ile Thr Ile Val Asn Xaa Asp Gly Thr Arg Tyr Val Asn
1               5                   10                  15

Arg Asp Gly Thr Xaa Tyr Val
            20

<210> SEQ ID NO 292
<211> LENGTH: 27
<212> TYPE: PRT
<213> ORGANISM: Artificial Sequence
<220> FEATURE:
<223> OTHER INFORMATION: synthetic citrullinated CD44 peptide CD44-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(18)
<223> OTHER INFORMATION: Xaa = citrulline
<220> FEATURE:
<221> NAME/KEY: AMIDATION
<222> LOCATION: (27)...(27)
<223> OTHER INFORMATION: glycinamide

<400> SEQUENCE: 292

Gly Ser Ser Gly Ser Ser Ser Glu Xaa Ser Trp Ile Thr Asp Ser Thr
1               5                   10                  15

Asp Xaa Ile Pro Ala Thr Thr Leu Met Ser Gly
            20                  25

<210> SEQ ID NO 293
<211> LENGTH: 25
<212> TYPE: PRT
<213> ORGANISM: Artificial Sequence
```

```
<220> FEATURE:
<223> OTHER INFORMATION: synthetic CD44 peptide CD44-4 core sequence
<220> FEATURE:
<221> NAME/KEY: MOD_RES
<222> LOCATION: (8)...(17)
<223> OTHER INFORMATION: Xaa = citrulline

<400> SEQUENCE: 293

Ser Ser Gly Ser Ser Ser Glu Xaa Ser Trp Ile Thr Asp Ser Thr Asp
 1               5                  10                  15

Xaa Ile Pro Ala Thr Thr Leu Met Ser
                20                  25

<210> SEQ ID NO 294
<211> LENGTH: 30
<212> TYPE: PRT
<213> ORGANISM: Artificial Sequence
<220> FEATURE:
<223> OTHER INFORMATION: synthetic citrullinated CD44 peptide CD44-5
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(28)
<223> OTHER INFORMATION: Xaa = citrulline
<220> FEATURE:
<221> NAME/KEY: AMIDATION
<222> LOCATION: (30)...(30)
<223> OTHER INFORMATION: glycinamide

<400> SEQUENCE: 294

Arg Ser Thr Ile Ser Thr Thr Pro Xaa Ala Glu Val Leu Leu Gln Thr
 1               5                  10                  15

Thr Thr Xaa Met Thr Arg Met Thr Asp Val Asp Xaa Asn Gly
                20                  25                  30

<210> SEQ ID NO 295
<211> LENGTH: 28
<212> TYPE: PRT
<213> ORGANISM: Artificial Sequence
<220> FEATURE:
<223> OTHER INFORMATION: synthetic CD44 peptide CD44-5 core sequence
<220> FEATURE:
<221> NAME/KEY: MOD_RES
<222> LOCATION: (8)...(27)
<223> OTHER INFORMATION: Xaa = citrulline

<400> SEQUENCE: 295

Ser Thr Ile Ser Thr Thr Pro Xaa Ala Glu Val Leu Leu Gln Thr Thr
 1               5                  10                  15

Thr Xaa Met Thr Arg Met Thr Asp Val Asp Xaa Asn
                20                  25

<210> SEQ ID NO 296
<211> LENGTH: 38
<212> TYPE: PRT
<213> ORGANISM: Artificial Sequence
<220> FEATURE:
<223> OTHER INFORMATION: synthetic citrullinated CD44 peptide CD44-6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (7)...(30)
<223> OTHER INFORMATION: Xaa = citrulline
<220> FEATURE:
<221> NAME/KEY: AMIDATION
```

```
<222> LOCATION: (38)...(38)
<223> OTHER INFORMATION: glycinamide

<400> SEQUENCE: 296

Gly Tyr Arg Gln Thr Pro Xaa Glu Asp Ser Met Gln Gly Xaa Thr Thr
 1               5                  10                  15

Pro Ser Pro Xaa Arg Met Asp Met Asp Ser Ser His Arg Xaa Met Asp
             20                  25                  30

Met Asp Ser Ser His Gly
             35

<210> SEQ ID NO 297
<211> LENGTH: 37
<212> TYPE: PRT
<213> ORGANISM: Artificial Sequence
<220> FEATURE:
<223> OTHER INFORMATION: synthetic CD44 peptide CD44-6 core sequence
<220> FEATURE:
<221> NAME/KEY: MOD_RES
<222> LOCATION: (7)...(30)
<223> OTHER INFORMATION: Xaa = citrulline

<400> SEQUENCE: 297

Gly Tyr Arg Gln Thr Pro Xaa Glu Asp Ser Met Gln Gly Xaa Thr Thr
 1               5                  10                  15

Pro Ser Pro Xaa Arg Met Asp Met Asp Ser Ser His Arg Xaa Met Asp
             20                  25                  30

Met Asp Ser Ser His
             35

<210> SEQ ID NO 298
<211> LENGTH: 28
<212> TYPE: PRT
<213> ORGANISM: Artificial Sequence
<220> FEATURE:
<223> OTHER INFORMATION: synthetic citrullinated CD44 peptide CD44-7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(21)
<223> OTHER INFORMATION: Xaa = citrulline
<220> FEATURE:
<221> NAME/KEY: AMIDATION
<222> LOCATION: (28)...(28)
<223> OTHER INFORMATION: glycinamide

<400> SEQUENCE: 298

Gly Ser Thr Leu Thr Ser Ser Asn Xaa Asn Arg Asn Asp Val Thr Gly
 1               5                  10                  15

Gly Xaa Gly Arg Xaa Asp Pro Asn His Ser Glu Gly
             20                  25

<210> SEQ ID NO 299
<211> LENGTH: 26
<212> TYPE: PRT
<213> ORGANISM: Artificial Sequence
<220> FEATURE:
<223> OTHER INFORMATION: synthetic CD44 peptide CD44-7 core sequence
<220> FEATURE:
<221> NAME/KEY: MOD_RES
<222> LOCATION: (8)...(20)
<223> OTHER INFORMATION: Xaa = citrulline

<400> SEQUENCE: 299

Ser Thr Leu Thr Ser Ser Asn Xaa Asn Arg Asn Asp Val Thr Gly Gly
```

```
                1               5                  10                  15
Xaa Gly Arg Xaa Asp Pro Asn His Ser Glu
            20                  25

<210> SEQ ID NO 300
<211> LENGTH: 21
<212> TYPE: PRT
<213> ORGANISM: Artificial Sequence
<220> FEATURE:
<223> OTHER INFORMATION: synthetic citrullinated CD44 peptide CD44-8
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(16)
<223> OTHER INFORMATION: Xaa = citrulline
<220> FEATURE:
<221> NAME/KEY: AMIDATION
<222> LOCATION: (21)...(21)
<223> OTHER INFORMATION: argininamide

<400> SEQUENCE: 300

Arg Asp Ser Asn Ser Asn Val Asn Xaa Ser Leu Ser Gly Pro Ile Xaa
1               5                  10                  15

Thr Pro Gln Ile Arg
            20

<210> SEQ ID NO 301
<211> LENGTH: 19
<212> TYPE: PRT
<213> ORGANISM: Artificial Sequence
<220> FEATURE:
<223> OTHER INFORMATION: synthetic CD44 peptide CD44-8 core sequence
<220> FEATURE:
<221> NAME/KEY: MOD_RES
<222> LOCATION: (8)...(15)
<223> OTHER INFORMATION: Xaa = citrulline

<400> SEQUENCE: 301

Asp Ser Asn Ser Asn Val Asn Xaa Ser Leu Ser Gly Pro Ile Xaa Thr
1               5                  10                  15

Pro Gln Ile

<210> SEQ ID NO 302
<211> LENGTH: 24
<212> TYPE: PRT
<213> ORGANISM: Artificial Sequence
<220> FEATURE:
<223> OTHER INFORMATION: synthetic citrullinated ICAM-I peptide ICAM-I-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (5)...(23)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 302

Arg Gly Ala Pro Xaa Ala Asn Leu Thr Val Val Leu Leu Xaa Leu Arg
1               5                  10                  15

Gly Glu Lys Glu Leu Lys Xaa Gly
            20
```

```
<210> SEQ ID NO 303
<211> LENGTH: 22
<212> TYPE: PRT
<213> ORGANISM: Artificial Sequence
<220> FEATURE:
<223> OTHER INFORMATION: synthetic ICAM-I peptide ICAM-I-1 core sequence
<220> FEATURE:
<221> NAME/KEY: MOD_RES
<222> LOCATION: (4)...(22)
<223> OTHER INFORMATION: Xaa = citrulline

<400> SEQUENCE: 303

Gly Ala Pro Xaa Ala Asn Leu Thr Val Val Leu Leu Xaa Leu Arg Gly
 1               5                  10                  15

Glu Lys Glu Leu Lys Xaa
             20

<210> SEQ ID NO 304
<211> LENGTH: 31
<212> TYPE: PRT
<213> ORGANISM: Artificial Sequence
<220> FEATURE:
<223> OTHER INFORMATION: synthetic citrullinated ICAM-I peptide ICAM-I-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(29)
<223> OTHER INFORMATION: Xaa = citrulline
<220> FEATURE:
<221> NAME/KEY: AMIDATION
<222> LOCATION: (31)...(31)
<223> OTHER INFORMATION: glycinamide

<400> SEQUENCE: 304

Gly Glu Val Thr Thr Thr Val Leu Val Xaa Arg Asp His Gly Ala Asn
 1               5                  10                  15

Phe Ser Ser Xaa Thr Ser Arg Thr Glu Leu Asp Leu Xaa Pro Gly
             20                  25                  30

<210> SEQ ID NO 305
<211> LENGTH: 29
<212> TYPE: PRT
<213> ORGANISM: Artificial Sequence
<220> FEATURE:
<223> OTHER INFORMATION: synthetic ICAM-I peptide ICAM-I-2 core sequence
<220> FEATURE:
<221> NAME/KEY: MOD_RES
<222> LOCATION: (9)...(28)
<223> OTHER INFORMATION: Xaa = citrulline

<400> SEQUENCE: 305

Glu Val Thr Thr Thr Val Leu Val Xaa Arg Asp His Gly Ala Asn Phe
 1               5                  10                  15

Ser Ser Xaa Thr Ser Arg Thr Glu Leu Asp Leu Xaa Pro
             20                  25

<210> SEQ ID NO 306
<211> LENGTH: 27
<212> TYPE: PRT
<213> ORGANISM: Artificial Sequence
<220> FEATURE:
<223> OTHER INFORMATION: synthetic citrullinated ICAM-I peptide ICAM-I-3
<220> FEATURE:
<221> NAME/KEY: MOD_RES
<222> LOCATION: (1)...(1)
<223> OTHER INFORMATION: Gly modified by biotin
<220> FEATURE:
```

```
<221> NAME/KEY: MOD_RES
<222> LOCATION: (6)...(24)
<223> OTHER INFORMATION: Xaa = citrulline
<220> FEATURE:
<221> NAME/KEY: AMIDATION
<222> LOCATION: (27)...(27)
<223> OTHER INFORMATION: glycinamide

<400> SEQUENCE: 306

Gly Leu Ser Arg Ala Xaa Ser Thr Gln Gly Glu Val Thr Xaa Lys Val
 1               5                  10                  15

Thr Val Asn Val Leu Ser Pro Xaa Tyr Glu Gly
            20                  25

<210> SEQ ID NO 307
<211> LENGTH: 25
<212> TYPE: PRT
<213> ORGANISM: Artificial Sequence
<220> FEATURE:
<223> OTHER INFORMATION: synthetic ICAM-I peptide ICAM-I-3 core sequence
<220> FEATURE:
<221> NAME/KEY: MOD_RES
<222> LOCATION: (5)...(23)
<223> OTHER INFORMATION: Xaa = citrulline

<400> SEQUENCE: 307

Leu Ser Arg Ala Xaa Ser Thr Gln Gly Glu Val Thr Xaa Lys Val Thr
 1               5                  10                  15

Val Asn Val Leu Ser Pro Xaa Tyr Glu
            20                  25

<210> SEQ ID NO 308
<211> LENGTH: 27
<212> TYPE: PRT
<213> ORGANISM: Artificial Sequence
<220> FEATURE:
<223> OTHER INFORMATION: synthetic citrullinated VCAM-I peptide VCAM-I-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(18)
<223> OTHER INFORMATION: Xaa = citrulline
<220> FEATURE:
<221> NAME/KEY: AMIDATION
<222> LOCATION: (27)...(27)
<223> OTHER INFORMATION: argininamide

<400> SEQUENCE: 308

Gly Pro Lys Gln Xaa Gln Ser Thr Gln Thr Leu Tyr Val Asn Val Ala
 1               5                  10                  15

Pro Xaa Asp Thr Thr Val Leu Val Ser Pro Arg
            20                  25

<210> SEQ ID NO 309
<211> LENGTH: 25
<212> TYPE: PRT
<213> ORGANISM: Artificial Sequence
<220> FEATURE:
<223> OTHER INFORMATION: synthetic VCAM-I peptide VCAM-I-1 core sequence
<220> FEATURE:
<221> NAME/KEY: MOD_RES
<222> LOCATION: (4)...(17)
<223> OTHER INFORMATION: Xaa = citrulline

<400> SEQUENCE: 309

Pro Lys Gln Xaa Gln Ser Thr Gln Thr Leu Tyr Val Asn Val Ala Pro
 1               5                  10                  15
```

```
Xaa Asp Thr Thr Val Leu Val Ser Pro
            20                  25

<210> SEQ ID NO 310
<211> LENGTH: 30
<212> TYPE: PRT
<213> ORGANISM: Artificial Sequence
<220> FEATURE:
<223> OTHER INFORMATION: synthetic citrullinated glypican peptide
      Glypican-I-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline
<220> FEATURE:
<221> NAME/KEY: AMIDATION
<222> LOCATION: (30)...(30)
<223> OTHER INFORMATION: argininamide

<400> SEQUENCE: 310

Gly Thr Ala Leu Xaa Asp Ser Ser Arg Val Ala Leu Arg Asp Ser Ser
 1               5                  10                  15

Xaa Val Leu Gln Ala Met Leu Ala Thr Gln Leu Xaa Ser Arg
            20                  25                  30

<210> SEQ ID NO 311
<211> LENGTH: 28
<212> TYPE: PRT
<213> ORGANISM: Artificial Sequence
<220> FEATURE:
<223> OTHER INFORMATION: synthetic glypican peptide Glypican-I-1 core
      sequence
<220> FEATURE:
<221> NAME/KEY: MOD_RES
<222> LOCATION: (4)...(27)
<223> OTHER INFORMATION: Xaa = citrulline

<400> SEQUENCE: 311

Thr Ala Leu Xaa Asp Ser Ser Arg Val Ala Leu Arg Asp Ser Ser Xaa
 1               5                  10                  15

Val Leu Gln Ala Met Leu Ala Thr Gln Leu Xaa Ser
            20                  25

<210> SEQ ID NO 312
<211> LENGTH: 37
<212> TYPE: PRT
<213> ORGANISM: Artificial Sequence
<220> FEATURE:
<223> OTHER INFORMATION: synthetic citrullinated glypican peptide
      Glypican-I-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(31)
<223> OTHER INFORMATION: Xaa = citrulline
<220> FEATURE:
<221> NAME/KEY: AMIDATION
<222> LOCATION: (37)...(37)
<223> OTHER INFORMATION: glycinamide

<400> SEQUENCE: 312

Gly Glu Leu Tyr Thr Gln Asn Ala Xaa Ala Arg Ala Phe Xaa Asp Leu
 1               5                  10                  15
```

```
Tyr Ser Phe Arg Asp Leu Tyr Ser Glu Leu Xaa Leu Tyr Tyr Xaa Gly
            20                  25                  30

Ala Asn Leu His Gly
            35

<210> SEQ ID NO 313
<211> LENGTH: 36
<212> TYPE: PRT
<213> ORGANISM: Artificial Sequence
<220> FEATURE:
<223> OTHER INFORMATION: synthetic glypican peptide Glypican-I-2 core
      sequence
<220> FEATURE:
<221> NAME/KEY: MOD_RES
<222> LOCATION: (9)...(31)
<223> OTHER INFORMATION: Xaa = citrulline

<400> SEQUENCE: 313

Gly Glu Leu Tyr Thr Gln Asn Ala Xaa Ala Arg Ala Phe Xaa Asp Leu
1               5                   10                  15

Tyr Ser Phe Arg Asp Leu Tyr Ser Glu Leu Xaa Leu Tyr Tyr Xaa Gly
            20                  25                  30

Ala Asn Leu His
            35

<210> SEQ ID NO 314
<211> LENGTH: 28
<212> TYPE: PRT
<213> ORGANISM: Artificial Sequence
<220> FEATURE:
<223> OTHER INFORMATION: synthetic citrullinated glypican peptide
      Glypican-I-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(23)
<223> OTHER INFORMATION: Xaa = citrulline
<220> FEATURE:
<221> NAME/KEY: AMIDATION
<222> LOCATION: (28)...(28)
<223> OTHER INFORMATION: glycinamide

<400> SEQUENCE: 314

Gly Leu Arg Ala Thr Xaa Ala Phe Val Ala Leu Arg Leu Xaa Ala Thr
1               5                   10                  15

Arg Ala Phe Val Ala Ala Xaa Ser Phe Val Gln Gly
            20                  25

<210> SEQ ID NO 315
<211> LENGTH: 26
<212> TYPE: PRT
<213> ORGANISM: Artificial Sequence
<220> FEATURE:
<223> OTHER INFORMATION: synthetic glypican peptide Glypican-I-3 core
      sequence
<220> FEATURE:
<221> NAME/KEY: MOD_RES
<222> LOCATION: (5)...(22)
<223> OTHER INFORMATION: Xaa = citrulline

<400> SEQUENCE: 315

Leu Arg Ala Thr Xaa Ala Phe Val Ala Leu Arg Leu Xaa Ala Thr Arg
1               5                   10                  15

Ala Phe Val Ala Ala Xaa Ser Phe Val Gln
            20                  25
```

```
<210> SEQ ID NO 316
<211> LENGTH: 26
<212> TYPE: PRT
<213> ORGANISM: Artificial Sequence
<220> FEATURE:
<223> OTHER INFORMATION: synthetic citrullinated glypican peptide
      Glypican-I-4
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(23)
<223> OTHER INFORMATION: Xaa = citrulline
<220> FEATURE:
<221> NAME/KEY: AMIDATION
<222> LOCATION: (26)...(26)
<223> OTHER INFORMATION: argininamide

<400> SEQUENCE: 316

Arg Leu Gly Val Ala Ser Asp Val Val Xaa Lys Val Ala Gln Val Pro
 1               5                  10                  15

Leu Gly Pro Glu Ser Ser Xaa Ala Val Arg
            20                  25

<210> SEQ ID NO 317
<211> LENGTH: 24
<212> TYPE: PRT
<213> ORGANISM: Artificial Sequence
<220> FEATURE:
<223> OTHER INFORMATION: synthetic glypican peptide Glypican-I-4 core
      sequence
<220> FEATURE:
<221> NAME/KEY: MOD_RES
<222> LOCATION: (9)...(22)
<223> OTHER INFORMATION: Xaa = citrulline

<400> SEQUENCE: 317

Leu Gly Val Ala Ser Asp Val Val Xaa Lys Val Ala Gln Val Pro Leu
 1               5                  10                  15

Gly Pro Glu Ser Ser Xaa Ala Val
            20

<210> SEQ ID NO 318
<211> LENGTH: 27
<212> TYPE: PRT
<213> ORGANISM: Artificial Sequence
<220> FEATURE:
<223> OTHER INFORMATION: synthetic citrullinated glypican peptide
      Glypican-I-5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(21)
<223> OTHER INFORMATION: Xaa = citrulline
<220> FEATURE:
<221> NAME/KEY: AMIDATION
<222> LOCATION: (27)...(27)
<223> OTHER INFORMATION: argininamide

<400> SEQUENCE: 318

Gly Gln Leu Lys Ile Met Thr Asn Xaa Leu Arg Ser Leu Lys Ile Met
 1               5                  10                  15

Thr Asn Arg Leu Xaa Ser Ala Tyr Asn Gly Arg
            20                  25
```

```
<210> SEQ ID NO 319
<211> LENGTH: 25
<212> TYPE: PRT
<213> ORGANISM: Artificial Sequence
<220> FEATURE:
<223> OTHER INFORMATION: synthetic glypican peptide Glypican-I-5 core
      sequence
<220> FEATURE:
<221> NAME/KEY: MOD_RES
<222> LOCATION: (8)...(20)
<223> OTHER INFORMATION: Xaa = citrulline

<400> SEQUENCE: 319

Gln Leu Lys Ile Met Thr Asn Xaa Leu Arg Ser Leu Lys Ile Met Thr
 1               5                  10                  15

Asn Arg Leu Xaa Ser Ala Tyr Asn Gly
            20                  25

<210> SEQ ID NO 320
<211> LENGTH: 25
<212> TYPE: PRT
<213> ORGANISM: Artificial Sequence
<220> FEATURE:
<223> OTHER INFORMATION: synthetic citrullinated glypican peptide
      Glypican-I-6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(23)
<223> OTHER INFORMATION: Xaa = citrulline
<220> FEATURE:
<221> NAME/KEY: AMIDATION
<222> LOCATION: (25)...(25)
<223> OTHER INFORMATION: glycinamide

<400> SEQUENCE: 320

Gly Ser Gly Arg Lys Val Ser Xaa Lys Ser Ser Ser Ser Arg Thr Ser
 1               5                  10                  15

Arg Lys Ser Ser Ser Ser Xaa Thr Gly
            20                  25

<210> SEQ ID NO 321
<211> LENGTH: 23
<212> TYPE: PRT
<213> ORGANISM: Artificial Sequence
<220> FEATURE:
<223> OTHER INFORMATION: synthetic glypican peptide Glypican-I-6 core
      sequence
<220> FEATURE:
<221> NAME/KEY: MOD_RES
<222> LOCATION: (7)...(22)
<223> OTHER INFORMATION: Xaa = citrulline

<400> SEQUENCE: 321

Ser Gly Arg Lys Val Ser Xaa Lys Ser Ser Ser Ser Arg Thr Ser Arg
 1               5                  10                  15

Lys Ser Ser Ser Ser Xaa Thr
            20

<210> SEQ ID NO 322
<211> LENGTH: 23
<212> TYPE: PRT
<213> ORGANISM: Artificial Sequence
<220> FEATURE:
<223> OTHER INFORMATION: synthetic citrullinated glypican peptide
      Glypican-II-1
<220> FEATURE:
<221> NAME/KEY: MOD_RES
```

```
<222> LOCATION: (1)...(1)
<223> OTHER INFORMATION: Gly modified by biotin
<220> FEATURE:
<221> NAME/KEY: MOD_RES
<222> LOCATION: (10)...(21)
<223> OTHER INFORMATION: Xaa = citrulline
<220> FEATURE:
<221> NAME/KEY: AMIDATION
<222> LOCATION: (23)...(23)
<223> OTHER INFORMATION: argininamide

<400> SEQUENCE: 322

Gly Ser Ser Ser Ser Glu Thr Glu Gln Xaa Arg Leu Ile Xaa Glu Thr
1               5                   10                  15

Glu Ala Thr Phe Xaa Gly Arg
            20

<210> SEQ ID NO 323
<211> LENGTH: 21
<212> TYPE: PRT
<213> ORGANISM: Artificial Sequence
<220> FEATURE:
<223> OTHER INFORMATION: synthetic glypican peptide Glypican-II-1 core
      sequence
<220> FEATURE:
<221> NAME/KEY: MOD_RES
<222> LOCATION: (9)...(20)
<223> OTHER INFORMATION: Xaa = citrulline

<400> SEQUENCE: 323

Ser Ser Ser Ser Glu Thr Glu Gln Xaa Arg Leu Ile Xaa Glu Thr Glu
1               5                   10                  15

Ala Thr Phe Xaa Gly
            20

<210> SEQ ID NO 324
<211> LENGTH: 30
<212> TYPE: PRT
<213> ORGANISM: Artificial Sequence
<220> FEATURE:
<223> OTHER INFORMATION: synthetic citrullinated glypican peptide
      Glypican-II-2
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (3)...(25)
<223> OTHER INFORMATION: Xaa = citrulline
<220> FEATURE:
<221> NAME/KEY: AMIDATION
<222> LOCATION: (30)...(30)
<223> OTHER INFORMATION: argininamide

<400> SEQUENCE: 324

Arg Leu Xaa Leu Gln Ile Thr Arg Thr Leu Val Ala Ala Xaa Ala Phe
1               5                   10                  15

Val Gln Leu Arg Leu Gln Ile Thr Xaa Thr Leu Val Ala Arg
            20                  25                  30

<210> SEQ ID NO 325
<211> LENGTH: 29
<212> TYPE: PRT
<213> ORGANISM: Artificial Sequence
<220> FEATURE:
<223> OTHER INFORMATION: synthetic glypican peptide Glypican-II-2 core
      sequence
<220> FEATURE:
<221> NAME/KEY: MOD_RES
<222> LOCATION: (3)...(25)
```

```
<223> OTHER INFORMATION: Xaa = citrulline

<400> SEQUENCE: 325

Arg Leu Xaa Leu Gln Ile Thr Arg Thr Leu Val Ala Ala Xaa Ala Phe
1               5                   10                  15

Val Gln Leu Arg Leu Gln Ile Thr Xaa Thr Leu Val Ala
            20                  25

<210> SEQ ID NO 326
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-II-3
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(22)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 326

Arg Gln Gly Phe Ser Leu Asn Val Val Xaa Gly Ser Leu Ser Ser Arg
1               5                   10                  15

Gly Ser Leu Ser Ser Xaa Gly Gly
            20

<210> SEQ ID NO 327
<211> LENGTH: 22
<212> TYPE: PRT
<213> ORGANISM: Artificial Sequence
<220> FEATURE:
<223> OTHER INFORMATION: synthetic glypican peptide Glypican-II-3 core
      sequence
<220> FEATURE:
<221> NAME/KEY: MOD_RES
<222> LOCATION: (9)...(21)
<223> OTHER INFORMATION: Xaa = citrulline

<400> SEQUENCE: 327

Gln Gly Phe Ser Leu Asn Val Val Xaa Gly Ser Leu Ser Ser Arg Gly
1               5                   10                  15

Ser Leu Ser Ser Xaa Gly
            20

<210> SEQ ID NO 328
<211> LENGTH: 29
<212> TYPE: PRT
<213> ORGANISM: Artificial Sequence
<220> FEATURE:
<223> OTHER INFORMATION: synthetic citrullinated glypican peptide
      Glypican-II-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(27)
<223> OTHER INFORMATION: Xaa = citrulline
<220> FEATURE:
<221> NAME/KEY: AMIDATION
<222> LOCATION: (29)...(29)
<223> OTHER INFORMATION: glycinamide
```

-continued

<400> SEQUENCE: 328

Gly Pro Val Pro Ala Xaa Asn Arg Arg Ala Pro Val Pro Ala Arg Asn
1               5                   10                  15

Xaa Arg Ala Pro Val Pro Ala Arg Asn Arg Xaa Ala Gly
            20                  25

<210> SEQ ID NO 329
<211> LENGTH: 27
<212> TYPE: PRT
<213> ORGANISM: Artificial Sequence
<220> FEATURE:
<223> OTHER INFORMATION: synthetic glypican peptide Glypican-II-4 core
      sequence
<220> FEATURE:
<221> NAME/KEY: MOD_RES
<222> LOCATION: (5)...(26)
<223> OTHER INFORMATION: Xaa = citrulline

<400> SEQUENCE: 329

Pro Val Pro Ala Xaa Asn Arg Arg Ala Pro Val Pro Ala Arg Asn Xaa
1               5                   10                  15

Arg Ala Pro Val Pro Ala Arg Asn Arg Xaa Ala
            20                  25

<210> SEQ ID NO 330
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-II-5
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (10)...(22)
<223> OTHER INFORMATION: Xaa = citrulline
<220> FEATURE:
<221> NAME/KEY: AMIDATION
<222> LOCATION: (24)...(24)
<223> OTHER INFORMATION: lysinamide

<400> SEQUENCE: 330

Arg Ser Gly Pro Asp Val Pro Thr Arg Xaa Arg Arg Xaa Leu Gln Leu
1               5                   10                  15

Arg Ala Ala Thr Ala Xaa Met Lys
            20

<210> SEQ ID NO 331
<211> LENGTH: 23
<212> TYPE: PRT
<213> ORGANISM: Artificial Sequence
<220> FEATURE:
<223> OTHER INFORMATION: synthetic glypican peptide Glypican-II-5
      core sequence
<220> FEATURE:
<221> NAME/KEY: MOD_RES
<222> LOCATION: (9)...(21)
<223> OTHER INFORMATION: Xaa = citrulline

<400> SEQUENCE: 331

Ser Gly Pro Asp Val Pro Thr Arg Xaa Arg Arg Xaa Leu Gln Leu Arg
1               5                   10                  15

Ala Ala Thr Ala Xaa Met Lys
            20

```
<210> SEQ ID NO 332
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-IV-1
<220> FEATURE:
<221> NAME/KEY: MOD_RES
<222> LOCATION: (1)...(1)
<223> OTHER INFORMATION: Arg modified by biotin
<220> FEATURE:
<221> NAME/KEY: MOD_RES
<222> LOCATION: (9)...(16)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 332

Arg Met Leu Asn Asp Phe Trp Ala Xaa Leu Leu Glu Arg Met Phe Xaa
 1               5                  10                  15

Leu Val Asn Ser Gln Tyr His Gly
            20

<210> SEQ ID NO 333
<211> LENGTH: 22
<212> TYPE: PRT
<213> ORGANISM: Artificial Sequence
<220> FEATURE:
<223> OTHER INFORMATION: synthetic glypican peptide Glypican-IV-1 core
      sequence
<220> FEATURE:
<221> NAME/KEY: MOD_RES
<222> LOCATION: (8)...(15)
<223> OTHER INFORMATION: Xaa = citrulline

<400> SEQUENCE: 333

Met Leu Asn Asp Phe Trp Ala Xaa Leu Leu Glu Arg Met Phe Xaa Leu
 1               5                  10                  15

Val Asn Ser Gln Tyr His
            20

<210> SEQ ID NO 334
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-IV-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(19)
<223> OTHER INFORMATION: Xaa = citrulline
<220> FEATURE:
<221> NAME/KEY: AMIDATION
<222> LOCATION: (24)...(24)
<223> OTHER INFORMATION: argininamide

<400> SEQUENCE: 334

Gly Leu Lys Leu Gln Val Thr Xaa Ala Phe Val Thr Arg Ala Phe Val
 1               5                  10                  15

Ala Ala Xaa Thr Phe Ala Gln Arg
            20
```

```
<210> SEQ ID NO 335
<211> LENGTH: 22
<212> TYPE: PRT
<213> ORGANISM: Artificial Sequence
<220> FEATURE:
<223> OTHER INFORMATION: synthetic glypican peptide Glypican-IV-2 core
      sequence
<220> FEATURE:
<221> NAME/KEY: MOD_RES
<222> LOCATION: (7)...(18)
<223> OTHER INFORMATION: Xaa = citrulline

<400> SEQUENCE: 335

Leu Lys Leu Gln Val Thr Xaa Ala Phe Val Thr Arg Ala Phe Val Ala
 1               5                  10                  15

Ala Xaa Thr Phe Ala Gln
            20

<210> SEQ ID NO 336
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-IV-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (3)...(15)
<223> OTHER INFORMATION: Xaa = citrulline
<220> FEATURE:
<221> NAME/KEY: AMIDATION
<222> LOCATION: (24)...(24)
<223> OTHER INFORMATION: argininamide

<400> SEQUENCE: 336

Gly Gly Xaa Ile Ser Arg Ser Ile Ser Glu Gly Arg Ile Ser Xaa Ser
 1               5                  10                  15

Ile Ser Glu Ser Ala Phe Ser Arg
            20

<210> SEQ ID NO 337
<211> LENGTH: 22
<212> TYPE: PRT
<213> ORGANISM: Artificial Sequence
<220> FEATURE:
<223> OTHER INFORMATION: synthetic glypican peptide Glypican-IV-3 core
      sequence
<220> FEATURE:
<221> NAME/KEY: MOD_RES
<222> LOCATION: (2)...(14)
<223> OTHER INFORMATION: Xaa = citrulline

<400> SEQUENCE: 337

Gly Xaa Ile Ser Arg Ser Ile Ser Glu Gly Arg Ile Ser Xaa Ser Ile
 1               5                  10                  15

Ser Glu Ser Ala Phe Ser
            20

<210> SEQ ID NO 338
<211> LENGTH: 23
<212> TYPE: PRT
<213> ORGANISM: Artificial Sequence
<220> FEATURE:
<223> OTHER INFORMATION: synthetic citrullinated glypican peptide
      Glypican-IV-4
<220> FEATURE:
<221> NAME/KEY: MOD_RES
```

```
<222> LOCATION: (1)...(1)
<223> OTHER INFORMATION: Arg modified by biotin
<220> FEATURE:
<221> NAME/KEY: MOD_RES
<222> LOCATION: (3)...(15)
<223> OTHER INFORMATION: Xaa = citrulline
<220> FEATURE:
<221> NAME/KEY: AMIDATION
<222> LOCATION: (23)...(23)
<223> OTHER INFORMATION: glycinamide

<400> SEQUENCE: 338

Arg Leu Xaa Gln Ile Met Ala Leu Arg Val Ile Met Ala Leu Xaa Val
 1               5                  10                  15

Met Thr Ser Lys Met Lys Gly
             20

<210> SEQ ID NO 339
<211> LENGTH: 21
<212> TYPE: PRT
<213> ORGANISM: Artificial Sequence
<220> FEATURE:
<223> OTHER INFORMATION: synthetic glypican peptide Glypican-IV-4 core
      sequence
<220> FEATURE:
<221> NAME/KEY: MOD_RES
<222> LOCATION: (2)...(14)
<223> OTHER INFORMATION: Xaa = citrulline

<400> SEQUENCE: 339

Leu Xaa Gln Ile Met Ala Leu Arg Val Ile Met Ala Leu Xaa Val Met
 1               5                  10                  15

Thr Ser Lys Met Lys
             20

<210> SEQ ID NO 340
<211> LENGTH: 29
<212> TYPE: PRT
<213> ORGANISM: Artificial Sequence
<220> FEATURE:
<223> OTHER INFORMATION: synthetic citrullinated glypican peptide
      Glypican-V-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(23)
<223> OTHER INFORMATION: Xaa = citrulline
<220> FEATURE:
<221> NAME/KEY: AMIDATION
<222> LOCATION: (29)...(29)
<223> OTHER INFORMATION: argininamide

<400> SEQUENCE: 340

Gly Thr Arg Lys Met Glu Glu Xaa Tyr Gln Ile Ala Ala Arg Gln Glu
 1               5                  10                  15

Arg Tyr Gln Ile Ala Ala Xaa Gln Asp Met Gln Gln Arg
             20                  25

<210> SEQ ID NO 341
<211> LENGTH: 27
<212> TYPE: PRT
<213> ORGANISM: Artificial Sequence
<220> FEATURE:
<223> OTHER INFORMATION: synthetic glypican peptide Glypican-V-1 core
      sequence
<220> FEATURE:
<221> NAME/KEY: MOD_RES
<222> LOCATION: (7)...(22)
```

```
<223> OTHER INFORMATION: Xaa = citrulline

<400> SEQUENCE: 341

Thr Arg Lys Met Glu Glu Xaa Tyr Gln Ile Ala Ala Arg Gln Glu Arg
 1               5                  10                  15

Tyr Gln Ile Ala Ala Xaa Gln Asp Met Gln Gln
            20                  25

<210> SEQ ID NO 342
<211> LENGTH: 32
<212> TYPE: PRT
<213> ORGANISM: Artificial Sequence
<220> FEATURE:
<223> OTHER INFORMATION: synthetic citrullinated glypican peptide
      Glypican-V-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (7)...(27)
<223> OTHER INFORMATION: Xaa = citrulline
<220> FEATURE:
<221> NAME/KEY: AMIDATION
<222> LOCATION: (32)...(32)
<223> OTHER INFORMATION: argininamide

<400> SEQUENCE: 342

Gly Ile Arg Met Ala Arg Xaa Asp Val Ser Pro Phe Gly Ala Xaa Arg
 1               5                  10                  15

Asp Val Ser Pro Phe Gly Asn Ile Pro Gln Xaa Val Met Gly Gln Arg
            20                  25                  30

<210> SEQ ID NO 343
<211> LENGTH: 30
<212> TYPE: PRT
<213> ORGANISM: Artificial Sequence
<220> FEATURE:
<223> OTHER INFORMATION: synthetic glypican peptide Glypican-V-2 core
      sequence
<220> FEATURE:
<221> NAME/KEY: MOD_RES
<222> LOCATION: (6)...(26)
<223> OTHER INFORMATION: Xaa = citrulline

<400> SEQUENCE: 343

Ile Arg Met Ala Arg Xaa Asp Val Ser Pro Phe Gly Ala Xaa Arg Asp
 1               5                  10                  15

Val Ser Pro Phe Gly Asn Ile Pro Gln Xaa Val Met Gly Gln
            20                  25                  30

<210> SEQ ID NO 344
<211> LENGTH: 34
<212> TYPE: PRT
<213> ORGANISM: Artificial Sequence
<220> FEATURE:
<223> OTHER INFORMATION: synthetic citrullinated glypican peptide
      Glypican-V-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(32)
<223> OTHER INFORMATION: Xaa = citrulline
<220> FEATURE:
<221> NAME/KEY: AMIDATION
<222> LOCATION: (34)...(34)
<223> OTHER INFORMATION: argininamide
```

```
<400> SEQUENCE: 344

Gly Lys Leu Leu Glu Gln Val Asn Xaa Ile Ser Gly Xaa Pro Val Arg
1               5                   10                  15

Thr Pro Thr Gln Gly Arg Pro Val Xaa Thr Pro Thr Gln Ser Pro Xaa
            20                  25                  30

Ser Arg

<210> SEQ ID NO 345
<211> LENGTH: 32
<212> TYPE: PRT
<213> ORGANISM: Artificial Sequence
<220> FEATURE:
<223> OTHER INFORMATION: synthetic glypican peptide Glypican-V-3 core
      sequence
<220> FEATURE:
<221> NAME/KEY: MOD_RES
<222> LOCATION: (8)...(31)
<223> OTHER INFORMATION: Xaa = citrulline

<400> SEQUENCE: 345

Lys Leu Leu Glu Gln Val Asn Xaa Ile Ser Gly Xaa Pro Val Arg Thr
1               5                   10                  15

Pro Thr Gln Gly Arg Pro Val Xaa Thr Pro Thr Gln Ser Pro Xaa Ser
            20                  25                  30

<210> SEQ ID NO 346
<211> LENGTH: 30
<212> TYPE: PRT
<213> ORGANISM: Artificial Sequence
<220> FEATURE:
<223> OTHER INFORMATION: synthetic citrullinated glypican peptide
      Glypican-V-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(25)
<223> OTHER INFORMATION: Xaa = citrulline
<220> FEATURE:
<221> NAME/KEY: AMIDATION
<222> LOCATION: (30)...(30)
<223> OTHER INFORMATION: argininamide

<400> SEQUENCE: 346

Gly Lys Glu Phe Ile Asn Ser Leu Xaa Leu Tyr Arg Ser Phe Tyr Gly
1               5                   10                  15

Phe Ile Asn Ser Leu Arg Leu Tyr Xaa Ser Phe Tyr Gly Arg
            20                  25                  30

<210> SEQ ID NO 347
<211> LENGTH: 28
<212> TYPE: PRT
<213> ORGANISM: Artificial Sequence
<220> FEATURE:
<223> OTHER INFORMATION: synthetic glypican peptide Glypican-V-4 core
      sequence
<220> FEATURE:
<221> NAME/KEY: MOD_RES
<222> LOCATION: (8)...(24)
<223> OTHER INFORMATION: Xaa = citrulline

<400> SEQUENCE: 347

Lys Glu Phe Ile Asn Ser Leu Xaa Leu Tyr Arg Ser Phe Tyr Gly Phe
1               5                   10                  15

Ile Asn Ser Leu Arg Leu Tyr Xaa Ser Phe Tyr Gly
            20                  25
```

<210> SEQ ID NO 348
<211> LENGTH: 24
<212> TYPE: PRT
<213> ORGANISM: Artificial Sequence
<220> FEATURE:
<223> OTHER INFORMATION: synthetic citrullinated glypican peptide
      Glypican-VI-1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(22)
<223> OTHER INFORMATION: Xaa = citrulline
<220> FEATURE:
<221> NAME/KEY: AMIDATION
<222> LOCATION: (24)...(24)
<223> OTHER INFORMATION: glycinamide

<400> SEQUENCE: 348

Gly Ser His Phe Val Xaa Thr Thr Phe Val Ser Arg His Phe Val Arg
1               5                   10                  15

Thr Thr Phe Val Ser Xaa His Gly
            20

<210> SEQ ID NO 349
<211> LENGTH: 22
<212> TYPE: PRT
<213> ORGANISM: Artificial Sequence
<220> FEATURE:
<223> OTHER INFORMATION: synthetic glypican peptide Glypican-VI-1 core
      sequence
<220> FEATURE:
<221> NAME/KEY: MOD_RES
<222> LOCATION: (5)...(21)
<223> OTHER INFORMATION: Xaa = citrulline

<400> SEQUENCE: 349

Ser His Phe Val Xaa Thr Thr Phe Val Ser Arg His Phe Val Arg Thr
1               5                   10                  15

Thr Phe Val Ser Xaa His
            20

<210> SEQ ID NO 350
<211> LENGTH: 31
<212> TYPE: PRT
<213> ORGANISM: Artificial Sequence
<220> FEATURE:
<223> OTHER INFORMATION: synthetic citrullinated glypican peptide
      Glypican-VI-2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(25)
<223> OTHER INFORMATION: Xaa = citrulline
<220> FEATURE:
<221> NAME/KEY: AMIDATION
<222> LOCATION: (31)...(31)
<223> OTHER INFORMATION: glycinamide

<400> SEQUENCE: 350

Gly Lys Leu Lys Ile Gln Val Thr Xaa Ala Phe Ile Ala Ala Xaa Thr
1               5                   10                  15

Phe Val Gln Gly Leu Thr Val Gly Xaa Glu Val Ala Asn Arg Gly
            20                  25                  30

```
<210> SEQ ID NO 351
<211> LENGTH: 29
<212> TYPE: PRT
<213> ORGANISM: Artificial Sequence
<220> FEATURE:
<223> OTHER INFORMATION: synthetic glypican peptide Glypican-VI-2 core
      sequence
<220> FEATURE:
<221> NAME/KEY: MOD_RES
<222> LOCATION: (8)...(24)
<223> OTHER INFORMATION: Xaa = citrulline

<400> SEQUENCE: 351

Lys Leu Lys Ile Gln Val Thr Xaa Ala Phe Ile Ala Ala Xaa Thr Phe
1               5                   10                  15

Val Gln Gly Leu Thr Val Gly Xaa Glu Val Ala Asn Arg
            20                  25

<210> SEQ ID NO 352
<211> LENGTH: 18
<212> TYPE: PRT
<213> ORGANISM: Artificial Sequence
<220> FEATURE:
<223> OTHER INFORMATION: synthetic citrullinated glypican peptide
      Glypican-VI-3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(10)
<223> OTHER INFORMATION: Xaa = citrulline
<220> FEATURE:
<221> NAME/KEY: AMIDATION
<222> LOCATION: (18)...(18)
<223> OTHER INFORMATION: argininamide

<400> SEQUENCE: 352

Gly Thr Val Gly Arg Glu Val Ala Asn Xaa Val Ser Lys Val Ser Pro
1               5                   10                  15

Thr Arg

<210> SEQ ID NO 353
<211> LENGTH: 16
<212> TYPE: PRT
<213> ORGANISM: Artificial Sequence
<220> FEATURE:
<223> OTHER INFORMATION: synthetic glypican peptide Glypican-VI-3 core
      sequence
<220> FEATURE:
<221> NAME/KEY: MOD_RES
<222> LOCATION: (9)...(9)
<223> OTHER INFORMATION: Xaa = citrulline

<400> SEQUENCE: 353

Thr Val Gly Arg Glu Val Ala Asn Xaa Val Ser Lys Val Ser Pro Thr
1               5                   10                  15

<210> SEQ ID NO 354
<211> LENGTH: 27
<212> TYPE: PRT
<213> ORGANISM: Artificial Sequence
<220> FEATURE:
<223> OTHER INFORMATION: synthetic citrullinated glypican peptide
      Glypican-VI-4
<220> FEATURE:
<221> NAME/KEY: MOD_RES
<222> LOCATION: (1)...(1)
<223> OTHER INFORMATION: Gly modified by biotin
```

```
<220> FEATURE:
<221> NAME/KEY: MOD_RES
<222> LOCATION: (9)...(19)
<223> OTHER INFORMATION: Xaa = citrulline
<220> FEAT

<400> SEQUENCE: 357

Thr Arg Ser Ser Ala Val Arg Leu Gln
1               5

<210> SEQ ID NO 358
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 358

Arg Ser Ser Ala Val Arg Leu Gln Ser
1               5

<210> SEQ ID NO 359
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 359

Ser Ser Ala Val Arg Leu Gln Ser Ser
1               5

<210> SEQ ID NO 360
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 360

Ser Ala Val Arg Leu Gln Ser Ser Val
1               5

<210> SEQ ID NO 361
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 361

Ala Val Arg Leu Gln Ser Ser Val Pro
1               5

<210> SEQ ID NO 362
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 362

Val Arg Leu Gln Ser Ser Val Pro Gly
1               5

<210> SEQ ID NO 363
<211> LENGTH: 9
<212> TYPE: PRT

```
<213> ORGANISM: Artificial Sequence
<220> FEATURE:
<223> OTHER INFORMATION: synthetic vimentin peptide epitope with R
      mutated to Q

<400> SEQUENCE: 363

Arg Leu Gln Ser Ser Val Pro Gly Val
 1               5

<210> SEQ ID NO 364
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 364

Leu Gln Ser Ser Val Pro Gly Val Arg
 1               5

<210> SEQ ID NO 365
<211> LENGTH: 9
<212> TYPE: PRT
<213> ORGANISM: Artificial Sequence
<220> FEATURE:
<223> OTHER INFORMATION: synthetic vimentin peptide epitope with R
      mutated to Q

<400> SEQUENCE: 365

Gln Ser Ser Val Pro Gly Val Arg Leu
 1               5

<210> SEQ ID NO 366
<211> LENGTH: 32
<212> TYPE: PRT
<213> ORGANISM: Artificial Sequence
<220> FEATURE:
<223> OTHER INFORMATION: synthetic vimentin Peptide (1), VMT6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(29)
<223> OTHER INFORMATION: Xaa = citrulline

<400> SEQUENCE: 366

Gly Ser Thr Xaa Ser Val Ser Ser Ser Tyr Arg Xaa Arg Ser Val
 1               5                  10                  15

Ser Ser Ser Ser Tyr Xaa Ser Arg Pro Ser Ser Ser Xaa Ser Tyr Val
             20                  25                  30

<210> SEQ ID NO 367
<211> LENGTH: 33
<212> TYPE: PRT
<213> ORGANISM: Artificial Sequence
<220> FEATURE:
<223> OTHER INFORMATION: synthetic vimentin Peptide (2), VMT7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(27)
<223> OTHER INFORMATION: Xaa = citrulline

<400> SEQUENCE: 367
```

-continued

Gly Arg Ser Tyr Val Thr Thr Ser Thr Xaa Thr Tyr Ser Ala Leu Arg
1               5                   10                  15

Pro Ser Thr Ser Xaa Ser Leu Tyr Ala Thr Xaa Ser Ser Ala Val Arg
                20                  25                  30

Leu

<210> SEQ ID NO 368
<211> LENGTH: 26
<212> TYPE: PRT
<213> ORGANISM: Artificial Sequence
<220> FEATURE:
<223> OTHER INFORMATION: synthetic vimentin Peptide (3), VMT8
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (8)...(21)
<223> OTHER INFORMATION: Xaa = citrulline

<400> SEQUENCE: 368

Gly Thr Arg Ser Ser Ala Val Xaa Leu Arg Ser Ser Val Pro Gly Val
1               5                   10                  15

Xaa Val Arg Leu Xaa Ser Ser Val Pro Gly
                20                  25

<210> SEQ ID NO 369
<211> LENGTH: 27
<212> TYPE: PRT
<213> ORGANISM: Artificial Sequence
<220> FEATURE:
<223> OTHER INFORMATION: synthetic vimentin Peptide (4), VMT9
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(20)
<223> OTHER INFORMATION: Xaa = citrulline

<400> SEQUENCE: 369

Gly Phe Lys Asn Thr Xaa Thr Asn Glu Lys Asn Tyr Ile Asp Lys Val
1               5                   10                  15

Xaa Phe Leu Xaa Arg Gln Val Asp Gln Leu Thr
                20                  25

<210> SEQ ID NO 370
<211> LENGTH: 32
<212> TYPE: PRT
<213> ORGANISM: Artificial Sequence
<220> FEATURE:
<223> OTHER INFORMATION: synthetic vimentin Peptide (5), VMT10
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline

<400> SEQUENCE: 370

Gly Leu Arg Xaa Gln Val Asp Gln Leu Thr Ser Phe Xaa Gln Asp Val
1               5                   10                  15

Asp Asn Ala Ser Leu Ala Xaa Ala Arg Leu Asp Leu Glu Xaa Lys Val
                20                  25                  30

```
<210> SEQ ID NO 371
<211> LENGTH: 21
<212> TYPE: PRT
<213> ORGANISM: Artificial Sequence
<220> FEATURE:
<223> OTHER INFORMATION: synthetic vimentin Peptide (6), VMT11
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(14)
<223> OTHER INFORMATION: Xaa = citrulline

<400> SEQUENCE: 371

Gly Thr Ala Ala Leu Xaa Asp Val Arg Gln Gln Tyr Arg Xaa Gln Val
 1               5                  10                  15

Gln Ser Leu Thr Ser
            20

<210> SEQ ID NO 372
<211> LENGTH: 27
<212> TYPE: PRT
<213> ORGANISM: Artificial Sequence
<220> FEATURE:
<223> OTHER INFORMATION: synthetic vimentin Peptide (7), VMT12
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(20)
<223> OTHER INFORMATION: Xaa = citrulline

<400> SEQUENCE: 372

Gly Ala Asn Arg Asn Asn Asp Ala Leu Xaa Gln Ala Lys Gln Glu Ser
 1               5                  10                  15

Thr Glu Tyr Xaa Arg Gln Val Gln Ser Leu Thr
            20                  25

<210> SEQ ID NO 373
<211> LENGTH: 32
<212> TYPE: PRT
<213> ORGANISM: Artificial Sequence
<220> FEATURE:
<223> OTHER INFORMATION: synthetic vimentin Peptide (8), VMT13
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (11)...(29)
<223> OTHER INFORMATION: Xaa = citrulline

<400> SEQUENCE: 373

Gly Arg Ala Asn Tyr Gln Asp Thr Ile Gly Xaa Leu Asp Ile Glu Ile
 1               5                  10                  15

Ala Thr Tyr Xaa Lys Leu Leu Glu Gly Glu Glu Ser Xaa Ile Ser Arg
            20                  25                  30

<210> SEQ ID NO 374
<211> LENGTH: 37
<212> TYPE: PRT
<213> ORGANISM: Artificial Sequence
<220> FEATURE:
<223> OTHER INFORMATION: synthetic vimentin Peptide (9), VMT14
<220> FEATURE:
```

```
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(35)
<223> OTHER INFORMATION: Xaa = citrulline

<400> SEQUENCE: 374

Gly Asn Phe Ser Ser Leu Asn Leu Xaa Glu Thr Asn Leu Asp Ser Leu
 1               5                  10                  15

Pro Leu Val Asp Thr His Ser Lys Xaa Thr Leu Leu Ile Lys Thr Val
            20                  25                  30

Glu Thr Xaa Asp Gly
        35

<210> SEQ ID NO 375
<211> LENGTH: 31
<212> TYPE: PRT
<213> ORGANISM: Artificial Sequence
<220> FEATURE:
<223> OTHER INFORMATION: synthetic fibrinogen alpha chain Peptide (1),
      Fib-A1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(29)
<223> OTHER INFORMATION: Xaa = citrulline

<400> SEQUENCE: 375

Gly Arg Gly Pro Arg Val Val Glu Xaa His Glu Val Asn Gln Asp Phe
 1               5                  10                  15

Thr Asn Xaa Ile Asn Lys Leu Lys Ile Arg Ser Ser Xaa Gly Ser
            20                  25                  30

<210> SEQ ID NO 376
<211> LENGTH: 31
<212> TYPE: PRT
<213> ORGANISM: Artificial Sequence
<220> FEATURE:
<223> OTHER INFORMATION: synthetic fibrinogen alpha chain Peptide (2),
      Fib-A2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(24)
<223> OTHER INFORMATION: Xaa = citrulline

<400> SEQUENCE: 376

Gly Thr Asn Ile Met Glu Ile Leu Xaa Gly Asp Phe Ser Ser Ala Asn
 1               5                  10                  15

Asn Arg Asp Asn Thr Tyr Asn Xaa Val Ser Glu Asp Leu Arg Ser
            20                  25                  30

<210> SEQ ID NO 377
<211> LENGTH: 32
<212> TYPE: PRT
<213> ORGANISM: Artificial Sequence
<220> FEATURE:
<223> OTHER INFORMATION: synthetic fibrinogen alpha chain Peptide (3),
      Fib-A3
<220> FEATURE:
<221> NAME/KEY: MOD_RES
<222> LOCATION: (1)...(1)
```

<223> OTHER INFORMATION: Gly modified by biotin
<220> FEATURE:
<221> NAME/KEY: MOD_RES
<222> LOCATION: (10)...(31)
<223> OTHER INFORMATION: Xaa = citrulline

<400> SEQUENCE: 377

Gly Tyr Asn Arg Val Ser Glu Asp Leu Xaa Ser Arg Ile Glu Val Leu
 1               5                  10                  15

Lys Xaa Lys Val Ile Glu Lys Gln Leu Leu Gln Lys Asn Val Xaa Ala
            20                  25                  30

<210> SEQ ID NO 378
<211> LENGTH: 33
<212> TYPE: PRT
<213> ORGANISM: Artificial Sequence
<220> FEATURE:
<223> OTHER INFORMATION: synthetic fibrinogen alpha chain Peptide (4),
      Fib-A4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (6)...(31)
<223> OTHER INFORMATION: Xaa = citrulline

<400> SEQUENCE: 378

Gly Asp Ile Lys Ile Xaa Ser Ser Arg Gly Ser Ser Xaa Ala Leu
 1               5                  10                  15

Leu Pro Ser Xaa Asp Arg Gln His Leu Leu Pro Ser Arg Asp Xaa Gln
            20                  25                  30

His

<210> SEQ ID NO 379
<211> LENGTH: 32
<212> TYPE: PRT
<213> ORGANISM: Artificial Sequence
<220> FEATURE:
<223> OTHER INFORMATION: synthetic fibrinogen alpha chain Peptide (5),
      Fib-A5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline

<400> SEQUENCE: 379

Gly Arg Phe Xaa Pro Asp Ser Pro Gly Ser Gly Thr Trp Asn Pro Gly
 1               5                  10                  15

Ser Ser Glu Xaa Gly Thr Ser Gly Ser Thr Thr Thr Xaa Arg Ser
            20                  25                  30

<210> SEQ ID NO 380
<211> LENGTH: 25
<212> TYPE: PRT
<213> ORGANISM: Artificial Sequence
<220> FEATURE:
<223> OTHER INFORMATION: synthetic fibrinogen alpha chain Peptide (6),
      Fib-A6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES

```
<222> LOCATION: (10)...(20)
<223> OTHER INFORMATION: Xaa = citrulline

<400> SEQUENCE: 380

Gly Ser Gly Ser Thr Thr Thr Thr Arg Xaa Ser Ser Ser Lys Thr Val
1               5                   10                  15

Phe Arg His Xaa His Pro Asp Glu Ala
            20                  25

<210> SEQ ID NO 381
<211> LENGTH: 30
<212> TYPE: PRT
<213> ORGANISM: Artificial Sequence
<220> FEATURE:
<223> OTHER INFORMATION: synthetic fibrinogen alpha chain Peptide (7),
      Fib-A7
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (11)...(22)
<223> OTHER INFORMATION: Xaa = citrulline

<400> SEQUENCE: 381

Gly Arg Glu Phe Val Ser Glu Thr Glu Ser Xaa Gly Ser Phe Thr Ser
1               5                   10                  15

Ser Thr Ser Tyr Asn Xaa Gly Asp Ser Thr Phe Glu Ser Lys
            20                  25                  30

<210> SEQ ID NO 382
<211> LENGTH: 28
<212> TYPE: PRT
<213> ORGANISM: Artificial Sequence
<220> FEATURE:
<223> OTHER INFORMATION: synthetic fibrinogen alpha chain Peptide (8),
      Fib-A8
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(19)
<223> OTHER INFORMATION: Xaa = citrulline

<400> SEQUENCE: 382

Gly His Glu Gly Thr His Ser Thr Lys Xaa Gly His Ala Lys Ser Arg
1               5                   10                  15

Pro Val Xaa Gly Ile His Thr Ser Pro Leu Gly Lys
            20                  25

<210> SEQ ID NO 383
<211> LENGTH: 32
<212> TYPE: PRT
<213> ORGANISM: Artificial Sequence
<220> FEATURE:
<223> OTHER INFORMATION: synthetic fibrinogen beta chain Peptide (1),
      Fib-B1
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline

<400> SEQUENCE: 383
```

```
Gly Tyr Arg Ala Xaa Pro Ala Lys Ala Ala Leu Leu Lys Asp Leu Trp
1               5                   10                  15

Gln Lys Xaa Asn Ser Asn Ile Pro Thr Asn Leu Xaa Val Leu Arg Ser
            20                  25                  30
```

```
<210> SEQ ID NO 384
<211> LENGTH: 35
<212> TYPE: PRT
<213> ORGANISM: Artificial Sequence
<220> FEATURE:
<223> OTHER INFORMATION: synthetic fibrinogen beta chain Peptide (2),
      Fib-B2
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(29)
<223> OTHER INFORMATION: Xaa = citrulline

<400> SEQUENCE: 384

Gly Pro Thr Asn Leu Arg Val Leu Xaa Ser Ile Leu Glu Asn Leu Arg
1               5                   10                  15

Ser Ile Leu Glu Asn Leu Xaa Ser Met Glu Tyr Ser Xaa Thr Pro Ser
            20                  25                  30

Thr Val Ser
        35
```

```
<210> SEQ ID NO 385
<211> LENGTH: 29
<212> TYPE: PRT
<213> ORGANISM: Artificial Sequence
<220> FEATURE:
<223> OTHER INFORMATION: synthetic fibrinogen beta chain Peptide (3),
      Fib-B3
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (9)...(27)
<223> OTHER INFORMATION: Xaa = citrulline

<400> SEQUENCE: 385

Gly Asp Lys Ile Ser Gln Leu Thr Xaa Met Gly Tyr Gln Ile Ser Val
1               5                   10                  15

Asn Lys Tyr Xaa Trp Leu Thr Ser Asp Pro Xaa Lys Gln
            20                  25
```

```
<210> SEQ ID NO 386
<211> LENGTH: 34
<212> TYPE: PRT
<213> ORGANISM: Artificial Sequence
<220> FEATURE:
<223> OTHER INFORMATION: synthetic alpha enolase Peptide (1), H-Enls-4
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline

<400> SEQUENCE: 386

Gly Phe Asp Ser Xaa Gly Asn Pro Thr Val Glu Val Gly Leu Phe Xaa
1               5                   10                  15
```

```
Ala Ala Val Pro Ser Gly Ala Ser Leu Glu Leu Xaa Asp Asn Asp Lys
            20                  25                  30

Thr Arg

<210> SEQ ID NO 387
<211> LENGTH: 33
<212> TYPE: PRT
<213> ORGANISM: Artificial Sequence
<220> FEATURE:
<223> OTHER INFORMATION: synthetic alpha enolase Peptide (2), H-Enls-5
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (4)...(30)
<223> OTHER INFORMATION: Xaa = citrulline

<400> SEQUENCE: 387

Gly Leu Tyr Xaa His Ile Ala Asp Leu Ala Gly Ser Xaa Tyr Ile Ser
  1               5                  10                  15

Pro Asp Gln Leu Ala Asp Leu Thr Val Thr Asn Pro Lys Xaa Ile Ala
            20                  25                  30

Lys

<210> SEQ ID NO 388
<211> LENGTH: 33
<212> TYPE: PRT
<213> ORGANISM: Artificial Sequence
<220> FEATURE:
<223> OTHER INFORMATION: synthetic alpha enolase Peptide (3), H-Enls-6
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (10)...(28)
<223> OTHER INFORMATION: Xaa = citrulline

<400> SEQUENCE: 388

Gly Gly Trp Gly Val Met Val Ser His Xaa Ser Gly Glu Thr Leu Xaa
  1               5                  10                  15

Ile Glu Glu Glu Leu Gly Ser Gly Arg Asn Phe Xaa Asn Pro Leu Ala
            20                  25                  30

Lys

<210> SEQ ID NO 389
<211> LENGTH: 32
<212> TYPE: PRT
<213> ORGANISM: Artificial Sequence
<220> FEATURE:
<223> OTHER INFORMATION: synthetic fibrin alpha-chain peptide alpha32
<220> FEATURE:
<221> NAME/KEY: MOD_RES
<222> LOCATION: (1)...(1)
<223> OTHER INFORMATION: Gly modified by biotin

<400> SEQUENCE: 389

Gly Gly Gly Pro Arg Val Val Glu Arg His Gln Ser Ala Gly Gly Gly
  1               5                  10                  15

Thr Lys Arg Gly His Ala Lys Ser Arg Pro Val Arg Gly Ile His Thr
            20                  25                  30

<210> SEQ ID NO 390
<211> LENGTH: 32
```

```
<212> TYPE: PRT
<213> ORGANISM: Artificial Sequence
<220> FEATURE:
<223> OTHER INFORMATION: synthetic citrullinated fibrin alpha-chain
      peptide Cit-alpha32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline

<400> SEQUENCE: 390

Gly Gly Gly Pro Xaa Val Val Glu Xaa His Gln Ser Ala Gly Gly Gly
1               5                   10                  15

Thr Lys Xaa Gly His Ala Lys Ser Xaa Pro Val Xaa Gly Ile His Thr
            20                  25                  30

<210> SEQ ID NO 391
<211> LENGTH: 32
<212> TYPE: PRT
<213> ORGANISM: Artificial Sequence
<220> FEATURE:
<223> OTHER INFORMATION: synthetic citrullinated fibrin alpha-chain
      peptide [25-Arg]Cit-alpha32
<220> FEATURE:
<221> NAME/KEY: MOD_RES
<222> LOCATION: (1)...(1)
<223> OTHER INFORMATION: Gly modified by biotin
<220> FEATURE:
<221> NAME/KEY: MOD_RES
<222> LOCATION: (5)...(28)
<223> OTHER INFORMATION: Xaa = citrulline

<400> SEQUENCE: 391

Gly Gly Gly Pro Xaa Val Val Glu Xaa His Gln Ser Ala Gly Gly Gly
1               5                   10                  15

Thr Lys Xaa Gly His Ala Lys Ser Arg Pro Val Xaa Gly Ile His Thr
            20                  25                  30

<210> SEQ ID NO 392
<211> LENGTH: 19
<212> TYPE: PRT
<213> ORGANISM: Artificial Sequence
<220> FEATURE:
<223> OTHER INFORMATION: synthetic citrullinated alpha enolase peptide
      Pg-Enls 1
<220> FEATURE:
<221> NAME/KEY: MOD_RES
<222> LOCATION: (1)...(1)
<223> OTHER INFORMATION: Cys modified by biotin
<220> FEATURE:
<221> NAME/KEY: MOD_RES
<222> LOCATION: (6)...(12)
<223> OTHER INFORMATION: Xaa = citrulline

<400> SEQUENCE: 392

Cys Lys Ile Ile Gly Xaa Glu Ile Leu Asp Ser Xaa Gly Asn Pro Thr
1               5                   10                  15

Val Glu Cys

<210> SEQ ID NO 393
<211> LENGTH: 19
<212> TYPE: PRT
<213> ORGANISM: Artificial Sequence
<220> FEATURE:
<223> OTHER INFORMATION: synthetic citrullinated alpha enolase peptide
      Pg-Enls 2
<220> FEATURE:
```

```
<221> NAME/KEY: MOD_RES
<222> LOCATION: (1)...(1)
<223> OTHER INFORMATION: Ala modified by biotin
<220> FEATURE:
<221> NAME/KEY: MOD_RES
<222> LOCATION: (12)...(12)
<223> OTHER INFORMATION: Xaa = citrulline

<400> SEQUENCE: 393

Ala Lys Ile Ile Gly Arg Glu Ile Leu Asp Ser Xaa Gly Asn Pro Thr
1               5                   10                  15

Val Glu Ala

<210> SEQ ID NO 394
<211> LENGTH: 12
<212> TYPE: PRT
<213> ORGANISM: Artificial Sequence
<220> FEATURE:
<223> OTHER INFORMATION: synthetic vimentin fragment residues 2-13

<400> SEQUENCE: 394

Ser Thr Arg Ser Val Ser Ser Ser Ser Tyr Arg Arg
1               5                   10

<210> SEQ ID NO 395
<211> LENGTH: 9
<212> TYPE: PRT
<213> ORGANISM: Artificial Sequence
<220> FEATURE:
<223> OTHER INFORMATION: synthetic vimentin fragment residues 4-12

<400> SEQUENCE: 395

Arg Ser Val Ser Ser Ser Ser Tyr Arg
1               5

<210> SEQ ID NO 396
<211> LENGTH: 10
<212> TYPE: PRT
<213> ORGANISM: Artificial Sequence
<220> FEATURE:
<223> OTHER INFORMATION: synthetic vimentin fragment residues 22-31

<400> SEQUENCE: 396

Ser Arg Pro Ser Ser Ser Arg Ser Tyr Val
1               5                   10

<210> SEQ ID NO 397
<211> LENGTH: 31
<212> TYPE: PRT
<213> ORGANISM: Artificial Sequence
<220> FEATURE:
<223> OTHER INFORMATION: synthetic vimentin composite fragment of
      residues 2-13, residues 4-12 and residues 22-31, native composite
      sequence

<400> SEQUENCE: 397

Ser Thr Arg Ser Val Ser Ser Ser Ser Tyr Arg Arg Arg Ser Val Ser
1               5                   10                  15

Ser Ser Ser Tyr Arg Ser Arg Pro Ser Ser Ser Arg Ser Tyr Val
            20                  25                  30

<210> SEQ ID NO 398
<211> LENGTH: 32
<212> TYPE: PRT
<213> ORGANISM: Artificial Sequence
<220> FEATURE:
<223> OTHER INFORMATION: synthetic variant of vimentin Peptide (1) with
      valine residues substituted with alanines
```

```
<220> FEATURE:
<221> NAME/KEY: MOD_RES
<222> LOCATION: (4)...(29)
<223> OTHER INFORMATION: Xaa = citrulline

<400> SEQUENCE: 398

Gly Ser Thr Xaa Ser Ala Ser Ser Ser Ser Tyr Arg Xaa Arg Ser Ala
 1               5                  10                  15

Ser Ser Ser Ser Tyr Xaa Ser Arg Pro Ser Ser Xaa Ser Tyr Ala
            20                  25                  30

<210> SEQ ID NO 399
<211> LENGTH: 31
<212> TYPE: PRT
<213> ORGANISM: Artificial Sequence
<220> FEATURE:
<223> OTHER INFORMATION: synthetic vimentin variant composite sequence
<220> FEATURE:
<221> NAME/KEY: MOD_RES
<222> LOCATION: (3)...(28)
<223> OTHER INFORMATION: Xaa = citrulline

<400> SEQUENCE: 399

Ser Thr Xaa Ser Ala Ser Ser Ser Ser Tyr Arg Xaa Arg Ser Ala Ser
 1               5                  10                  15

Ser Ser Ser Tyr Xaa Ser Arg Pro Ser Ser Xaa Ser Tyr Ala
            20                  25                  30

<210> SEQ ID NO 400
<211> LENGTH: 25
<212> TYPE: PRT
<213> ORGANISM: Artificial Sequence
<220> FEATURE:
<223> OTHER INFORMATION: synthetic vimentin peptide VMT8 core sequence
<220> FEATURE:
<221> NAME/KEY: MOD_RES
<222> LOCATION: (7)...(20)
<223> OTHER INFORMATION: Xaa = Arg or citrulline (Cit)

<400> SEQUENCE: 400

Thr Arg Ser Ser Ala Val Xaa Leu Arg Ser Ser Val Pro Gly Val Xaa
 1               5                  10                  15

Val Arg Leu Xaa Ser Ser Val Pro Gly
            20                  25

<210> SEQ ID NO 401
<211> LENGTH: 32
<212> TYPE: PRT
<213> ORGANISM: Artificial Sequence
<220> FEATURE:
<223> OTHER INFORMATION: synthetic vimentin peptide VMT7 core sequence
<220> FEATURE:
<221> NAME/KEY: MOD_RES
<222> LOCATION: (9)...(26)
<223> OTHER INFORMATION: Xaa = Arg or citrulline (Cit)

<400> SEQUENCE: 401

Arg Ser Tyr Val Thr Thr Ser Thr Xaa Thr Tyr Ser Ala Leu Arg Pro
 1               5                  10                  15

Ser Thr Ser Xaa Ser Leu Tyr Ala Thr Xaa Ser Ser Ala Val Arg Leu
            20                  25                  30

<210> SEQ ID NO 402
<211> LENGTH: 28
<212> TYPE: PRT
<213> ORGANISM: Artificial Sequence
<220> FEATURE:
<223> OTHER INFORMATION: synthetic vimentin peptide VMT13 core sequence
```

```
-continued
<220> FEATURE:
<221> NAME/KEY: MOD_RES
<222> LOCATION: (9)...(26)
<223> OTHER INFORMATION: Xaa = Arg or citrulline (Cit)

<400> SEQUENCE: 402

Ala Asn Tyr Gln Asp Thr Ile Gly Xaa Leu Asp Glu Ile Ala Thr Tyr
 1               5                  10                  15

Xaa Lys Leu Leu Glu Gly Glu Glu Ser Xaa Ile Ser
            20                  25
```

What is claimed is:

1. A synthetic peptide comprising an amino acid sequence selected from the group consisting of SEQ ID NOS:41, 43, 45, 47, 49, 51, 53, 55, 57, 59, 61, 63, 65, and 67, wherein said peptide is immunologically reactive with an anti-citrullinated protein antibody.

2. The synthetic peptide of claim 1, wherein said peptide further comprises a tag.

3. The synthetic peptide of claim 2, wherein said tag is biotin.

4. A synthetic peptide comprising an amino acid sequence selected from the group consisting of SEQ ID NOS:40, 42, 44, 46, 48, 50, 52, 54, 56, 58, 60, 62, 64, and 66 wherein said peptide is immunologically reactive with an anti-citrullinated protein antibody.

5. The synthetic peptide of claim 1 or 4, wherein the C-terminus of said peptide is amidated.

6. The synthetic peptide of claim 1 or 4, wherein said peptide further comprises a detectable moiety.

7. The synthetic peptide of claim 6, wherein said detectable moiety is a fluorescent moiety.

8. A method for detecting an anti-citrullinated protein antibody in a biological sample, the method comprising the steps of:
   (a) contacting the biological sample with a synthetic peptide of claim 1 or 4 under conditions suitable to transform said peptide into a complex comprising said peptide and anti-citrullinated protein antibody; and
   (b) detecting the presence or level of said complex.

9. The method of claim 8, wherein step (b) comprises the detection of a detectable moiety conjugated to said peptide.

10. The method of claim 9, wherein said detectable moiety is a fluorescent moiety.

11. The method of claim 8, wherein step (b) comprises the sub-steps of:
   (i) contacting said complex with a detection reagent comprising a reporter group to transform said complex into a labeled complex; and
   (ii) detecting the presence or level of said labeled complex.

12. The method of claim 11, wherein said detection reagent is selected from the group consisting of an anti-IgA antibody, an anti-IgG antibody, an anti-IgM antibody, Protein L, Protein A, Protein G, and mixtures thereof.

13. The method of claim 11, wherein said reporter group is selected from the group consisting of radioactive groups, fluorescent groups, luminescent groups, enzymes, biotin, and dyes.

14. The method of claim 11, wherein detecting the presence or level of said labeled complex comprises detecting the presence or level of a signal generated from said reporter group.

15. The method of claim 11, wherein said anti-citrullinated protein antibodies comprise IgG anti-citrullinated protein antibodies.

16. A kit comprising:
   (a) at least one synthetic peptide of claim 1 or 4; and
   (b) a detection reagent comprising a detectable moiety.

17. A kit comprising:
   (a) at least one synthetic peptide of claim 1 or 4; and
   (b) a detectable moiety linked to said at least one synthetic peptide.

18. The kit of claim 16 or 17, wherein said detectable moiety is selected from the group consisting of radioactive groups, fluorescent groups, luminescent groups, enzymes, biotin, and dyes.

19. The kit of claim 16, wherein said detection reagent is selected from the group consisting of an anti-IgA antibody, an anti-IgG antibody, an anti-IgM antibody, Protein L, Protein A, Protein G, and mixtures thereof.

20. The kit of claim 16 or 17, wherein said at least one synthetic peptide is immobilized on a solid support.

* * * * *